United States Patent
Jiang et al.

(10) Patent No.: US 12,195,734 B2
(45) Date of Patent: Jan. 14, 2025

(54) DEAMINASE-BASED RNA SENSORS

(71) Applicants: Massachusetts Institute of Technology, Cambridge, MA (US); The Broad Institute, Inc., Cambridge, MA (US); President and Fellows of Harvard College, Cambridge, MA (US)

(72) Inventors: Kaiyi Jiang, Cambridge, MA (US); Rohan Neil Krajeski, Boston, MA (US); Omar Osama Abudayyeh, Cambridge, MA (US); Jonathan S. Gootenberg, Cambridge, MA (US); Yifan Zhang, Cambridge, MA (US); Fei Chen, Cambridge, MA (US); Xi Chen, Roxbury Crossing, MA (US); Jeremy G. Koob, Somerville, MA (US)

(73) Assignees: Massachusetts Institute of Technology, Cambridge, MA (US); The Broad Institute, Inc., Cambridge, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 17/806,879

(22) Filed: Jun. 14, 2022

(65) Prior Publication Data
US 2023/0123513 A1    Apr. 20, 2023

Related U.S. Application Data

(60) Provisional application No. 63/267,177, filed on Jan. 26, 2022, provisional application No. 63/210,829, filed on Jun. 15, 2021.

(51) Int. Cl.
*C12N 15/113* (2010.01)
*C12N 9/50* (2006.01)
*C12N 9/78* (2006.01)
*C12N 15/10* (2006.01)
*C12Q 1/6897* (2018.01)

(52) U.S. Cl.
CPC .......... *C12N 15/113* (2013.01); *C12N 9/50* (2013.01); *C12N 9/78* (2013.01); *C12N 15/1055* (2013.01); *C12Q 1/6897* (2013.01); *C12N 2310/14* (2013.01)

(58) Field of Classification Search
None
See application file for complete search history.

(56) References Cited

U.S. PATENT DOCUMENTS

2017/0191057 A1* 7/2017 Jamieson ............. C12N 5/0693
2019/0032141 A1* 1/2019 Weiss ................. A61K 31/7125
2020/0263180 A1* 8/2020 Mali ...................... A61P 21/00
2021/0355494 A1* 11/2021 Wei ..................... C12N 15/102
2023/0242906 A1* 8/2023 Levanon ............ C12N 15/1086
506/10

FOREIGN PATENT DOCUMENTS

WO        2019071048 A1    4/2019
WO    WO-2023077135 A1 *  5/2023
WO    WO-2023164630 A1 *  8/2023

OTHER PUBLICATIONS

Qu et al. Nature Biotechnology vol. 37 pp. 1059-1069 (Year: 2019).*
Dabrowski et al. RNA Biology 12: 950-958 (Year: 2015).*
Yeh et al. ACS Chem. Biol 14, 959-965 (Year: 2019).*
Rodriguez et al. Trends in Biochemical Sciences vol. 42, pp. 111-129 (Year: 2017).*
PCT Application No. PCT/US2022/033459, International Search Report and Written Opinion, dated Feb. 6, 2023, 19 pages.
David B.T. Cox et al., RNA Editing with CRISPR-Cas13, Science, vol. 358, No. 6366, Nov. 24, 2017.
Abudayyeh et al., "A cytosine deaminase for programable single-base RNA editing", Science, Jul. 26, 2019, 365(6451): 382-386.
GEO Gene Expression Online, "In vivo RNA editing of point mutations via RNA-guided adenosine deaminases", Dec. 17, 2018, Series GSE123905, retrieved from url: <https://www.ncbi.nlm.nih.gov/geo/query/acc.cgi>.
Savva et al., "The ADAR protien family", Genome Biol., Dec. 28, 2012, 13(12): 252.

(Continued)

*Primary Examiner* — Brian Whiteman
(74) *Attorney, Agent, or Firm* — Lathrop GPM LLP; Laura A. Labeots

(57) ABSTRACT

RNA editing tools for use in systems designed to measure RNA in vivo and manipulate specific cell types are disclosed herein. An RNA sensor system comprising a) a single-stranded RNA (ssRNA) sensor comprising a stop codon and a payload; optionally wherein the ssRNA sensor further comprises a normalizing gene; and b) an adenosine deaminase acting on RNA (ADAR) deaminase; wherein the sensor is capable of binding to a ssRNA target to form a double-stranded RNA (dsRNA) duplex that becomes a substrate for the ADAR deaminase; wherein the substrate comprises a mispairing within the stop codon; and wherein the mispairing is editable by the ADAR deaminase, which editing can effectively remove the stop codon so as to enable translation and expression of the payload. A method of quantifying ribonucleic acid (RNA) levels using the RNA sensor system is also disclosed.

14 Claims, 111 Drawing Sheets
Specification includes a Sequence Listing.

(56) References Cited

OTHER PUBLICATIONS

Abe et al., "Rolling Circle Translation of Circular RNA in Living Human Cells", Scientific Reports, Nov. 10, 2015, vol. 5, Article 16435.
Chao et al., "Structural basis for the coevolution of a viral RNA-protein complex", Nature Structural & Molecular Biology, 2008, 15(1): 103-105, Published Dec. 9, 2007.
Galipon et al., "Differential Binding of Three Major Human ADAR Isoforms to Coding and Long Non-Coding Transcripts", Genes, Feb. 11, 2017, 8(68): 1-13.
Karlsson et al., "The human exposome and health in the Anthropocene", International Journal of Epidemiology, Apr. 2021, 50(2): 378-389, Epublished Dec. 8, 2020.
Katrekar et al., "In vivo RNA editing of point mutations via RNA-guided adenosine deaminases", Nat Methods, Mar. 2019, 16(3): 239-242, Epublished Feb. 8, 2019.
Kauffman et al., "Materials for non-viral intracellular delivery of messenger RNA therapeutics", Journal of Controlled Release, Oct. 28, 2016, 240: 227-234.
Litke et al., "Highly efficient expression of circular RNA aptamers in cells using autocatalytic transcripts", Nat. Biotechnol., Jun. 2019, 37(6): 667-675, Epublished Apr. 8, 2019.
Matthews et al., "Structures of human ADAR2 bound to dsRNA reveal base-flipping mechanism and basis for site selectivity", Apr. 11, 2016, 23(5): 426-433.
Merkle et al., "Precise RNA editing by recruiting endogenous ADARs with antisense oligonucleotides", Nat Biotechnol., Feb. 2019, 37(2): 133-138.
Reautschnig et al., "Cluster guide RNAs enable precise and efficient RNA editing with endogenous ADAR enzymes in vivo", Nature Biotechnology, Jan. 3, 2022, 40: 759-768.
Straathof et al., "An inducible caspase 9 safety switch for T-cell therapy", Blood, Jun. 1, 2005, 105(11): 4247-4254.
Uhlén, et al., "Tissue-based map of the human proteome", Science, Jan. 23, 2015, 347(6220): 1260419-1-1260419-9.

* cited by examiner

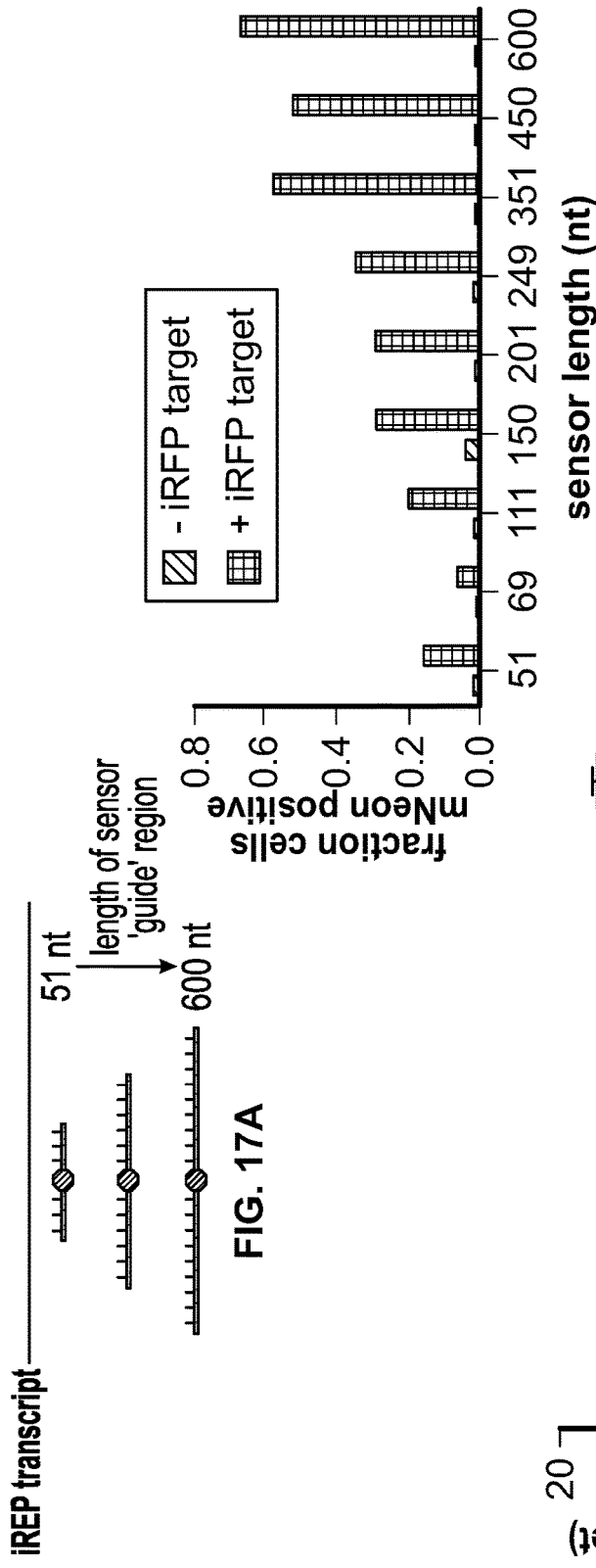
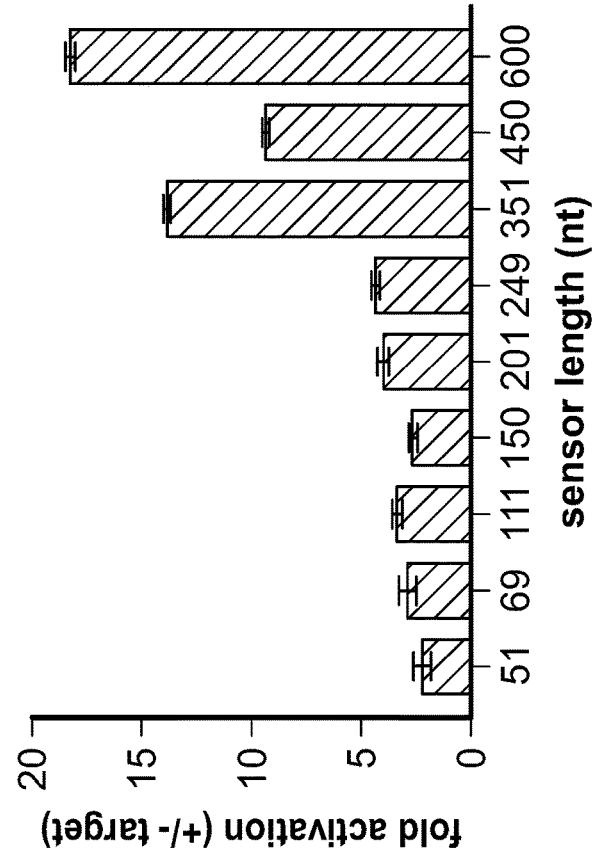

1. Find CCA sites on the target transcript
Human IL6
5'-agagtaacatgtgaaagcagcaaagaggcactggcagaaacaacctgaaccttCCAaagatggctgaaaaagatgatgcttccaatctgattcaatgaggagacttgcct -3'

2. Identify Center 51nt containing stop codon
5'-agagtaacatgtgaaagcagcaaagaggcactggcagaaacaacctgaaccttCCAaagatggctgaaaaagatgatgcttccaatctgattcaatgaggagacttgcct -3'
                                                       |||||||||||||||||||||||||||||||||||||||||||||||||||
                              3'- gaccgtcttttgttggacttggaaGATttctaccgacttttctacctacg -5'

3. Insert MS2 hairpin loops on both side
5'-agagtaacatgtgaaagcagcaaagaggcactggcagaaacaacctgaaccttCCAaagatggctgaaaaagatgatgcttccaatctgattcaatgaggagacttgcct -3'
                                                       |||||||||||||||||||||||||||||||||||||||||||||||||||
                              3'- t — a gaccgtcttttgttggacttggaaGATttctaccgacttttctacctacg t — a -5'
                                   g — c                                                    g — c
                                   t — a                                                    t — a
                                   a — t                                                    a — t
                                   c — g                                                    c — g
                                   g — a                                                    g — a
                                     c — g      MS2 Hairpin                                   c — g
                                     c — g                                                    c — g
                                     a — a                                                    a — a
                                     c — t                                                    c — t

FIG. 24

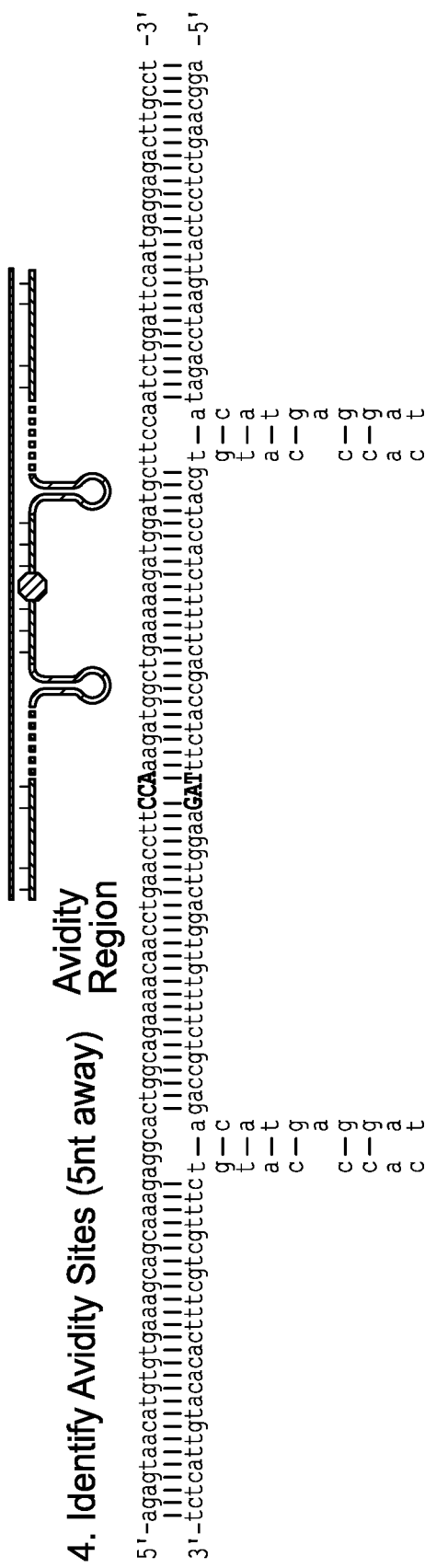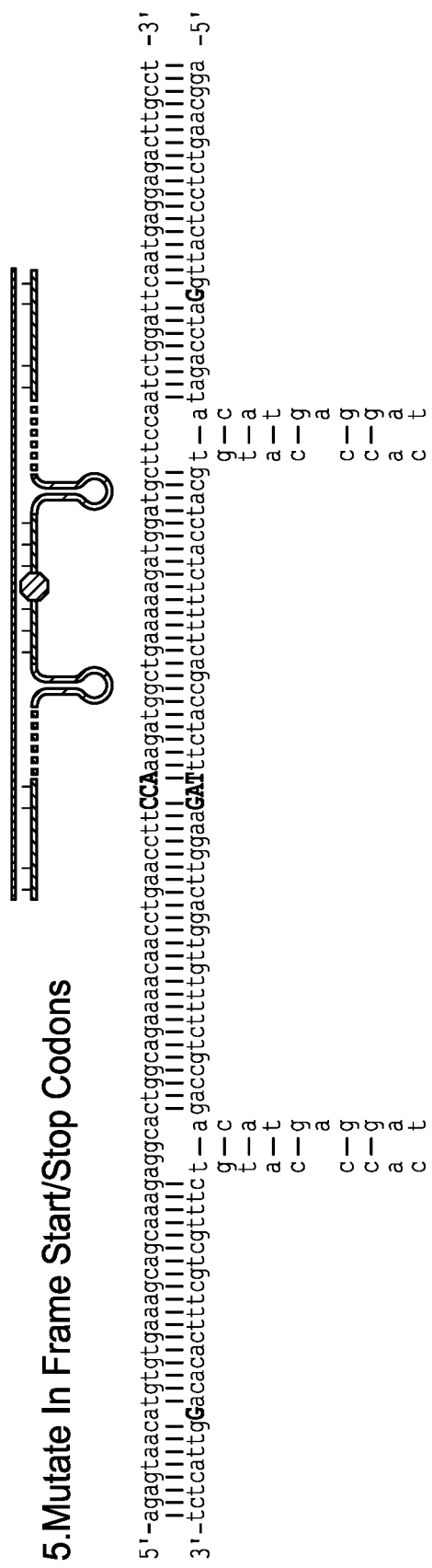
FIG. 24
(Continued)

AND gate RADARS

OR gate RADARS

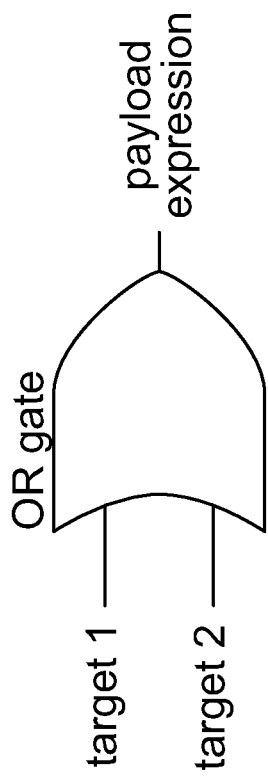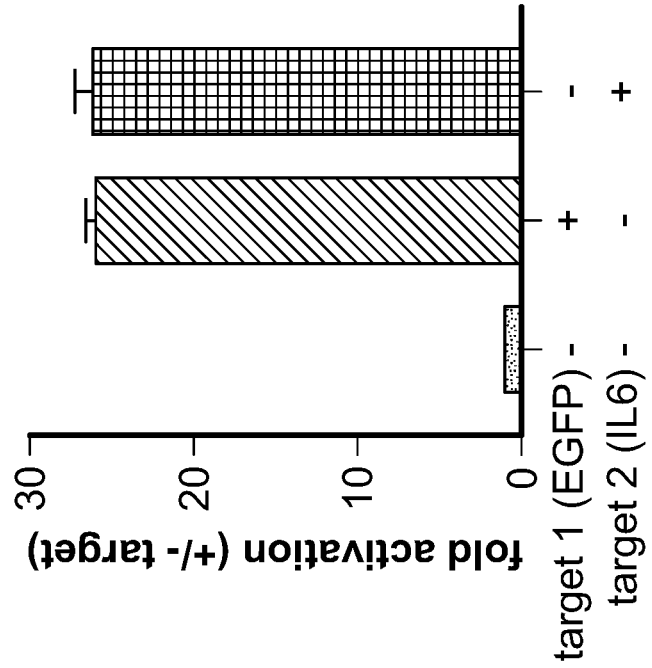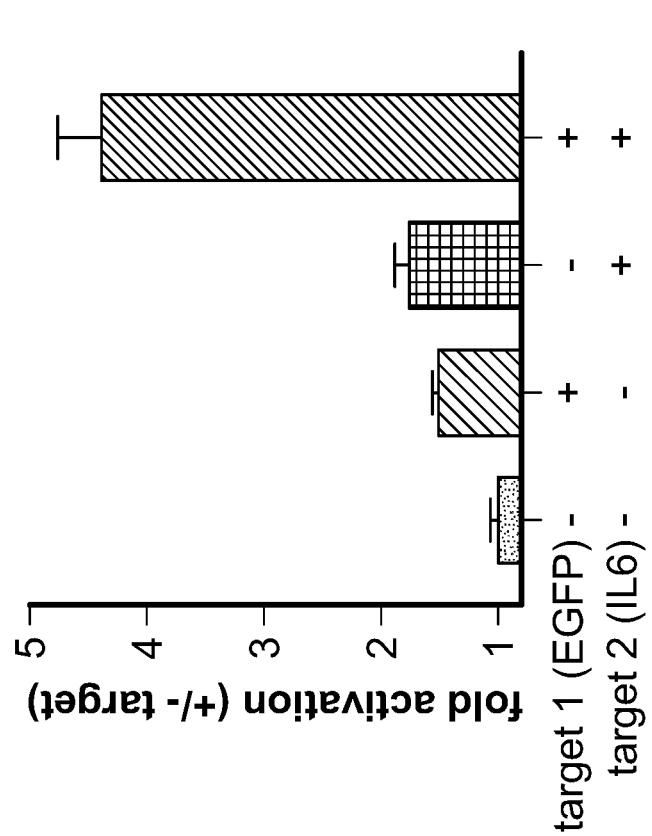
FIG. 41A
FIG. 41B

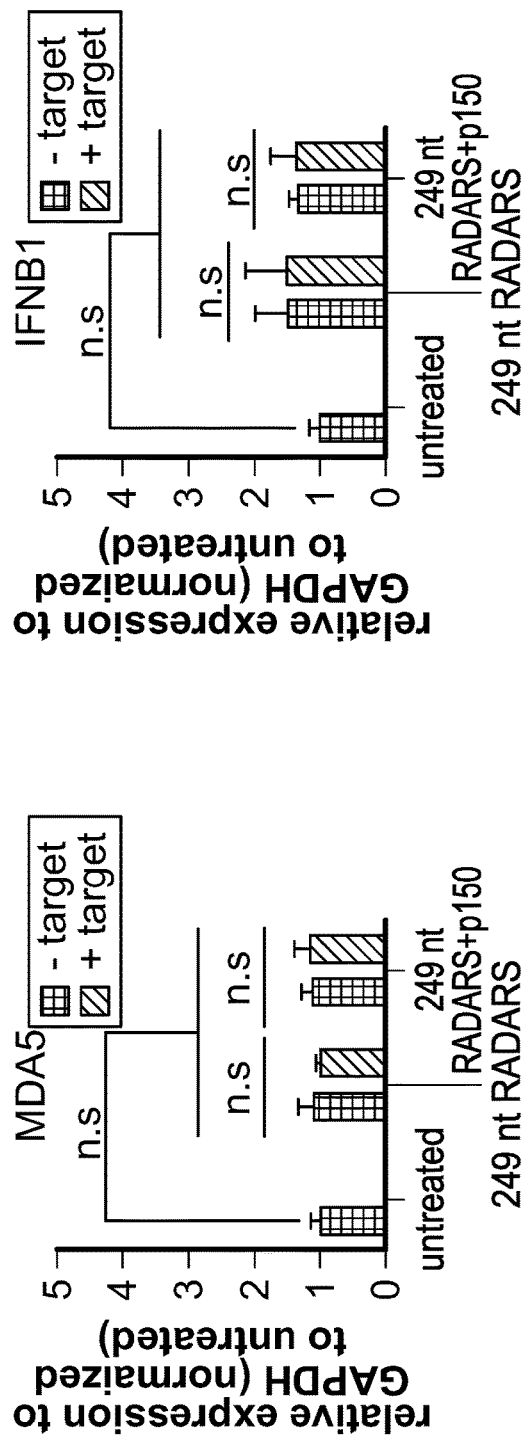
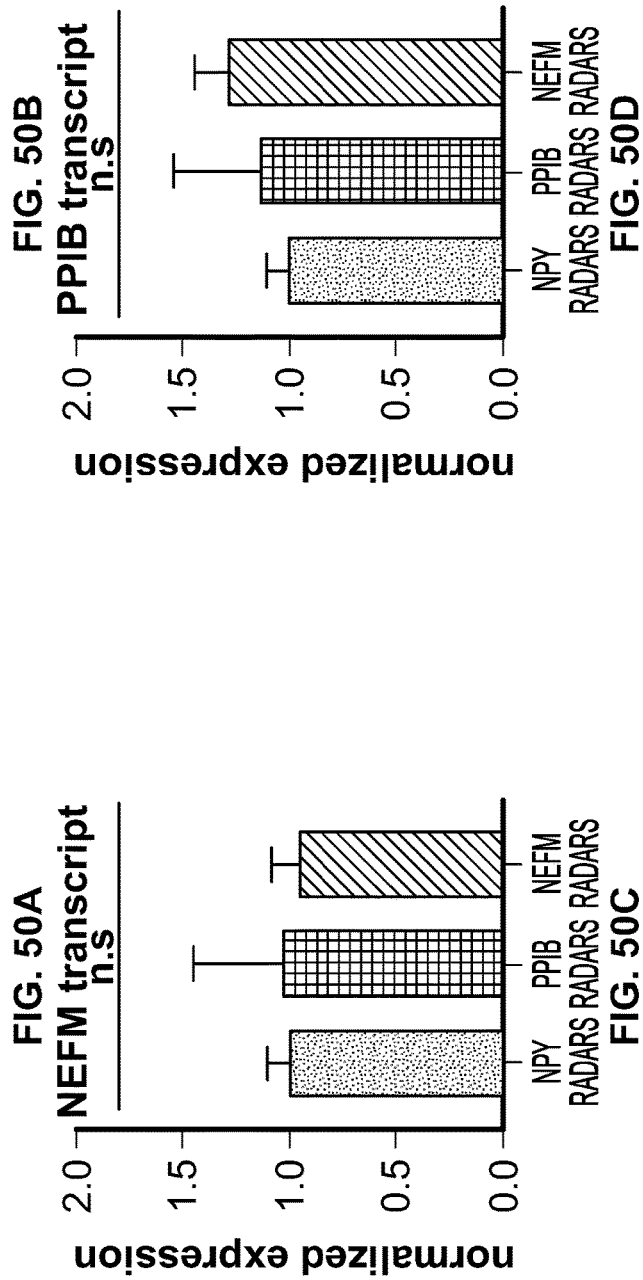
FIG. 50A
FIG. 50B
FIG. 50C
FIG. 50D

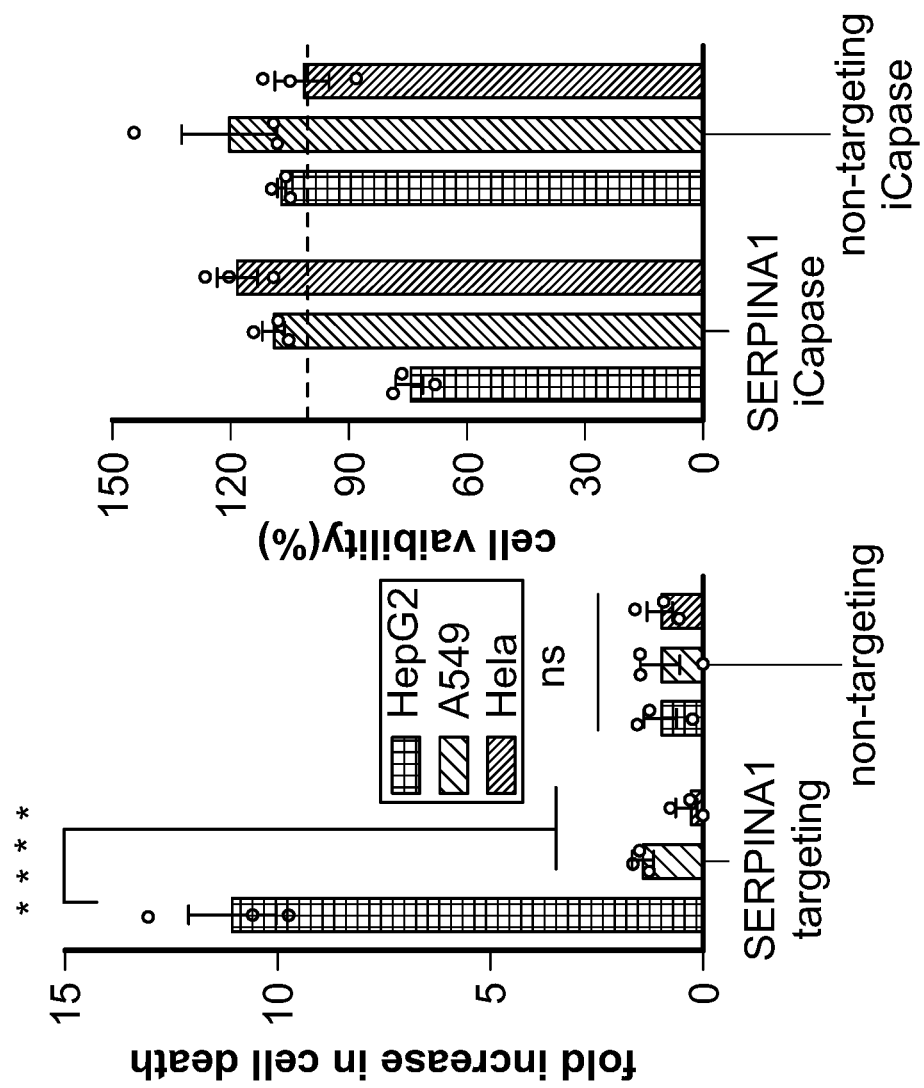
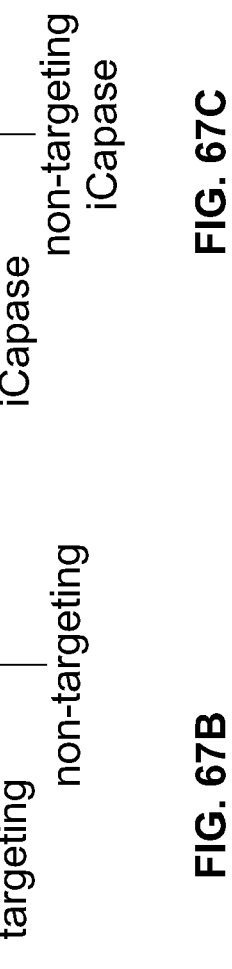
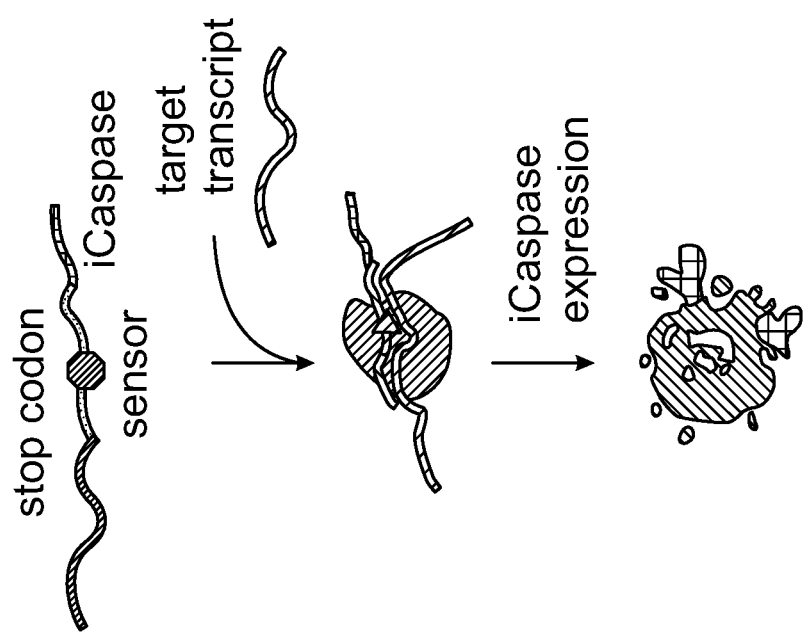
FIG. 67C
FIG. 67B
FIG. 67A
cell type specific apoptosis

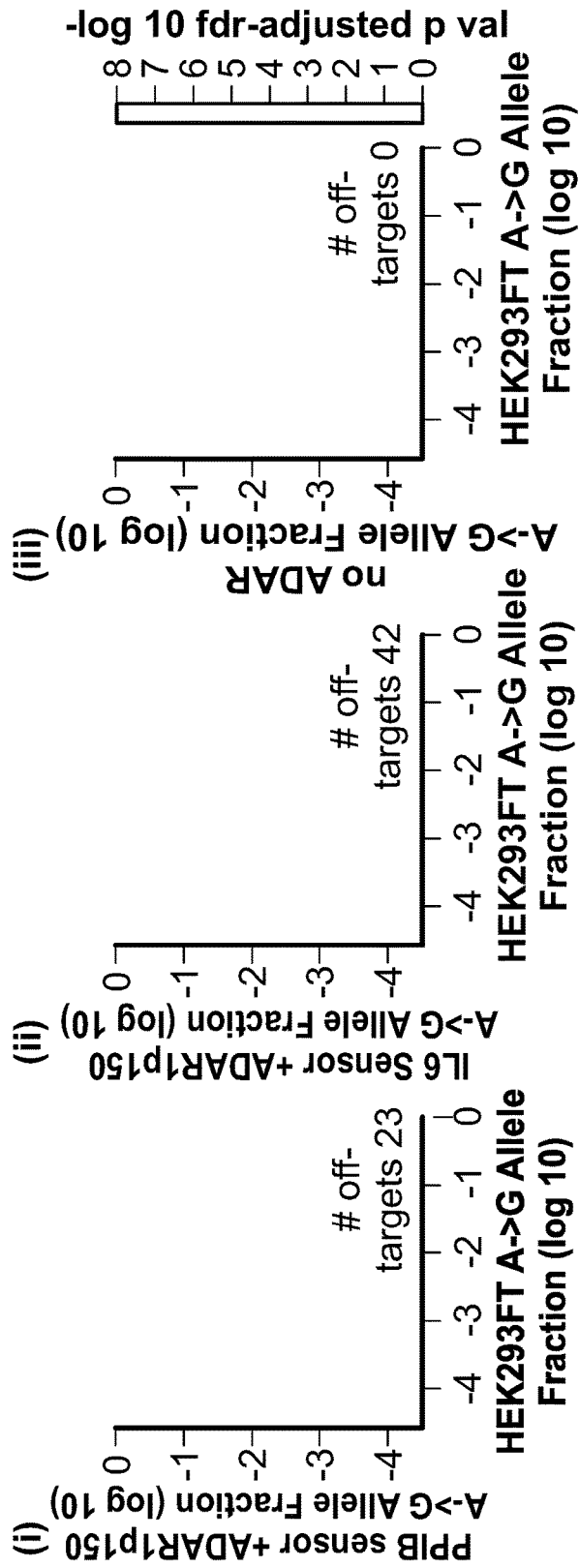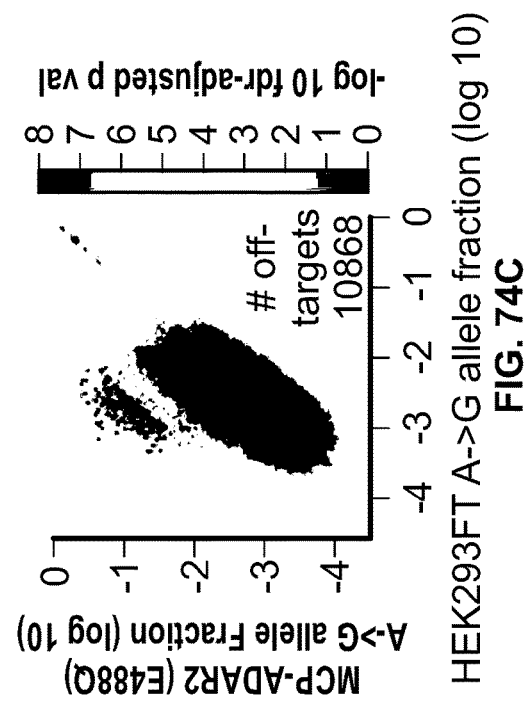
FIG. 74B
FIG. 74C

SEQUENCE LISTING

```
<160> NUMBER OF SEQ ID NOS: 7

<210> SEQ ID NO 1
<211> LENGTH: 115
<212> TYPE: DNA
<213> ORGANISM: Homo sapiens

<400> SEQUENCE: 1
agagtaacat gtgtgaaagc agcaaagagg cactggcaga aaacaacctg aaccttccaa        60
agatggctga aaaagatgga tgcttccaat ctggattcaa tgaggagact tgcct           115

<210> SEQ ID NO 2
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 2
gcatccatct ttttcagcca tctttagaag gttcaggttg ttttctgcca g        51

<210> SEQ ID NO 3
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acatgaggat cacccatgtg catccatctt tttcagccat ctttagaagg ttcaggttgt    60
tttctgccag acatgaggat cacccatgt                                     89

<210> SEQ ID NO 4
<211> LENGTH: 143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
aggcaagtct cctcattgaa tccagataca tgaggatcac ccatgtgcat ccatcttttt    60
cagccatctt tagaaggttc aggttgtttt ctgccagaca tgaggatcac ccatgtcttt   120
gctgctttca cacatgttac tct                                          143

<210> SEQ ID NO 5
<211> LENGTH: 143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
aggcaagtct cctcattgga tccagataca tgaggatcac ccatgtgcat ccatcttttt    60
cagccatctt tagaaggttc aggttgtttt ctgccagaca tgaggatcac ccatgtcttt   120
gctgctttca cacaggttac tct                                          143

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gccttcatac atacatctca agttagggac aaaaaagggg gaag                    44

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cctcctgtgc catctcccct agtggagtct ccgccctgga t                       41
```

DEAMINASE-BASED RNA SENSORS

CROSS REFERENCE TO RELATED APPLICATIONS

This application claims the priority benefit of U.S. Provisional Patent Application Ser. No. 63/267,177, filed Jan. 26, 2022 and U.S. Provisional Patent Application Ser. No. 63/210,829, filed Jun. 15, 2021. The entirety of those applications is hereby incorporated by reference.

SEQUENCE LISTING

The instant application contains a Sequence Listing which has been submitted electronically in ASCII format and is hereby incorporated by reference in its entirety. Said ASCII copy, created on Sep. 29, 2022, is named 727966_083474-020PC_SL.txt and is 2,422 bytes in size.

STATEMENT REGARDING FEDERALLY SPONSORED RESEARCH OR DEVELOPMENT

This invention was made with Government support under Grant No. 5DP5OD024583 awarded by the National Institutes of Health (NIH). The Government has certain rights in the invention.

BACKGROUND

The ability to edit nucleic acids in a precise and programmable manner has become refined in recent years. New technologies allow for this precision editing in vivo, opening the possibility of treating patients at the genotype level. However, there are no viable tools to measure and track RNA levels in vivo without genetic engineering or tagging. Genetic engineering, rather than being a strictly observational sensor system that can measure changes, often requires manipulation of the genome, which can have unforeseen consequences on expression and overall cellular activity. Further, manipulation at the genome level to fully integrate a sensor requires transgenic organisms, which is an unfeasible approach in many scenarios.

Although recent advances have allowed for determination of numerous specific cell types, the ability to track and manipulate these cells is still lacking. The present disclosure relates to RNA editing tools for use in systems designed to measure RNA in vivo and manipulate specific cell types.

BRIEF SUMMARY

The present disclosure is directed to RNA sensor systems. The present disclosure provides an RNA sensor system comprising a) a single-stranded RNA (ssRNA) sensor comprising a stop codon and a payload; optionally wherein the ssRNA sensor further comprises a normalizing gene; and b) an adenosine deaminase acting on RNA (ADAR) deaminase; wherein the sensor is capable of binding to a ssRNA target to form a double-stranded RNA (dsRNA) duplex that becomes a substrate for the ADAR deaminase; wherein the substrate comprises a mispairing within the stop codon; and wherein the mispairing is editable by the ADAR deaminase, which editing can effectively remove the stop codon so as to enable translation and expression of the payload.

The present disclosure provides an RNA sensor system wherein the mispairing between the ssRNA sensor and the ssRNA target comprises an adenine:cytidine mispairing in the dsRNA duplex.

The present disclosure provides an RNA sensor system wherein the mispairing between the ssRNA sensor and the ssRNA target comprises an adenine:cytidine mispairing and wherein the ADAR deaminase edits the adenine to inosine in the mispairing of the dsRNA duplex. In one embodiment, the RNA system comprises more than one mispairing.

The sensor strand of the RNA sensor system can comprise a payload, wherein the payload comprises a reporter protein, a transcription factor, an enzyme, a transgene protein, or a therapeutic protein. The present disclosure also provides an RNA sensor system, wherein the payload comprises a fluorescent reporter. The present disclosure also provides an RNA sensor system, wherein the payload comprises an EGFP reporter or a luciferase reporter. The present disclosure also provides an RNA sensor system, wherein the payload comprises a caspase.

The present disclosure also provides an RNA sensor system, wherein the ADAR is endogenous or exogenous. The present disclosure also provides an RNA sensor system, wherein the ADAR is a modified ADAR.

The present disclosure also provides an RNA sensor system, wherein the ADAR comprises an RNA editing for programmable A to I (G) replacement (REPAIR) molecule, a Cas13b-ADAR fusion molecule, a Cas13d-ADAR fusion molecule, a Cas7-11-ADAR fusion molecule, and MS2-ADAR fusion molecule, a deaminase domain of ADAR2, a full-length ADAR2, or a truncated ADAR2.

The present disclosure also provides an RNA sensor system comprising multiple RNA sensors.

The present disclosure also provides a cell logic system comprising a) an AND gate comprising a ssRNA sensor comprising one or more payloads and multiple stop codons that are complementary to different ssRNA targets; wherein the ssRNA sensor is capable of binding to the ssRNA targets to form a double-stranded RNA (dsRNA) duplex that becomes a substrate for an ADAR deaminase; wherein the substrate comprises a mispairing within each stop codon; and wherein the mispairing in each stop codon is editable by the ADAR deaminase, which editing can effectively remove the stop codon so as to enable translation and expression of the one or more payloads; and/or b) an OR gate comprising multiple independent ssRNA sensors, each of the multiple independent ssRNA sensors comprising a payload and a stop codon that is complementary to one or more different RNA targets; wherein each ssRNA sensor is capable of binding to a different ssRNA target to form a double-stranded RNA (dsRNA) duplex that becomes a substrate for an ADAR deaminase; wherein the substrate comprises a mispairing within each stop codon; and wherein the mispairing in each stop codon is editable by the ADAR deaminase, which editing can effectively remove the stop codon so as to enable translation and expression of the one or more payloads. The present disclosure also discloses a cell logic system comprising: a) an AND gate comprising a ssRNA sensor comprising one or more payloads and multiple stop codons that are complementary to different ssRNA targets; wherein the ssRNA sensor is capable of binding to the ssRNA targets to form a double-stranded RNA (dsRNA) duplex that becomes a substrate for an ADAR deaminase; wherein the substrate comprises a mispairing within each stop codon; wherein the mispairing in each stop codon is editable by the ADAR deaminase, which editing can effectively remove the stop codon so as to enable translation and expression of the one or more payloads; or b) an OR gate comprising multiple independent ssRNA sensors comprising a payload and a stop codon that is complementary to one or more different RNA targets; wherein each ssRNA sensor is capable of binding to a ssRNA target to form a double-stranded RNA (dsRNA) duplex that becomes a substrate for an ADAR deaminase, wherein the substrate comprises a mispairing within each stop codon; and wherein the mispairing in each stop codon is editable by the ADAR deaminase, which editing can effectively remove the stop codon so as to enable translation and expression of the one or more payloads.

The present disclosure provides a method of detecting or quantifying ribonucleic acid (RNA) levels with an RNA sensor system comprising a) providing a single-stranded RNA (ssRNA) sensor comprising a stop codon and a payload; optionally wherein the ssRNA sensor further comprises a normalizing gene; and b) providing an adenosine deaminase acting on RNA (ADAR) deaminase; wherein the sensor is capable of binding to a ssRNA target of interest to form a double-stranded RNA (dsRNA) duplex that becomes a substrate for the ADAR deaminase; wherein the substrate comprises a mispairing within the stop codon; and wherein the mispairing is editable by the ADAR deaminase, which editing can effectively remove the stop codon so as to enable translation and expression of the payload.

The present disclosure also provides an RNA sensor system, wherein the mispairing comprises an adenine:cytidine mispairing in the dsRNA duplex.

The present disclosure provides a method of detecting or quantifying ribonucleic acid (RNA) levels with an RNA sensor system, wherein the mispairing comprising an adenine to cytidine and wherein the ADAR deaminase edits the adenine to inosine in the dsRNA duplex. The present disclosure provides a method of detecting or quantifying ribonucleic acid (RNA) levels with an RNA sensor system, wherein the RNA sensor system comprises more than one mispairing.

The present disclosure provides a method of detecting or quantifying ribonucleic acid (RNA) levels with an RNA sensor system comprising a payload, wherein the payload is translated to a reporter protein, a transcription factor, an enzyme, a transgene protein, or a therapeutic protein.

The present disclosure also provides an RNA sensor system, wherein the ADAR is endogenous or exogenous. In some embodiments, the ADAR is a modified ADAR. In some embodiments, the ADAR is an ADAR endogenous to a cell type in which the sensor may be used.

The present disclosure also provides an RNA sensor system comprising: a) a single-stranded RNA (ssRNA) sensor comprising at least a first stop codon and a payload; optionally wherein the ssRNA sensor further comprises a normalizing gene; and b) an adenosine deaminase acting on RNA (ADAR) deaminase; wherein the sensor is capable of binding to a ssRNA target to form a double-stranded RNA (dsRNA) duplex that becomes a substrate for the ADAR deaminase; wherein the substrate comprises a mispairing within the first stop codon; wherein the mispairing is editable by the ADAR deaminase, which editing can effectively remove the stop codon so as to enable translation and expression of the payload.

The present disclosure also provides an RNA sensor system, wherein the single stranded RNA sensor comprises more than one stop codon. The present disclosure also provides an RNA sensor system, wherein the single stranded RNA sensor further comprises a second stop codon. The present disclosure also provides an RNA sensor system, wherein the single stranded RNA sensor further comprises a third stop codon.

The present disclosure also provides an RNA sensor system, wherein the mispairing comprises a CCA on the target strand and a TAG/UAG on the sensor strand. The present disclosure also provides an RNA sensor system, wherein sensor strand comprises a TAG/UAG stop codon, but does not mismatch with a CCA codon on the target strand. The present disclosure also provides an RNA sensor system, wherein the sensor strand comprises a stop codon that can create a match or mismatch with a codon on a target strand selected from the group consisting of ACA, ACT, ACC, ACG, TCA, TCT, TCC, TCG, GCA, GCT, GCC, GCG, CCA, CCT, CCC, and CCG.

The present disclosure also provides an RNA sensor system comprising: a) a single-stranded RNA (ssRNA) sensor comprising a stop codon and a payload; optionally wherein the ssRNA sensor further comprises a normalizing gene; and b) an adenosine deaminase acting on RNA (ADAR) deaminase; wherein the sensor is capable of binding to a ssRNA target to form a double-stranded RNA (dsRNA) duplex that becomes a substrate for the ADAR deaminase; wherein the substrate comprises a stop codon editable by the ADAR deaminase, which editing can effectively remove the stop codon so as to enable translation and expression of the payload. In some embodiments, the ssRNA sensor comprises a TAG/UAG stop codon. In some embodiments, a TAG/UAG stop codon forms a dsRNA duplex with the ssRNA target at a codon having the formula nCn, wherein n is any nucleotide, and C is cytidine.

The present disclosure also provides an RNA sensor system as described herein, wherein the ssRNA sensor is 50 nt or longer, 100 nt or longer, 150 nt or longer, 200 nt or longer, 250 nt or longer, 300 nt or longer, or 500 nt or longer. In some embodiments, the ssRNA sensor is 51 nt. In some embodiments, the ssRNA sensor is 81 nt. In some embodiments, the ssRNA sensor is 171 nt. In some embodiments, the ssRNA sensor is 225 nt. In some embodiments, the ssRNA sensor is 279 nt. In some embodiments, the ssRNA sensor is longer than 279 nt.

The present disclosure also provides an RNA sensor system as described herein, wherein the ssRNA sensor is a circular sensor. In some embodiments, the circular sensor is a Rolling Circle Translation Sensor. In some embodiments, the circular sensor is a Regular Circular Sensor.

The present disclosure also provides an RNA sensor system as described herein, wherein the ssRNA sensor comprises two stop codons. In some embodiments, wherein the ssRNA sensor comprises three stop codons. In some embodiments, wherein the ssRNA sensor comprises two stop codons, wherein only one stop codon is targeted for ADAR editing. In some embodiments, wherein the ssRNA sensor comprises three stop codons, wherein only one stop codon is targeted for ADAR editing.

The present disclosure also provides an RNA sensor system as described herein, wherein the ssRNA sensor comprises at least one avidity binding region. In some embodiments, the ssRNA sensor comprises at least three avidity binding regions. In some embodiments, the ssRNA sensor comprises at least five avidity binding regions. In some embodiments, the ssRNA sensor comprises at least seven avidity binding regions. In some embodiments, the ssRNA sensor comprises more than seven avidity binding regions. In some embodiments, the avidity binding regions are separated by a MS2 hairpin region.

The present disclosure also provides an RNA sensor system as described herein, wherein the payload comprises a Cre recombinase. In some embodiments, the payload comprises a Cas protein. In some embodiments, wherein the payload comprises Cas9. In some embodiments, wherein the payload comprises a transcription factor. In some embodiments, wherein the payload comprises a payload ADAR. In some embodiments, wherein the payload is a reporter for a cellular stress response.

The present disclosure also provides a composition comprising the RNA sensor system of as described herein, and a delivery vehicle. In some embodiments, the composition comprising an RNA sensor system and a lipid nanoparticle, wherein the RNA sensor system comprises: a) a single-stranded RNA (ssRNA) sensor comprising a stop codon and a payload; optionally wherein the ssRNA sensor further comprises a normalizing gene; and b) an adenosine deaminase acting on RNA (ADAR) deaminase; wherein the sensor is capable of binding to a ssRNA target to form a double-stranded RNA (dsRNA) duplex that becomes a substrate for the ADAR deaminase; wherein the substrate comprises a stop codon editable by the ADAR deaminase, which editing can effectively remove the stop codon so as to enable translation and expression of the payload, and wherein the RNA sensor system is encapsulated in the lipid nanoparticle.

The present disclosure also provides for a method of killing a specific cell or cell type, wherein the method comprises supplying a single-stranded RNA (ssRNA) sensor or guide comprising a stop codon and a payload; optionally wherein the ssRNA sensor further comprises a normalizing gene; wherein the payload is a self-dimerizing caspase, and wherein the ssRNA sensor or guide is capable of binding to a ssRNA target to form a double stranded RNA duplex that becomes a substrate for an adenosine deaminase acting on RNA (ADAR) deaminase, and wherein the ssRNA target is enriched in expression in the specific cell or cell type.

The present disclosure also provides for an RNA sensor system comprising: a) an RNA sensor comprising a stop codon and a payload; optionally wherein the RNA sensor further comprises a normalizing gene; and b) an adenosine deaminase acting on RNA (ADAR) deaminase; wherein the sensor is capable of binding to an RNA target to form a double-stranded RNA (dsRNA) duplex region that becomes a substrate for the ADAR deaminase; wherein the substrate comprises a mispairing within the stop codon; wherein the mispairing is editable by the ADAR deaminase, which editing can effectively remove the stop codon so as to enable translation and expression of the payload. In some embodiments, the RNA sensor is a single stranded RNA. In some embodiments, the RNA sensor comprises one or more double stranded RNA (dsRNA) domains. In some embodiments, the RNA target is a single stranded RNA. In some embodiments, wherein the RNA comprises one or more double stranded RNA (dsRNA) domains.

The present disclosure also provides for an RNA sensor system as described herein, wherein the RNA sensor is 50 nt or longer, 100 nt or longer, 150 nt or longer, 200 nt or longer, 250 nt or longer, 300 nt or longer, or 500 nt or longer. In some embodiments, the RNA sensor is 51 nt. In some embodiments, the ssRNA sensor is 81 nt. In some embodiments, the ssRNA sensor is 171 nt. In some embodiments, the ssRNA sensor is 225 nt. In some embodiments, the ssRNA sensor is 279 nt. In some embodiments, the ssRNA sensor is longer than 279 nt.

The present disclosure also provides for an RNA sensor system as described herein, wherein the ssRNA sensor is a circular sensor. In some embodiments, wherein the circular sensor is a Rolling Circle Translation Sensor. In some embodiments, the circular sensor is a Regular Circular Sensor. In some embodiments, the RNA sensor comprises two stop codons. In some embodiments, the RNA sensor comprises three stop codons. In some embodiments, the RNA sensor comprises two stop codons, wherein only one stop codon is targeted for ADAR editing. In some embodiments, the RNA sensor comprises three stop codons, wherein only one stop codon is targeted for ADAR editing.

The present disclosure also provides for an RNA sensor system as described herein, wherein the RNA sensor comprises at least one avidity binding region. In some embodiments, the RNA sensor comprises at least three avidity binding regions. In some embodiments, the RNA sensor comprises at least five avidity binding regions. In some embodiments, the RNA sensor comprises at least seven avidity binding regions. In some embodiments, the RNA sensor comprises more than seven avidity binding regions. In some embodiments, the avidity binding regions are separated by a MS2 hairpin region.

In some embodiments, the payload comprises a Cre recombinase. In some embodiments, the payload comprises a Cas protein. In some embodiments, the payload comprises Cas9. In some embodiments, the payload comprises a transcription factor. In some embodiments, the payload comprises a payload ADAR. In some embodiments, the payload is a reporter for a cellular stress response.

In some embodiments, the ADAR is selected from the group consisting of ADAR2, ADAR1, ADAR1 p150, ADAR1 p110, ADAR2 R455G, ADAR2 R455G, ADAR2 S486T, ADAR2 T375G E488Q T490A, ADAR2 T375G, ADAR2 T375S, ADAR2 N473D, ADAR2 deaminase domain, ADAR2 T490S, ADAR2 T490A, MCP-ADAR2 deaminase domain, ADAR2 R455E, ADAR2 T375G T490A, ADAR2 E488Q, MCP-ADAR2 deaminase domain E488Q T490A, ADAR2 R510E, ADAR2 R455S, ADAR2 V351L, and derivatives or modified variants thereof. In some embodiments, the ADAR is endogenously expressed in a target cell in which the RNA sensor system may be used.

BRIEF DESCRIPTION OF THE DRAWINGS

FIG. 4A Expression of the Gluc luciferase gene was quantified in HEK293FT cells to which two distinct guide strands (Design 2 and Design 4) targeting EGFP or a negative control scramble sequence (Neg control) was introduced.

FIG. 2, white bars), or in the presence of a fusion construct expressing a catalytically inactive Cas13b enzyme fused to the deaminase domain of ADAR2 (dPspCas13b-ADAR2dd; FIG. 2, red bars). All fold-increases are relative to a scramble guide that is designed not to target EGFP serving as a negative control.

FIG. 11A, FIG. 11C, FIG. 11E, FIG. 11G: sensor fluorescent ratio (mNeon/mCherry) fold change showing + target condition normalized to − target condition for each target and sensor combination.

(RNA editing for programmable A to I (G) replacement (REPAIR)), or to a catalytically inactive version (REPAIR K370A). Guide strands were tested in cells containing only endogenous ADAR2 (FIG. 15, blue bars), cells containing endogenous ADAR2 in addition to an exogenous catalytically inactive REPAIR molecule (REPAIR K370A; FIG. 15, white bars), or in cells containing a catalytically active REPAIR molecule (REPAIR; FIG. 15, red bars).

FIG. 17A is a schematic showing different length sensors screened against an iRFP target transcript. FIG. 17B Bar graph showing increasing sensor activation with increasing sensor length. Sensor activation indicates that normalized fluorescence (mNeon/mCherry) values in the presence of target are divided by normalized fluorescence (mNeon/mCherry) values in the absence of target for each sensor. FIG. 17C Fraction mNeon positive cells show proportion of cells that have higher expression than a predefined threshold. All conditions represent data from n=3 technical replicates.

FIG. 24 is a schematic of step-by-step generation of a three avidity ADAR SENSOR with 5 nt spacing between the avidity guide regions. FIG. 24 discloses SEQ ID NOS 1, 1, 2, 1, 3, 1, 4, 1, and 5, respectively, in order of appearance.

FIG. 29A is a schematic representation of the mismatch tolerance.

FIG. 41A is a graphical illustration of normalized sensor activation of AND gate ADAR SENSOR for EGFP and IL6 transcript inputs across all four possible target combinations. FIG. 41B is a graphical illustration of normalized sensor activation of OR gate ADAR SENSOR for EGFP and IL6 transcript inputs across different target combinations.

FIG. 44A is a bar plot comparing SERPINA1 expression across HEK293FT, SERPINA1, and Hela cells.

FIG. 50A, FIG. 50B is a graphical illustration showing characterization of RADARS safety regarding immune response and endogenous RNA knockdown. Effect of sensor-target duplex formation on the innate antiviral pathways. RADARS sensors were transfected in the presence or absence of complementary target sequences. Total RNA was analyzed using quantitative PCR (qPCR) to determine the relative expression levels of MDA5 FIG. 50A and IFN-β FIG. 50B. FIG. 50C, FIG. 50D Effect of sensor-target duplex formation on the abundance of endogenous targeted transcripts. The relative abundance of NEFM and PPIP transcripts upon the transfection of complementary or non-targeting RADARS sensors were assessed by qPCR. Data are presented as the mean±s.d. (n=4); unpaired two-sided Student's t-test, ns, p>0.05.

FIG. 67A is a schematic representation of a SERPINA1–targeting RADARS with an inducible Caspase9 payload. FIG. 67B is a graphical depiction of cell viability of A549, Hela and HepG2 cells after transfection of SERPINA1 sensing RADARS expressing iCaspase9 in combination with exogenous ADAR1p150. Non-targeting control engineered guide RNA contain a scramble sequence with stop codon in front of the payload. Data are mean of technical replicates (n=3)±s.e.m. FIG. 67C is a graphical depiction of cell viability of HepG2, Hela and A549 cells are determined 48 hours after transfection of a SERPINA1 or non-targeting RADARS expressing iCaspase9 construct and ADAR1p150 using MTS assay and normalized to a control group transfected with only a GFP expressing plasmid.

FIG. 74B is a scatter plot analysis of transcriptome-wide off target editing. Scatter plots show the allele fraction of A→G mutations in (i) PPIB sensor and ADAR1p150 overexpression versus non-transfected HEK293T cells (n=3.17×106 sites); (ii) same as (i) but for IL6 sensor (n=3.07×106 sites); (iii) same as (i) but for no ADAR overexpression and a non-targeting RADAR sensor (n=3.14×106 sites). Sites are colored by fdr-corrected p-value (color bar left). For i, and iii, experiments were generated from 3 independent replicates. FIG. 74C is a scatter plot analysis of transcriptome-wide off target editing with MCP-ADAR2(E488Q) using a dataset from NCBI Geo accession number GSE123905 (Katrekar et al., 2019). Scatter plots show the allele fraction of A→G mutations in MCP-ADAR2 (E488Q) overexpression versus non-transfected HEK293T cells (n=2.35×106 sites). Sites are colored by fdr-corrected p-value (color bar left).

DETAILED DESCRIPTION

Figure 1:
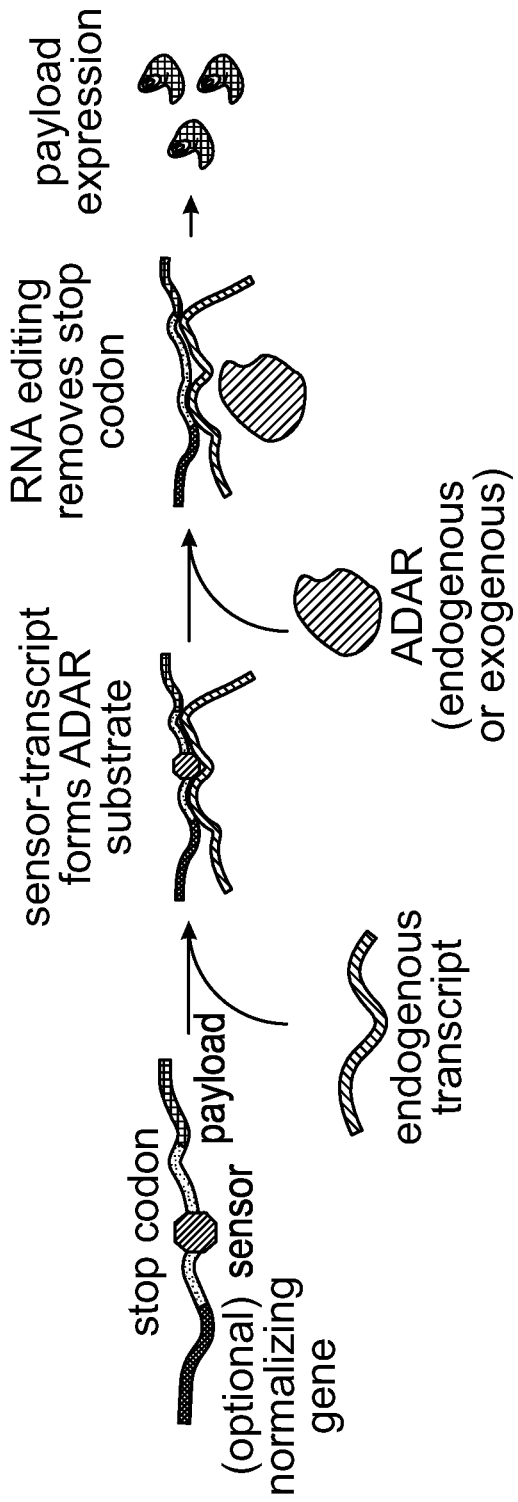
FIG. 1 is a graphic illustration of how RNA sensors harnessing ADAR technology provides new gene outputs. The sensor RNA contains an optional marker protein, a guide RNA region with a stop codon (red octagon), and a downstream payload protein. Sensor association with a target RNA forms a duplex with an A-C mismatch, which serves as a substrate for RNA editing by ADAR protein (brown). For example, RNA editing can convert a UAG stop codon to UIG, allowing translation of the payload (green protein).

This disclosure provides systems and sensors for detecting and quantifying RNA. The disclosure also provides systems and methods for genetic editing. Also disclosed are systems for in vivo imaging of RNA expression. The present disclosure provides sensor systems that convert adenine to inosine. Inosine is recognized as guanosine (G) by translational machinery. Conversion of adenine to inosine is a result of hydrolytic deamination adenosine. (Cox et al. Science 358(6366):1019-1027 (2017)). Thus, the adenosine deaminase acting on RNA (ADAR) family of enzymes are able to convert codons within a transcript such that the translation product is functionally altered. The present disclosure provides, among other functional alterations, editing of a transcript to remove a stop codon and thus enable expression of a payload.

Definitions

Unless stated otherwise, terms and techniques used within this application have the meaning generally known to one of skill in the art.

The term "about" as used herein is understood to modify the specified value. Unless explicitly stated otherwise, the term about is understood to modify the specified values+/− 10%. As used herein, the term about applied to a range modifies both endpoints of the range. By way of example, a range of "about 5 to 10" is understood to mean "about 5 to about 10."

As used herein, the terms "sensor" and "sensor strand" are used interchangeably. "Sensor" or "sensor strand" as used herein is understood to relate to the single stranded RNA that comprises at least a stop codon, where the RNA strand is capable of hybridizing or forming a duplex with another RNA strand. "Sensor" and "guide" strand may be used interchangeably throughout this disclosure.

As used herein, the terms "ADAR," "ADAR enzyme," and "deaminating enzyme" are used interchangeably unless explicitly stated otherwise. Thus, within the present disclosure, "wherein the ADAR enzyme is a prokaryotic RNA editing enzyme" is understood to also mean "wherein the deaminating enzyme is a prokaryotic RNA editing enzyme."

As used herein, the terms "RNA sensor system" or "sensor system" are understood to mean the minimum components required for (i) hybridization of a single-stranded RNA to a transcript of interest, such that the resulting hybridized RNA comprises at least one mispairing and at least one stop codon, (ii) recognition of the hybridized RNA as a substrate, and (iii) editing of the single stranded RNA to remove a stop codon.

As used herein, the terms "cell logic system" or "logic system" refers to a system comprised of multiple individual sensor systems. The cell logic systems or logic systems of the disclosure are complex systems, which may be comprised of one or more individual RNA sensor systems. An individual RNA sensor system, when incorporated into a larger cell logic system, may be dependent upon a separate RNA sensor system in the same cell for activation. Alternatively, multiple individual RNA sensor systems may be incorporated into a cell logic system such that no individual RNA sensor system is necessary for another.

It is generally understood, unless explicitly stated otherwise, that the term "payload" as used herein means a portion of single stranded RNA that may either hybridize to another single stranded RNA, be an invading strand for an already duplexed RNA molecule, or may be translated to express a protein. Thus, if an embodiment of the disclosure states, by way of example, that "the payload comprises a therapeutic protein," it is generally understood that the payload is a fragment or portion of single-stranded RNA that can be translated to express a therapeutic protein.

As used herein, "cell-specific," "cell-type specific," and "activatable by a specific cell type" would be understood by one of skill in the art to mean that the activation of the RNA sensor requires the presence of a factor that is present in a specific cell type at substantially higher levels than in other cell types. One of skill in the art would recognize that while the expression of these factors may occur in other cell types, such that activation of the RNA sensor is a possibility, it is not highly probable.

As used herein and unless stated otherwise. "avidity region" or "avidity binding region" may be used interchangeably to describe a region on the guide strand that has a degree of complementarity to the target transcript. Avidity refers to the design of multiple binding sites within a guide. These binding sites can be separated by linkers. Avidity regions may optionally be separated from the main sensor region of the guide strand by one or more secondary structures, including a hairpin structure. In some embodiments, the hairpin structure is an MS2 hairpin. Avidity regions may optionally contain a stop codon that is not targeted for editing by an ADAR. In some embodiments, the avidity region comprises a linker sequence. In some embodiments, the avidity region comprises one or more linker sequences.

Adenosine Deaminase Acting on RNA (ADAR) and Other RNA Editing Enzymes

ADAR enzymes are evolutionarily conserved among animals. Mammals have three known ADAR enzymes: ADAR1, ADAR2, and ADAR3. ADAR1 and ADAR2 are known to be catalytically active. By contrast, ADAR3, despite substantial similarity to ADAR2, is generally considered catalytically inactive. (Savva et al. Genome Biol. 13(12):252. (2012)). ADAR enzymes contemplated in the present disclosure include mammalian ADAR enzymes or modified enzymes derived therefrom. In some embodiments, the ADAR enzyme of the RNA sensor is human ADAR1. In some embodiments, the ADAR enzyme of the RNA sensor is a modified human ADAR1. In some embodiments, the ADAR enzyme of the RNA sensor is human ADAR2. In some embodiments, the ADAR enzyme of the RNA sensor is a modified human ADAR2. In some embodiments, the ADAR enzyme of the RNA sensor is a modified human ADAR3. In some embodiments, the ADAR enzyme of the RNA sensor is a synthetic enzyme. In some embodiments, the ADAR enzyme of the RNA sensor is a non-mammalian ADAR enzyme.

ADAR enzymes of the present disclosure include enzymes that have been modified. ADAR enzymes contemplated in the present disclosure include enzymes that have been modified to increase the affinity of the enzyme to the sensor strand. In some embodiments, the ADAR has been modified to include an additional RNA binding domain. In some embodiments, the ADAR has been modified to exclude one or more non-catalytic domains. In some embodiments, the ADAR enzyme of the sensor system comprises the ADAR2 deaminase domain. In some embodiment the ADAR consists of the ADAR2 deaminase domain. In some embodiments the ADAR comprises the ADAR2 deaminase domain fused to the MS2 binding protein. In some embodiments the ADAR consists of the ADAR2 deaminase domain fused to the MS2 binding protein. In some embodiments the ADAR is fused to a CRISPR-associated protein (Cas protein), or a fragment or derivate thereof. In some embodiments, the ADAR is fused to a modified Cas protein. In some embodiments, the modified Cas protein has been mutated to lack catalytic activity. In some embodiments, the ADAR is fused to a modified Cas13. In some embodiments, the ADAR is fused to a Cas13b comprising a mutation at an amino acid corresponding to K370. In some embodiments the ADAR is fused to Cas13b comprising a K370A mutation. In some embodiments, the ADAR is fused to a modified Cas13d. In some embodiments, the ADAR is fused to a modified Cas7-11.

ADAR enzymes of this disclosure can be endogenous to cells in which the sensor is being delivered. ADAR enzymes contemplated in this disclosure may be exogenous, being delivered to the cell either simultaneously or separately from the sensor. In some embodiments, the exogenous ADAR is delivered separately from the sensor. In some embodiments, the exogenous ADAR is delivered concurrently with the sensor. In some embodiments, an exogenous ADAR may be used to supplement an endogenous ADAR. In some embodiments, more than one exogenous ADAR is supplied to the cell.

Additional RNA Editing Enzymes

Additional deaminating enzymes may be used in the methods of this disclosure. In some embodiments, the deaminating enzyme may be a modified ADAR enzyme. Modified ADAR enzymes may include ADAR enzymes that have been modified to have increased cytidine deamination activity, such as RESCUE (Abudayyeh et al., Science 365, 382-386 (2019)).

In some embodiments, the deaminating enzyme is a modified cytidine to uracil editing enzyme. In some embodiments, the deaminating enzyme may be a member of the apolipoprotein B mRNA-editing enzyme, catalytic polypeptide like (APOBEC) family of cytidine deaminases. In some embodiments, the deaminating enzyme is a modified APOBEC1. In some embodiments, the deaminating enzyme is a modified APOBEC2. In some embodiments, the deaminating enzyme is a modified APOBEC3. In some embodiments, the deaminating enzyme is a modified APOBEC3A. In some embodiments, the deaminating enzyme is a modified APOBEC3B. In some embodiments, the deaminating enzyme is a modified APOBEC3C. In some embodiments, the deaminating enzyme is a modified APOBEC3D. In some embodiments, the deaminating enzyme is a modified APOBEC3E. In some embodiments, the deaminating enzyme is a modified APOBEC3F. In some embodiments, the deaminating enzyme is a modified APOBEC3G. In some embodiments, the deaminating enzyme is a modified APOBEC3H.

In some embodiments, the deaminating enzyme may be a prokaryotic RNA editing enzyme. In some embodiments, the deaminating enzyme is derived from *Escherichia coli* (*E. coli*).

Sensors/Sensor Strands

Sensors of the present disclosure comprise at least one stop codon. The sensors may be located on the same RNA strand as a payload, a normalizing gene, or both a payload and a normalizing gene. The sensors of the disclosure may be designed such that when the single strand RNA (ssRNA) sensor strand binds to a target ssRNA strand to create a double-stranded RNA (dsRNA) duplex, the duplex comprises a mispairing within the region corresponding to the stop codon in the sensor strand. Disclosed sensors may be modified in a number of ways. In some embodiments the sensor is provided to the cell as a DNA template, which can be subsequently transcribed to a single strand RNA sensor molecule.

Also provided by the present disclosure are sensor strands that comprise more than one stop codon. In some embodiments, the sensor strand comprises 1, 2, 3, 4, 5, 6, 7, 8, 9, or 10 stop codons. In some embodiments, the sensor strand comprises more than 10 stop codons. In some embodiments, the sensor strand comprises 2 stop codons. In some embodiments, the sensor strand comprises 3 stop codons. In some embodiments, the sensor strand comprises 4 stop codons. In some embodiments, the sensor strand comprises 5 stop codons. In some embodiments, the sensor strand comprises 6 stop codons. In some embodiments, the sensor strand comprises 7 stop codons. In some embodiments, the sensor strand comprises 8 stop codons. In some embodiments, the sensor strand comprises 9 stop codons. In some embodiments, the sensor strand comprises 10 stop codons.

Also provided in this disclosure are sensor/guide strands that contain one or more avidity binding regions. In some embodiments, the sensor strand comprises 3 avidity regions. In some embodiments, the sensor strand comprises 5 avidity regions. In some embodiments, the sensor strand comprises 7 avidity regions. Avidity regions may incorporate a stop codon that is not a target for ADAR editing. Avidity binding regions may also contain stop codons that are targets for ADAR editing. In some embodiments, the avidity binding region comprises the stop codon intended for ADAR editing.

Also provided within this disclosure are sensor/guide strands that incorporate one or more MS2 hairpin. In some embodiments, the sensor strand comprises two MS2 hairpins. In some embodiments, the sensor strand comprises three MS2 hairpins.

In some embodiments, the sensor/guide strand comprises both avidity regions and MS2 hairpin regions.

In some embodiments, the sensor/guide strand comprises RNA modifications. In some embodiments, the modified RNA comprises 5-methylcytosine. In some embodiments, the modified RNA comprises pseudouridine.

Payloads

In some embodiments the payload comprises a reporter transcript. In some embodiments the payload consists of a reporter transcript. In some embodiments, the reporter transcript is a fluorescent reporter. In some embodiments, the reporter transcript comprises a luciferase transcript. In some embodiments, the reporter transcript comprises a GFP transcript.

The sensor systems of the present disclosure may be designed to deliver a payload that encodes a therapeutic protein. In some embodiments, the therapeutic protein can be used in conjunction with another therapeutic.

In some embodiments the payload comprises a transcription factor. In some embodiments, the payload comprises an enzyme. In some embodiments, the payload comprises a transgene protein.

In some embodiments, the payload comprises a protein for use in editing the genome of the cell. In some embodiments, the payload comprises a Cas protein. In some embodiments, the payload comprises a Cas9 protein.

In some embodiments, the payload comprises a protein that is capable of converting one cell type to another.

In some embodiments, the payload comprises an ADAR. In some embodiments, the payload comprises an ADAR that is capable of initiating a positive feedback loop.

In some embodiments, the payload comprises a protein that is capable of killing a specific cell type. In some embodiments, the payload comprises a protein that is capable of killing a tumor cell. In some embodiments, the payload comprises an immune modulating protein.

Logic Gates

This disclosure also relates to complex multi-sensor reporter systems. In some embodiments these multi-sensor reporter systems employ logic gates. These logic gates may be comprised of AND gates, OR gates, or AND OR gates as individual decision points in the same reporter system.

An AND gate for use in the reporter system of this disclosure may be implemented by having multiple guide strand binding sections on the same ssRNA sensor. In this type of AND gate, each individual guide section senses a separate, endogenous transcript in the cell. "Activation" of the AND gate in this type of gate is the same as activation of the whole ssRNA sensor strand, that is, removal of the stop codon and expression of a terminal payload. This type of logic gate requires that each guide section interact with a target sequence and an ADAR or other deaminating molecule. Deamination of the stop codon in each guide section would allow for full expression of the payload. In some embodiments, each guide section is further separated by an individual reporter. In some embodiments, each guide section is further separated by an individual, distinct reporter. In some embodiments, each reporter on a ssRNA sensor for use in an AND gate is a distinct fluorescent reporter.

In some embodiments. AND gates can operate in a sequential manner. In this type of AND gate, each of the multiple guide strand binding sections is located on a separate ssRNA sensor. Activation of the gate in this type of AND gate involves activation of multiple sensors in a defined sequence. In this type of AND gate, activation of a first sensor results in expression of an intermediate payload. This intermediate payload, in a specific cellular environment, allows for expression of a second RNA sensor. In such a system, a cascade of RNA sensor activation may occur upon activation, and only in the context of specifically determined cellular stimuli.

An OR gate for use in the reporter system of this disclosure may be implemented through the use of multiple independent ssRNA sensors within the same cell. Each of the multiple independent sensors can deliver a payload without activation of another sensor.

Delivery Systems

This disclosure also provides systems for delivering an ADAR sensor.

In some embodiments, the ADAR sensor is delivered directly to a cell. In some embodiments, the ADAR sensor is encapsulated in a lipid nanoparticle. In some embodiments, the ADAR sensor is delivered via a viral vector.

In some embodiments, the ADAR sensor is a circular RNA.

Methods of the Disclosure

This disclosure also provides methods for using the sensor systems described herein.

In some embodiments, the RNA sensor delivers a payload that may be optically observed. In some embodiments, the RNA sensor is tracked through an imaging system. The imaging system may be any suitable imaging system compatible with the system. In some embodiments, the imaging system uses a fluorescent molecule. In some embodiments, the RNA sensor system comprises multiple fluorescent molecules. In other embodiments, the imaging system is non-invasive. In some embodiments, the RNA sensor system is compatible with a fluorescence activated cell sorting (FACS) system.

In some embodiments, the RNA sensor system is tracked through a non-invasive imaging system. In some embodiments, the imaging system tracks a deep red luciferase.

The present disclosure also provides for methods of quantifying RNA in vivo. Quantification methods of the present disclosure may rely on incorporation of a normalizing gene on the sensor strand. Translation of this normalizing gene occurs independent of RNA editing. Quantification of the normalizing gene provides a reference of total sensor strand delivered to each individual cell. Reference to this normalizing gene allows for determination of activated RNA sensor as a percentage of the total delivered sensor.

The present disclosure also contemplates live cell imaging. In some embodiments, a fluorescent reporter is visualized. In some embodiments, multiple fluorescent reporters are tracked. The present disclosure also provides long-term cell lineage tracking. In some embodiments, activation of the RNA sensor system creates effects a permanent change in the expression of a reporter molecule, such that cells in which the RNA sensor system has been previously activated, can be identified at a later time.

In some embodiments, the RNA sensor system may be used to target a specific cell type. In some embodiments, the RNA sensor system is engineered to be activated by a specific cell type. In some embodiments, the RNA sensor system targets a specific cell type. In some embodiments, the RNA sensor system targets a tumor cell. In some embodiments, the RNA sensor system delivers a payload that kills a specific cell type. In some embodiments, the RNA sensor system delivers a payload that converts one cell type to another cell type. In some embodiments, the RNA sensor system delivers a payload that edits the genome of the cell.

In some embodiments, the RNA sensor system is druggable. In some embodiments, the RNA sensor system is drug sensitive. In some embodiments, the RNA sensor system is only activated in the presence of a single drug or compound. In some embodiments, the RNA sensor system is only activated in the presence of multiple drugs or compounds.

The present disclosure also contemplates the use of the RNA sensor systems described herein for use in in vitro diagnostic assays. For instance, the RNA sensor systems may be in diagnostic assays, wherein the payload comprises a fluorescent protein, luciferase protein, antigen, or epitope. In some embodiments, the diagnostic assay is a lateral flow strip.

Having now described the present technology in detail, the same will be more clearly understood by reference to the following examples. The following examples are included solely for purposes of illustration and are not considered limiting embodiments of the technology. All patents and publications referred to herein are expressly incorporated by reference.

EXAMPLES

Example 1. Methods of the Examples

Unless indicated otherwise, the following experimental techniques were employed in the examples provided herein.

Measurement of Luciferase Activity.

Media containing secreted luciferase was harvested 48 h after transfection, unless otherwise noted, 20 μL of media is used to measure luciferase activity using Targeting Systems Cypridinia and Targeting systems *Gaussia* luciferase assay kits (Targeting Systems) on a Biotek Synergy 4 plate reader with an injection protocol. All replicates were performed as biological replicates.

Transfection for Fluorescence Sensors.

Cells were plated at 10K the day prior to transfection in Corning 96-well tissue-culture treated plates (black), resulting in approximately 40-50% confluency the day of transfection. For all fluorescence sensors, HEK293FT cells were transfected with 100 ng total plasmid DNA using TransIT-LTI according to manufacturer specifications (ratio 1 μg DNA:3 μL Trans reagent). Unless otherwise specified, ADAR sensor. ADAR, and target plasmid were mixed at equal concentrations (33.3 ng/condition); for experiments without one or more of the previous, pUC19 was substituted accordingly to keep the total concentration of DNA at 100 ng.

Confocal Microscopy of Fluorescent ADAR Sensors

At 48 hours post-transfection, all wells were measured via confocal microscopy under the following settings. For each well, a 2×2 image at 10× magnification was collected and stitched around the center point. Images were collected in 488 nm (32.8% power, 100 ms exposure), 561 nm (35.2% power, 100 ms exposure), 640 nm (80% power, 100 ms exposure), and brightfield channels (25 ms exposure).

Quantification of Fluorescence Signal from Images.

Images were opened in Matlab, and segmented via watershed in the mCherry channel. For each segmented cell, the total pixel area and mean intensity of the pixels was computed for mNeon (488 nM), mCherry (561 nM), and iRFP (640 nM) channels, and output into an aggregated csv file. Csv files were batch processed in R with the following steps: all csv files were merged, conditions with low aggregated area (few cells, or not transfected with sensor) were merged, fluorescence background for each channel was subtracted from all conditions in that channel, and aggregated values for each condition were divided by area to obtain average fluorescence intensity. Standard deviation was computed by comparing average values in three technical transfection replicates. For mNeon/mCherry ratio values, the average mNeon fluorescence intensity for a condition was divided by the average mCherry value for that same condition. For fluorescence ratio values and ratio fold change values, error was propagated according to the formula:

$$\sigma_{\frac{x}{y}} = \sqrt{\left(\frac{\sigma_x}{x}\right)^2 + \left(\frac{\sigma_y}{y}\right)^2}$$

Quantification of Percent mNeon Positive Cells in Confocal Images.

Some consistent leakiness of the mNeon in the fluorescent sensors was observed, either due to a very low level of plasmid contamination or ribosome slippage. Therefore, the detection of mNeon positive cells at 30 AU above background was gated, and determined the percent of mCherry positive cells in a condition that expressed mNeon higher than this threshold. mNeon values were plotted in log base 10 as a histogram with kernel density smoothing to generate the plots in FIG. 2E.

Extraction of RNA and Next-Generation Sequencing of ADAR SENSOR.

For calculating the editing rate of ADAR SENSOR sensors, cells were harvested 48 hours post-transfection, after imaging. Total RNA was extracted using the RNeasy 96 Kit (Qiagen) with DNase treatment. cDNA was prepared with SuperScript IV reverse transcriptase (Invitrogen) and a sensor-specific primer. The guide regions of the sensors were amplified, indexed, and sequenced on an Illumina MiSeq platform. Reads were demultiplexed and aligned to each sensor, and the A-to-1 editing rates were calculated with an in-house MATLAB pipeline.

Quantification of Protein Expression.

Two days after the transfection of HEK293FT cells, the Nano-Glo HiBiT Lytic Detection System (Promega) was used for the quantification of the HiBiT tags, in cell lysates. For the preparation of the Nano-Glo HiBiT Lytic Reagent, the Nano-Glo HiBit Lytic Buffer (Promega) was mixed with Nano-Glo HiBiT Lytic Substrate (Promega) and the LgBiT Protein (Promega) according to manufacturer's protocol. The volume of Nano-Glo HiBiT Lytic Reagent added was equal to the culture medium present in each well, and the samples were placed on an orbital shaker at 600 rpm for 3 minutes. After incubation of 10 minutes at room temperature, the readout took place with 125 gain and 2 seconds integration time using a plate reader (Biotek Synergy Neo 2). The control background was subtracted from the final measurements.

mRNA Synthesis.

Before in vitro transcription, the DNA template was obtained by PCR with targeted forward primers containing T7 promoters. The sensor mRNA and the MCP-ADAR2dd mRNA were transcribed and poly-A tailed using the HiScribe™ T7 ARCA mRNA Kit (NEB, E2065S) with 50% supplement of 5-Methyl-CTP and Pseudo-UTP (Jena Biosciences), following the manufacturer's protocol. The mRNA was then cleaned up using the MEGAclear™ Transcription Clean-Up Kit (Thermo Fisher, AM1908).

Harvest of Total RNA and Quantitative PCR.

For gene expression experiments in mammalian cells, cell harvesting and reverse transcription for cDNA generation was performed using a previously described modification of the commercial Cells-to-Ct kit (Thermo Fisher Scientific) 48 h after transfection. (Joung et al., 2017) Transcript expression was then quantified with qPCR using Fast Advanced Master Mix (Thermo Fisher Scientific) and TaqMan qPCR probes (Thermo Fisher Scientific) with GAPDH control probes (Thermo Fisher Scientific). All qPCR reactions were performed in 10-µl reactions with two technical replicates in a 384-well format, and read out using a LightCycler 480 Instrument II (Roche). For multiplexed targeting reactions, readout of different targets was performed in separate wells. Expression levels were calculated by subtracting housekeeping control (GAPDH) cycle threshold (Ct) values from target Ct values to normalize for total input, resulting in ΔCt levels. Relative transcript abundance was computed as 2-ΔCt. All replicates were performed as biological replicates.

Automatic Generation of Avidity Sensors.

Avidity sensors are generated using python scripts in the following repository. Schematic for generation of a typical three avidity guide ADAR SENSOR with two MS2 hairpin loops and 5 nt spacing between the guide regions (on the target) are shown in FIG. 24.

Animal Husbandry and Animal Protocol.

All experiments were carried out on female B6(Cg)-Tyrc-2J/J (Albino B6) and NOD.Cg-Prkdcscid Il2rgtml Wjl Tg(SERPINA1*E342K)#Slcw/SzJ (NSG-PiZ) (The Jackson Laboratory) mice with ad libitum access to food and water. NSG-PiZ mice express the mutant human SERPINA1 on the immunodeficient NOD scid gamma background. All mice were housed in individually ventilated cages, in a temperature-controlled animal facility (normal 12:12 hour light-dark cycles) and used in accordance with approved procedures by the Committee on Animal Care at MIT.

RADARSv2 Design

Figure 54A:
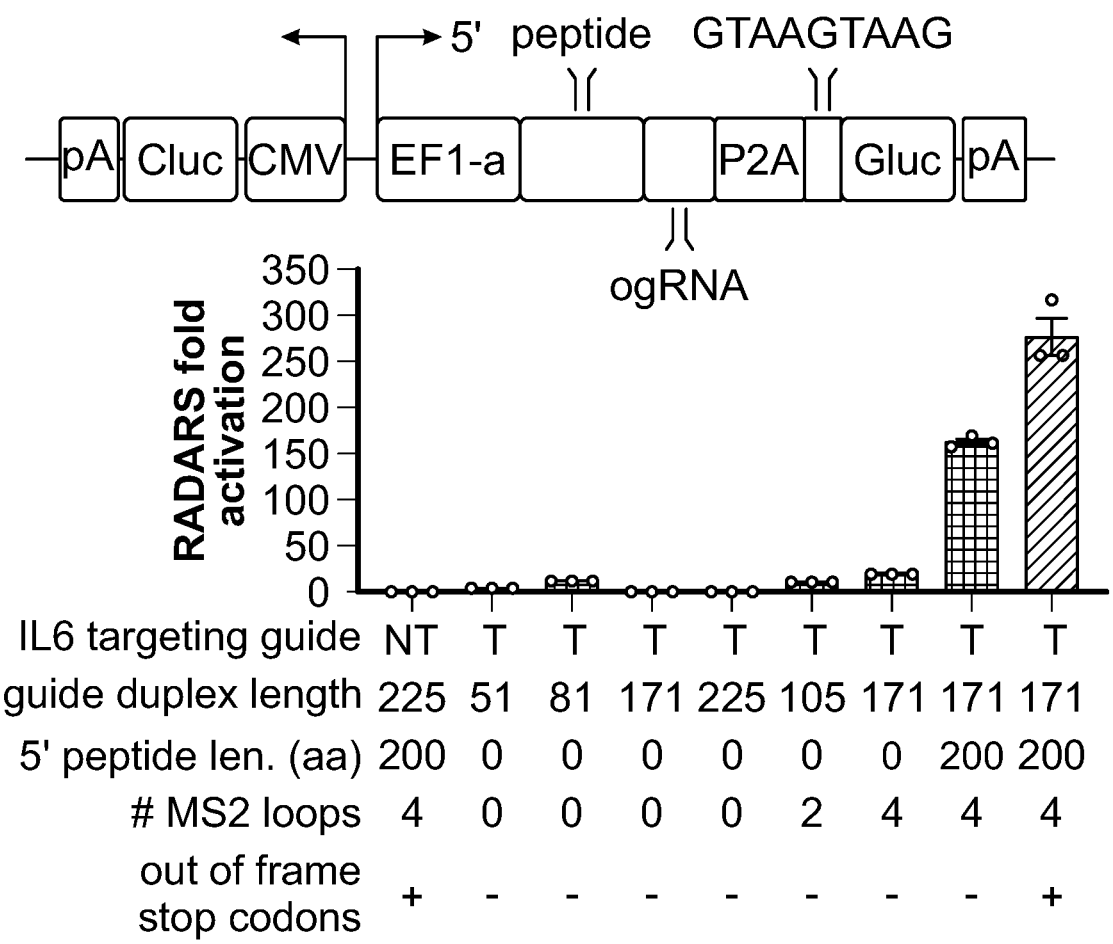
FIG. 54A is a visual characterization of the evolution of different RADARS sensor designs used in conjunction with exogenous ADAR1p150 supplementation. The inset depicts the backbone for different RADARS designs. RADARS fold activation is calculated as the ratio of *Gaussia* luciferase (Gluc) luminescence relative to constitutive *Cypridina* luciferase (Cluc) luminescence (Gluc/Cluc) in the presence of IL6 target relative to in the absence of target (see Methods). Sensor, target (IL6), and ADAR1p150 are co-delivered via transient transfection. Data are mean of technical replicates (n=3)±s.e.m.

Stop codons were engineered in the +1 and +2 frames following the engineered guide RNA region to trap the translating ribosome across all frames. These out-of-frame stop codon designs significantly decreased the background synergistically with long 5' peptides, generating ~200 fold activation. We chose this sensor design, termed RADARSv2, incorporating structured guides, upstream peptides, and out-of-frame stop codons, as a unified structure for future sensors (FIG. 54A).

Example 2. Development of Luciferase and Fluorescent Sensors and Detection of EGFP Transcript Cloning of Luciferase Sensors Luciferase sensors were cloned by Gibson assembly of PCR products. The sensor backbone is generated by cloning Cypridinia luciferase (Cluc) under expression of the CMV promoter and *Gaussia* luciferase (Gluc) under expression of the EF1-a promoter, both on a single vector. Expression of both luciferases on a single vector allowed one luciferase to serve as a dosing control for normalization of knockdown of the other luciferase, controlling for variation due to transfection conditions. Short sensors were ordered as primers and subsequently phosphorylated and annealed using T4 PNK. The annealed oligo is ligated into the backbone using T4 DNA Ligase (NEB) in a typical 10 µL ligation reaction with 1 µL of T4 DNA ligase, 30 ng of the insert, 50 ng of the backbone and 1 µL of 10× ligation buffer at room temperature for 20 minutes. Long avidity sensor regions ordered as Eblocks directly from Integrated DNA Technologies (IDT). PCR products were purified by gel extraction (Monarch gel extraction kit, NEB), and assembled into the backbones using NEB HiFi DNA Assembly master mix kit, with 2.5 µL of the mastermix, 30 ng of backbone, and 5 ng of the insert in a 5 µL reaction. The reaction is incubated in the thermocycler at 50 degrees for 30 minutes and 2 µL of assembled reactions were transformed into 20 µL of competent Stbl3 generated by Mix and Go! competency kit (Zymo) and plated on agar plates supplemented with appropriate antibiotics. After overnight growth at 37° C., colonies were picked into Terrific Broth (TB) media (Thermo Fisher Scientific)

and incubated with shaking at 37° C. for 24 hours. Cultures were harvested using QiAprep Spin Miniprep Kit (Qiagen) according to the manufacturer's instructions.

Figure 2A:
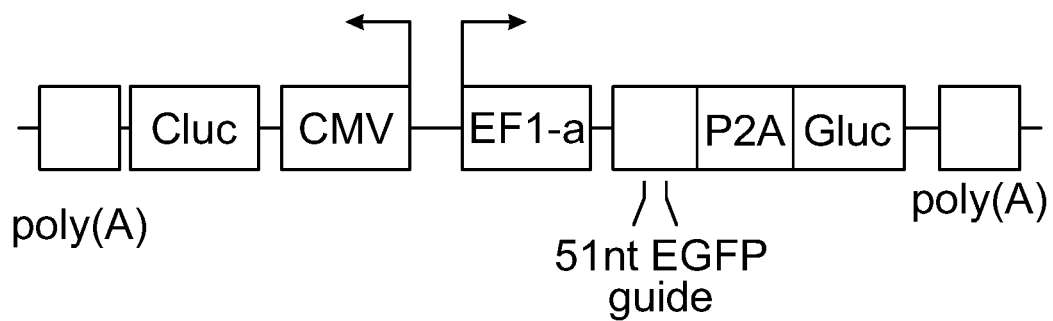
FIG. 2A is a graphic illustration of a dual transcript ADAR sensor design. The luciferase dual transcript ADAR sensor contains a normalizing protein under constitutive expression and a payload protein under ADAR sensor control. Ratio fold change can be calculated via calculating the normalized sensor activation (gluc/cluc) and then normalizing to the ratio value in the absence of target. Target can be delivered via exogenous transfection under the control of a doxycycline inducible promoter. The sensor can either recruit endogenous ADAR to sense target EGFP transcript or utilize exogenously delivered ADAR to sense target transcript with enhanced sensitivity.
Figure 2B:
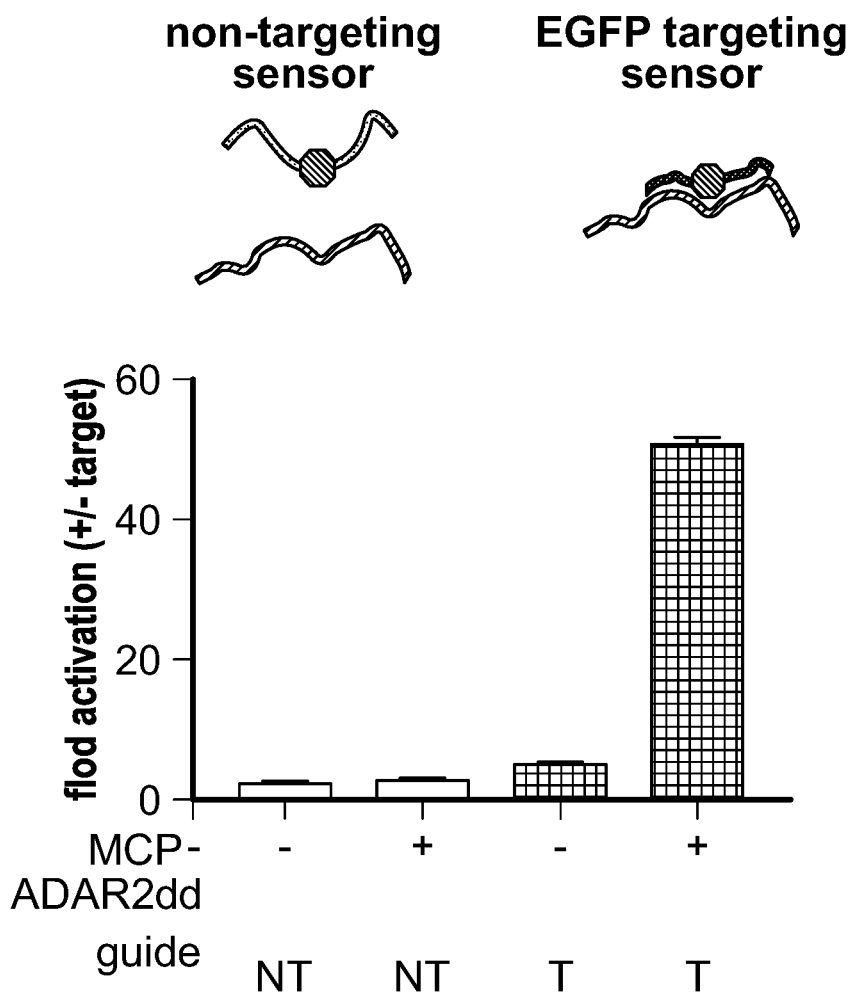
FIG. 2B is a graphical illustration of the comparison of the fold increase in activation in luciferase value in HEK293FT cells transfected with an eGFP plasmid or a control plasmid, as well as with an eGFP recognizing sensor strand, in either the presence or absence of supplemental ADAR.
Figure 2C:
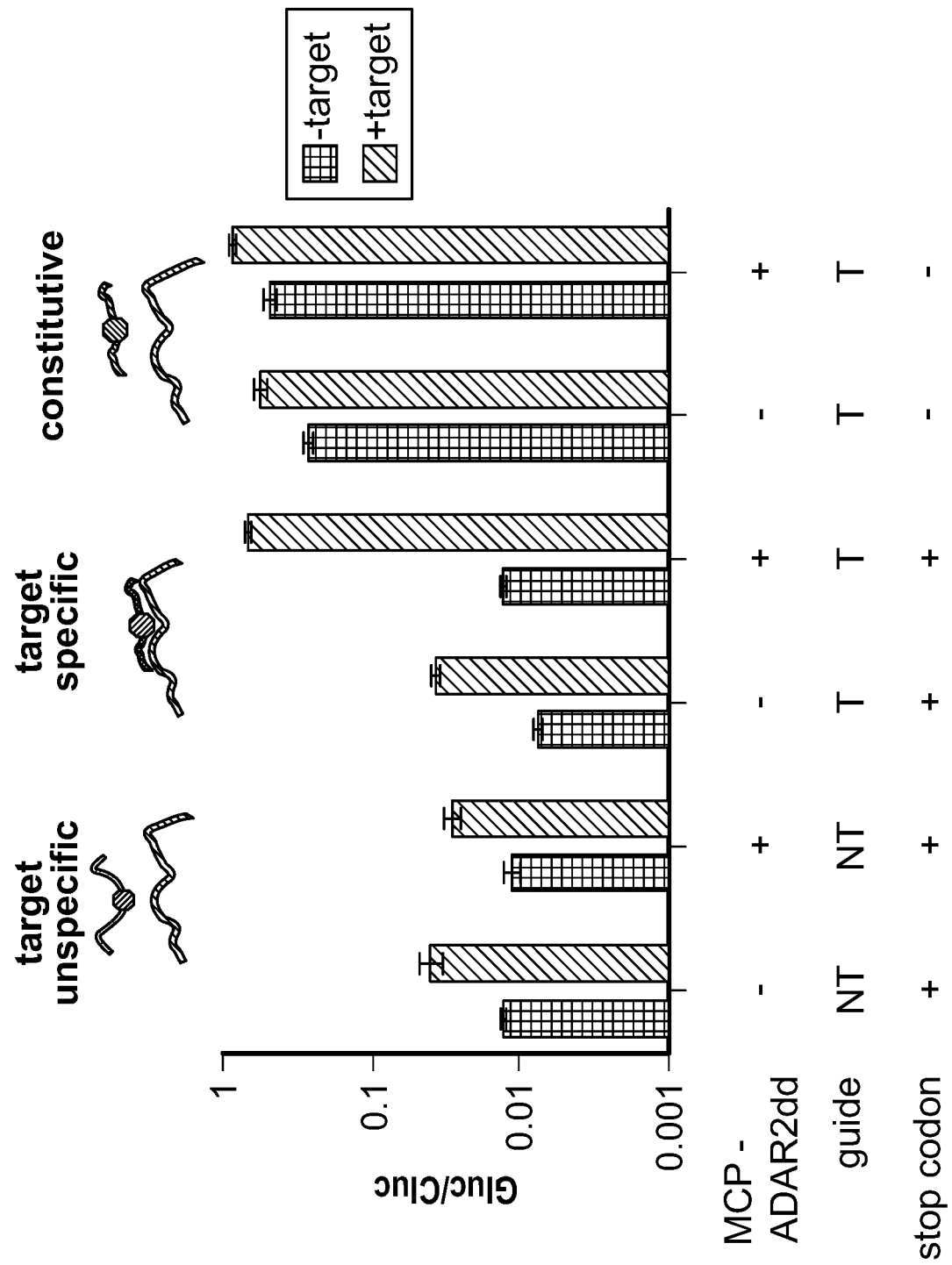
FIG. 2C is graphical illustration comparing luciferase value of a non-targeting sensor, a targeting sensor, or a constitutively active plasmid in the presence or absence of supplemental ADAR.
Figure 2D:
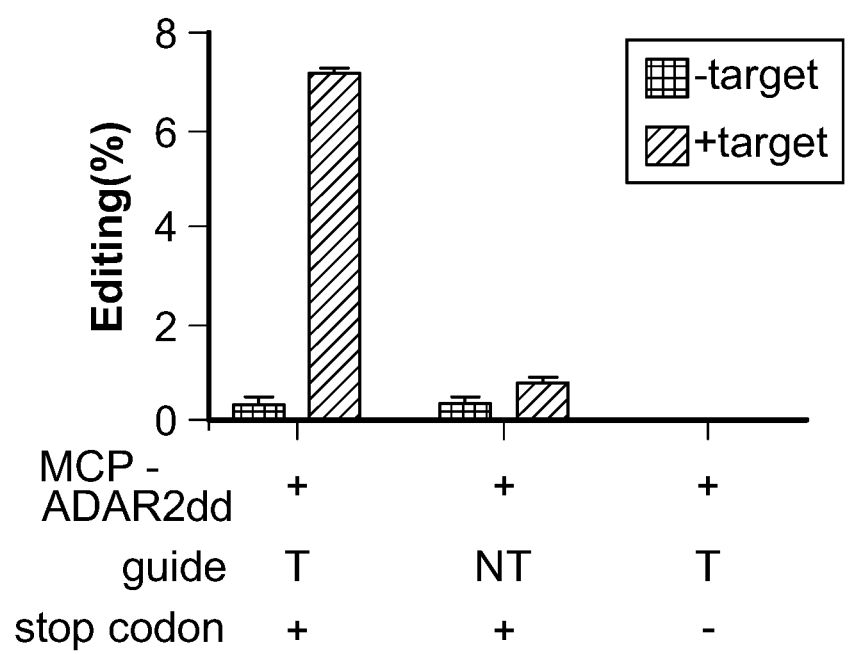
FIG. 2D is graphical illustration of the results of next generation sequencing to quantify the editing of a UAG stop codon in a targeting sensor, a non-targeting sensor, and a constitutively active plasmid.

This luciferase ADAR sensor contains a 51 nt EGFP transcript-sensing guide and a *Gaussia* luciferase (Gluc) payload (FIG. 2A). A constitutive *Cypridina* luciferase (Cluc) was included on a separate transcript, allowing for ratiometric control for transfection variance. This dual reporter, dual transcript luciferase reporter system targets a functional eGFP under control of a doxycycline inducible promoter. We tested this ADAR sensor design along with a scrambled guide control, in the presence or absence of exogenous ADAR2 deaminase domain with hyperactive mutation E488Q and specificity mutant T490A fused to the MS2 coat protein (MCP-ADAR2dd (E488Q, T490A)) (Kuttan and Bass 2012; Cox et al. 2017). ADAR sensor-expressing plasmids were co-transfected into HEK293FT cells with either a EGFP expressing plasmid or a control plasmid. We observed that the ADAR sensors resulted in up to a 5 fold increase in the normalized luciferase value, when only relying on endogenous ADAR, and a 51-fold activation in signal (fold change of luciferase expression in the presence of target/in the absence of target) when supplemented with exogenous MCP-ADAR2dd(E488Q, T490A) (FIG. 2B) In addition, we observed that the luciferase signal during ADAR sensor induction supplemented with exogenous ADAR is comparable (~78%, FIG. 2C) to a constitutive expression transcript without an upstream stop codon. Thus, this high protein production released upon ADAR SENSOR activation validates ADAR SENSOR for applications that demand high absolute payload expression. To confirm that payload expression is dependent on RNA editing, we harvested RNA from cells and quantified editing with next generation sequencing and observed a ~24-fold increase in the editing of the UAG stop codon in EGFP targeting sensor, but negligible increase in the editing of a non-targeting sensor. (FIG. 2D)

Cloning of Fluorescent Sensors

The fluorescence ADAR sensor parent was cloned via Gibson assembly in three pieces, using pcDNA3.1(+) cut with HindIII and NotI as the backbone. mCherry was amplified off the Addgene vector 109427, and T2A mNeon was ordered as a gBlock from IDT. All fluorescence ADAR SENSOR were subcloned into the parent fluorescence plasmid via golden gate cloning using the enzyme Esp3I (isoschizomer of BsmBI). Inserts were either ordered as complementary strands with overhangs and annealed with phosphorylation or produced via PCR. Golden-gate reactions used NEB BsmBIv2 golden gate assembly kit, or was assembled component-wise, in a 20 µL reaction containing 25 ng of vector and 2 µL of 1:200 diluted insert (approximately 5-10 ng). Reactions were thermocycled for 1 hour alternating between 25° C. and 37° C. for 5 minutes each, and then 0.75 µL of the reaction mix was transformed into 12.5 µL of Zymo Mix and Go competent cells. The transformed cells were diluted 1:1 with SOC media and 10 µL were streaked onto 50 µg/mL carbenicillin agar plates. After incubation overnight at 37° C. degrees, single colonies were picked into 4 mL of luria broth (LB) supplemented at 50 µg/mL carbencillin. Plasmids were prepared from culture as described above for the luciferase sensors.

Figure 3A:
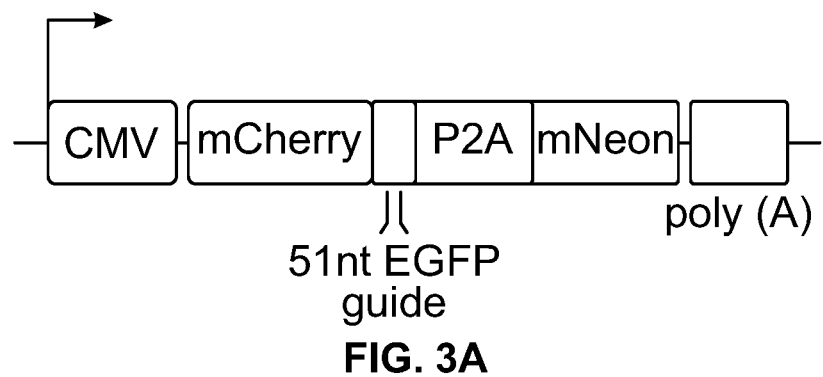
FIG. 3A is schematic showing fluorescence ADAR sensor with a single transcript design containing a constitutively expressed normalizing fluorescent protein (mCherry) upstream of an ADAR sensor guide controlling a second fluorescent protein (mNeon). Due to the dual fluorescence on a single transcript, a non-functional eGFP must be used with this format.
Figure 3B:
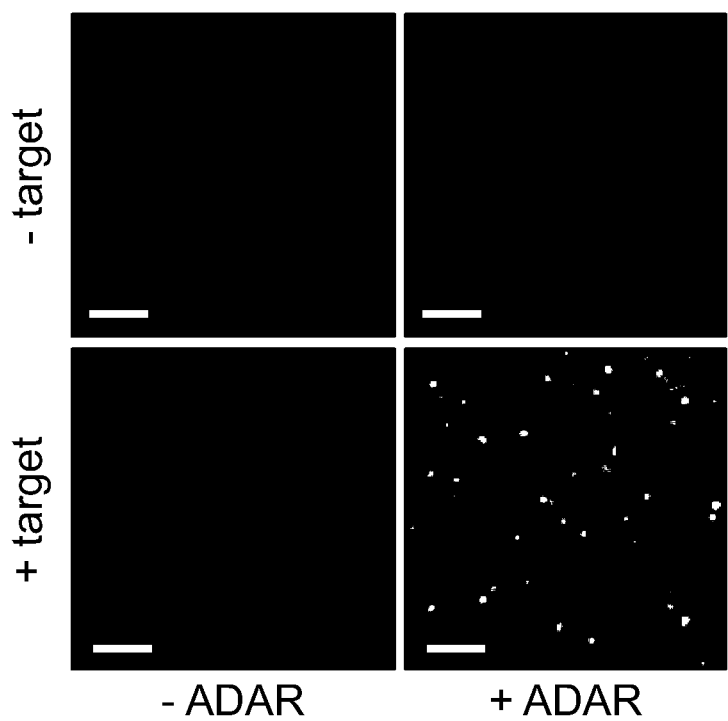
FIG. 3B is a series of representative images of HEK293FT cells transfected with a targeting sensor or a non-targeting sensor, non-functional eGFP, and with or without supplemental ADAR.
Figure 3C:
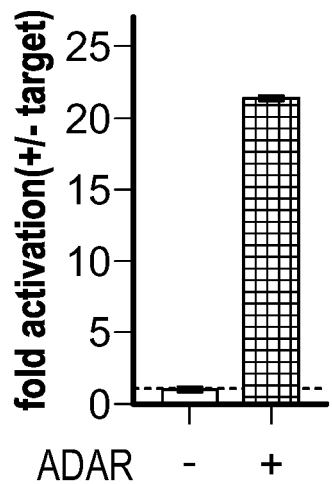
FIG. 3C is a quantification of the fold increase of mNeon activation by measuring fluorescence.
Figure 3D:
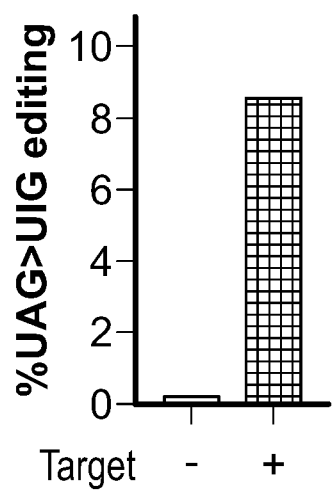
FIG. 3D is a graphical illustration of the results of next generation sequencing to quantify the editing of a UAG stop codon in the presence of supplemental ADAR of both non-targeting sensors and targeting sensors.

This dual reporter, single transcript fluorescent sensor contains a single transcript fluorescence reporter that constitutively expresses mCherry upstream of a 51 bp eGFP sensor, with a downstream mNeon reporter only activated upon interaction with the target (FIG. 3A). HEK293 cells were transfected with a non-functional eGFP under control of a doxycycline inducible promoter. Cells were also transfected with a dual reporter, single transcript targeting sensor or a non-targeting sensor in the presence of 1 µg/mL doxycycline. FIG. 3B displays representative images in experiments with and without target, and with and without exogenous ADAR. FIG. 3C displays the quantification of EGFP fluorescence fold change upon target induction, ratio fold change indicates that mNeon/mCherry fluorescence values (fluorescence ratio values) in the presence of target were divided by fluorescence ratio values in the absence of target for the ADAR variant. In the presence of exogenous MCP-ADAR2dd (E488Q, T490A) the targeting ADAR sensor exhibited a >21-fold increase in activation. Additionally, in the absence of a targeting ADAR sensor there was low background activation. The TAG→TIG editing rate of the sensor TAG codon was also measured in the presence or absence of target. In the presence of exogenous ADAR, the UAG stop codon in the presence of the targeting ADAR sensor was edited at a rate of 9.4%, while in the absence of a targeting ADAR sensor the UAG stop codon was edited at a rate of 0.2%, suggesting that target driven editing drives fluorescent payload expression.

Figure 4A:
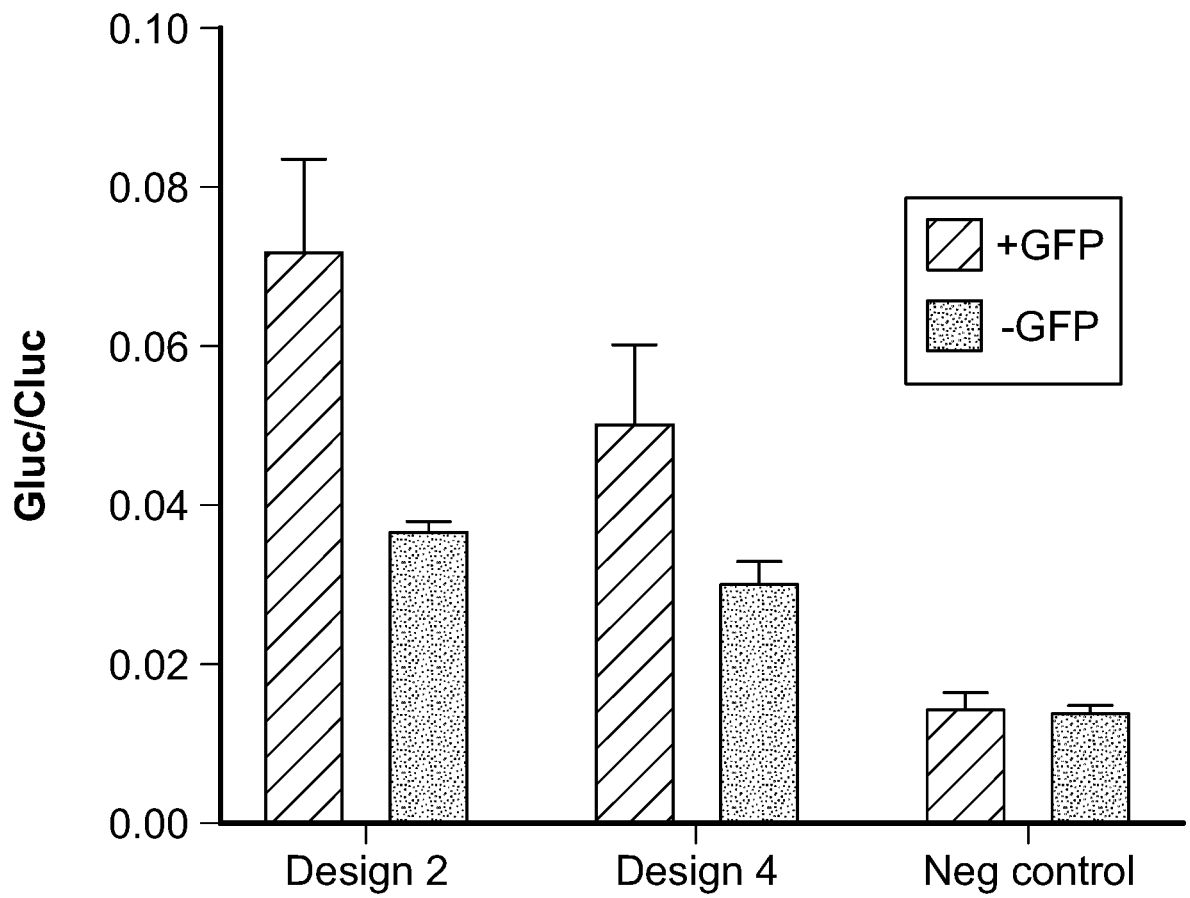
FIG. 4A is a graphic illustration of luciferase expression and fold increase in luciferase expression compared to a negative control in HEK293FT cells FIG. 4B Ratio fold change can be calculated via calculating the normalized sensor activation (gluc/cluc) and then normalizing to the ratio value in the absence of target.
Figure 4B:
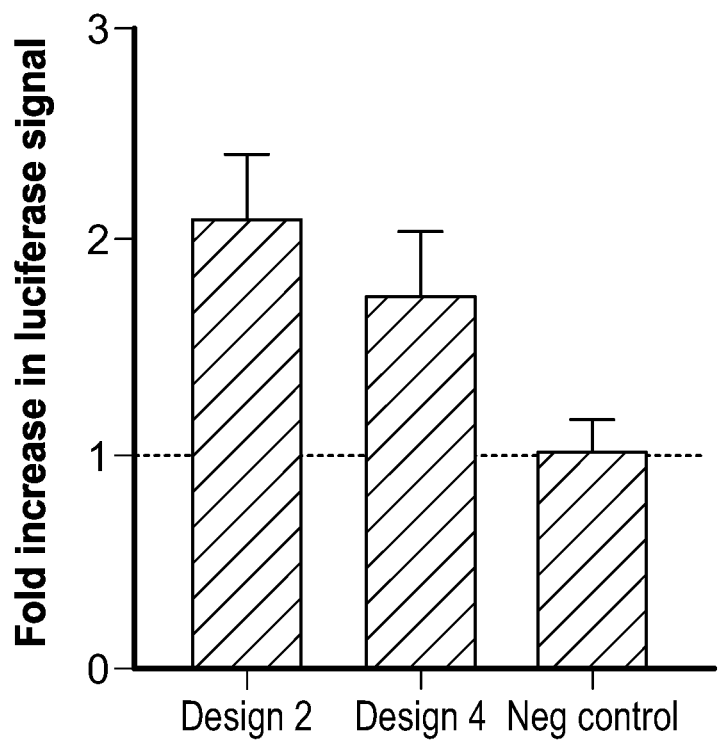
FIG. 4B increase in EGFP expression compared to the negative control guide strand was quantified.

To further establish proof of principle with respect to biological luciferase sensors, three guide strands were introduced into HEK293FT cells, simultaneously with an exogenous EGFP reporter transcript. The ADAR sensor was a dual transcript *Gaussia* luciferase (Gluc)/*Cypridina* luciferase (Cluc) transcript, allowing for ratiometric control for transfection variance. The dual reporter, dual transcript luciferase reporter system targeted the exogenous eGFP reporter transcript. Design 2 and 4 are different guides targeting the EGFP transcript. No exogenous ADAR was introduced into the cell. The negative control is a guide strand which does not recognize EGFP. When EGFP expression was analyzed following introduction of the three guide strands, both design 2 and design 4 showed a significant increase in the level of luciferase expression (FIG. 4A). Both design 2 and design 4 guide strands exhibited a significant increase in luciferase signal compared to the negative control scramble guide (FIG. 4B).

Figure 5:
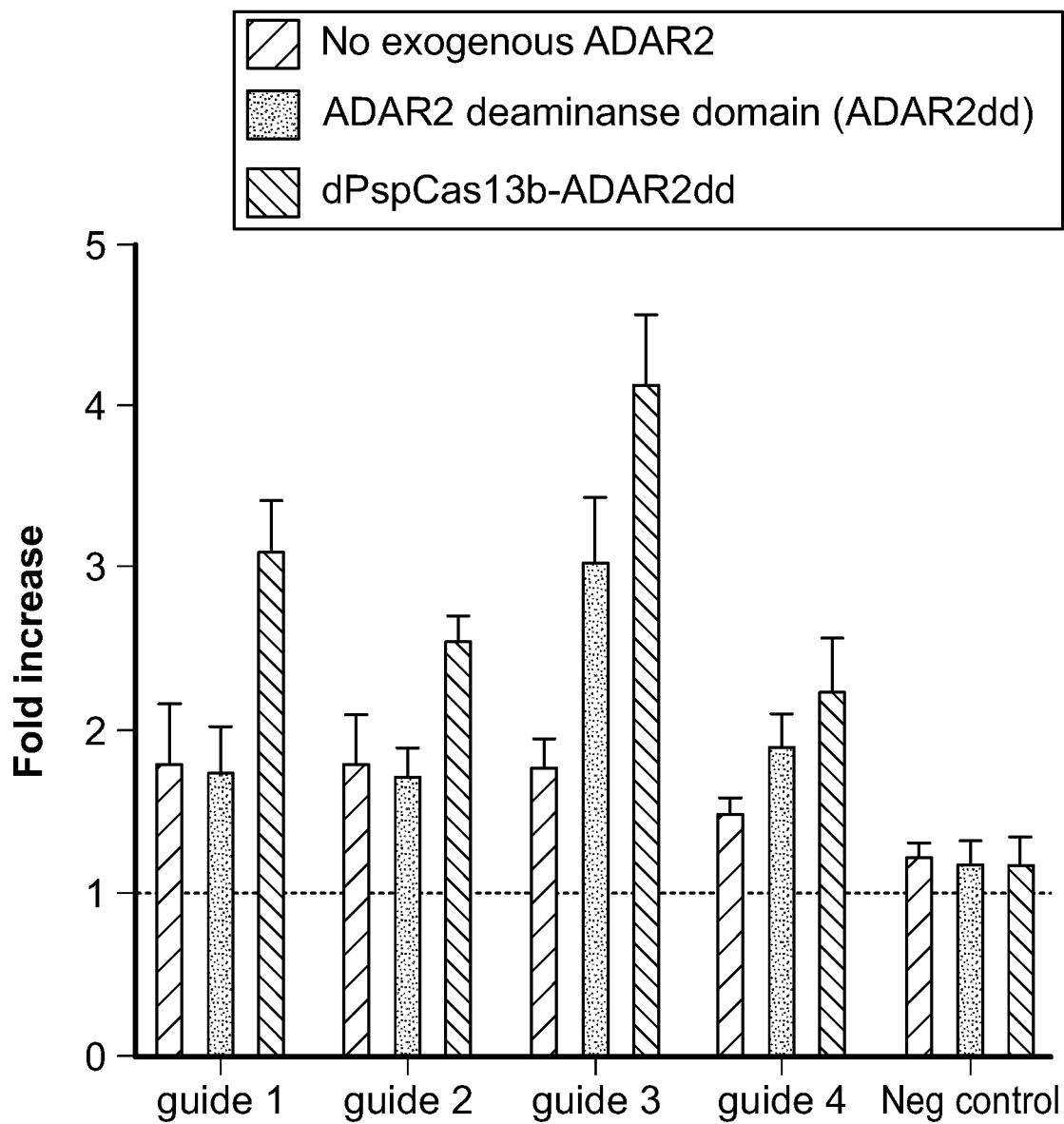
FIG. 5 is a graphic illustration of increase in luciferase expression of experimental guide strands 1-4, which target an EGFP transcript, in the presence of endogenous ADAR2 (FIG. 3, blue bars), endogenous ADAR2 supplemented by an exogenously supplied deaminase domain of ADAR2 (ADAR2dd.

Example 3. Increased Transcript Expression Following Exogenous ADAR2 Administration To determine if introducing an additional ADAR molecule would increase luciferase expression, 5 guide strands were introduced into HEK293FT cells, simultaneously with an exogenous EGFP reporter transcript. Guides 1-4 are different guides targeting the EGFP transcript. The negative control is a scrambled control designed not to recognize EGFP. Each guide strand was tested in three experimental conditions. First, each guide was introduced into HEK293FT cells into which no exogenous ADAR was introduced into the cell (FIG. 5, blue bars). Next, each guide was introduced to a HEK293FT cell simultaneously with the deaminase domain of ADAR2 (ADARdd) (FIG. 5, white bars). Finally, each guide was introduced to a HEK293FT cell simultaneously with a ADAR2dd overexpressing transcript dPspCas13b-ADAR2dd (FIG. 5, red bars).

Guide strands 1-4 exhibited between a 1.5-fold and a 2-fold increase in luciferase expression without the addition of any exogenous ADAR molecules, when normalized to the negative control (FIG. 5, blue bars). When the deaminase domain of ADAR2 (ADAR2dd) was simultaneously introduced to the cell, guides 1, 2, and 4 exhibited an increase in luciferase expression similar to the same guides in the presence of endogenous ADAR (FIG. 5, white bars). Guide strand 3 exhibited a 3-fold increase in luciferase expression in the presence of the additional ADAR2dd molecule (FIG. 5, white bars).

When an ADAR2dd overexpressing vector was simultaneously introduced with guide strands 1-4, luciferase expression was increased at least 2-fold (FIG. 5, red bars). Guide strand 3, specifically, displayed a 4-fold increase in luciferase expression when compared to the negative control. This data highlights the possibility of harnessing exogenous and modified ADAR molecules to enhance sensor capabilities.

Figure 6A:
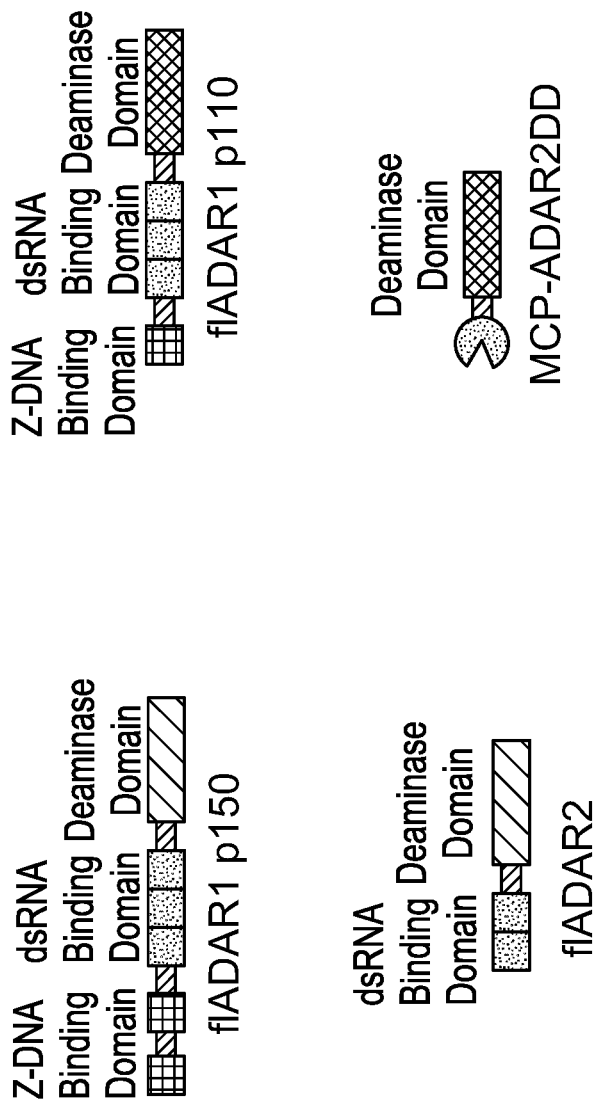
FIG. 6A is a visual depiction of an ADAR variant and catalytic domain mutation screen. Schematic of different ADARs tested, from left to right including ADAR1p150, ADAR1p110, ADAR2, and an MS2 coat protein (MCP)-ADAR fusion protein (MCP-ADAR), fl=full-length. DD=deaminase domain. Catalytic domain mutations are not shown in the schematic; are all in the deaminase domain.
Figure 6B:
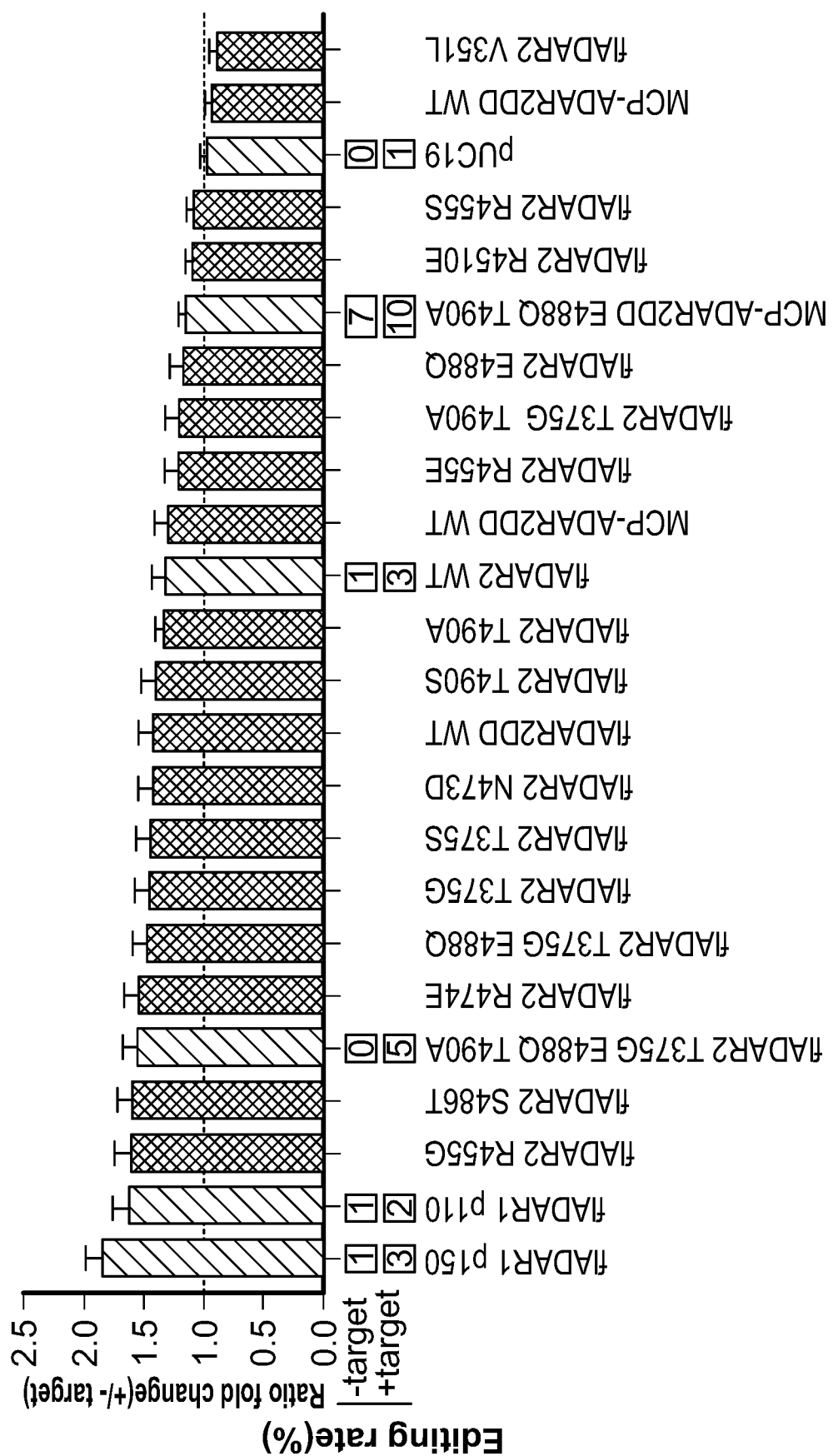
FIG. 6B Bar graph showing activation of exogenously transfected sensor in the presence of exogenously transfected iRFP and different ADAR variants. ADAR variants selected for screening across targets are shown in red with RNA sequencing data showing the conversion of TAG stop codons to TIG in the presence and absence of target. Error bars indicate standard deviation of n=3 technical replicates.
Figure 7A:
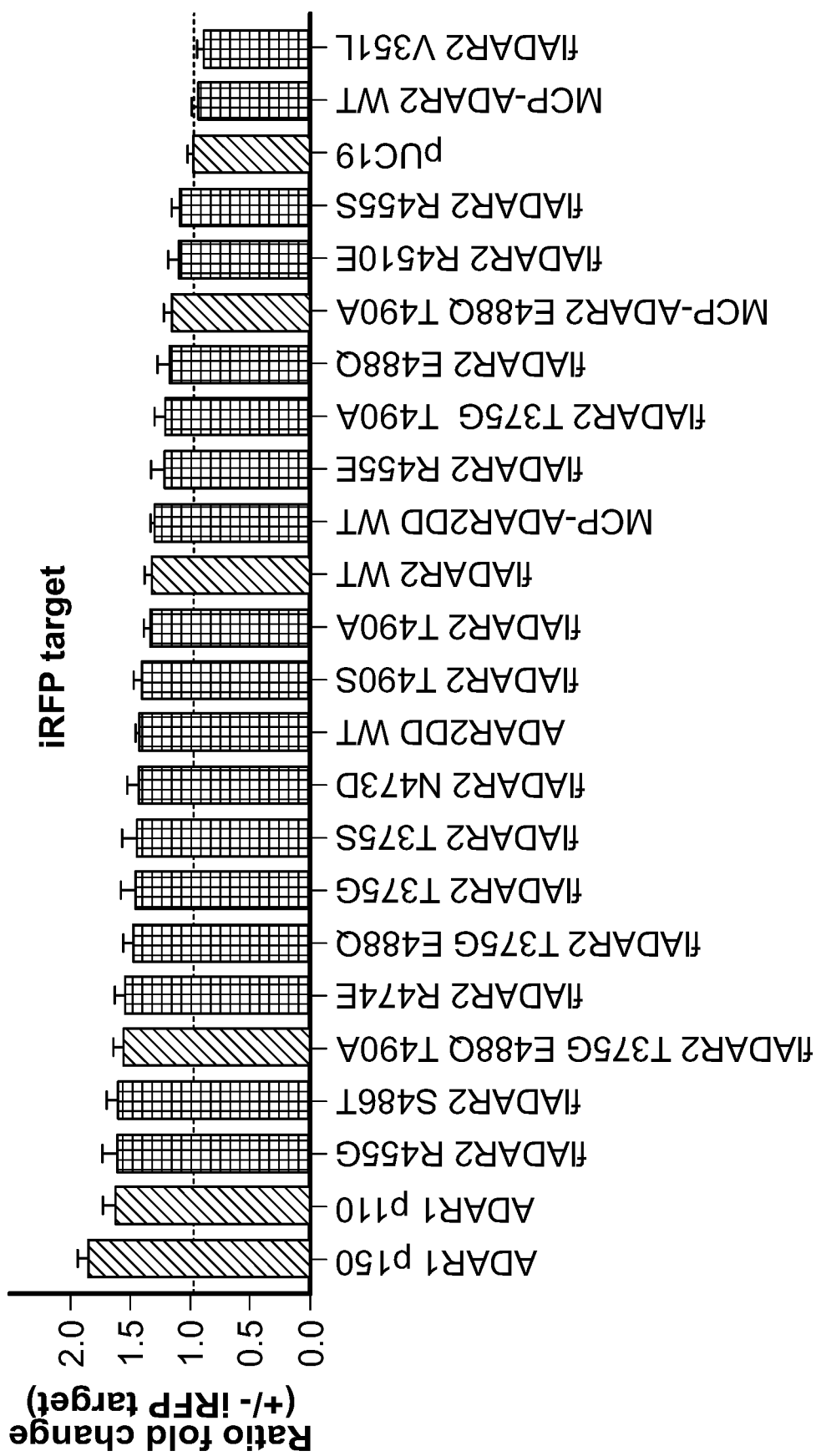
FIG. 7A is a graphical representation of the activation of ADAR sensors with eGFP and iRFP targets. Testing of ADAR variants on a 69 nt iRFP sensor. Fold change shown indicates fluorescence ratio values (mNeon/mCherry) in the presence of target divided by ratio values in the absence of target.
Figure 7B:
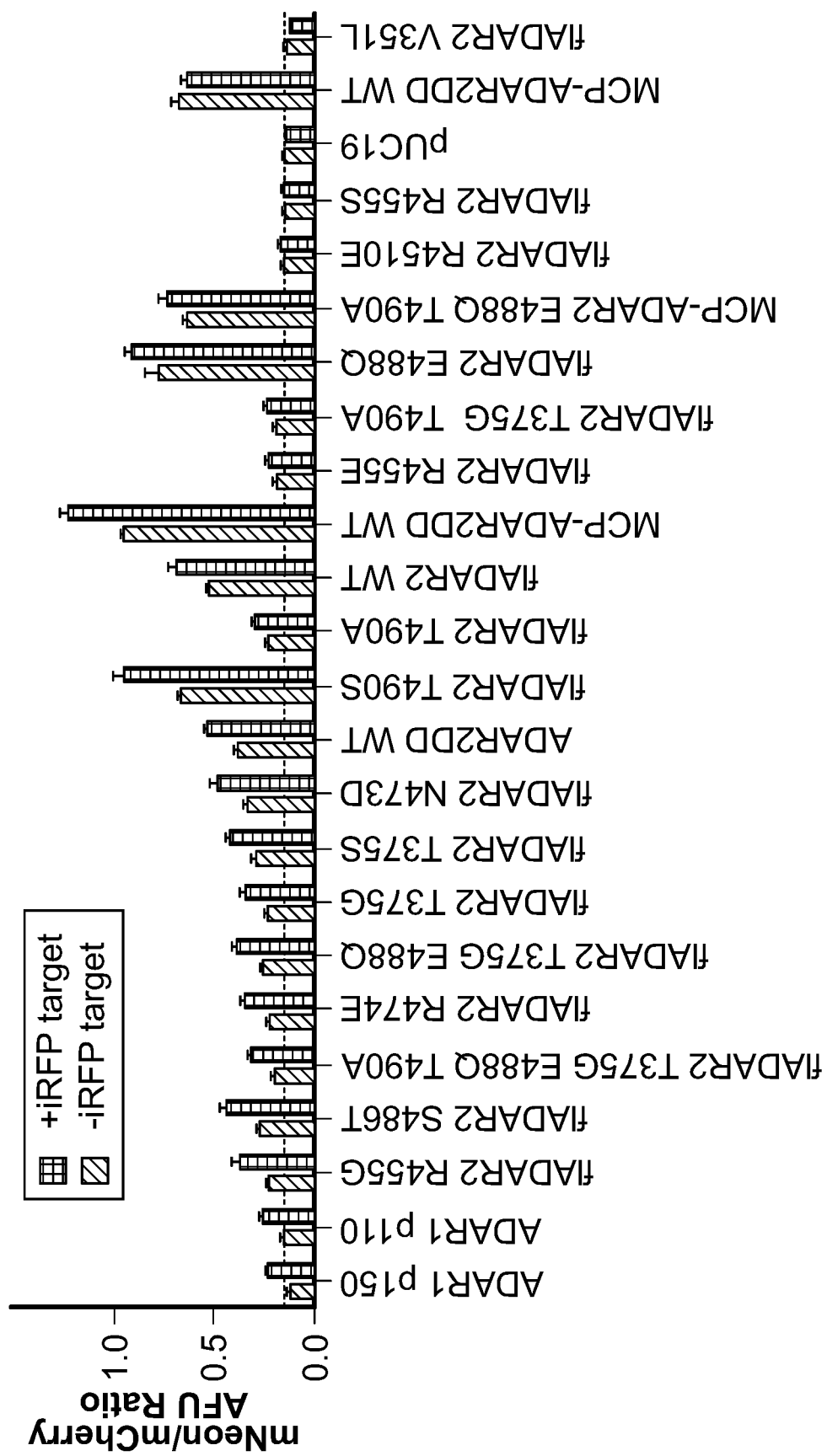
FIG. 7B Non-normalized mNeon/mCherry fluorescence ratio values for data shown in FIG. 7A.
Figure 7C:
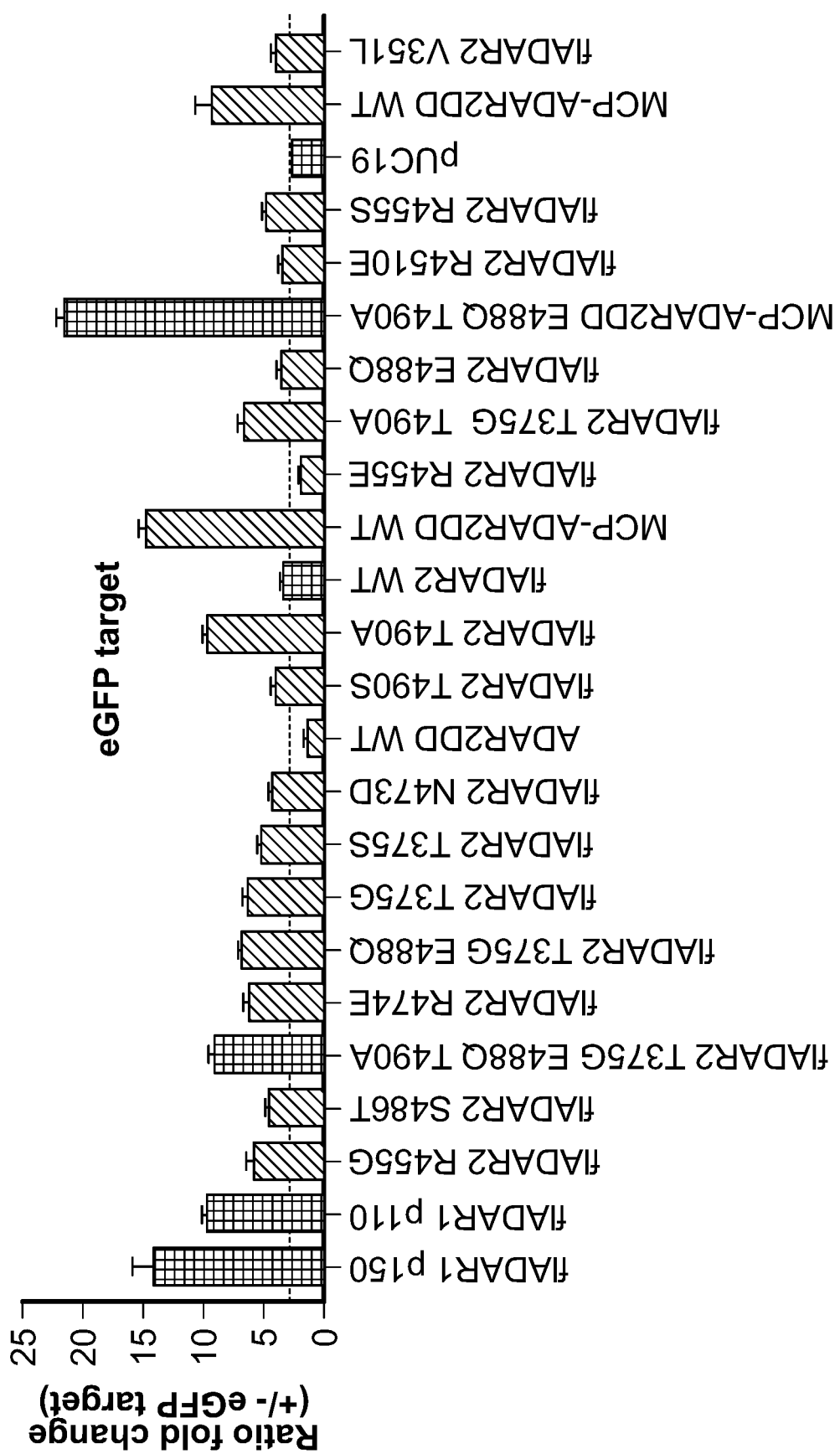
FIG. 7C Testing of ADAR variants on a 51 nt eGFP sensor. Fold change shown indicates fluorescence ratio values (mNeon/mCherry) in the presence of target divided by ratio values in the absence of target.
Figure 7D:
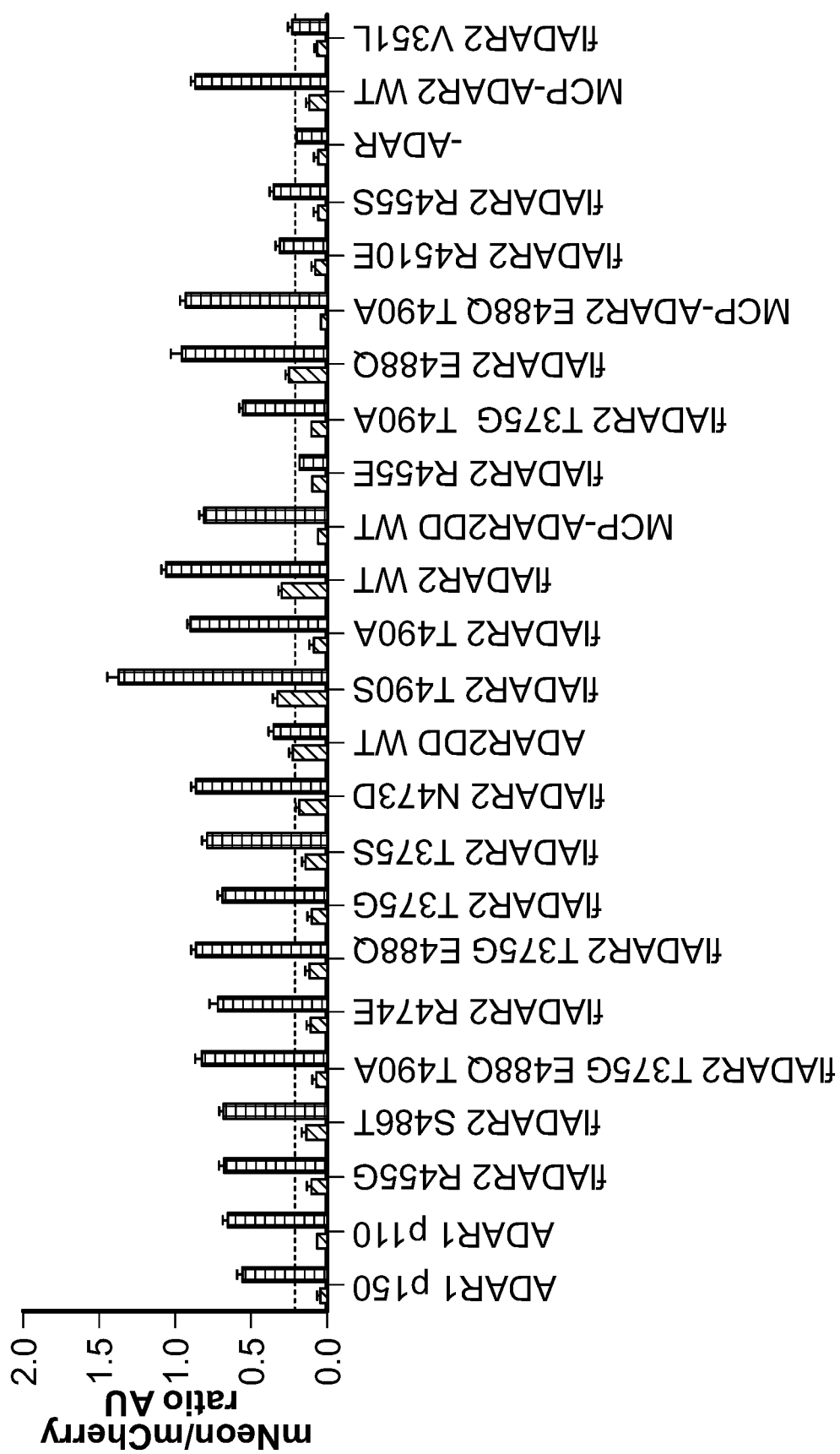
FIG. 7D Non-normalized mNeon/mCherry fluorescence ratio values for data shown in FIG. 7C. Error bars indicate standard deviation of n=3 technical replicates.
Figure 8A:
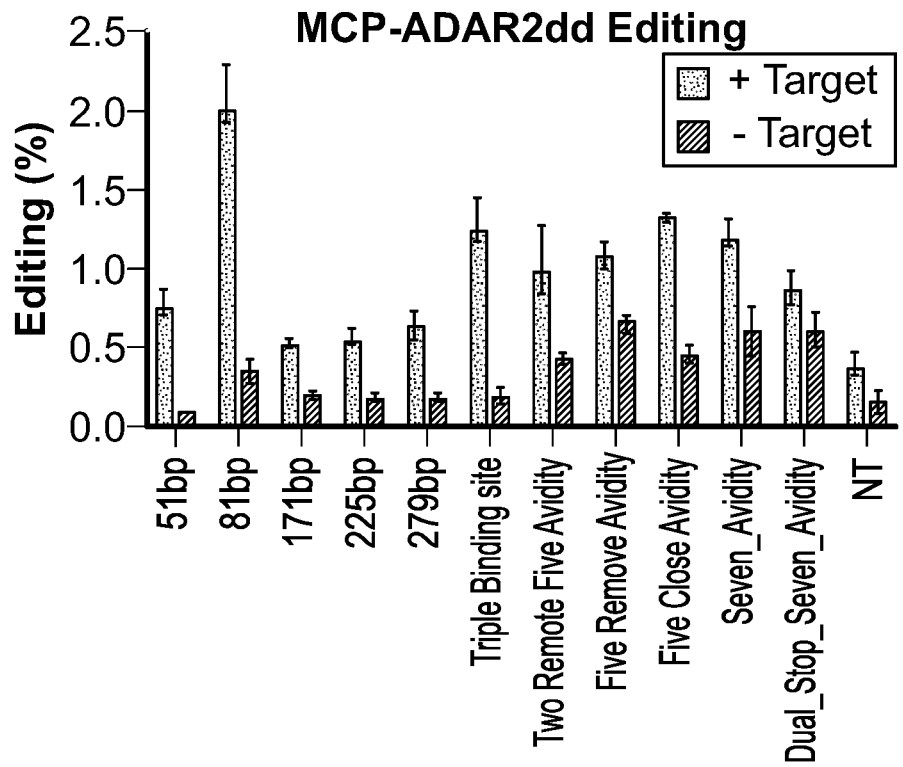
FIG. 8A is a graphical depiction of editing rate at the stop codon of panel of sensors in the + target group and − target group for MCP-ADAR2dd exogenous supplementation, FIG. 8B ADAR1 p150 isoform exogenous supplementation, FIG. 8C ADAR2 exogenous supplementation, and FIG. 8D no exogenous ADAR supplementation.
Figure 8B:
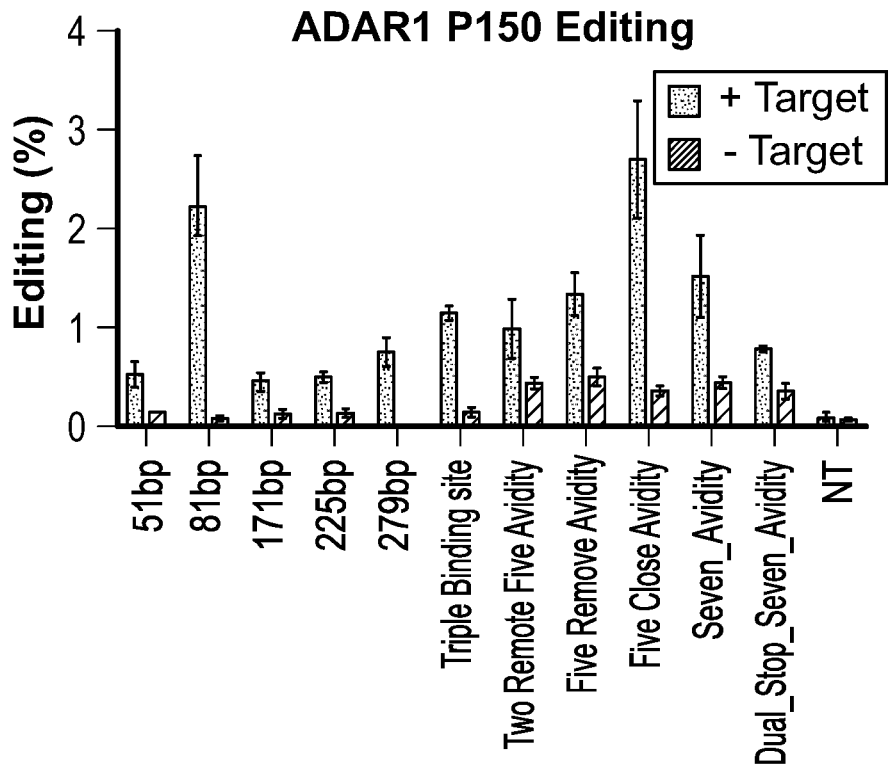
Figure 8C:
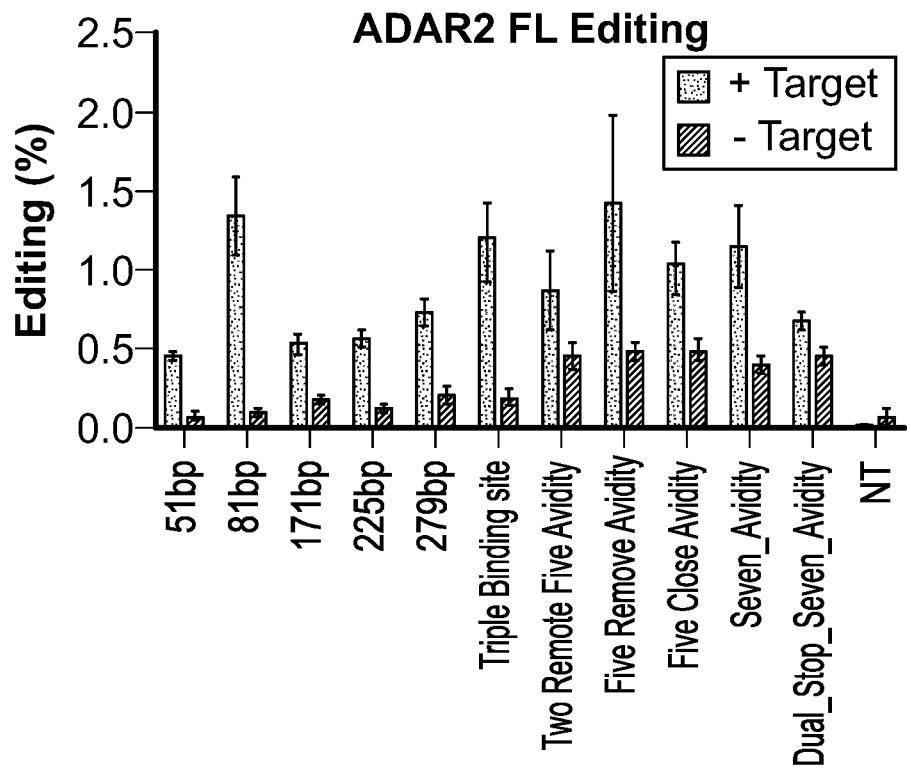
Figure 8D:
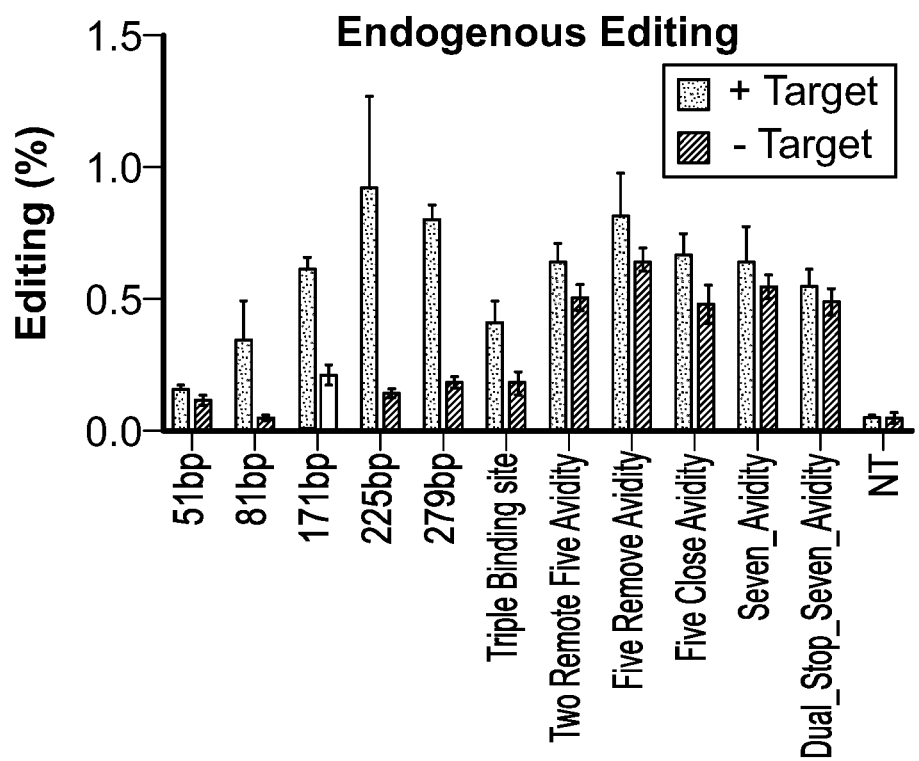

Example 4. ADAR Optimization and Length Screening Reduces Background and Increases ADAR Sensor Activation in the Presence of Target During the validation of these ADAR sensors, we observed that, for some guides, activation can happen in the presence of exogenous ADAR despite the absence of a target RNA (FIG. 2C, FIG. 3B). We set out to determine if ADAR activity could be optimized to increase activation and decrease background. To optimize the ADAR sensors and minimize this background, we selected and tested a panel of different ADAR1 and ADAR2 mutants in combination with 69 nt guide guides targeting a frame-shifted EGFP transcript or iRFP transcript (FIG. 6, FIG. 7). FIG. 6A shows a schematic of the different ADARs tested, from left to right including the p150 isoform of ADAR1, the p110 isoform of ADAR1, ADAR2, and an MS2 coat protein (MCP)-ADAR fusion protein (MCP-ADAR), fl=full-length. DD=deaminase domain. Catalytic domain mutations are not shown in the schematic: all are in the deaminase domain.

We screened full-length human ADAR isoforms (ADAR1 p110, ADAR1 p150, and ADAR2) (Galipon et al. 2017; Merkle et al. 2019) and their catalytic deaminase domains, along with specific mutants designed to destabilize ADAR-dsRNA interactions to decrease non-specific editing (Cox et al. 2017; Matthews et al. 2016). While our initial exogenous ADAR selection, MCP-ADAR2dd(E488Q. T490A), performed the best on the frame-shifted EGFP transcript, several candidates in our screen had comparable activation upon target co-transfection (FIG. 6B), with reduced background on the set of two targets (FIG. 7). We also examined the stop codon Editing rate for (FIG. 8A) MCP-ADAR2dd exogenous supplementation, (FIG. 8B) ADAR1 p150 isoform exogenous supplementation, (FIG. 8C) ADAR2 exogenous supplementation, and (FIG. 8D) no exogenous ADAR supplementation with various sensors. The Editing Rate of these candidates was also examined. Editing rate is calculated through RNA sequencing data showing the conversion of UAG stop codons to UIG in the presence and absence of target of the ADAR variants selected for further screening (FIG. 8).

Figure 9:
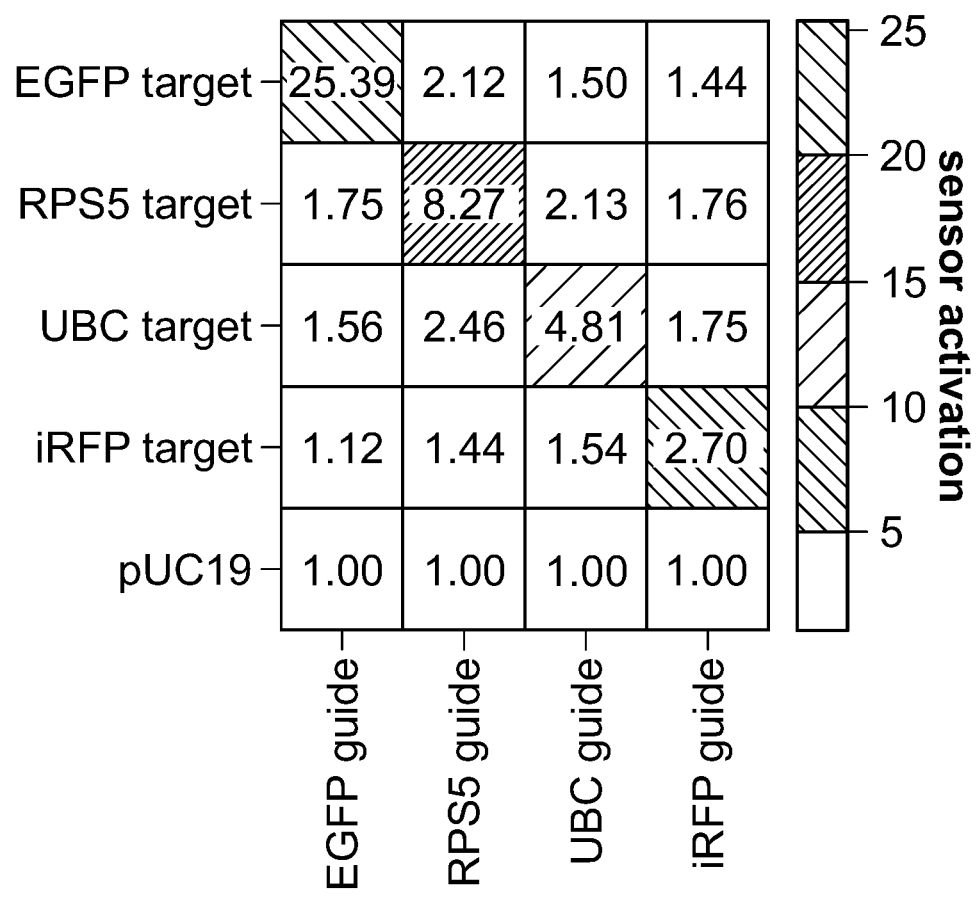
FIG. 9 is a heatmap displaying the results of an experiment in which HEK293FT cells were transfected with ADAR p150 and with plasmids expressing target transcripts and target-sensing ADAR sensor constructs in the combinations shown on the y- and x-axes, respectively. Data shown is fold change calculated as the fluorescent ratios (mNeon/mCherry) in the + target divided by − target (pUC19) conditions. All conditions represent data from n=3 technical replicates.
Figure 10A:
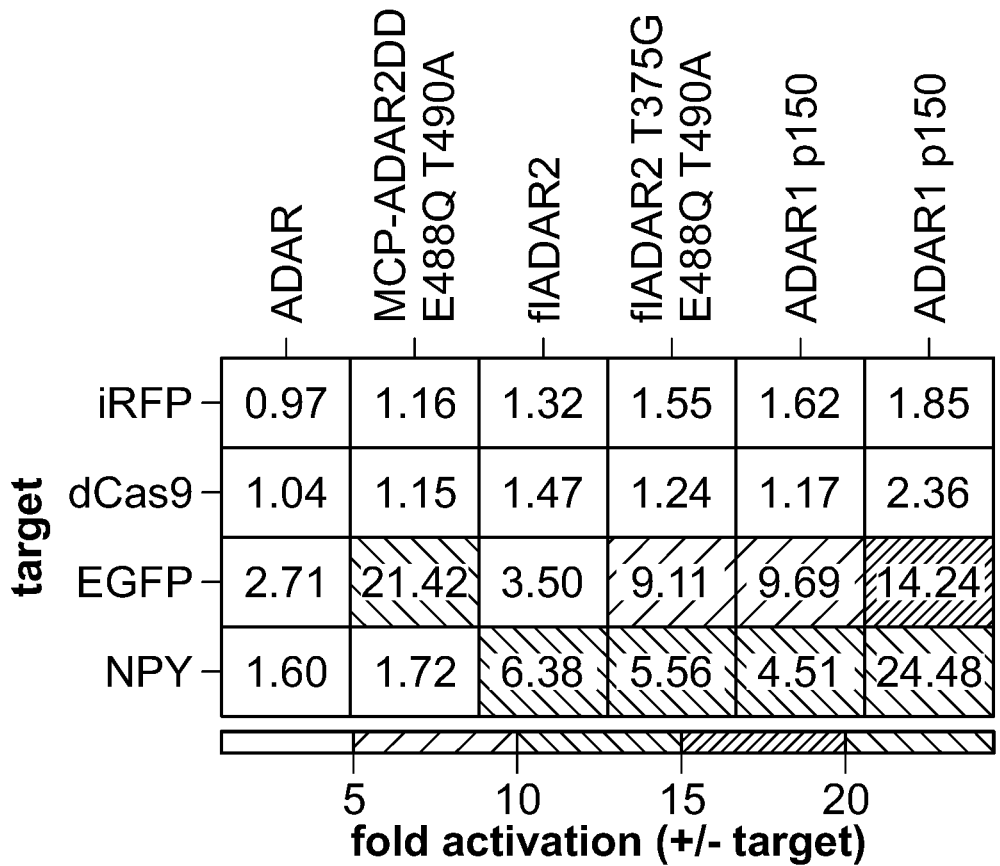
FIG. 10A Selected ADAR variants screened against four different targets in combination with respective RNA sensors. The numbers in the heat map represent ratio fold change. All conditions represent data from n=3 technical replicates.
Figure 10B:
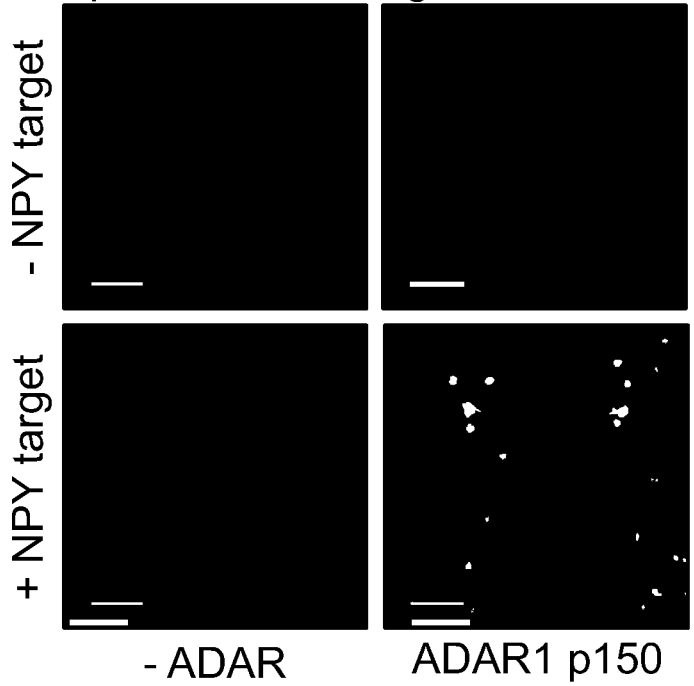
FIG. 10B Representative images are shown for the neuropeptide Y (NPY) target for ADAR1 p150. Cells were transfected with the NPY sensor, ADAR variants, and target in the combinations listed around the images. Image data obtained via confocal microscopy of HEK293 cells at 10× magnification and digitally enhanced 4×.
Figure 11A:
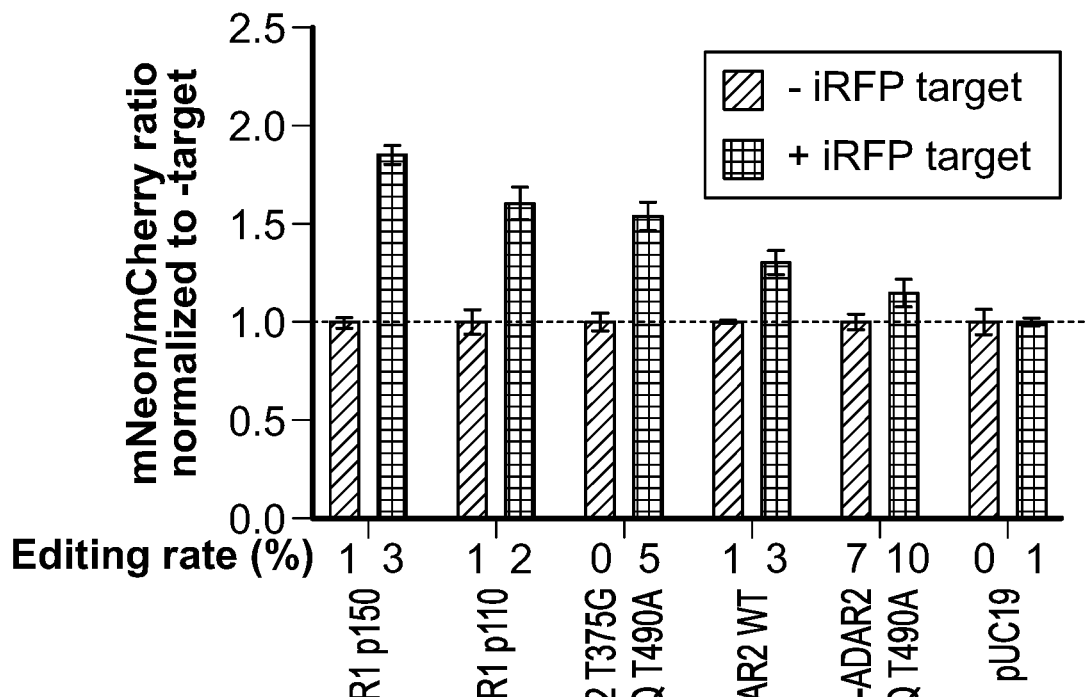
FIG. 11A, FIG. 11C, FIG. 11E, FIG. 11G is a graphical illustration of the normalized fluorescence ratio and the non-normalized FIG. 11B, FIG. 11D, FIG. 11F, FIG. 11H fluorescence values for target and ADAR sensor combinations when tested in HEK293FT cells. Targets tested were iRFP FIG. 11A, FIG. 11B, eGFP FIG. 11C, FIG. 11D, neuropeptide Y FIG. 11E, FIG. 11F and dCas9 FIG. 11G, FIG. 11H.
Figure 11B:
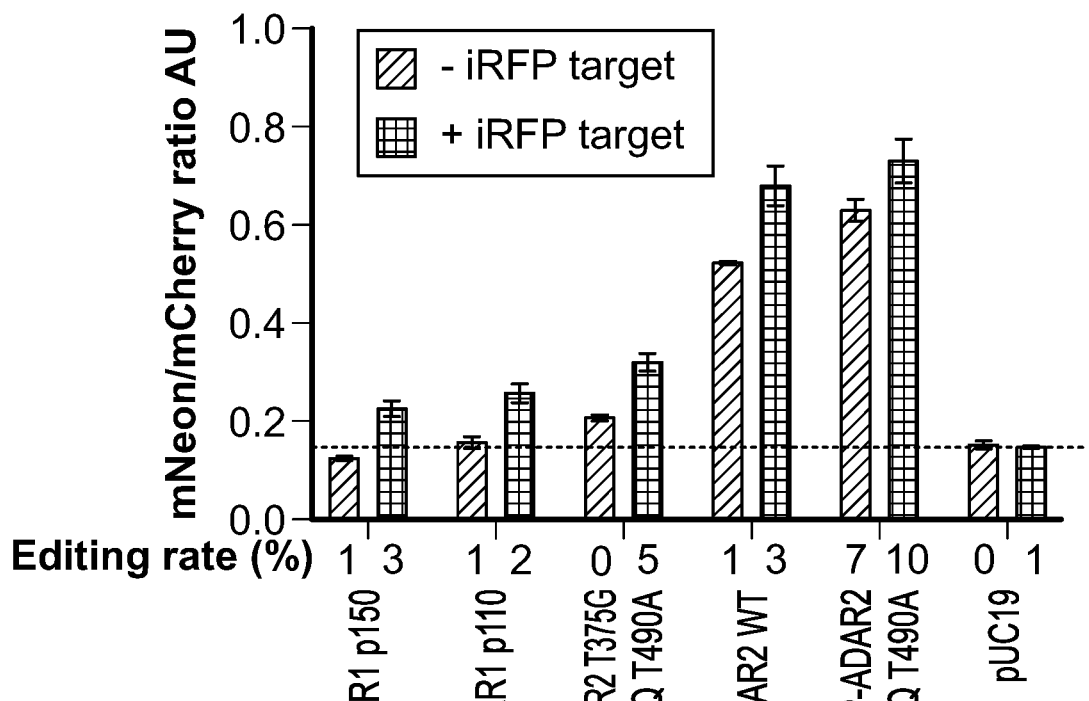
FIG. 11B, FIG. 11D, FIG. 11F, FIG. 11H: non-normalized mNeon/mCherry fluorescence ratio values for each sensor and target combination with different ADAR variants. For iRFP and EGFP targets, next-generation sequencing data of the RNA sensors for the UAG to UIG conversion. % editing indicates % reads that are A→I edited. All conditions represent data from n=3 technical replicates.
Figure 11C:
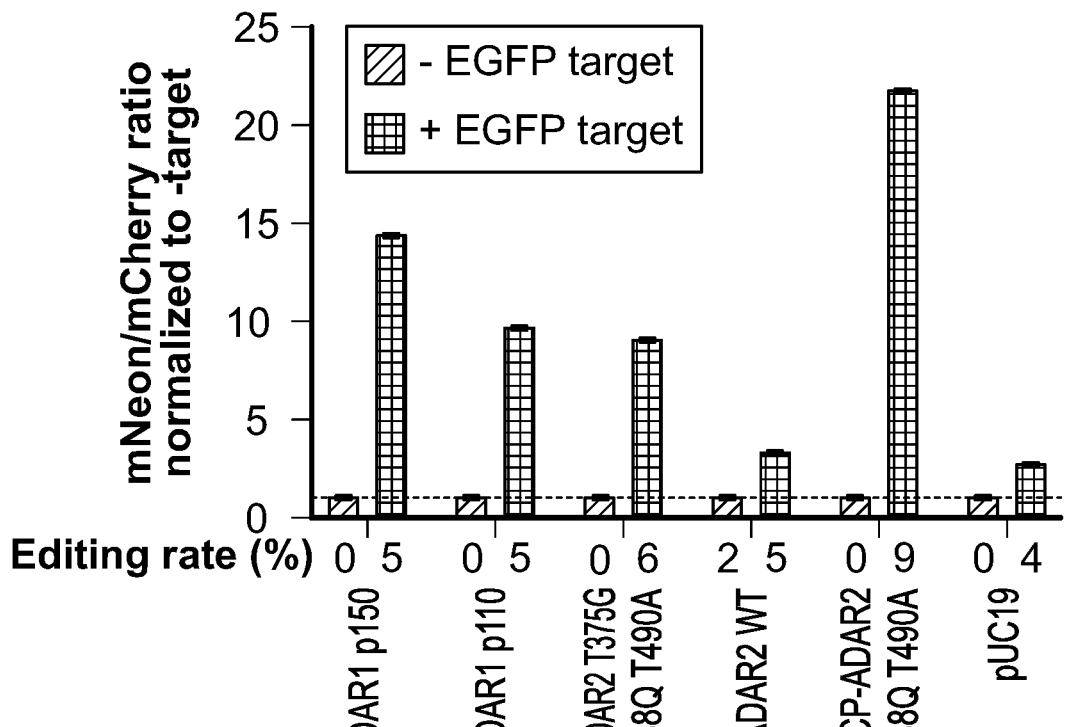
Figure 11D:
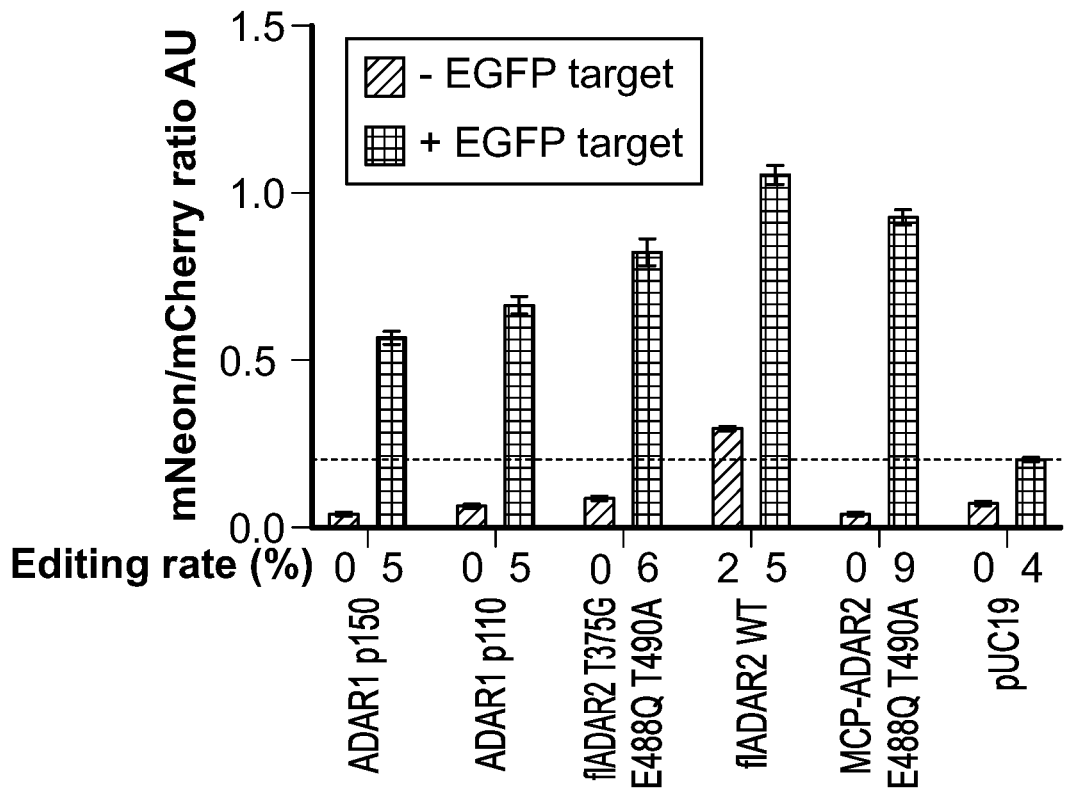
Figure 11E:
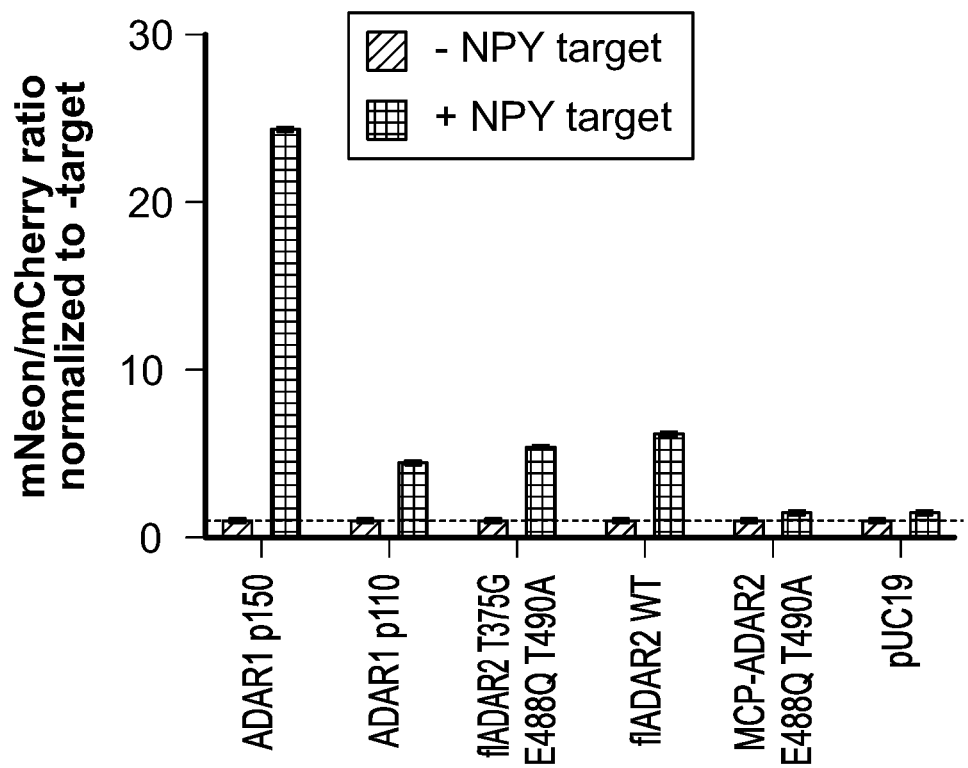
Figure 11F:
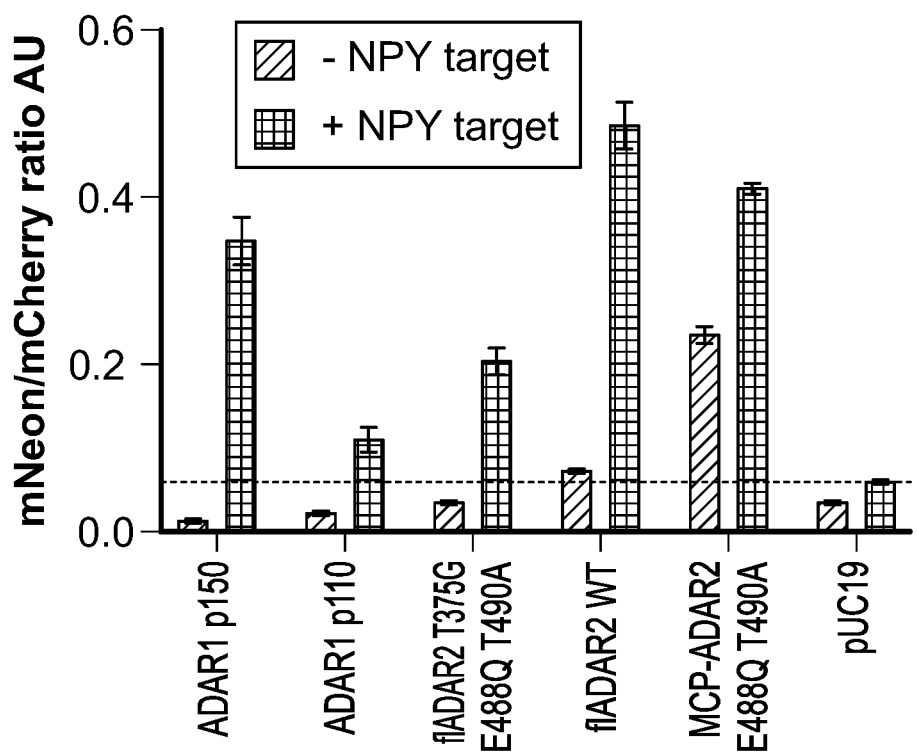
Figure 11G:
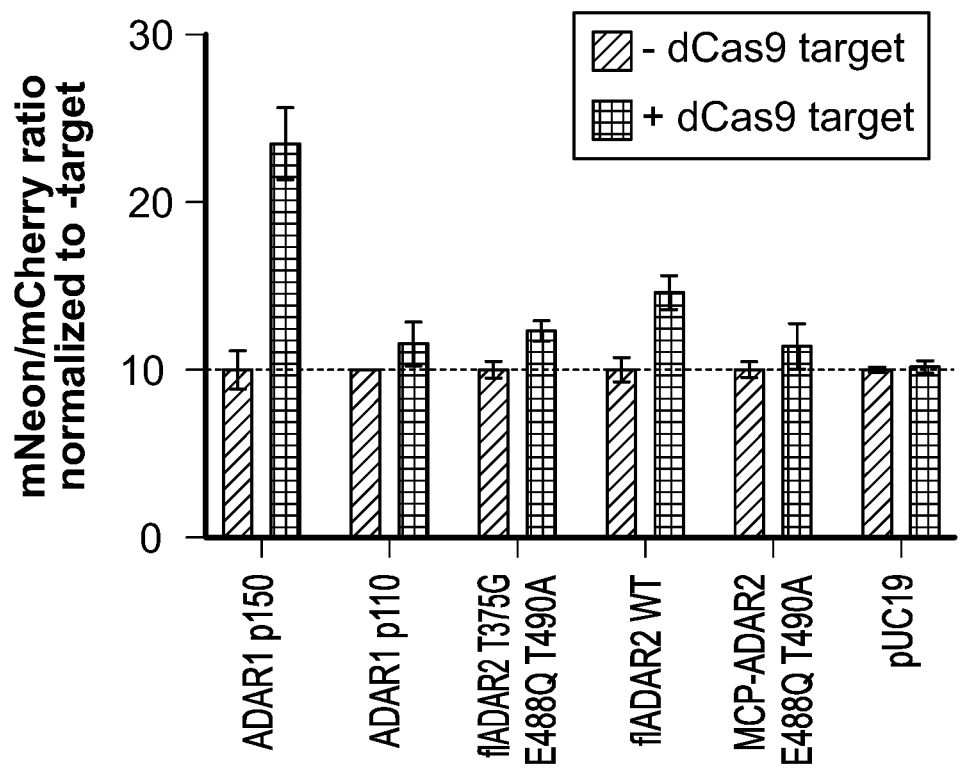
Figure 11H:
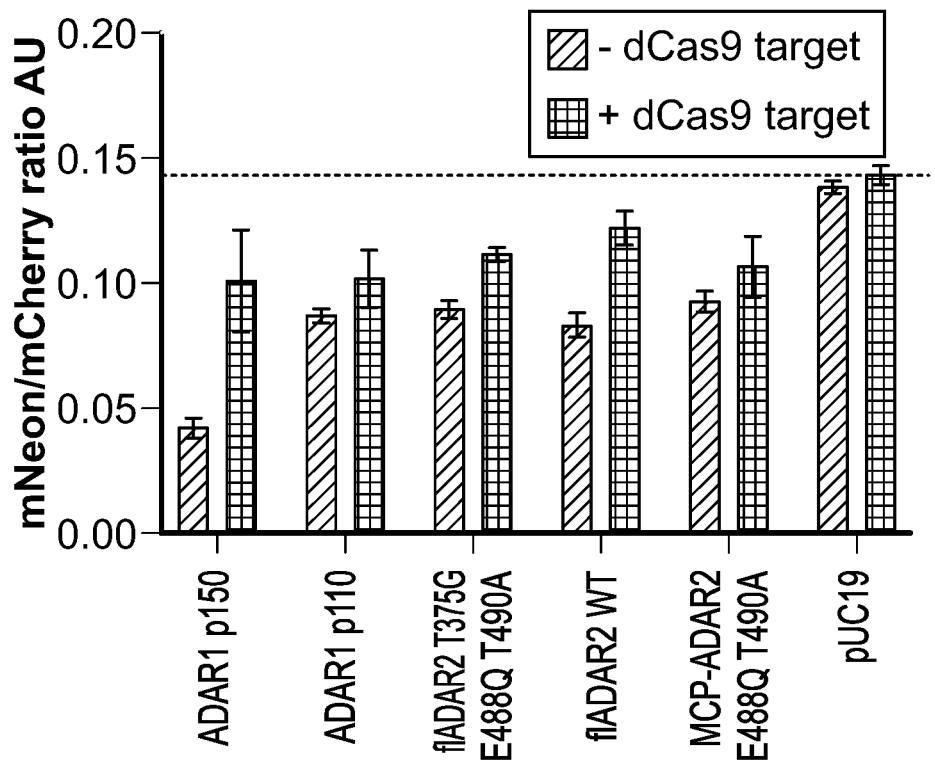
Figure 12A:
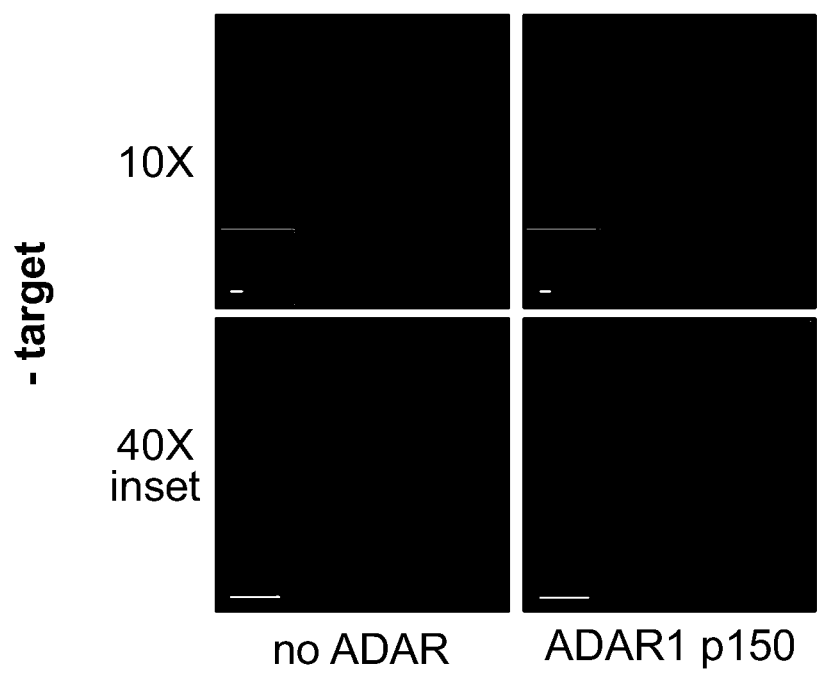
FIG. 12A are representative images of the full 10× images with insets for the ADAR p150 images shown in FIG. 10B either without target or with target (FIG. 12B). Scale bars are 100 μm.
Figure 12B:
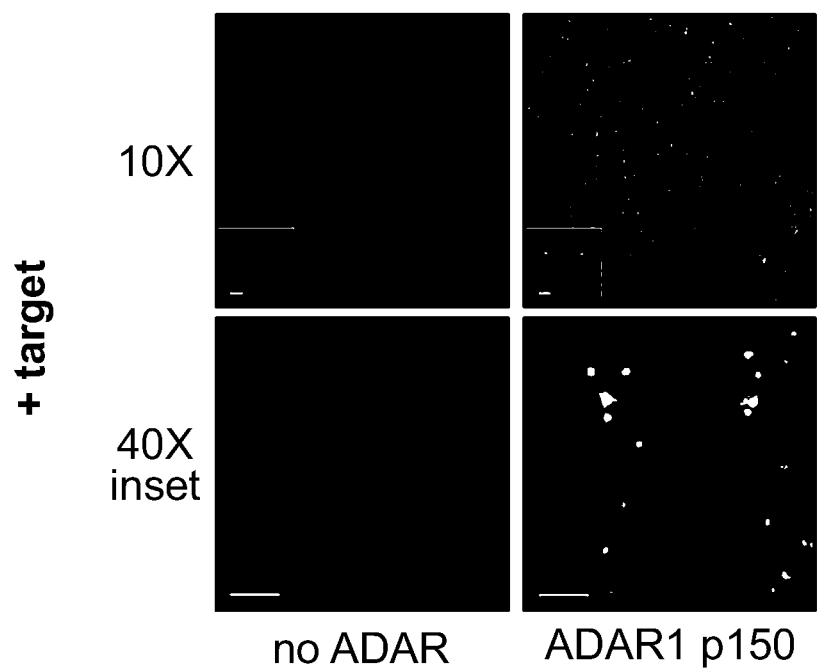

As guide choice could affect overall sensitivity of the sensor, we screened top ADAR candidates on multiple guide sequences and targets in an orthogonal panel (FIG. 10). First, we observed activation above background only in the correctly matched ADAR sensors and target transcripts (FIG. 9). ADAR1 p150 had highest fold activation on 3 of the 4 targets, driven by a generally low overall background signal in the absence of target, w % bile MCP-ADAR2dd (E488Q, T490A) performed best on the EGFP target due to its generally high level of absolute signal, but suffered from higher background on the other targets that reduced its overall activation (FIG. 6, FIG. 10. FIG. 11, FIG. 12).

Figure 13A:
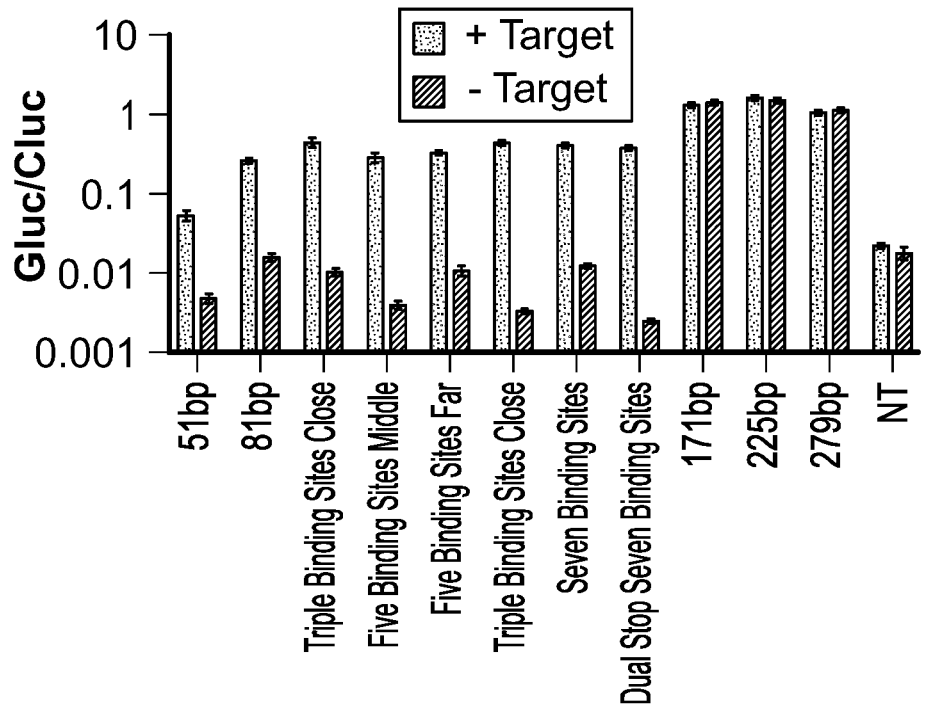
FIG. 13A is a graphical comparison of normalized luciferase values of panel of sensors in the + target group and − target group for MCP-ADAR2dd exogenous supplementation, FIG. 13B ADAR1 p150 isoform exogenous supplementation, FIG. 13C ADAR2 exogenous supplementation, and FIG. 13D no exogenous ADAR supplementation.
Figure 13B:
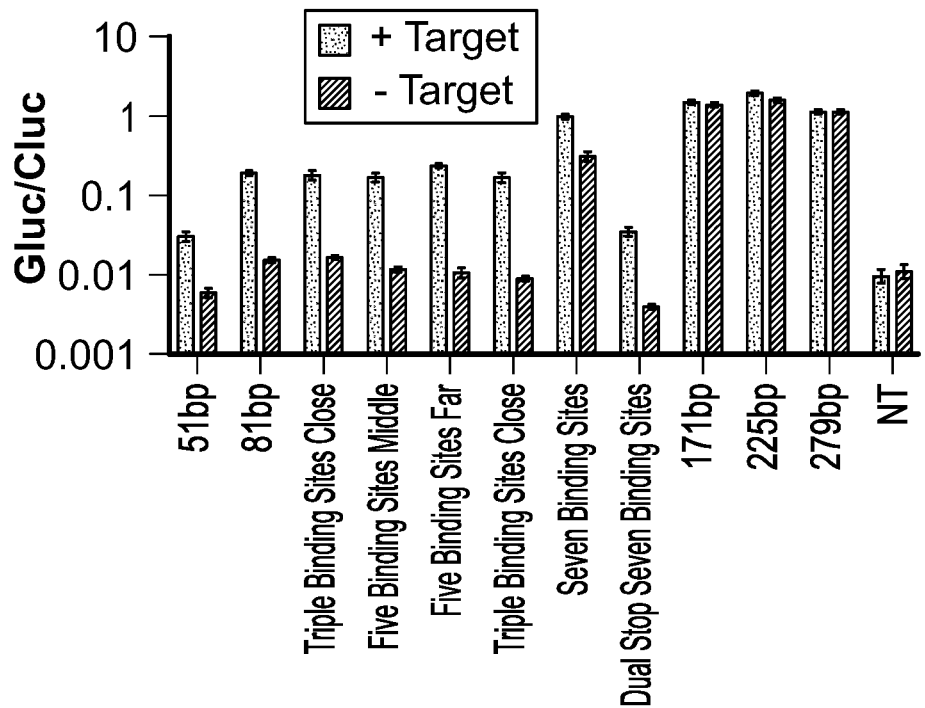
Figure 13C:
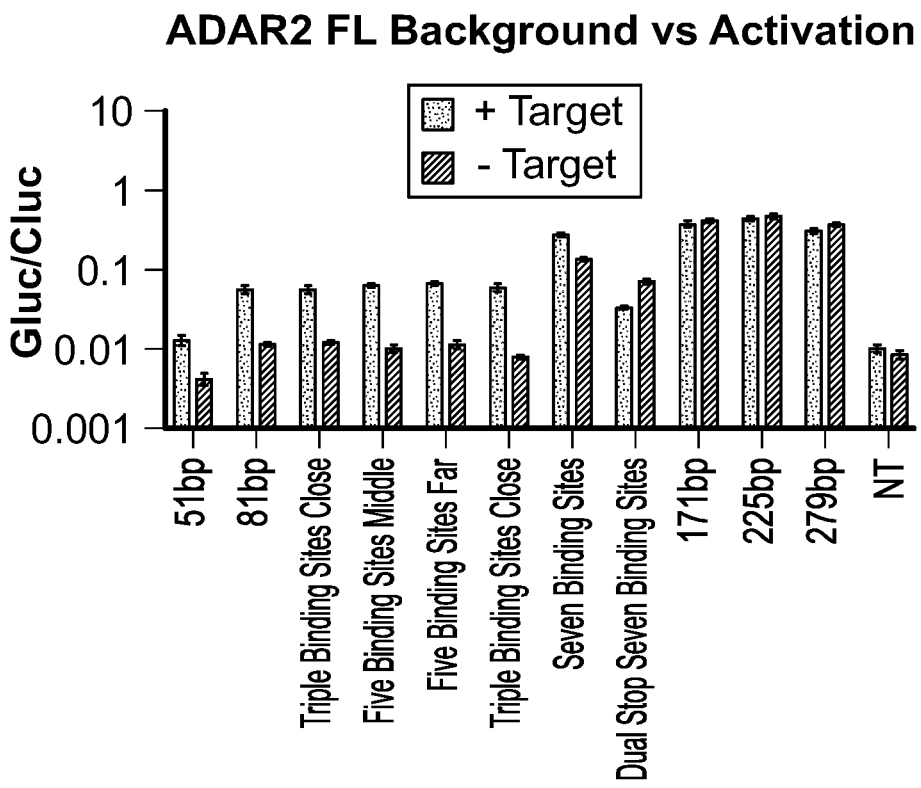
Figure 13D:
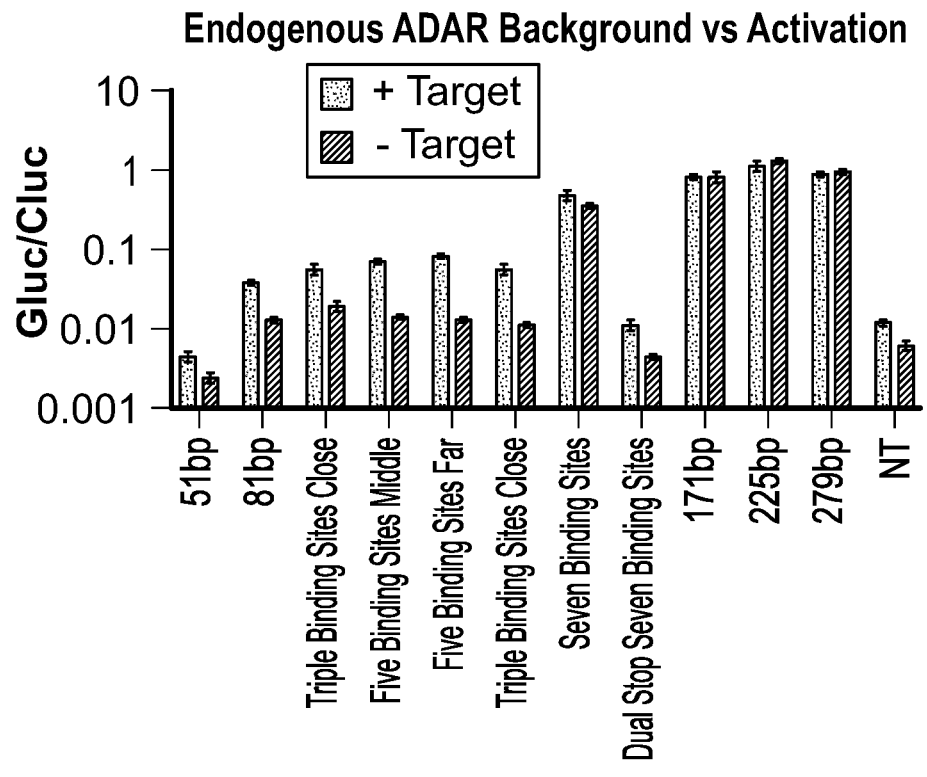

Analysis of the background vs activation of the panel of sensors was also performed for (FIG. 13A) MCP-ADAR2dd exogenous supplementation, (FIG. 13B) ADAR1 p150 isoform exogenous supplementation, (FIG. 13C) ADAR2 exogenous supplementation, and (FIG. 13D) no exogenous ADAR supplementation with various sensors.

Figure 14:
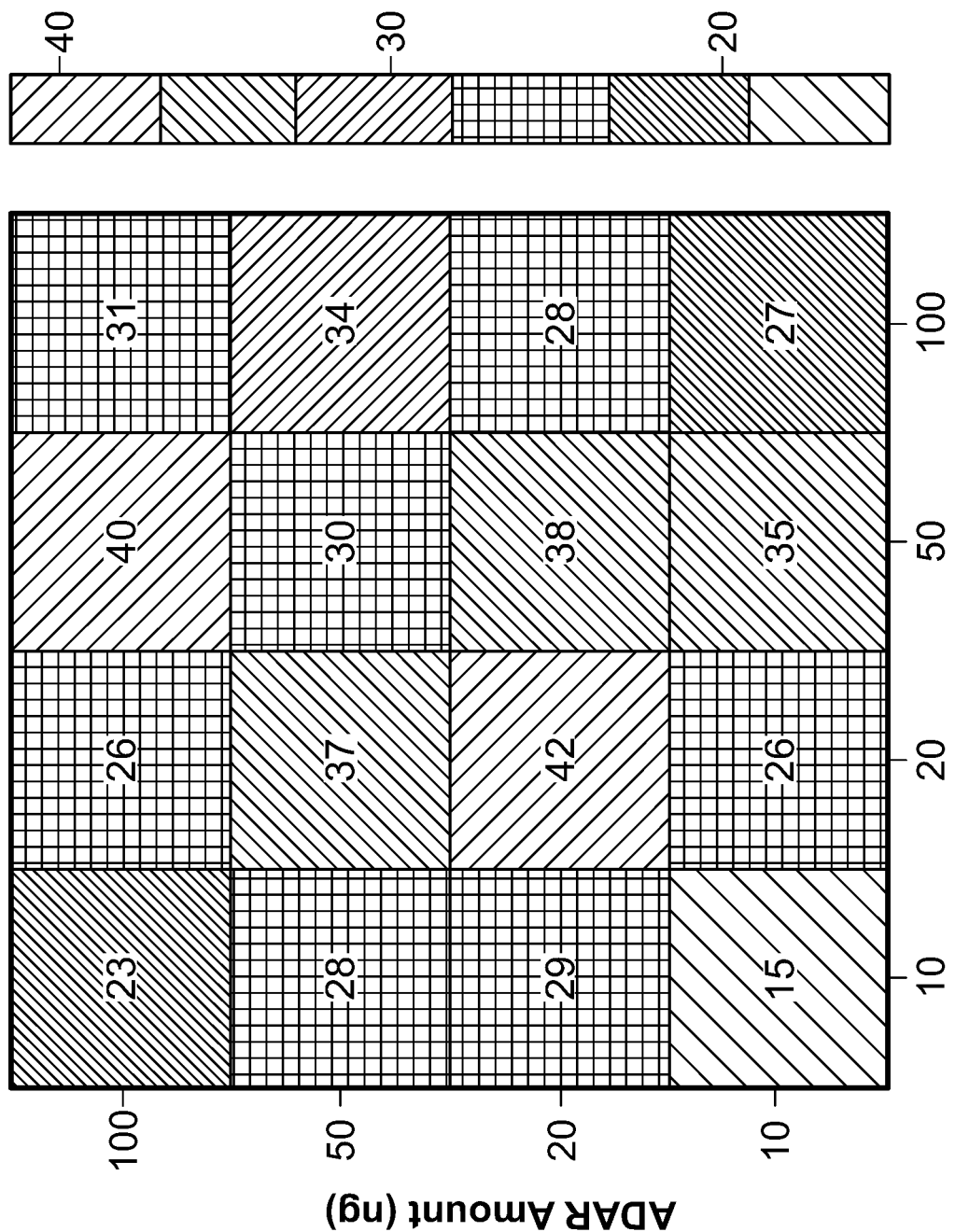
FIG. 14 is a heatmap of titration of exogenous supplemented MCP-ADAR2dd versus IL6 targeting sensor against 20 ng of transfected tetracycline inducible human IL6 transgene in IL6. Fold change denotes normalized luciferase ratio between the + target group and the − target group.

Optimal exogenous ADAR amount was also examined (FIG. 14). In a titration experiment, HEK293 cells were transfected with varying amounts of MCP-ADAR2dd from long to 100 ng as well as varying amounts of 3 site binding avidity IL6 sensor strand from 10 ng to 100 ng in a tetracycline inducible IL6 experiment, where the target's (IL6) amount is fixed at 20 ng. Fold change denotes normalized luciferase ratio between the + target group and the − target group.

Example 5. Use of the RNA Editing for Programmable A to I (G) Replacement (REPAIR) System for Biological Sensors Next, the feasibility of RNA editing for programmable A to I (G) replacement (REPAIR) system was evaluated pertaining to whether it could be harnessed as a mechanism for triggering these genetic sensors. The REPAIR system is made up of a fusion of catalytically active Cas13b enzyme fused to the deaminase domain of an ADAR2 molecule. A catalytically inactive Cas13b enzyme, which incorporates a K370A mutation, is also fused to deaminase domain of an ADAR2 molecule to form a fusion protein without the Cas13b activity (REPAIR K370A).

Figure 15:
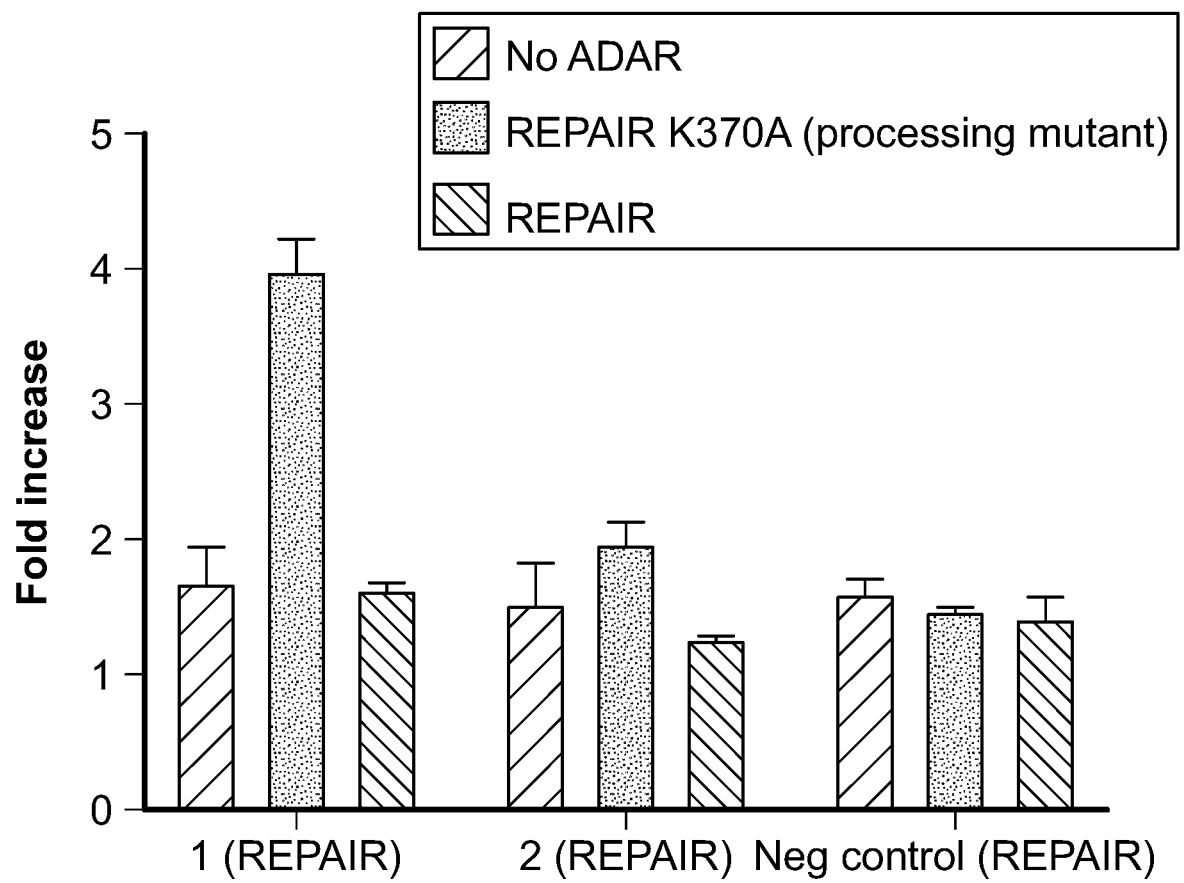
FIG. 15 is a graphic illustration of the fold increase in luciferase expression for guide strands 1 and 2, targeted to EGFP, compared to a scrambled guide strand designed not to specifically target EGFP. Each guide strand was introduced into a HEK293T cell. Cells were then tested using a Cas13b enzyme fused to the deaminase domain of ADAR2

Two guide strands designed to target EGFP, as well as a negative control designed to not target EGFP, were introduced into HEK293FT cells without the addition of any exogenous ADAR molecules (FIG. 15, blue bars). The guide strands were also introduced into HEK293FT cells simultaneously with a REPAIR molecule (FIG. 15, red bars), or with a catalytically inactive REPAIR K370A molecule (FIG. 15, white bars). Guides 1 and 2, designed to be targets for Cas13b, showed no increase in luciferase expression in cells compared to cells relying solely on endogenous ADAR expression. However, when the Cas13 activity is turned off (REPAIR K370A), guide 1 showed a 4-fold increase in luciferase expression when compared to cells relying solely on endogenous ADAR expression. This increase in expression underscores the potential for the REPAIR system to be used in conjunction with the genetic sensors of this this disclosure.

Figure 16:
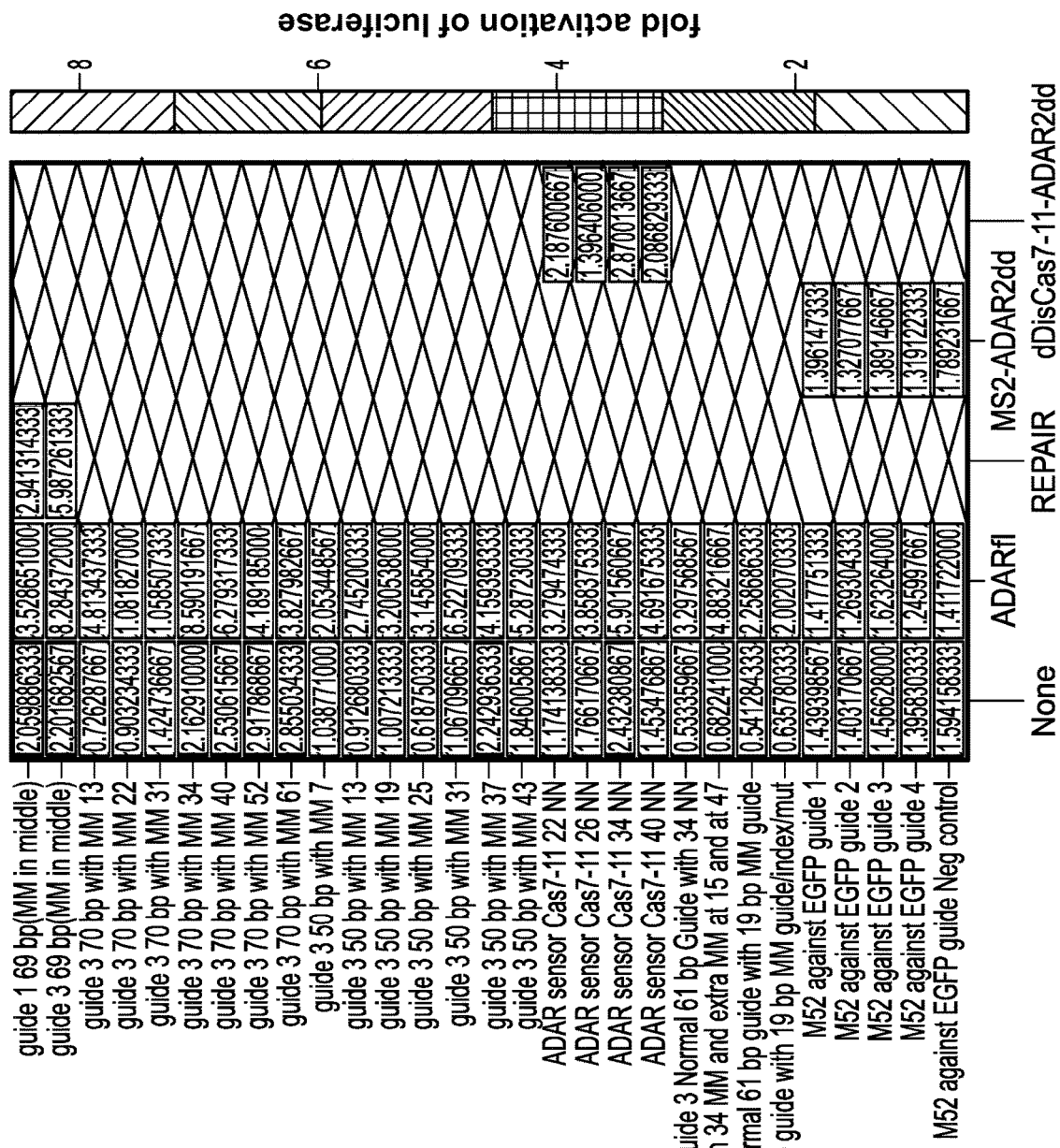
FIG. 16 is a heatmap displaying the fold increase in luciferase activation (white, lowest fold increase, to dark blue, highest fold increase) when tested in HEK293FT cells. The y-axis displays guide strands with multiple different designs of different lengths and mismatches targeting EGFP. The x-axis displays the exogenous ADAR molecule tested (None=endogenous only; ADAR2fl=ADAR2 full length, REPAIR=Cas13b enzyme fused to the deaminase domain of ADAR2; MS2-ADAR2dd=MS2 binding protein fused to ADAR2dd; dDisCas7-11-ADAR2dd=catalytically inactive Cas7-11 fused to the deaminase domain of ADAR2.

Example 6. Examination of Varying Guide Strand Characteristics for Increased Luciferase Expression Next, the characteristics of the guide strand design were varied to determine which variables could be adjusted to increase efficiency and expression of the genetic sensor. FIG. 16 displays a heatmap indicating fold luciferase expression for varying guide/ADAR combinations. Exogenously introduced full length ADAR (column 2) consistently exhibited the highest fold increase of luciferase expression. However, this was not the case for guide strands designed as an MS2 agonist, which exhibited largely consistent expression regardless of ADAR introduced.

Figure 18A:
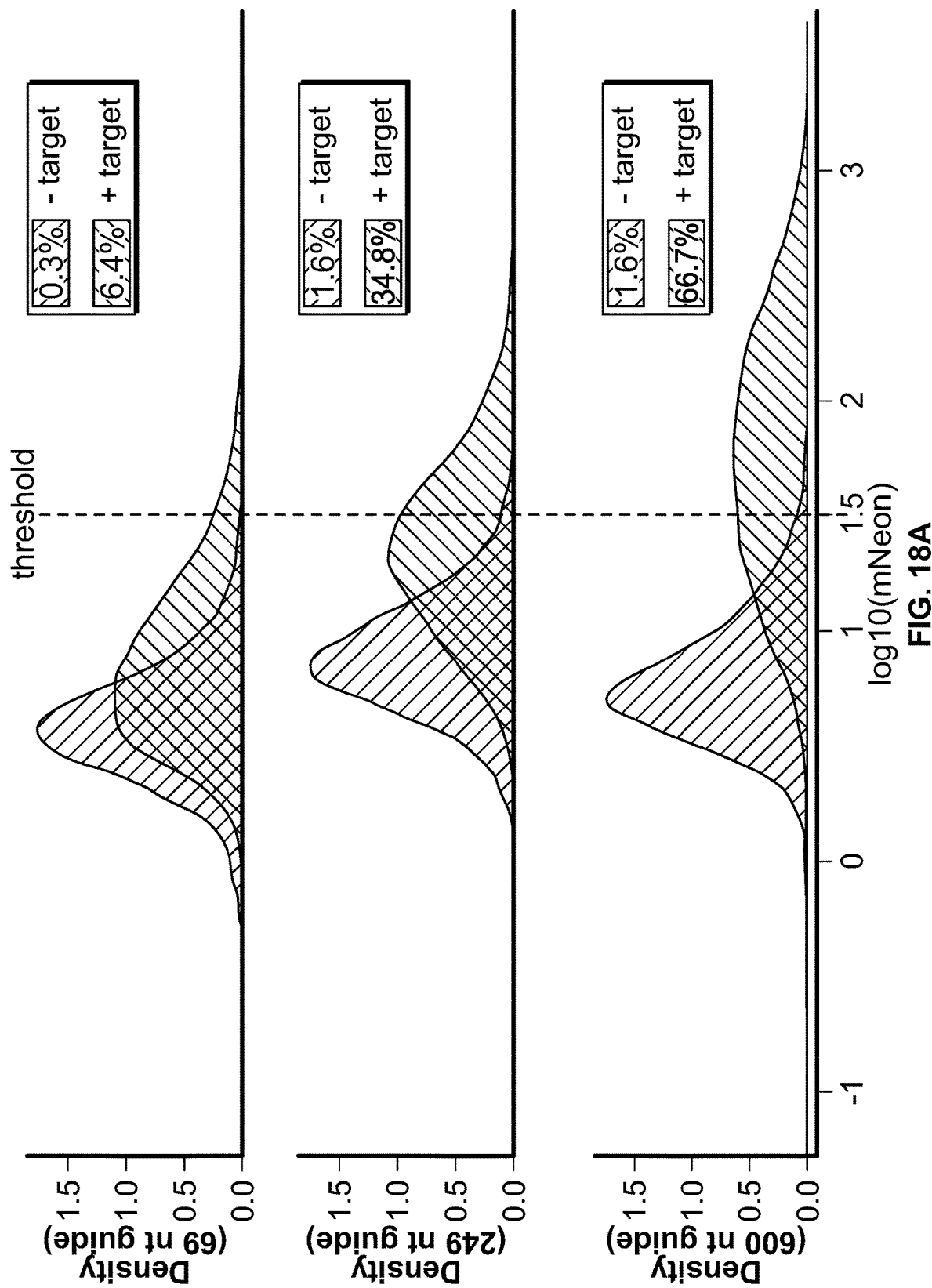
FIG. 18A Single-cell image analysis analogous to fluorescence cytometry for iRFP targeting ADAR SENSOR of guide lengths 69, 249, and 600 nt. Histograms show population density of mNeon expression across all cells for +iRFP (blue) and −iRFP (pink) target conditions. The dotted line shows a constant intensity threshold across all conditions gating individual cells as mNeon(+) or mNeon(−). Colored boxes show % mNeon positive cells for +iRFP (blue) and −iRFP (pink) target conditions.
Figure 18B:
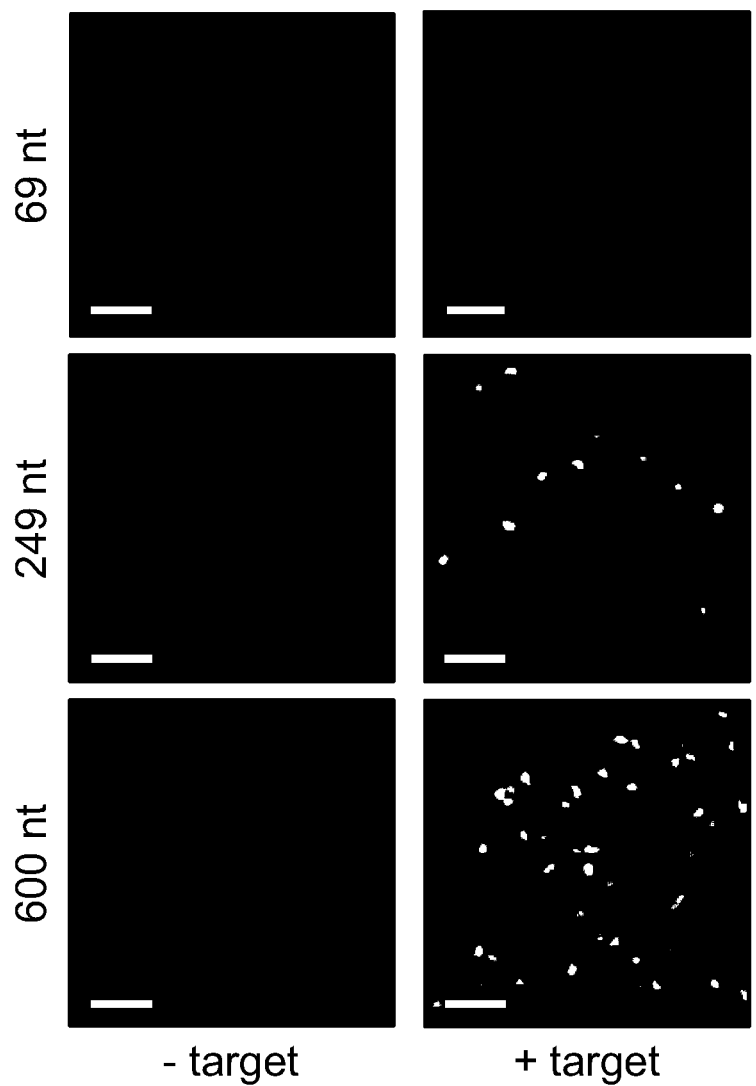
FIG. 18B Representative images are shown for (A). Cells were transfected with the iRFP target, ADAR p150, and different ADAR SENSOR guide lengths in the combinations listed around the images. Scale bars, 100 microns.
Figure 19A:
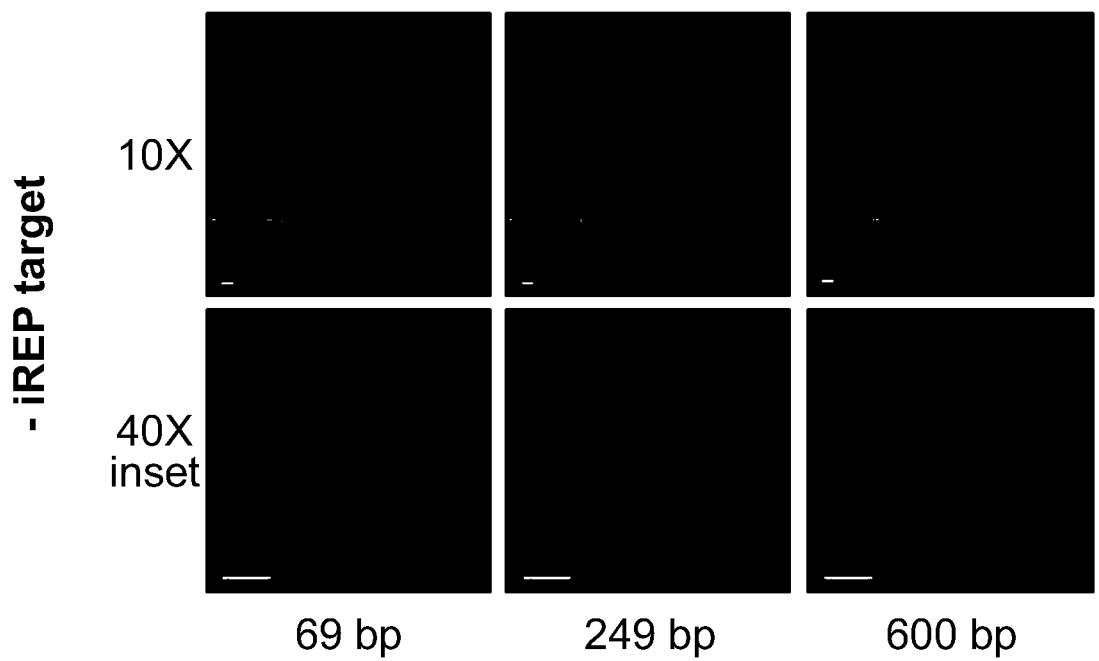
FIG. 19A, FIG. 19B are representative images of the full lox images with insets for images shown in FIG. 18B. Scale bars are 100 μm.
Figure 19B:
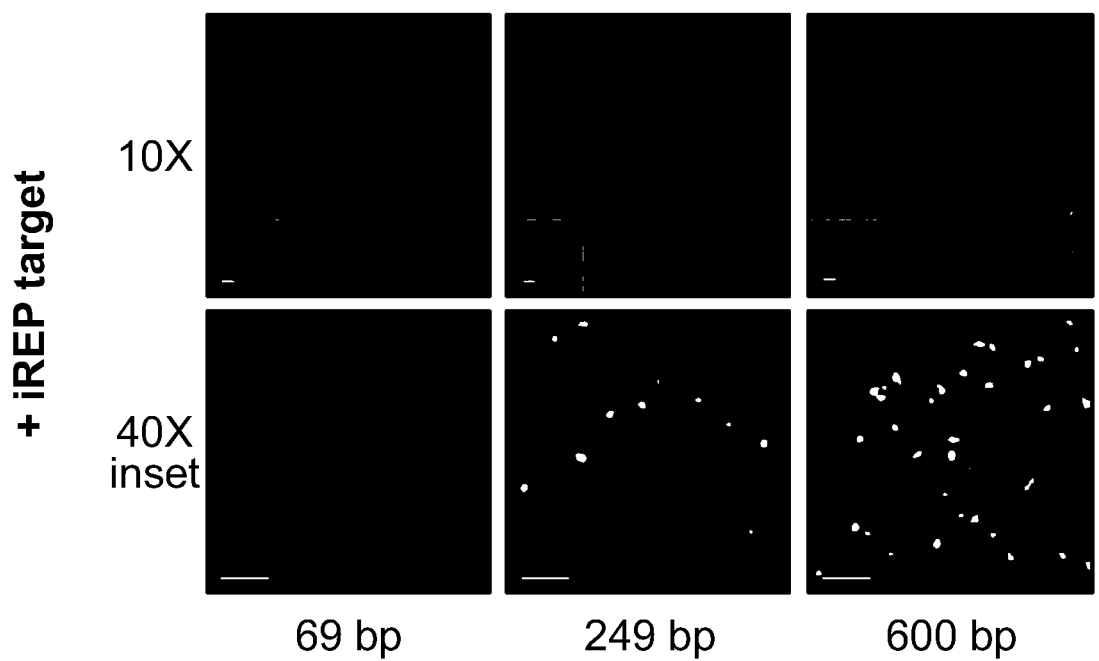

Electing lower background levels from Example 4, we began to further optimize the sensor with the ADAR1 p150 construct. To improve both binding stability and target search time, increasing guide lengths centered around a premature stop codon (Qu et al. 2019) were tested against a constitutive iRFP target. Sensor activation improved from 2.2-fold to 18.22-fold as guide length increased from 51 nt to 600 nt (FIG. 17B). Additionally, a marked shift was observed in the distribution of mNeon expression levels per cell for all guide lengths when target is present (FIG. 17C, FIG. 18A), with a more substantial mNeon(+) population at longer guide lengths. Meanwhile, the percent mNeon(+) cells in the absence of target consistently remained <5% for all guide lengths. At guide lengths of 600 nt, 66.7% mNeon (+) cells in the presence of target, and 1.6% in the absence of target, were observed, suggesting a robust capability to separate cellular populations based on target mRNA expression.

The two best performing ADARS from Example 4, ADAR1 p150 and MCP-ADAR2dd(E488Q,T490A), achieved optimal signal through either reducing background or increasing activation. Because MCP-ADAR2dd(E488Q, T490A) had the highest activation with a luciferase sensor (FIG. 20) when engineering the ADAR enzyme, we hypothesized that guide engineering strategies to lower background, when coupled with MCP-ADAR2dd (E488Q, T490A), would result in the most optimal sensor activation.

Figure 20:
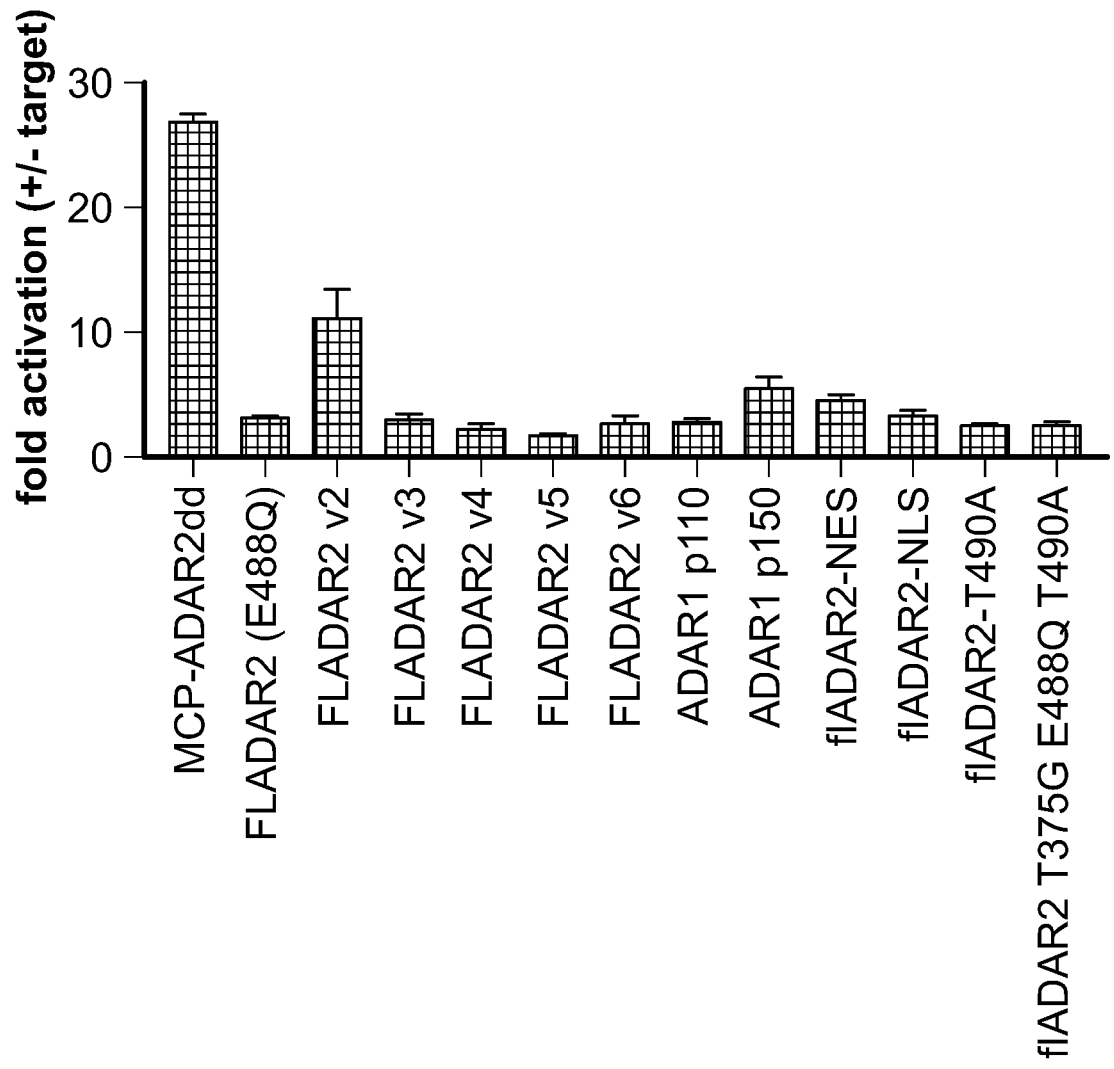
FIG. 20 is a graphical comparison of different exogenous supplemented ADAR variants on IL6 targeting sensors with transiently transfected tetracycline inducible human IL6 transgene.

A new sensor targeting IL6 mRNA was designed, a virtually unexpressed transcript in HEK293FT cells (Uhlén et al. 2015), enabling both supplementation of IL6 mRNA via exogenous transfection and generation of integrated lines with IL6 mRNA under the control of a dox-inducible promoter to modulate low levels of IL6 expression for sensitivity testing (See FIG. 20).

Figure 21A:
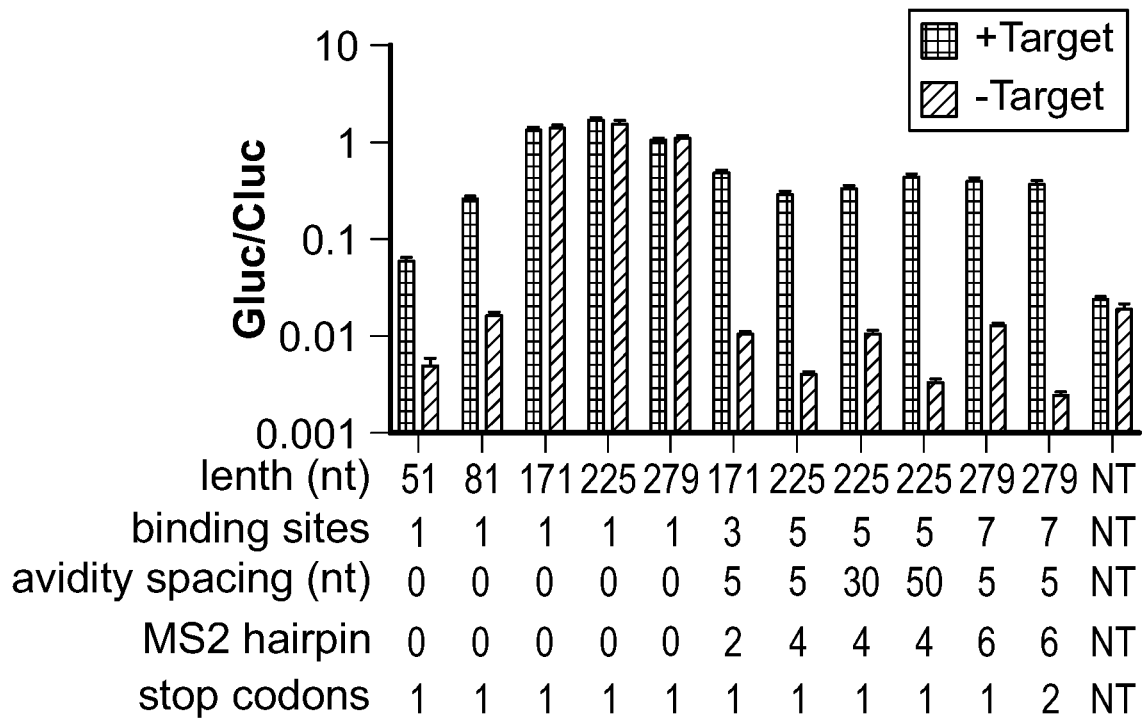
FIG. 21A, FIG. 21B, FIG. 21C, FIG. 21D are a series of graphical illustrations displaying normalized luciferase values of panel of sensors in the + target group and − target group for FIG. 21A MCP-ADAR2dd (E488Q, T490A) exogenous supplementation, FIG. 21B ADAR1 p150 isoform exogenous supplementation, FIG. 21C ADAR2 exogenous supplementation, and FIG. 21D no exogenous ADAR supplementation.
Figure 21B:
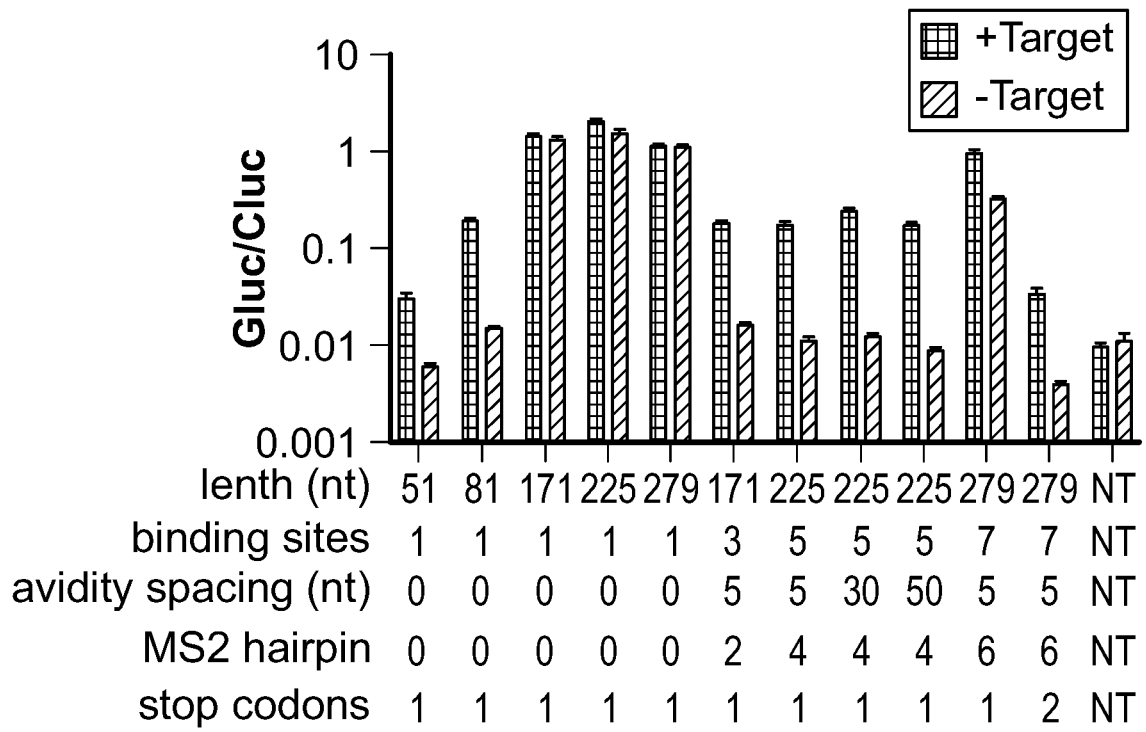
Figure 21C:
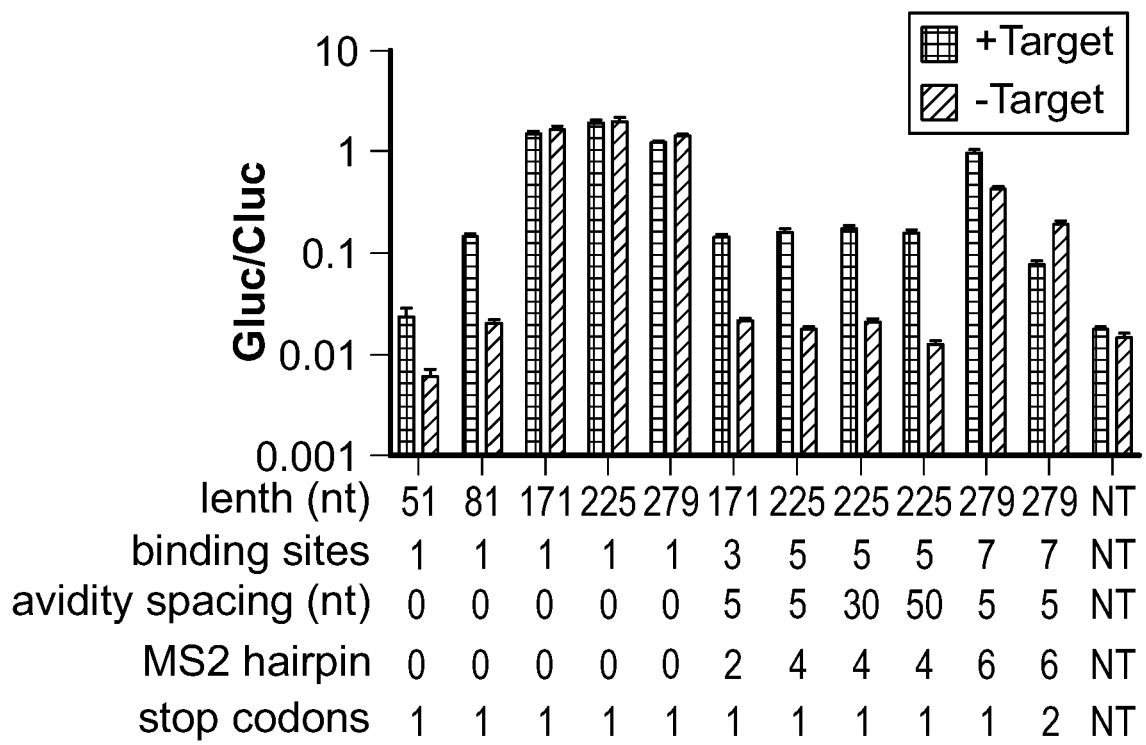
Figure 21D:
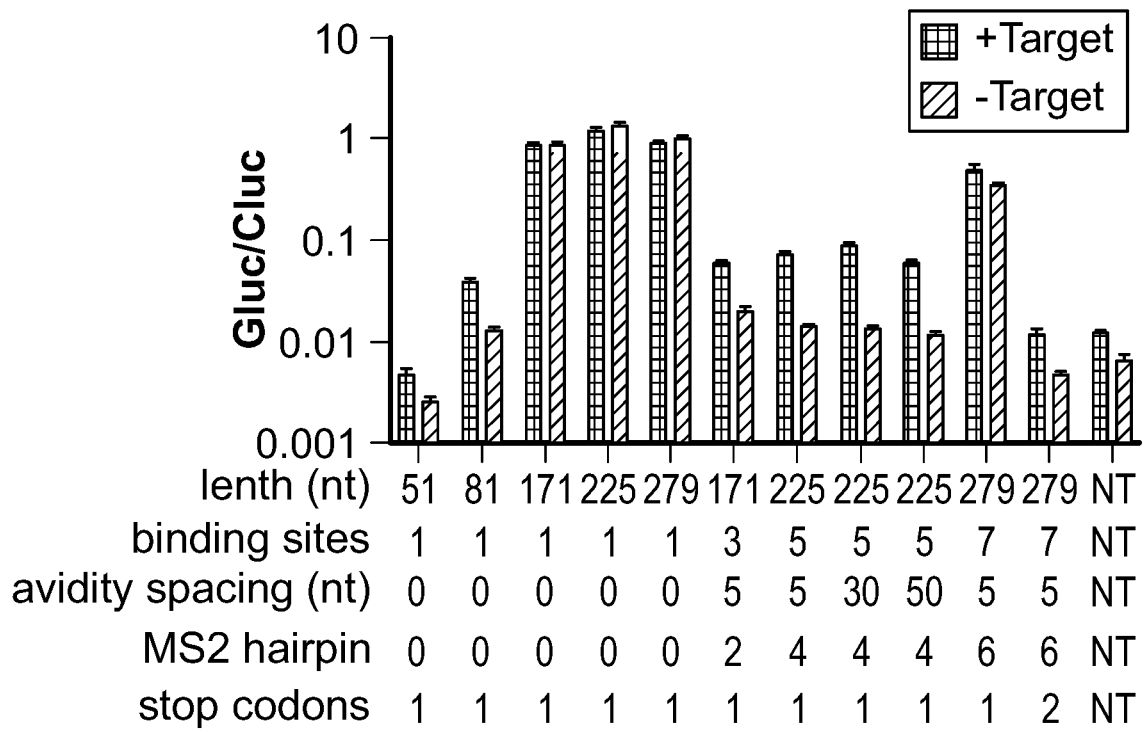
Figure 22:
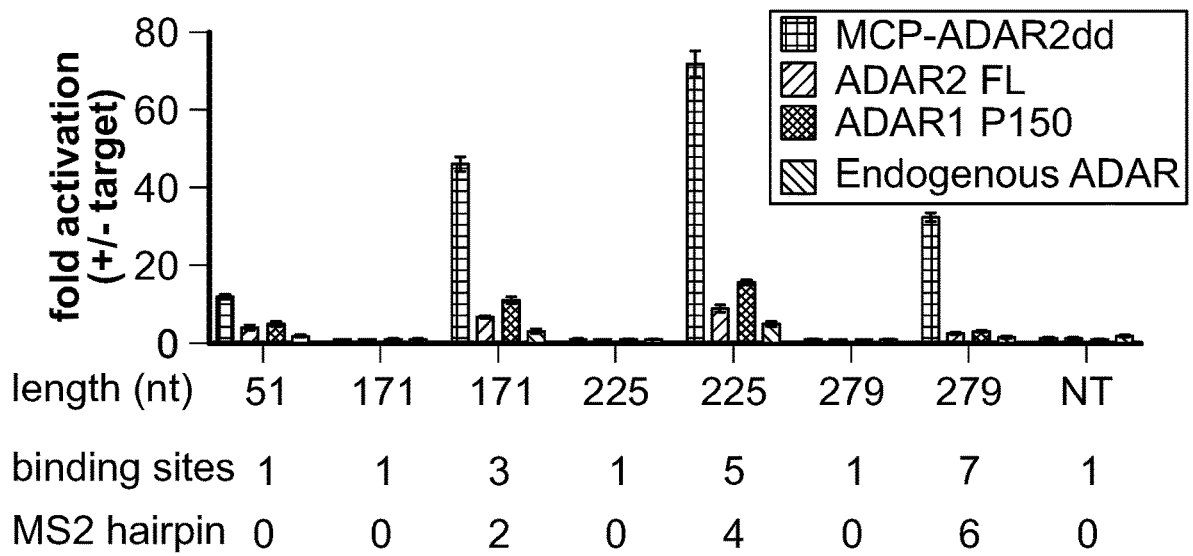
FIG. 22 is a graphical illustration of a comparison between sensors containing normal guides and guides containing multiple binding sites and MS2 hairpin loops against the human IL6 target with endogenous ADAR1 in HEK293 cells, exogenous supplemented ADAR1 p150 isoform, full length ADAR2, or MCP-ADAR2dd(E488Q, T490A). Fold change is calculated by the normalized luciferase values (Gluc/Cluc) of the + target condition over − target condition.
Figure 23:
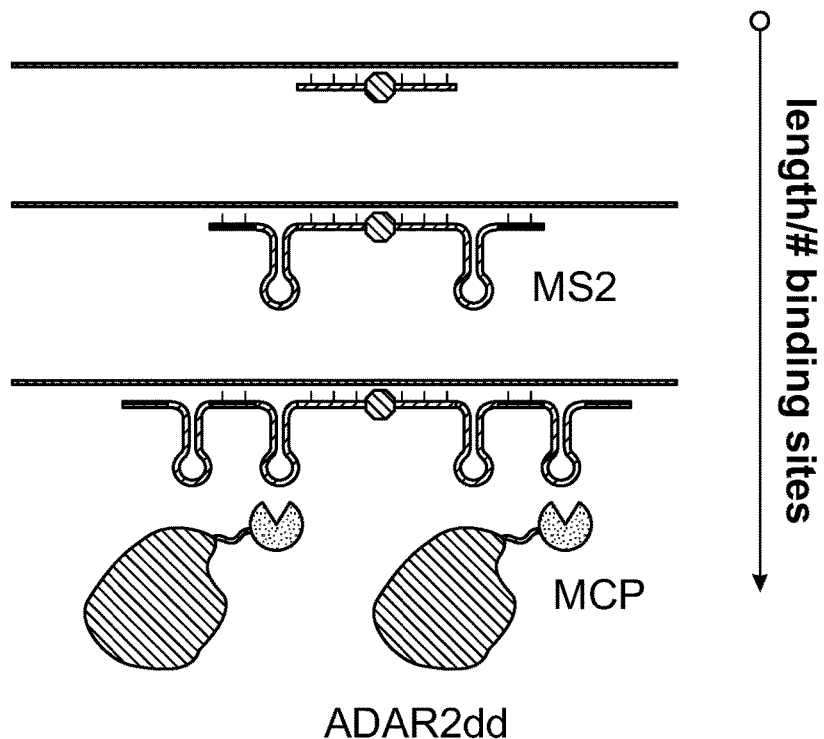
FIG. 23 is a visual representation of the engineering of ADAR sensors with MS2 hairpin loops and avidity regions. The addition of MS2 hairpin loops and avidity enhance sensitivity and dynamic range of ADAR sensors.

Due to an increase in background signal in the absence of target, potentially due to readthrough of the stop codon within longer guide regions (FIG. 21(A) MCP-ADAR2dd (E488Q, T490A) exogenous supplementation, (B) ADAR1 p150 isoform exogenous supplementation, (C) ADAR2 exogenous supplementation, and (D) no exogenous ADAR supplementation), we engineered the guide region to block aberrant translation by introduction of MS2 hairpin loops (Chao et al. 2008), which provides the added benefit of recruiting the MCP-ADAR2dd(E488Q, T490A) protein to the guide:target duplex (FIG. 23). We repeated our investigation of increased guide regions with the luciferase sensors targeting an IL6 transcript and found a significant reduction in the fold-change of ADAR sensor activation past 81 nt guides using the MCP-ADAR2dd(E488Q, T490A) construct (FIG. 22) when only one binding site is present on the guide strand. However, structural additions and modifications to the guide strand design implemented to determine if the addition of MS2 hairpin loops and additional engineered guide binding regions (termed "avidity binding regions") on the sensor/guide strand enhanced sensitivity exhibited a significant increase in ADAR sensor activation (FIG. 22). FIG. 22 displays the results of an experiment to determine the fold change for guide/sensor strands of differing formats. HEK293 cells were transfected (Lipofectamine 3000, Thermo Fisher Scientific) with a sensor comprising the naïve reverse complement (of the IL6 target) and MS2 hairpins with additional avidity regions (x-axis; a 51 bp sensor, a sensor with a consecutive 171 bp binding region, a sensor with the 171 bp avidity region separated by two MS2 hairpins, a sensor with a single consecutive 225 bp binding region, a sensor with a 225 bp binding region separated by four MS2 hairpins, a sensor with a consecutive 279 bp binding region, a sensor with the 279 bp binding region separated by six MS2 hairpins, and a non-target sensor). Separation of the binding regions by MS2 hairpins increased the expression of the target significantly in all varied avidity region lengths. Several types of ADAR proteins were tested, including a full-length ADAR 2 (ADAR2 FL), the p150 isoform of ADAR1, endogenous ADAR1, and a fusion protein of an MS2 coat binding protein fused to the deaminase domain of human ADAR2. Fold change (y-axis) of expression is calculated by the raw luciferase values of the + target condition over − target condition.

Figure 27A:
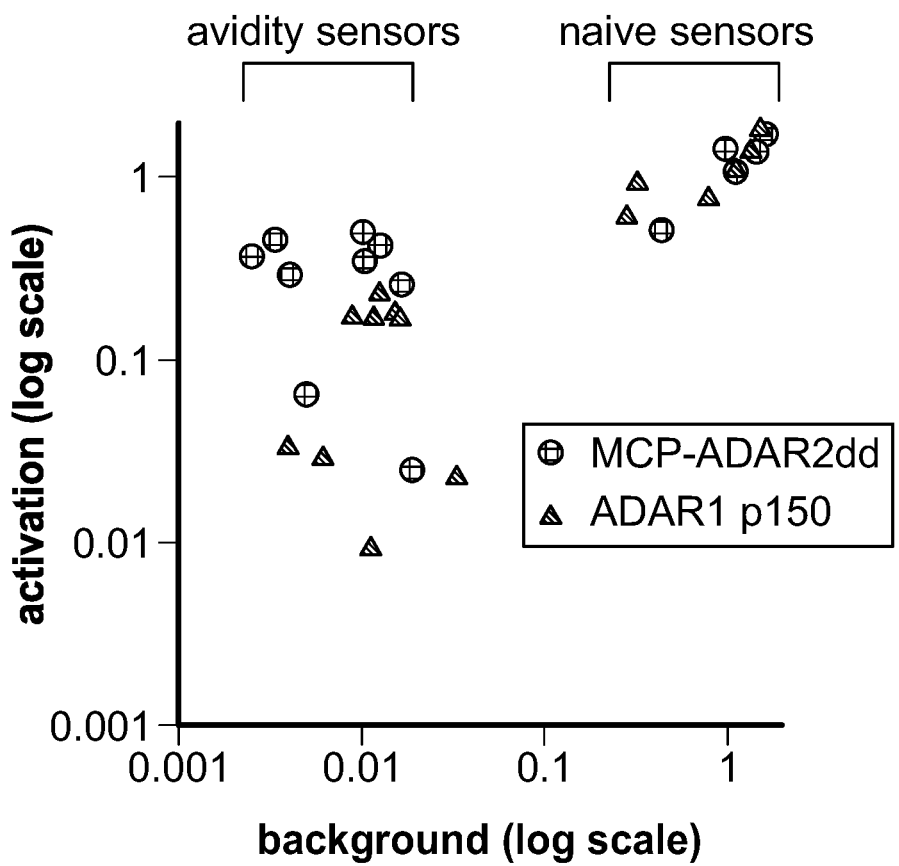
FIG. 27A is a comparison of background versus activation for avidity sensors against naïve ("long") sensors.
Figure 27B:
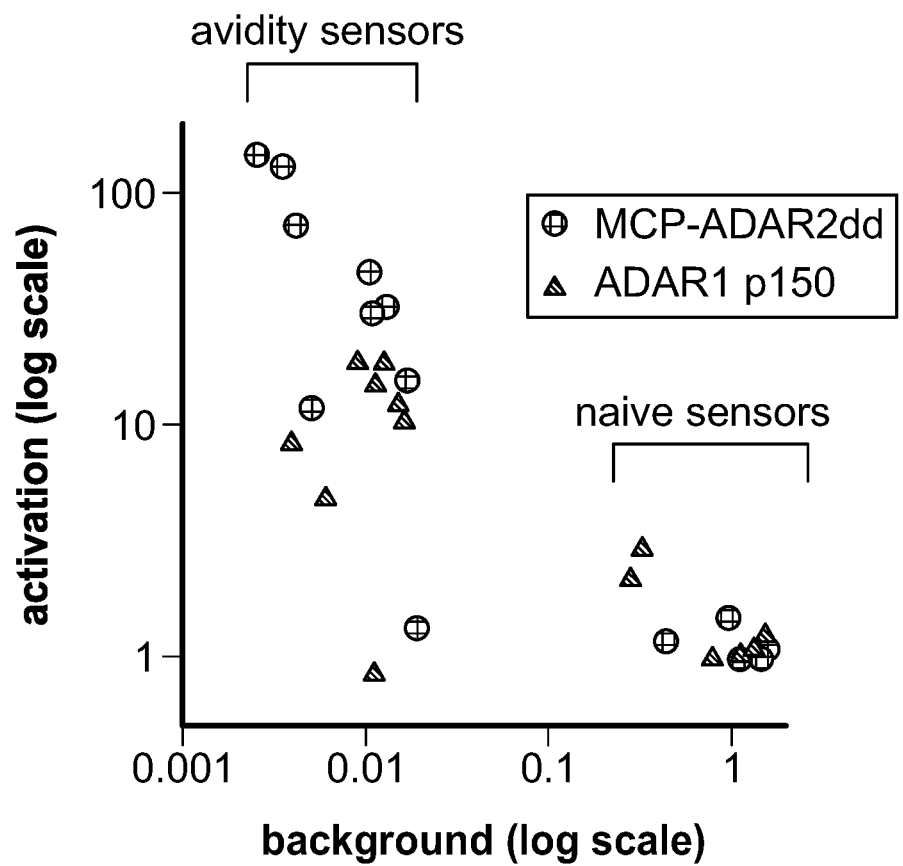
FIG. 27B is a scatter plot of fold change versus background luciferase values for avidity sensors versus naive ("long") sensors.

ADAR sensor activation was highest with 5 site avidity binding guides, achieving ~70-fold activation and substantially lower background than the uninterrupted guide designs (FIG. 27). Avidity binding guides improved performance for all exogenous ADAR constructs, but showed maximal performance increases with MCP-ADAR2dd supplementation. Avidity binding guides with 5 or 7 binding sites could produce detectable activation relying only on endogenous ADAR. FIG. 23 displays several formats of possible MS2 hairpin/avidity modifications, and FIG. 24 provides a design guide for avidity sensors and an easy to use software program to automatically generate avidity sensors for input target sequences (github.com/abugoot-lab/ADAR SENSOR).

Figure 52:
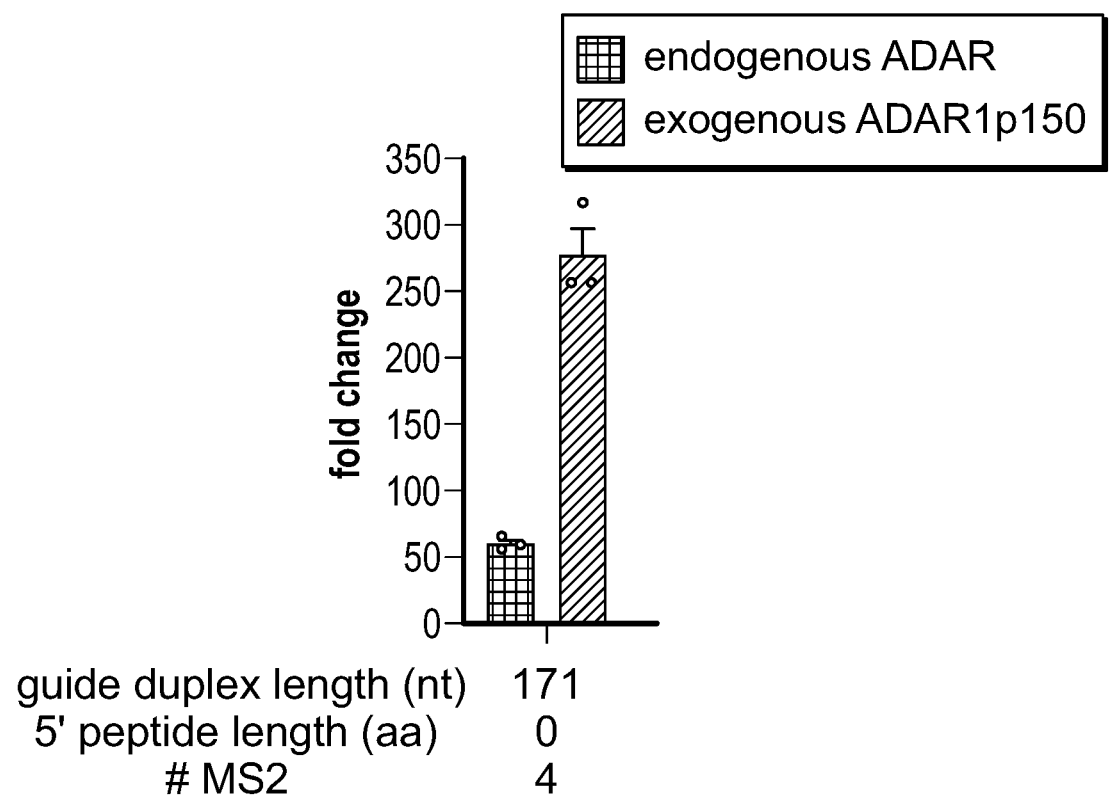
FIG. 52 is a graphical comparison of fold activation of #CCA8 IL6 engineered guide RNA with 171 nt guide and 4 MS2 loops when used in conjunction with exogenous supplemented ADAR1p150 or with endogenous ADAR. Data are mean of technical replicates (n=3)±s.e.m.

891. We tested whether the best performing IL6-targeting engineered guide RNA could utilize endogenous ADAR to sense a synthetic IL6 target transfected into cells. We observed more than 50 fold activation of the payload with endogenous ADAR, although exogenous ADAR1p150 supplementation improved the performance of RADARSv2 (FIG. 52).

Figure 25A:
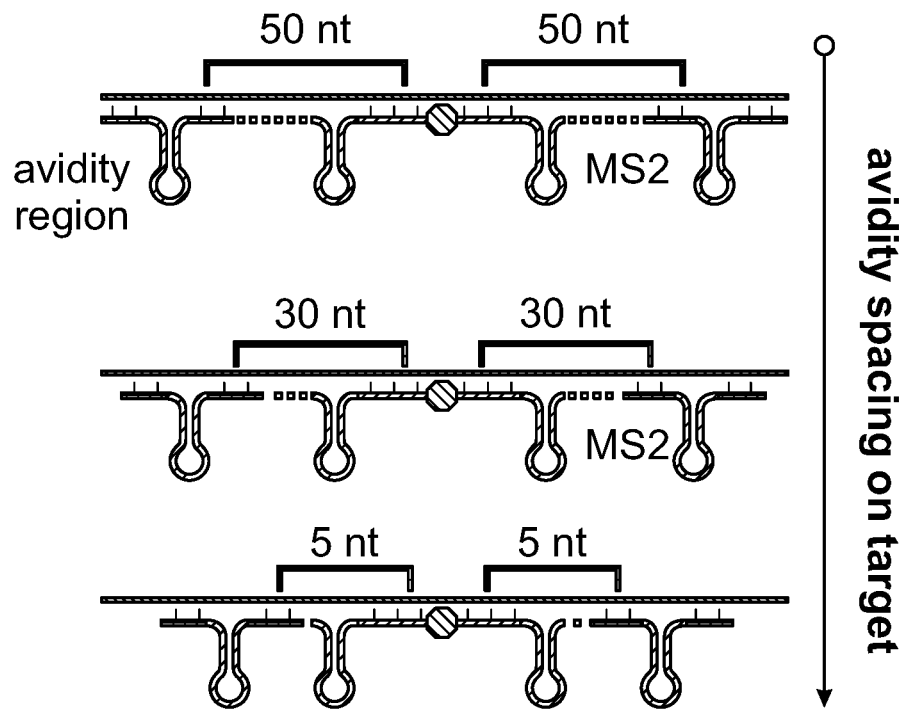
FIG. 25A is a schematic of varying linker lengths outside of the target region.
Figure 25B:
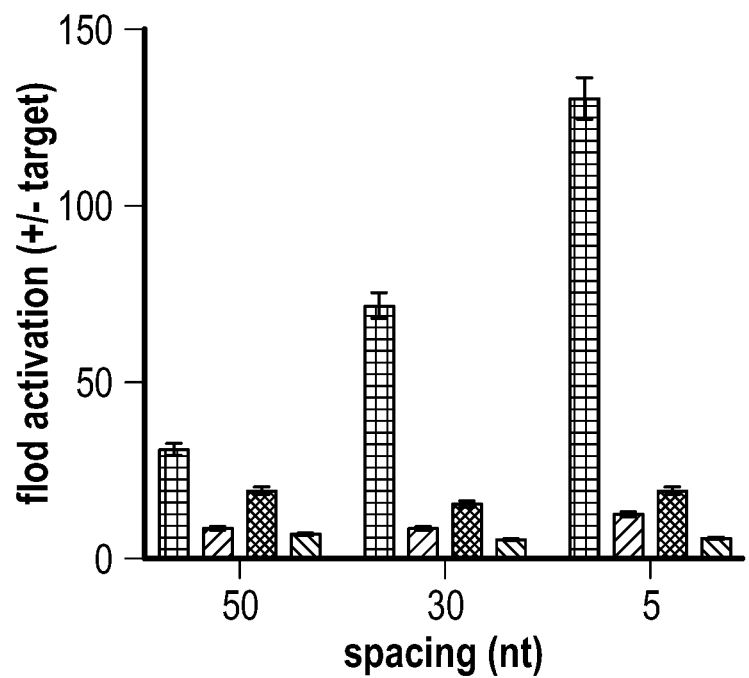
FIG. 25B is a graphical representation of the effect of linker length between the avidity regions. Linker lengths of 5 nt, 30 nt and 50 nt between the avidity region of a MS2 hairpin connected-5 avidity sensor against IL6 were tested.

To further explore the avidity binding guide concept, we varied the spacing between the binding sites (5, 30 and 50 nt). The length between the binding sites represents the number of nucleotides on the guide strand starting from immediately prior to the MS2 hairpin until another region of complementarity. Binding sites closer together on the target transcripts resulted in the highest activation (FIG. 25).

Figure 26A:
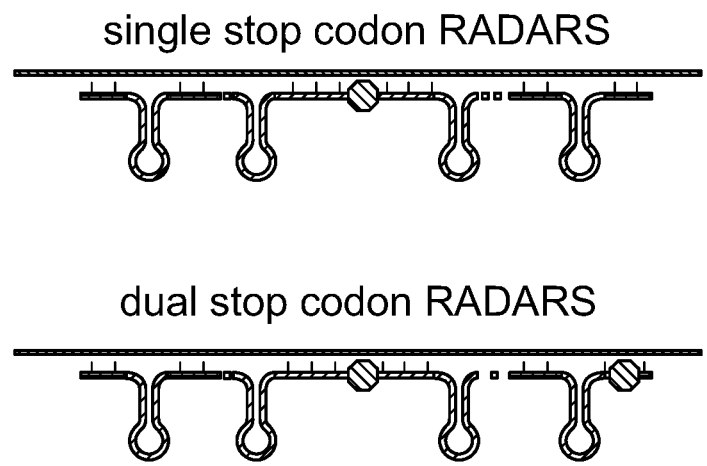
FIG. 26A is a schematic of dual and single stop codon avidity/MS2 hairpin sensors.
Figure 26B:
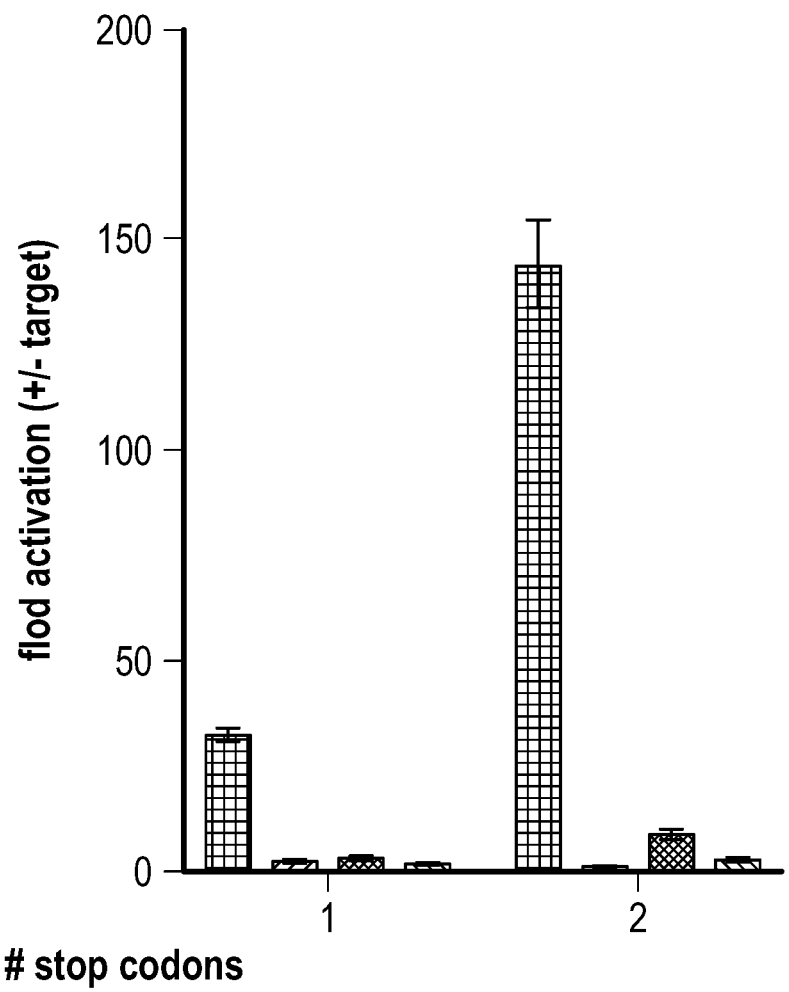
FIG. 26B is a comparison of sensor fold activation between regular MS2 hairpin connected seven avidity sensor and a dual stop codon seven avidity sensor with insertion of a 3' downstream stop codon inside the last avidity region.
Figure 28A:
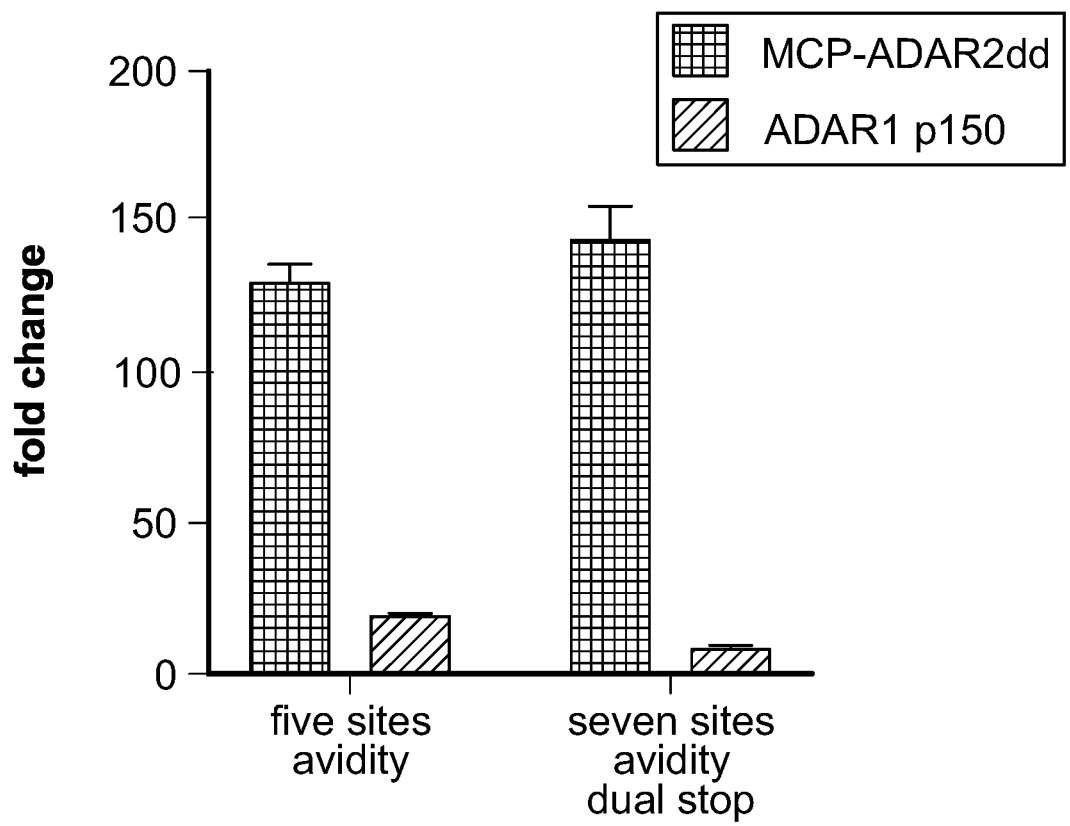
FIG. 28A is a bar plot showing comparison between five binding site avidity sensors versus seven binding site avidity dual stop codon sensors across MCP-ADAR2dd (E488Q, T490A) and ADAR1 p150.
Figure 28B:
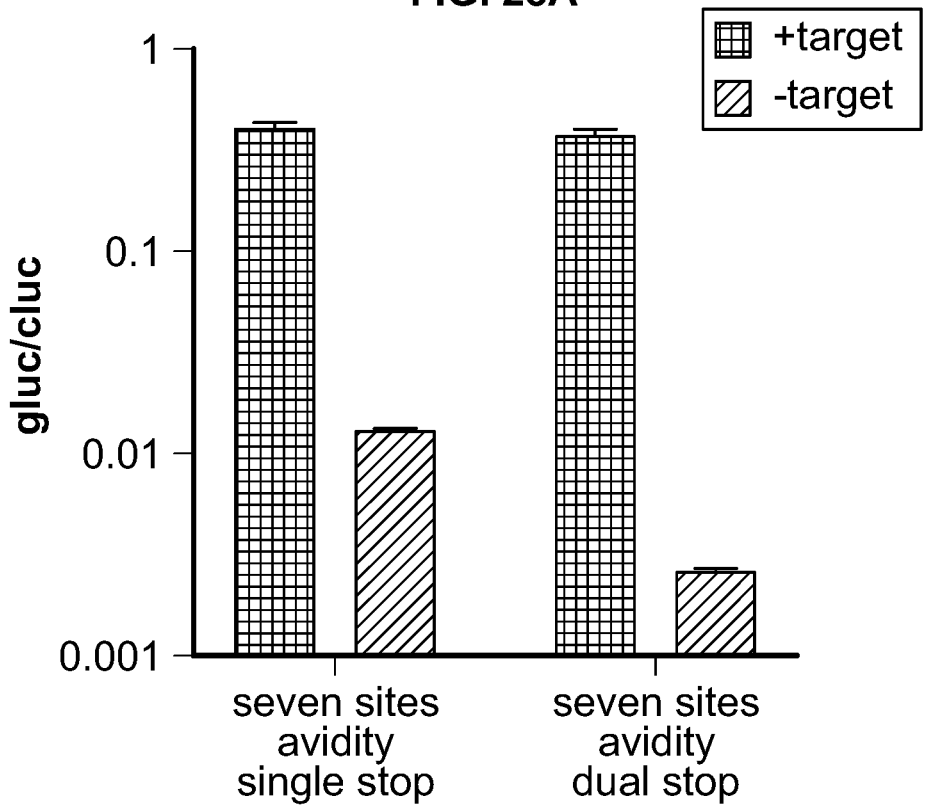
FIG. 28B is a bar plot showing comparison between the activation and background signal of seven binding site avidity single stop codon versus seven avidity dual stop codon sensor.

We also explored whether the avidity binding guide improvements could be combined with orthogonal methods to block translational readthrough, such as additional stop codons. We compared a single stop seven avidity region sensor or a dual stop seven avidity region sensor, with the additional stop codon in the final avidity region (FIG. 26). FIG. 26B exhibits the fold change in luciferase payload between the single and dual stop sensors. The dual stop sensor exhibited a significant increase in fold change compared to the single stop sensor, dependent on ADAR. We found that an additional stop codon increased the fold activation for the 7-site avidity binding guide, exceeding the performance of the 5-site avidity binding guide (FIG. 28A). This improvement was driven both by decreases in the background activation rate and increases in the editing rate of the stop codon in the presence of target (FIG. 28B, FIG. 8).

Figure 29A:
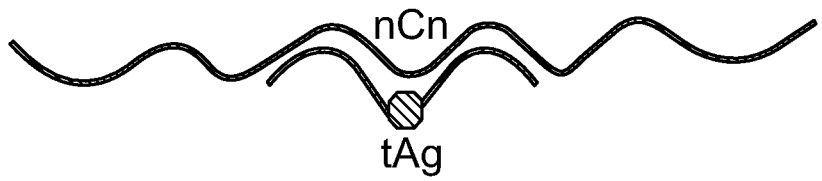
FIG. 29A is a comparison of the target mismatch tolerance across all 16 possible mismatches between the naïve 51 bp sensor, three avidity and the five-avidity sensor design. (16 Targets comprises either 5' or 3' nucleotide change from the regular CCA).
Figure 29B:
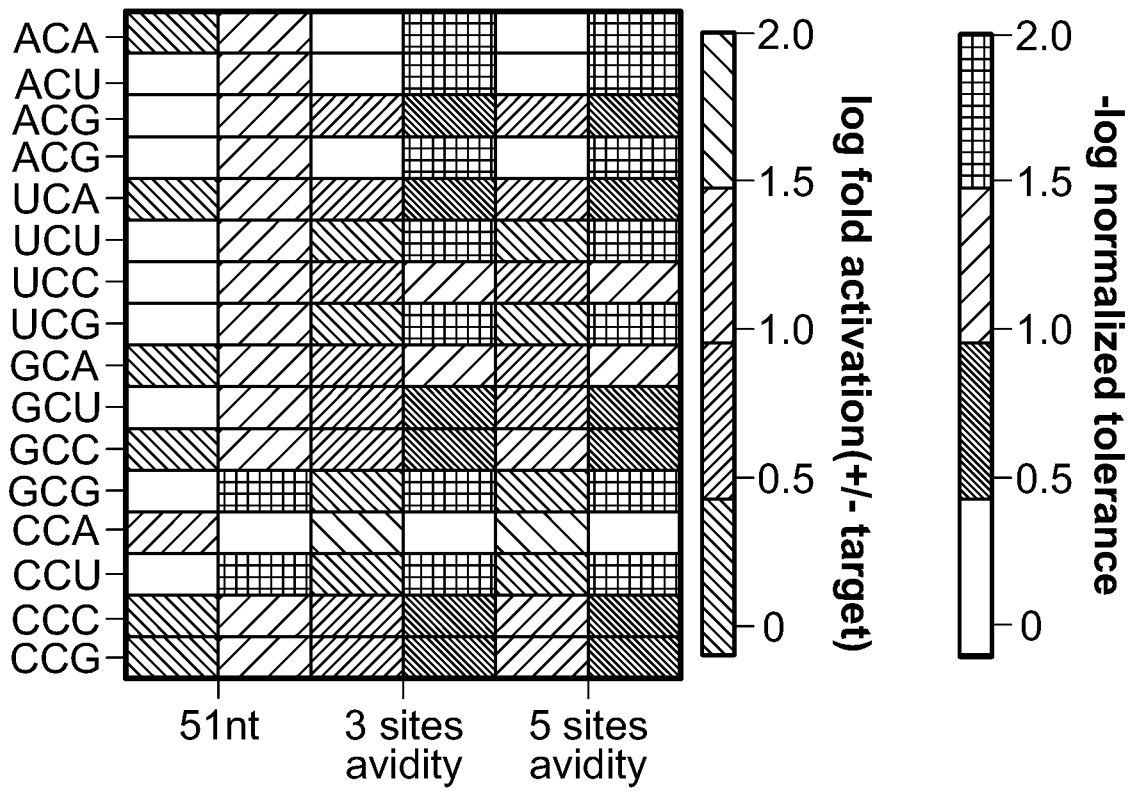
FIG. 29B is a heatmap that shows the log fold activation of all three sensor design across the 16 target mismatches (blue) and the log 10 of the normalized tolerance of the different target mismatch relative to the native CCA target (red).
Figure 30:
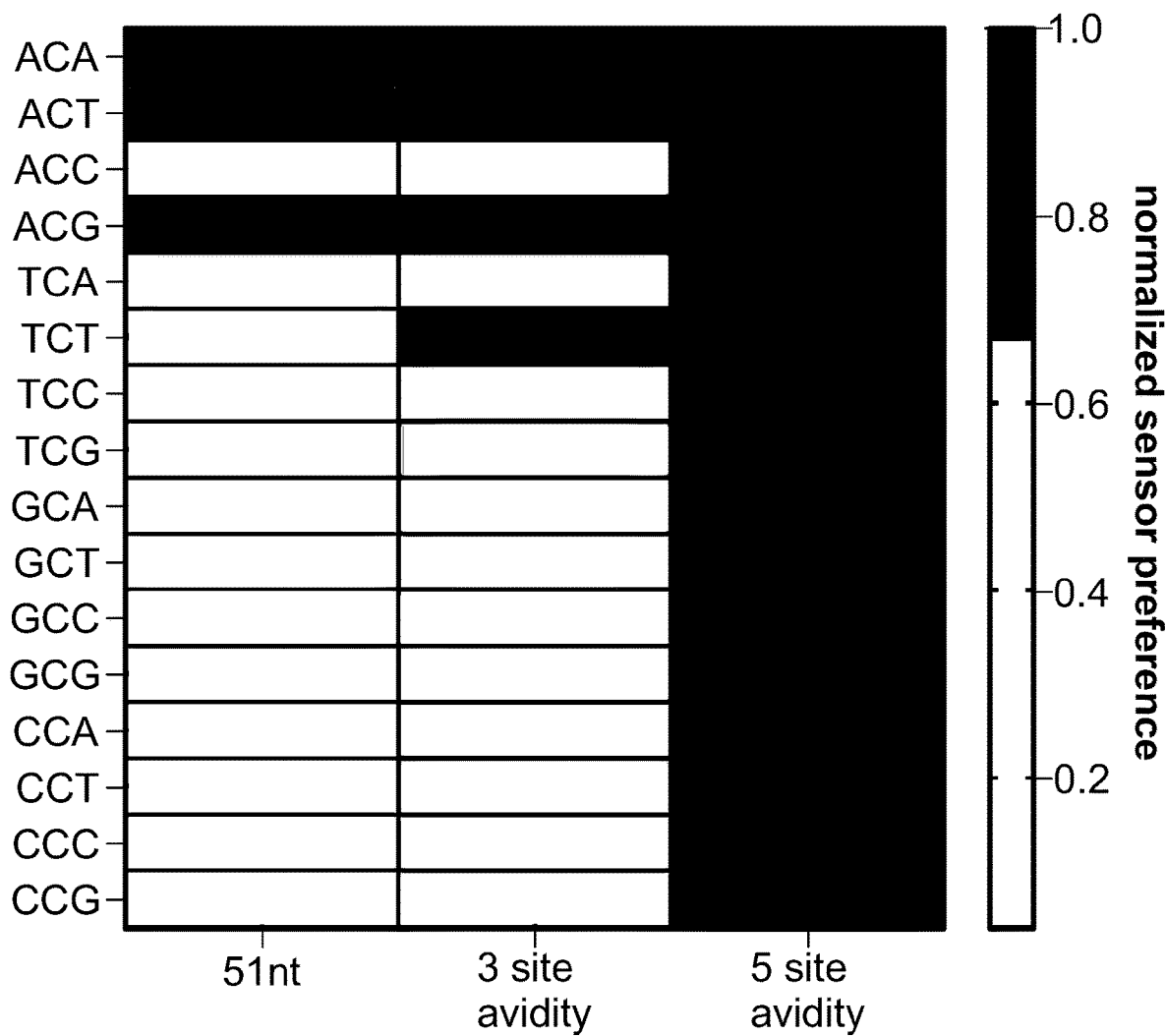
FIG. 30 is a heatmap displaying normalized preference of sensor design within each target mismatch combination between naive 51 bp sensor, triple binding sites sensor and five binding sites sensor.

Despite the abundance of CCA codons on potential target transcripts, we explored if progressive engineering of the avidity guide design allowed for improved mismatch tolerance to increase targeting flexibility. We also tested the target mismatch tolerance (FIG. 29A) in the 16 possible mismatches (from the regular CCA) between the naïve 51 bp sensor, the three-avidity sensor, and the five-avidity sensor. We designed 16 targets, covering all nucleotide changes to either the 5' cytosine or the Y adenosine (nCn). Testing a guide containing a UAG across from these varied codons, we found that guanine or cytosine mismatches were generally better tolerated than adenosine or uridine mismatches (FIG. 29B). Moreover, with the exception of the ACA and ACU targets, the 5-site avidity binding guide ADAR sensor design had the best activation fold change (FIG. 30).

Figure 31A:
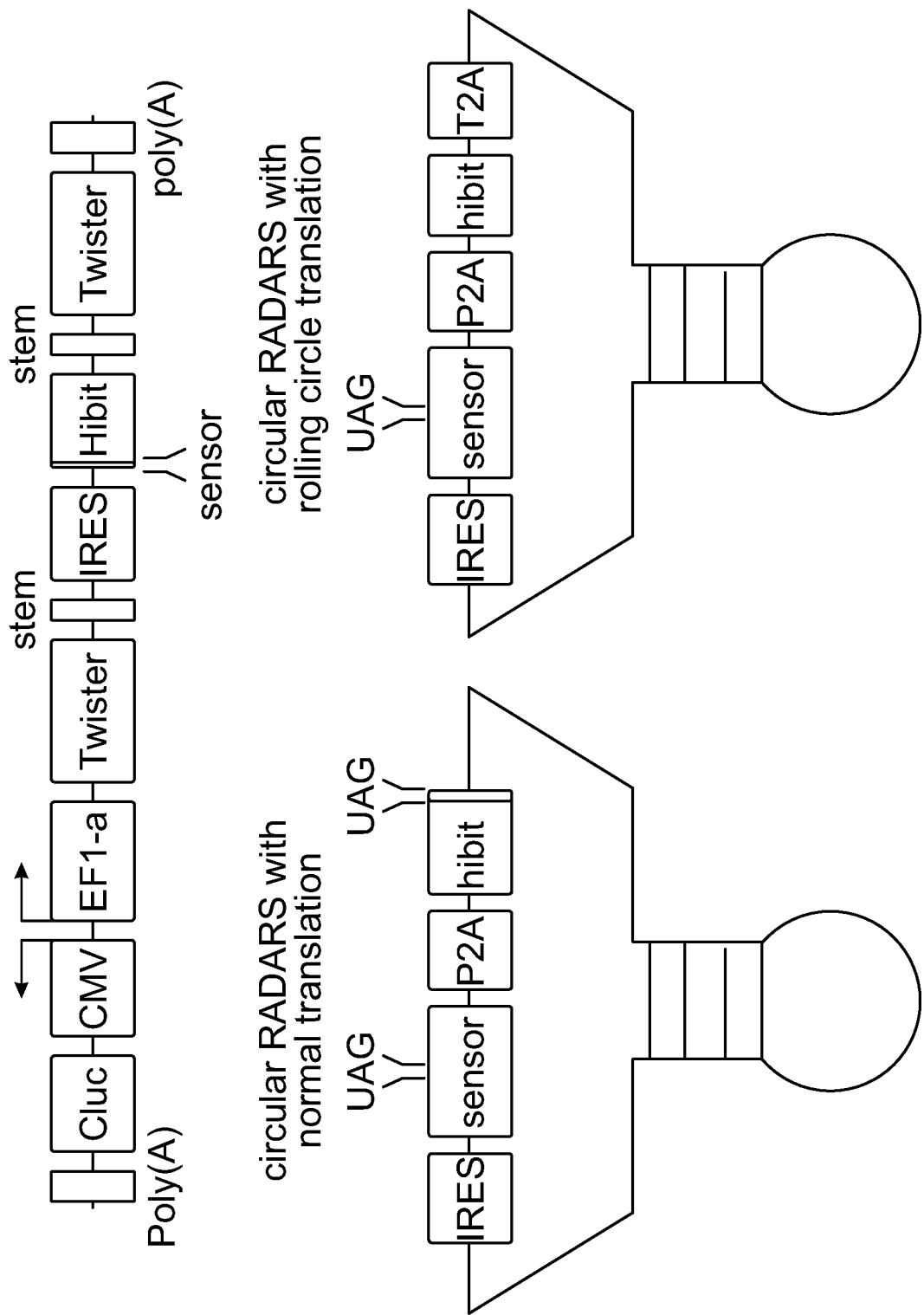
FIG. 31A is a visual representation of the creation and activation of circular sensors. A regular Circular sensor is created with a twister ribozyme backbone driven by a U6 promoter for in vitro self-circularization. Self-circularization of sensor-hibit tag utilizes mammalian cell RtcB ligase. A rolling circle translation version of the circular sensor is made by deleting the stop codon at the C-terminal of the hibit protein and insertion of T2A peptide to allow ribosomal readthrough in a circular fashion.
Figure 31B:
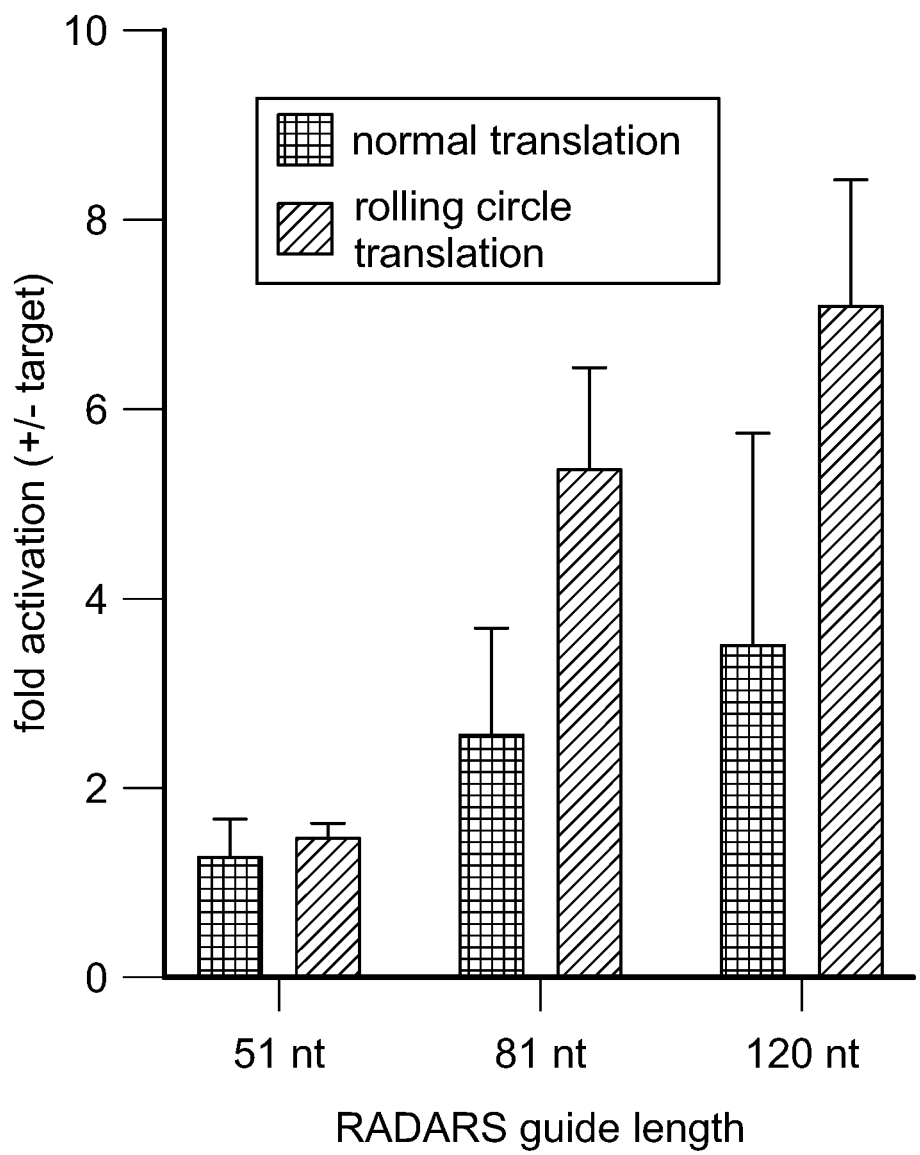
FIG. 31B Various length of sensors between 50 nt to 120 nt are compared for sensor activation fold change upon transgene target (human IL6) induction.

The modularity of protein payloads also allows for small payloads, such as Hibit payload (Schwinn et al. 2018), that allow for n vivo circularization of transcripts. Circular RNAs present a platform for enhanced residency time and minimum immunotoxicity (Katrekar et al. 2019) and we hypothesized that ADAR sensors with small payloads could be circularized to take advantage of these properties (FIG. 31A). Two forms of short circular sensors were initially developed. The Regular Circle Sensor is a dual Twister ribozyme system (Litke and JafTrey 2019) backbone driven by a U6 promoter which circularizes in vitro in the presence of RtcB ligase. The Regular Circular Sensor also contains a Hibit tag, with a stop codon at the c-terminal end of the Hibit. We found that circular ADAR sensors expressed the Hibit in a target (IL6) specific manner (FIG. 31B). For signal amplification, we augmented these circular ADAR sensors as endless ADAR sensors by removing the stop codon after the payload and inserting 2A peptides on either end of the Hibit tag, allowing for expression via rolling circle translation (RCT) (Abe et al. 2015). These Rolling Circle Translation sensors are similar to the Regular Circular sensor, except the stop codon in the Hibit is removed, and T2ToA peptide is inserted to allow ribosomal readthrough in a circular fashion. These circular sensors (targeting IL6) were transfected into HEK293 cells, with varying lengths of sensors compared for sensor activation. Longer sensors consistently increased sensor activation fold change. We found that Rolling Circle sensors can express protein in a target specific manner with minimum background leakage (FIG. 31B).

We examined the effect of mRNA modifications on the sensor activation fold change. Synthetic mRNAs have emerged as a useful therapeutic modality, but there are no methods to control their payload expression in a transcript-specific manner. We explored the application of synthetic mRNA ADAR sensors for transcript-specific expression in a mouse model that expresses human SERPINA1 transcripts in mouse hepatocytes. When delivering mRNA, incorporation of base modifications such as 5' methylcytosine (5mc) and pseudouridine ($\Psi$) are essential to reduce host immune responses (Kauffman et al., 2016), but these modifications may interfere with ADAR activity, impacting mADAR SENSOR function.

Figure 32A:
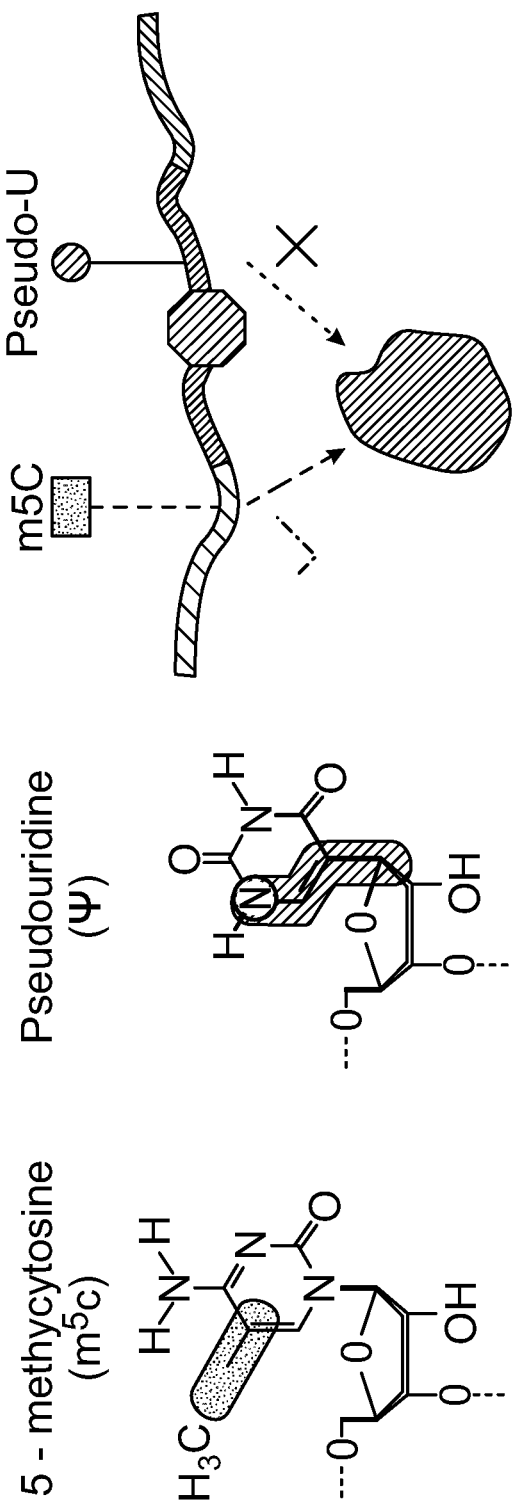
FIG. 32A is a schematic of the RNA modifications evaluated.
Figure 32B:
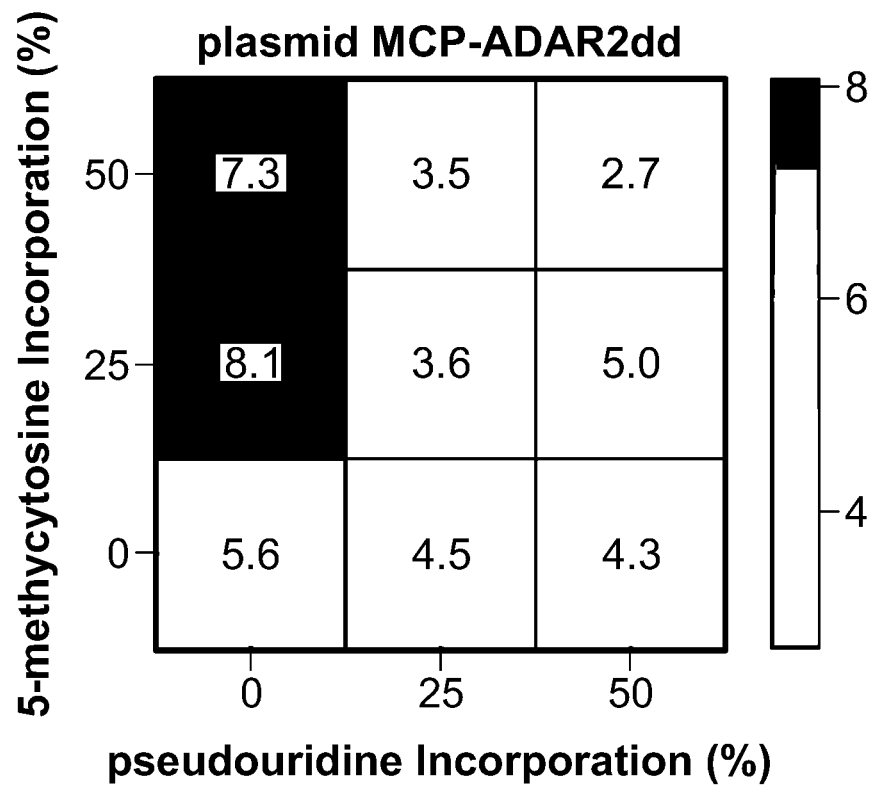
FIG. 32B A heatmap comparing different mRNA modifications for synthetic mRNA ADAR SENSOR detecting IL6 transgene expression in HEK293FT cells when supplemented with MCP-ADAR2dd (E488Q, T490A) by plasmid transient transfection 24 hours before mRNA sensor transfection.
Figure 32C:
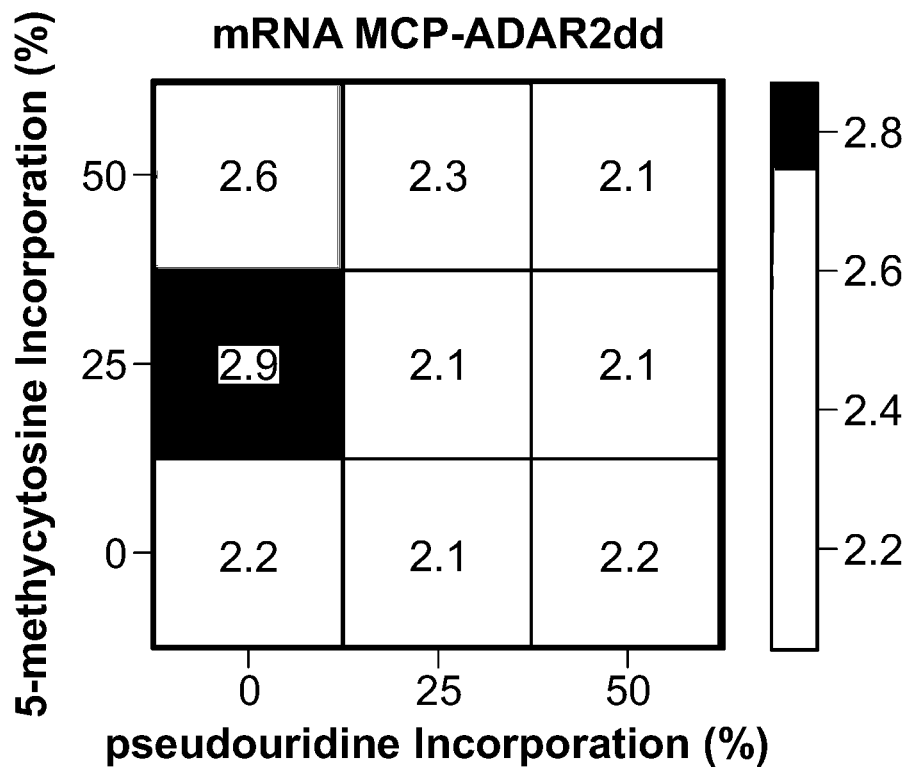
FIG. 32C A heatmap comparing different mRNA modifications for synthetic mRNA ADAR SENSOR detecting IL6 transgene expression in HEK293FT cells when supplemented with MCP-ADAR2dd (E488Q, T490A) mRNA at the time of sensor transfection.

Incorporation of 5-methylcytosine and pseudouridine was analyzed in HEK293 cells. 24 hours prior to mRNA transfection, HEK293 cells were supplemented with MCP-ADAR2dd as either a plasmid or directly as mRNA. An IL6 sensor with a tetracycline inducible IL6 was also used. We found that increased P amounts reduced ADAR sensor activation, while 5mc was more tolerated with 25% incorporation of 5mc having the highest signal activation (FIG. 32).

Figure 53A:
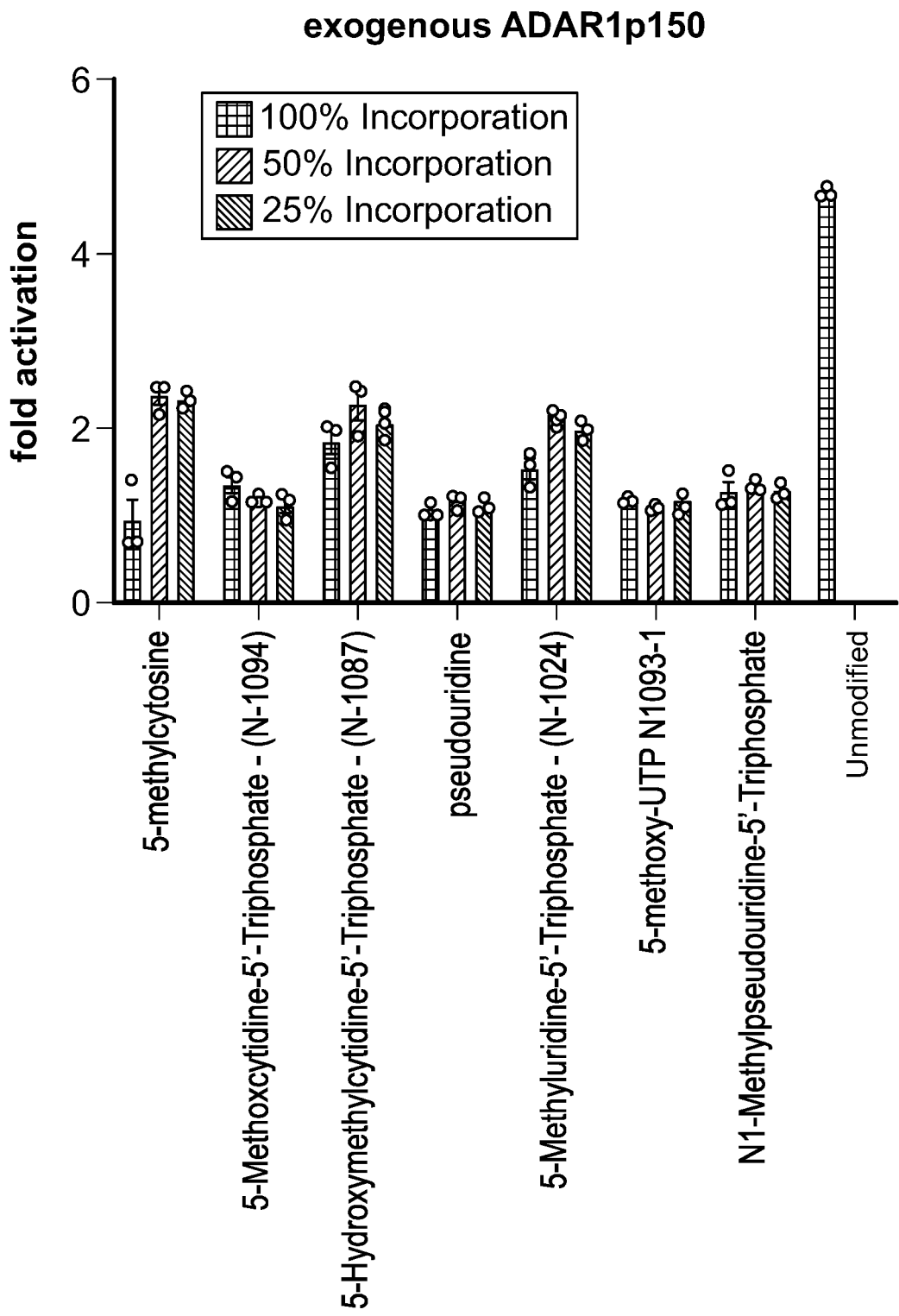
FIG. 53A is a graphical comparison of mRNA RADARS sensor activation fold activation in detecting IL6 transcript in conjunction with plasmid ADAR1p150 transfection. Synthetic mRNA sensors are synthesized with different chemically modified bases at different levels of incorporation ranging from 0 to 100%. Data are mean of technical replicates (n=3)±s.e.m.
Figure 53B:
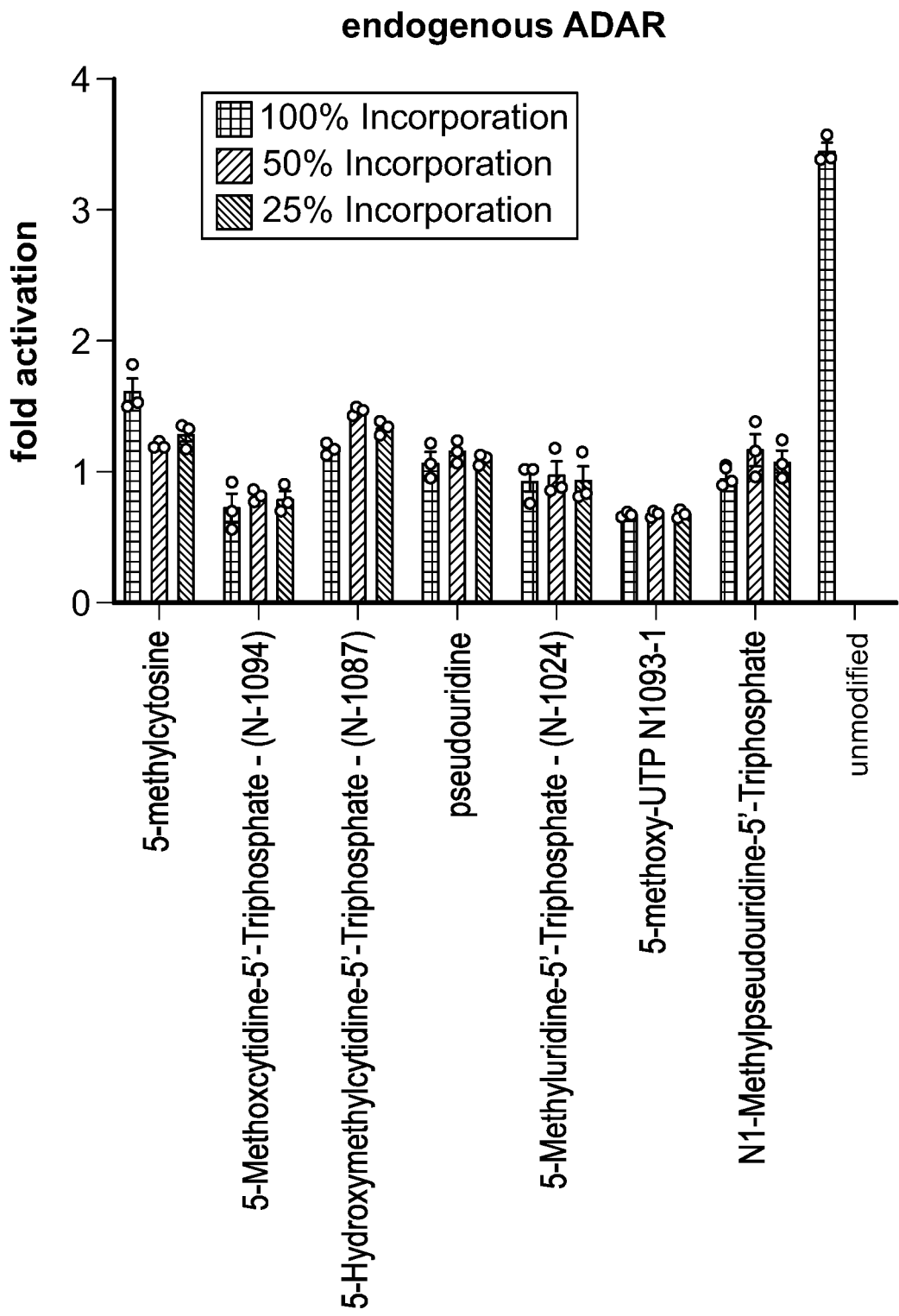
FIG. 53B is a graphical comparison of mRNA RADARS activation fold activation in detecting IL6 transcript utilizing endogenous ADAR when synthesized with different chemically modified bases at different levels of incorporation ranging from 0 to 100%. Data are mean of technical replicates (n=3)±s.e.m.
Figure 53C:
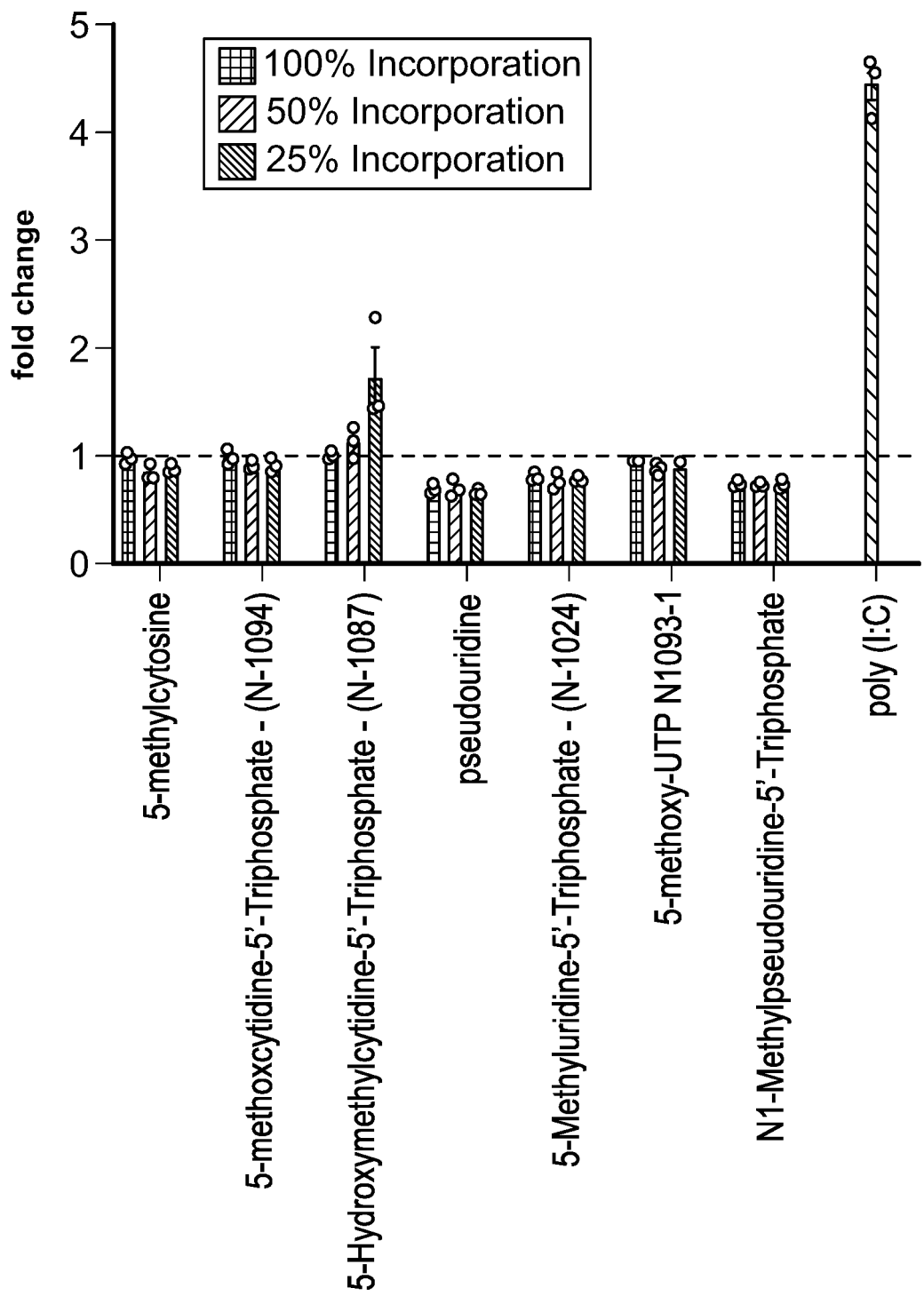
FIG. 53C is a graphical comparison of Induction of interferon beta response due to mRNA RADARS transfection. Synthetic mRNAs are synthesized with different levels of chemically modified bases and interferon response is measured by plasmid (One-Glo luciferase) reporter assay (Gentili et al., 2015).

Using our inducible IL6 system to measure sensor activation, we further assayed the effect on mRNA RADARS activation for different levels of incorporation of a broader panel of chemically modified bases and transfected modified IL6 sensing mRNA RADARS with either exogenous ADAR1p150 (FIG. 53A) or endogenous ADAR (FIG. 53B). We found that all tested modifications reduced the mRNA RADARS activation, likely due to interference with ADAR1p150's ability to edit modified mRNA. Among modifications, we found that 50% incorporation of modified bases such as 5-methylcytosine or 5-Methyluridine was best tolerated in the case of exogenous ADARp150, and 100% incorporation of 5-methylcytosine had highest activation with endogenous ADAR. To determine if this level of modification is sufficient to reduce the host immune responses, assayed induction of interferon beta related genes by chemically modified mRNA RADARS. We observed at even 25% incorporation levels of modified bases, we achieve minimal induction of inflammatory genes (FIG. 53C).

Figure 54B:
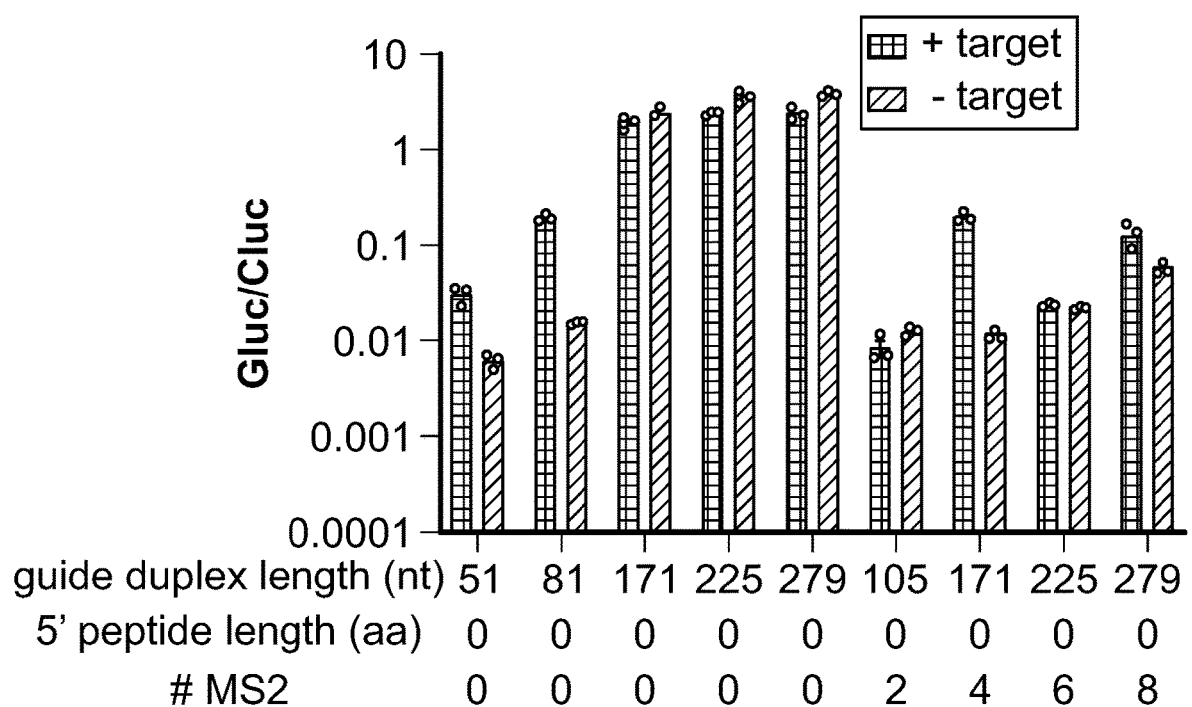
FIG. 54B is a graphical comparison of Gluc/Cluc ratio between + target and − target conditions for IL6 #CCA8 targeting engineered guide RNA with different length and different MS2 hairpin loops while keeping 0aa 5' peptide length. Error bars indicate standard error of the mean. (n=3 technical replicates).

We tested a sensor that contains a 51 nt IL6 transcript-sensing guide in front of a *Gaussia* luciferase (Gluc) payload, called RADARSv1, in combination with a constitutive *Cypridina* luciferase (Cluc) on a separate transcript to provide ratiometric control for transfection variance (FIG. 54A). With this RADARSv1 design and co-transfection with exogenous ADAR1p150, we observed approximately 5-fold activation (FIG. 54A), as quantified by an increase of Gluc/Cluc ratio in the presence of exogenous IL6 target expression (FIG. 54B, change in Gluc/Cluc ratio between conditions defined as RADARS fold activation in rest of manuscript). As ADAR1p150 prefers long double stranded RNA as a substrate, we titrated the length of the guide region from 51 nt to 279 nt, resulting in a modest increase in activation at 81 nt, with reduced activation at longer lengths due to increases in background payload expression in the absence of target RNA (FIG. 54A, FIG. 54B).

Three strategies were used to prevent dsRNA formation in the absence of target due partly to translational readthrough and self-folding. First, we introduced multiple MS2 hairpin loop-interspersed binding sites into the guide region to create a secondary structure to prevent self-folding and enable multivalent binding. We optimized these engineered guides termed organized guide RNA (engineered guide RNA) by varying the number of MS2 loops and binding sites on the guide. RADARS activation was highest with engineered guide RNAs containing 5 binding sites interspersed with MS2 hairpin loops, which reduced background payload expression in the absence of target compared to the uninterrupted guide designs and achieved ~20 fold activation, (FIG. 54A, FIG. 54B)

Figure 55A:
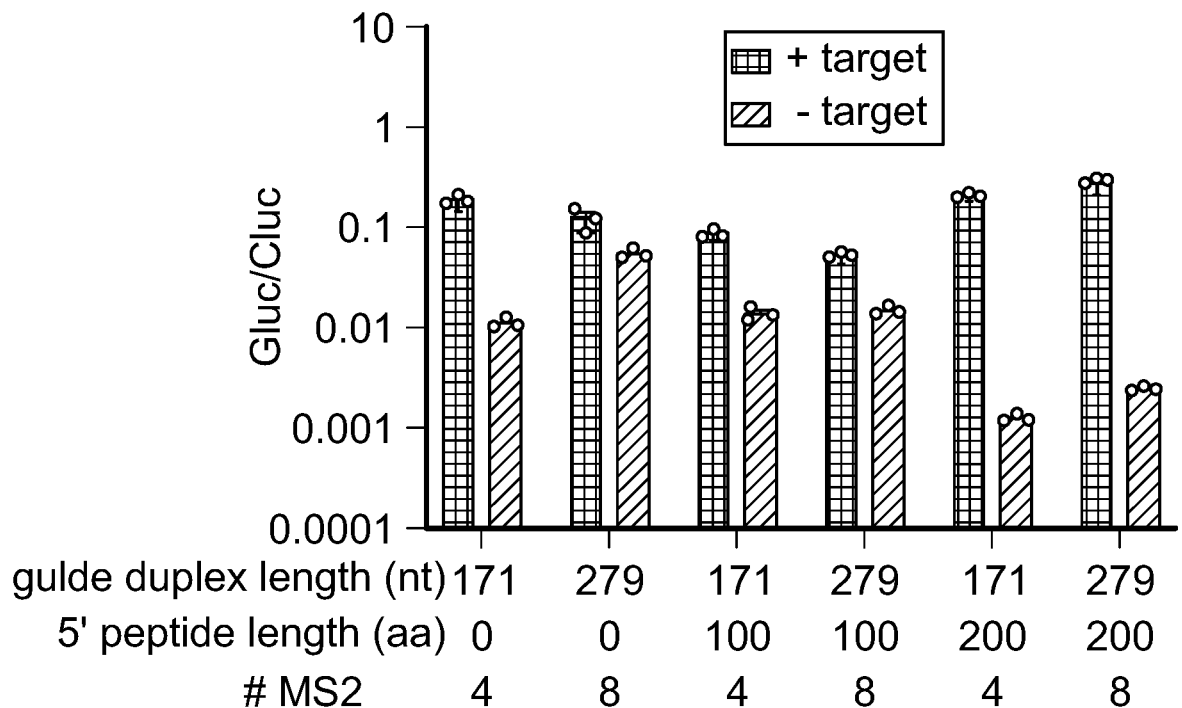
FIG. 55A is a graphical comparison of Gluc/Cluc ratio between + target and − target conditions for five avidity binding site (4 MS2 loops) and nine avidity binding site (8 MS2 loops) engineered guide RNA with varying length of 5' peptide. Error bars indicate standard error of the mean. (n=3 technical replicates).

Second, we increased the length of the translatable open reading frame (ORF) before the engineered guide RNA to promote termination and prevent ribosome reinitiation, which is known to be dependent on upstream ORF length. We tested 5' peptide lengths at 0, 100, and 200 residues, and found that, at 200 residues, we were able to substantially reduce the background translational readthrough (FIG. 55A), achieving >100 fold activation.

Figure 55B:
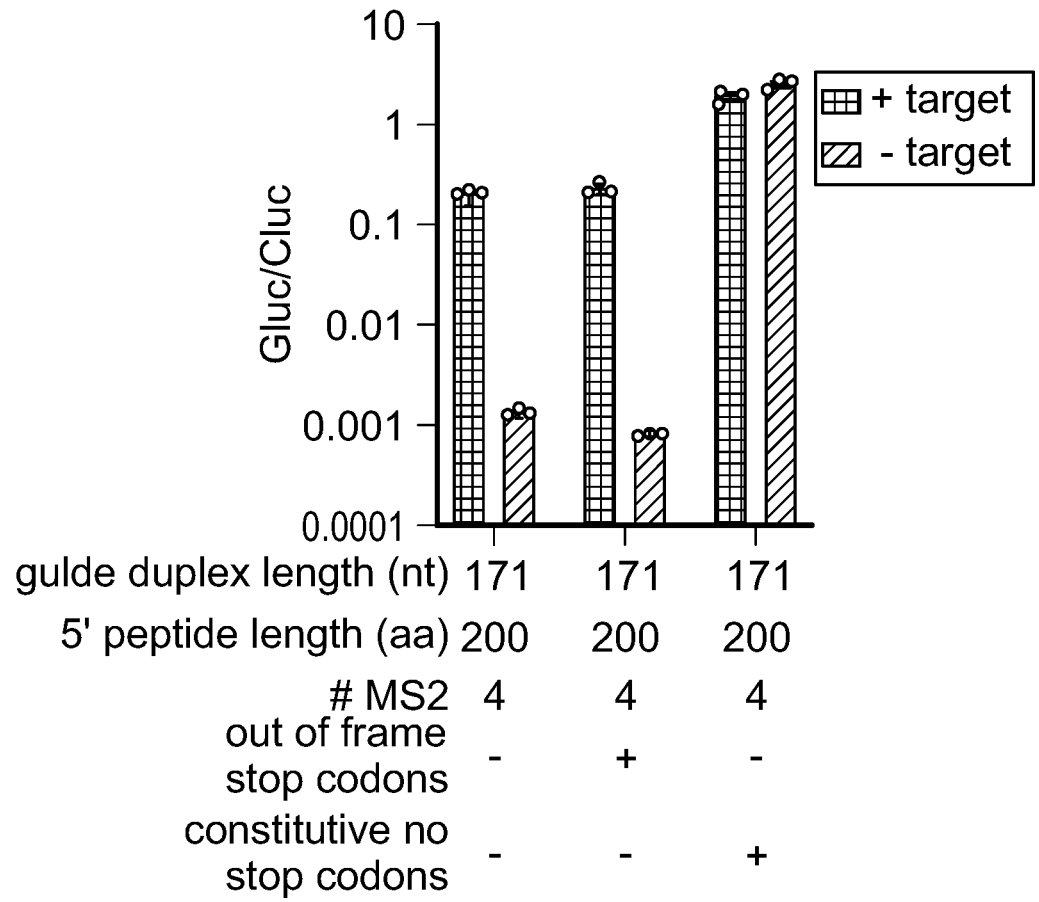
FIG. 55B is a graphical comparison of Gluc/Cluc ratio between no out of frame stop codons and addition of two out of frame stop codons for a five avidity binding site engineered guide RNA with 200aa 5' peptide residues. Last column represents a constitutive gluc driven under an Ef1-alpha promoter. Error bars indicate standard error of the mean. (n=3 technical replicates).

Finally, we engineered stop codons in the +1 and +2 frames following the engineered guide RNA region to trap the translating ribosome across all frames. These out-of-frame stop codon designs significantly decreased the background synergistically with long 5' peptides, generating ~200 fold activation. We chose this sensor design, termed RADARSv2, incorporating structured guides, upstream peptides, and out-of-frame stop codons, as a unified structure for future sensors. (FIG. 54A, FIG. 55B).

Figure 56A:
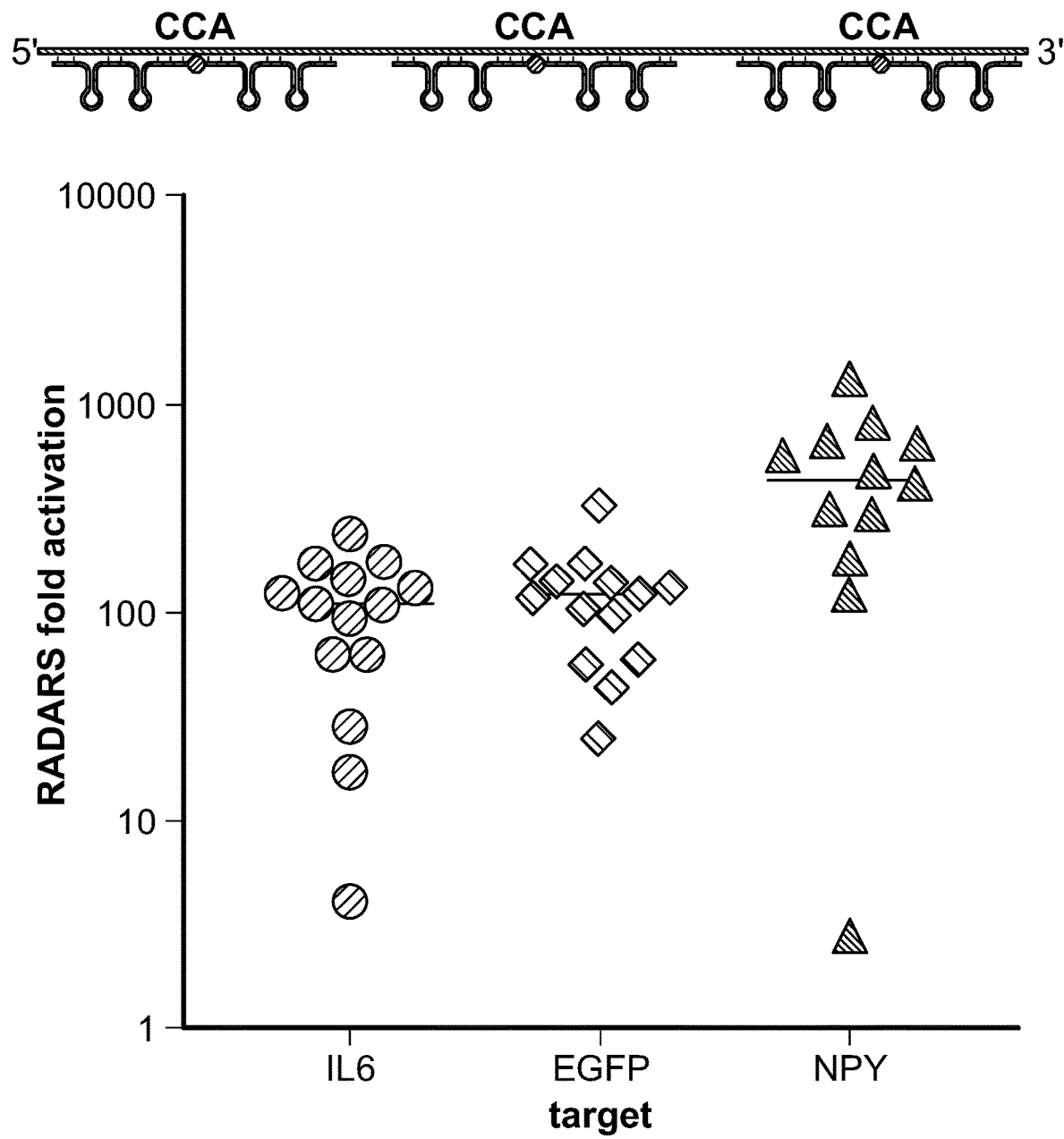
FIG. 56A is a graphical depiction of fold activation of IL6, EGFP and NPY targeting RADARS with exogenous ADAR1p150 supplementation. For each transcript, twelve engineered guide RNAs were engineered to target different CCA sites across the transcript. The CCA site number depicted follows the convention that #CCAx indicates the number of the CCA triplicate counting from 5' end of the transcript coding region. Each dot denotes the average of three technical replicates for an individual sensor. Horizontal solid lines represent the mean of all 12 engineered guide RNAs.
Figure 56B:
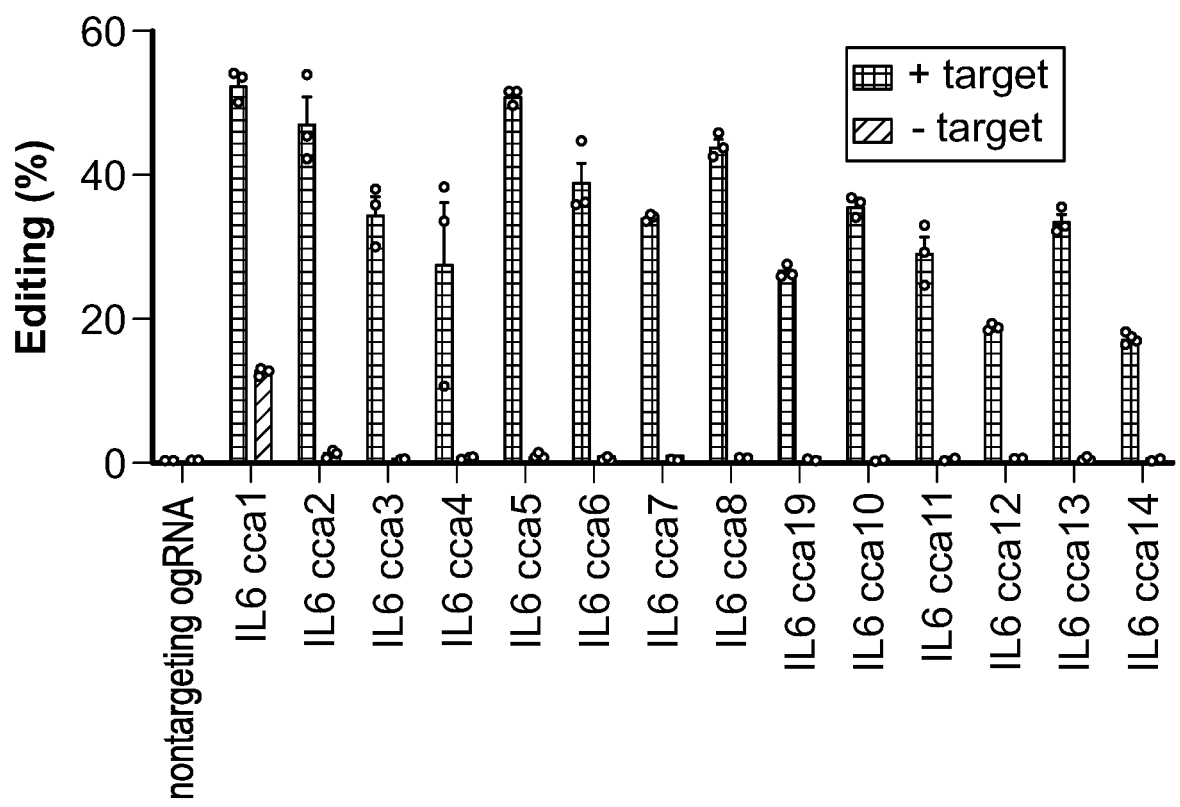
FIG. 56B graphically depicts the editing percentage of the target adenosine in the UAG stop codon for a non-targeting engineered guide RNA and fourteen IL6 targeting engineered guide RNAs tiling CCA sites on IL6 with exogenous ADAR1p150 supplementation using the RADARSv2 design in the presence and absence of the target IL6 transcript. Error bars indicate standard error of the mean (n=3 technical replicates).

We evaluated our RADARSv2 design across exogenously expressed IL6, EGFP, and Neuropeptide Y (NPY) targets by tiling engineered guide RNAs over fourteen CCA sites spaced across the transcript. We found that although RADARS activation depends on the hybridization site chosen for a given target, a majority of sensors had substantial payload activation in the presence of their target, with up to 1,000 fold activation, showing the generalizability of RADARSv2 designs (FIG. 56A). To confirm that payload expression resulted from RNA editing, we harvested RNA from cells transfected with a panel of fourteen IL6 targeting engineered guide RNA and quantified editing with next-generation sequencing. In the presence of the target transcript, all 14 engineered guide RNAs had greater than 15% editing, with an average of 35.1%+/−11.4%. In the absence of the target transcript, 13 out of 14 engineered guide RNAs had minimal editing (0.32%+/−0.34%). We also observed minimal editing of a non-targeting sensor, reaffirming that the RNA editing of RADARS sensors required specific engineered guide RNA target recognition (FIG. 56B).

Example 7. Quantitative and Correlative Analysis of Genetic Sensors

Figure 33A:
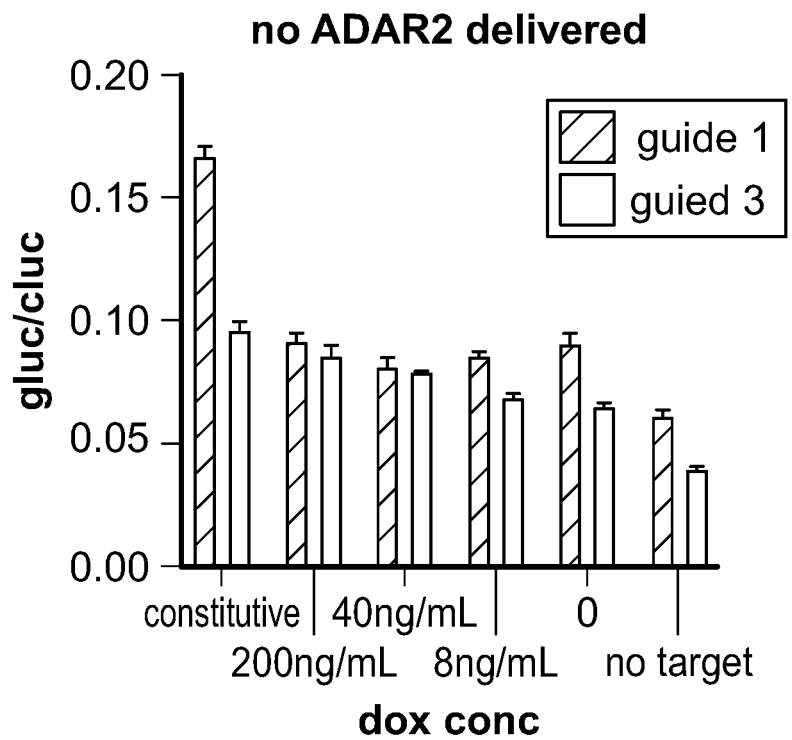
FIG. 33A, FIG. 33B is a graphic illustration depicting the expression of EGFP and the fold increase in GFP expression (FIG. 33C) in HEK293FT cells. EGFP expression was either constitutive or expressed as a gradient using a doxycycline inducible EGFP construct. HEK203T cells were then exposed to concentrations of doxycycline ranging from 8 ng/mL to 200 ng/mL.

To determine if the above genetic sensors could be accurately used as a "dose-sensitive" sensor, an inducible EGFP transcript was introduced into HEK293FT cells. This EGFP transcript was put under control of a doxycycline inducible promoter, and cells were then exposed to 0 ng/mL, 8 ng/mL, 40 ng/mL, or 200 ng/mL doxycycline to vary the expression of the EGFP transcript. In HEK293FT cells in which no exogenous ADAR was introduced (FIG. 6A), neither guide strand displayed significant differences in luciferase activity. However, guide strand 3 displayed a trend toward dose sensitivity (FIG. 33A, white bars).

Figure 33B:
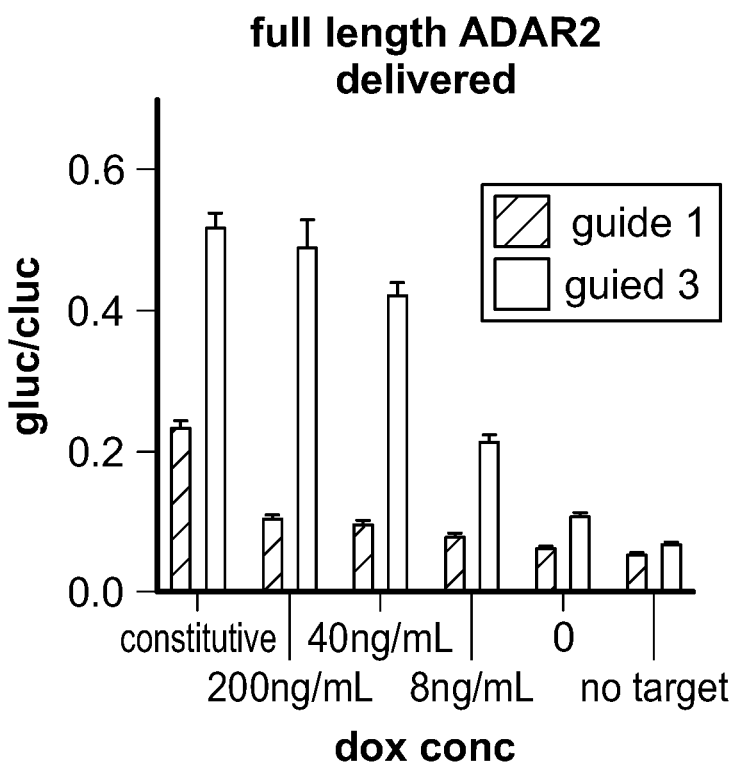
Figure 33C:
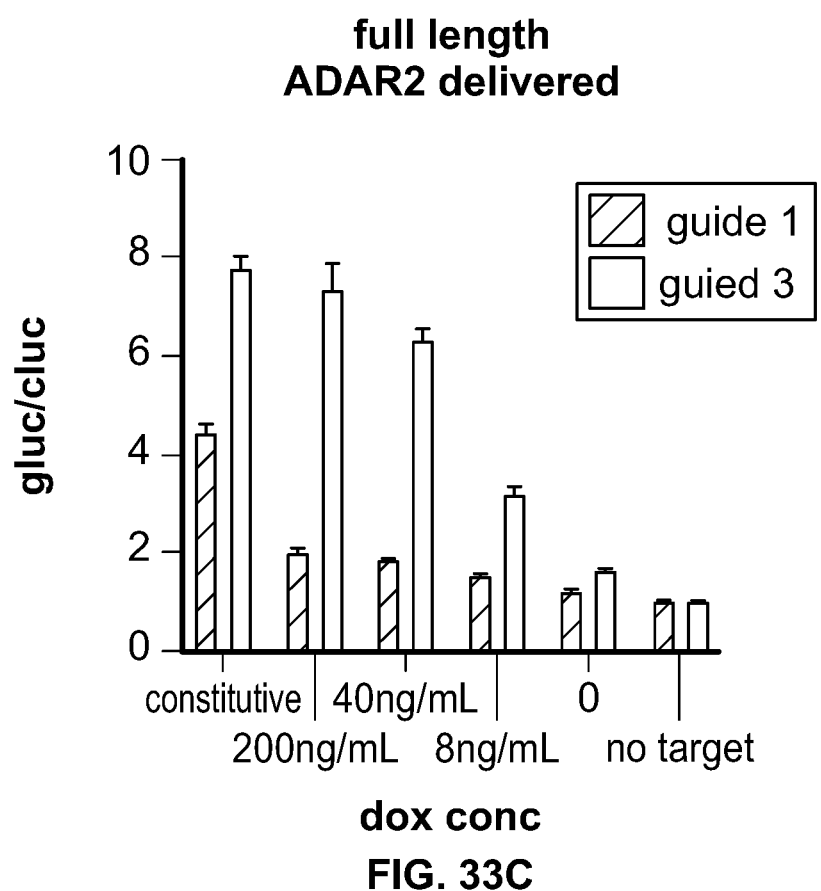
Figures 34A, 34B:
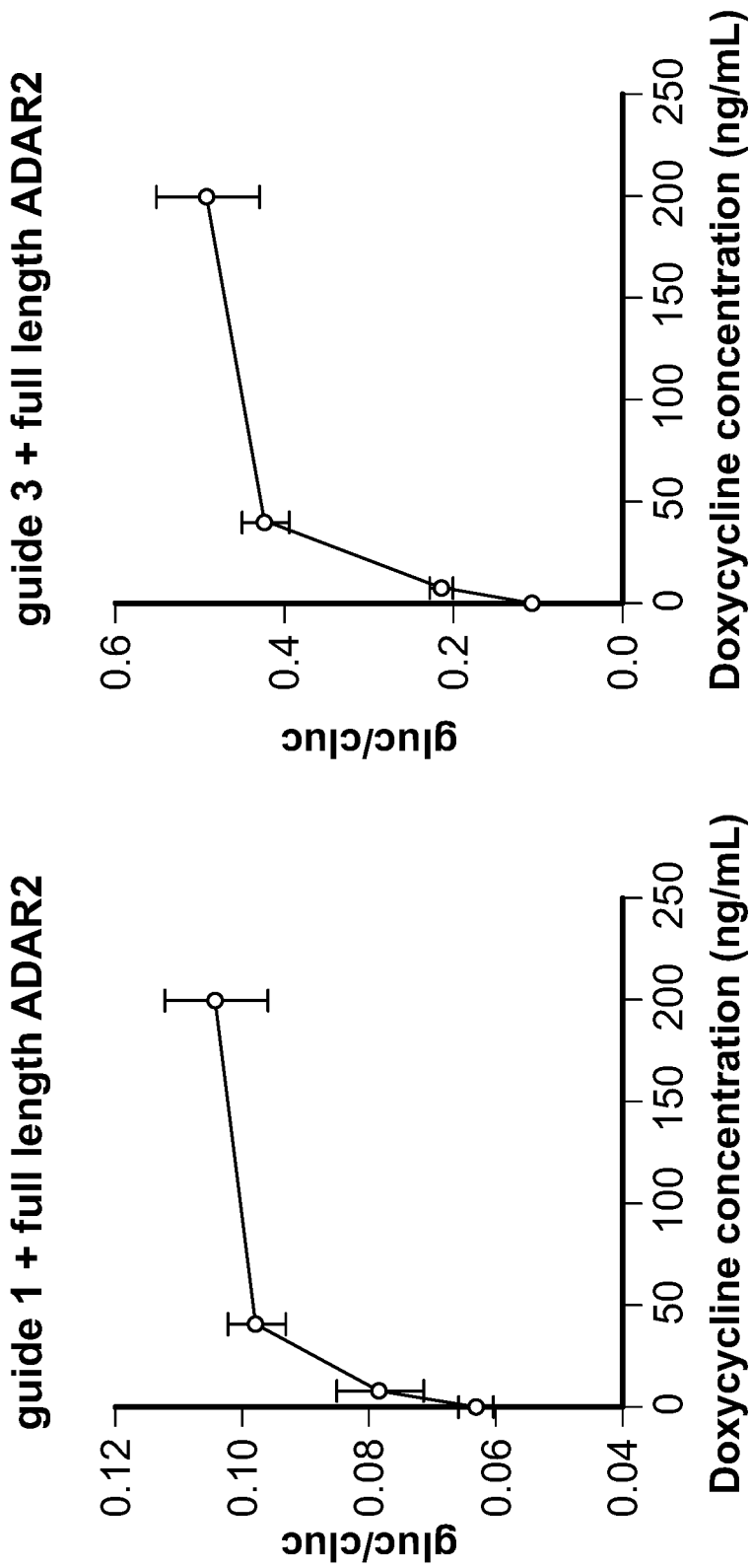
FIG. 34A is a graphic illustration depicting the dose-dependent luciferase activity of guide strand 1 and guide strand 3 FIG. 34B as a function of doxycycline dose in HEK293FT cells simultaneously exposed to full length-ADAR2 and the guide strands targeting EGFP, which is under the control of a doxycycline inducible promoter.
Figures 35A, 35B:
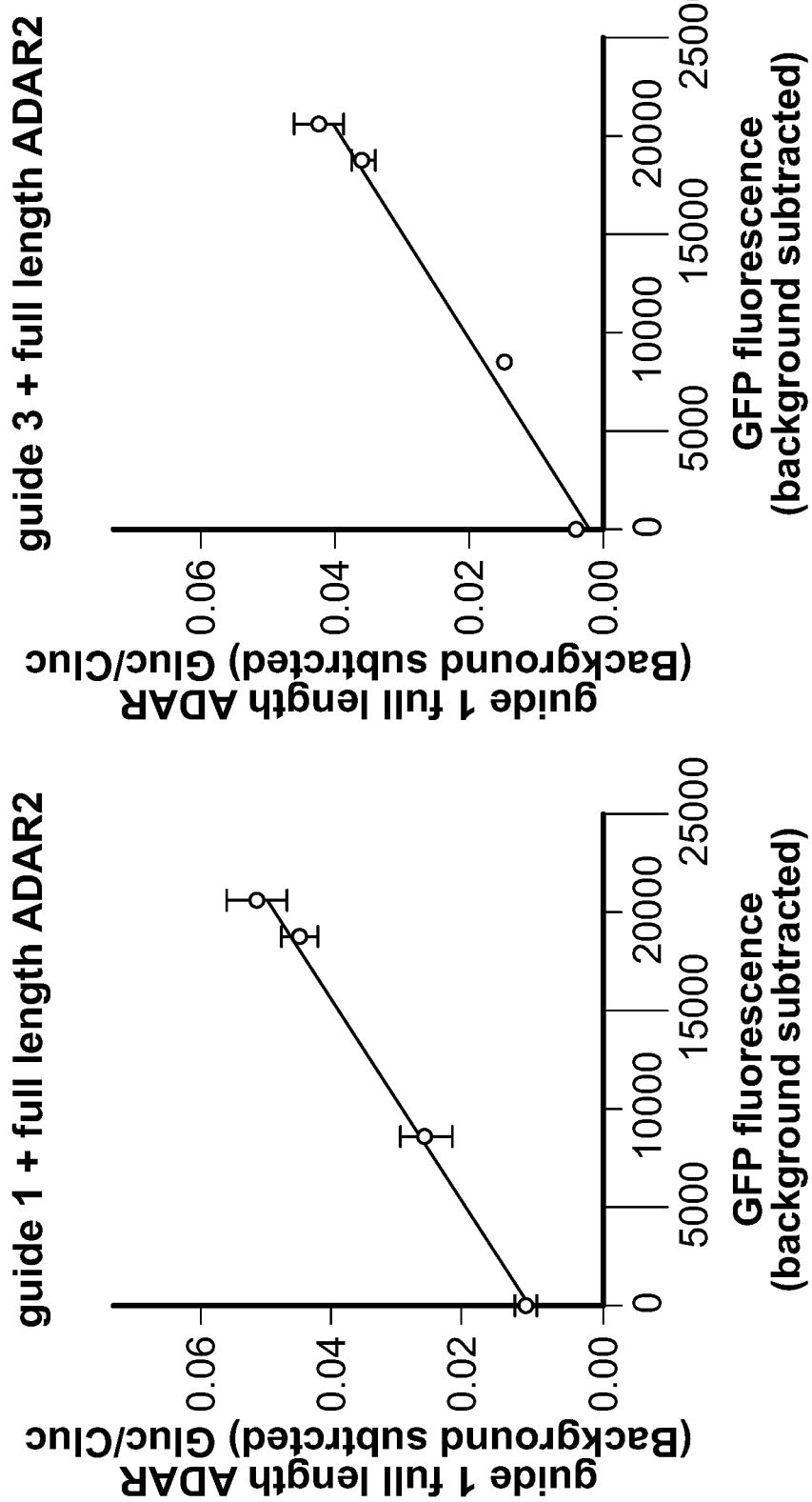
FIG. 35A is a graphic illustration depicting the luciferase activity of guide strand 1 and guide strand 3 FIG. 35B as a function of GFP fluorescence in HEK293FT cells simultaneously exposed to full length-ADAR2 and the guide strands targeting EGFP, which is under the control of a doxycycline inducible promoter.

When full length ADAR2 was introduced to the cells simultaneously with the guide strands (FIG. 33B), guide strand 3 displayed a clear dose sensitivity, while guide 1 had some dose sensitivity, but to a lesser extent (FIG. 33B-C, white bars). Cells given the 200 ng/mL dose of doxycycline showed similar luciferase activity to cells which were constitutively expressing the EGFP transcript. As the dose of doxycycline decreased, there was a corresponding decrease in luciferase activity identified in the cells. This same trend is seen in cells simultaneously exposed to full length ADAR2 and guide strand 1 (FIG. 33B, blue bars). FIG. 34 depicts the dose-dependent reporter expression when EGFP targeting guide strands 1 and (FIG. 34A) and guide strand 3 (FIG. 34B) are introduced into cells. The fold activation of luciferase also follows this dose-dependent trajectory (FIG. 33C). FIG. 35 depicts the level of luciferase activity as a function of GFP fluorescence. These results indicate that these genetic sensors may be valuable as quantitative sensors of transcript level, and not solely as "on-off" sensors.

Figure 57:
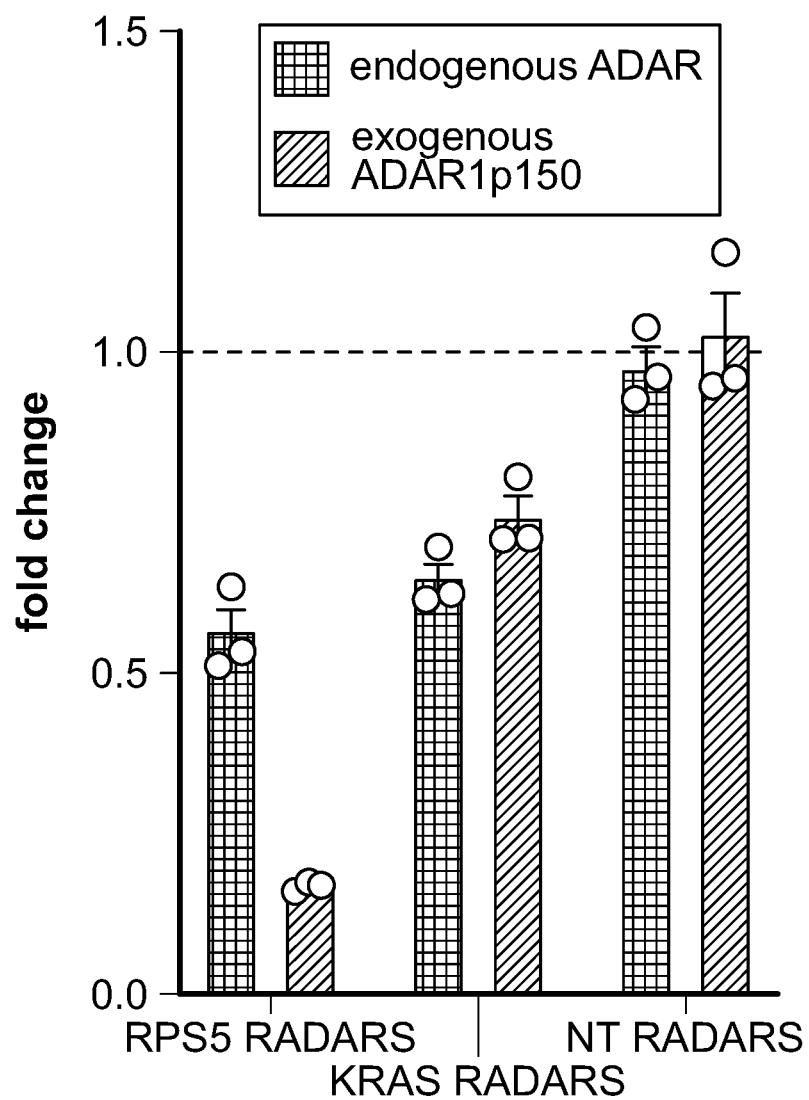
FIG. 57 is a graphical depiction of the RADARSv2 with engineered guide RNAs targeting a high TPM gene (RPS5), a low TPM gene (KRAS) or a non-targeting scrambled sequence used either with exogenous ADAR1p150 supplementation or with endogenous ADAR to sense the downregulation of their corresponding gene via gene-specific siRNA. Fold activation is calculated by the activation of payload in the on-target siRNA group over non-target siRNA group. Data are mean of technical replicates (n=3) ±s.e.m.

We compared target expression for the highest Transcript Per Million (TPM) gene (RPS5) and the lowest expressed gene (KRAS) with an siRNA perturbation experiment to compare how RADARSv2's performance varies between exogenous ADAR1p150 and endogenous ADAR. We observed that both sensors detected the siRNA knockdown without exogenous ADARp150 supplementation, however, with the RPS5 sensor benefited more from exogenous ADAR (FIG. 57), suggesting that larger expression changes may benefit more from exogenous ADAR.

Figure 36A:
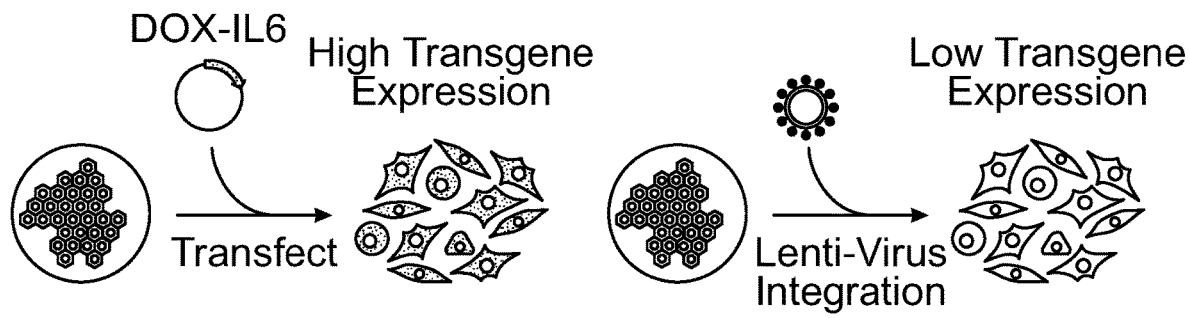
FIG. 36A is a visual representation of the results of a combined treatment of tetracycline inducible IL6 and stable lentiviral integration.
Figure 36B:
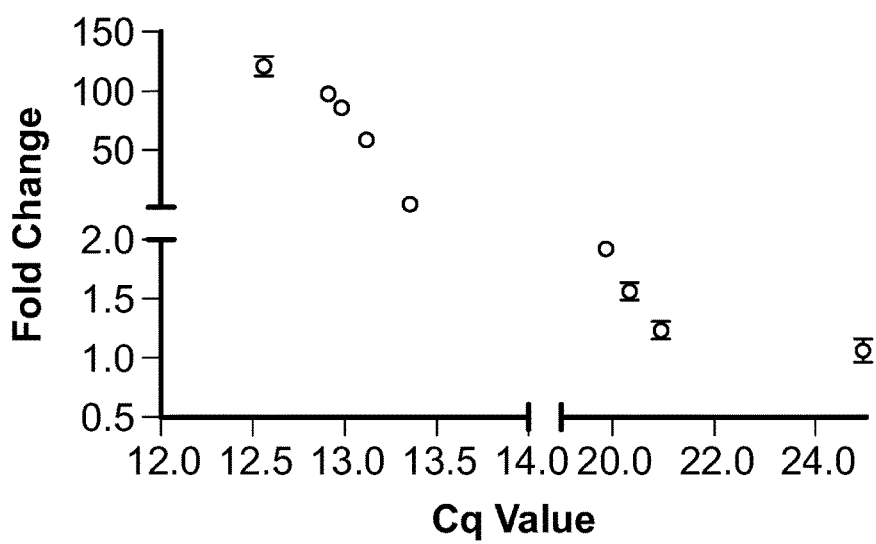
FIG. 36B Dual Stop Codon Seven Avidity IL6 sensor is then used to quantify the relative expression of IL6, and the corresponding luciferase fold change is plotted against the Cq value of the IL6 expression as detected by quantitative polymerase chain reaction (QCPR).
Figure 37:
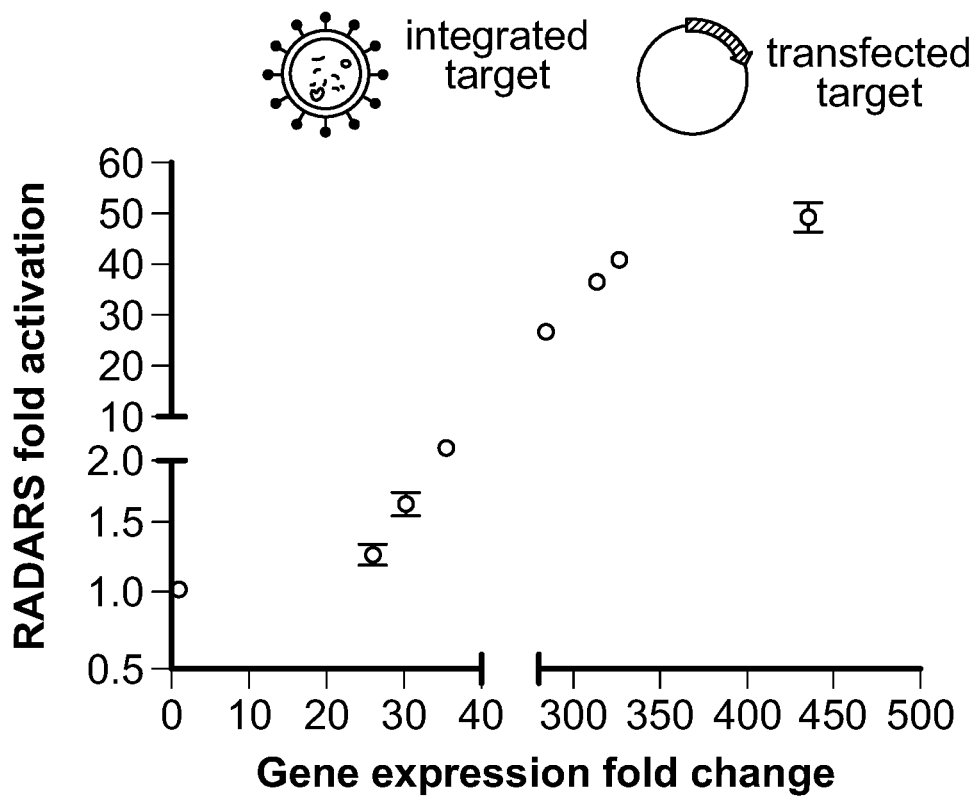
FIG. 37 is a scatter plot displaying that the dual stop codon seven avidity IL6 sensor is useful for quantifying the relative expression of IL6 with broad dynamic range. Target expression range is created through a combination of the transient overexpression of tetracycline inducible IL6 and stable lenti-virus integrated tetracycline-IL6 cassette in HEK293FT cells. ADAR SENSOR fold change relative to the basal condition is plotted against the IL6 gene expression change as determined by quantitative polymerase chain reaction (qPCR).
Figure 38:
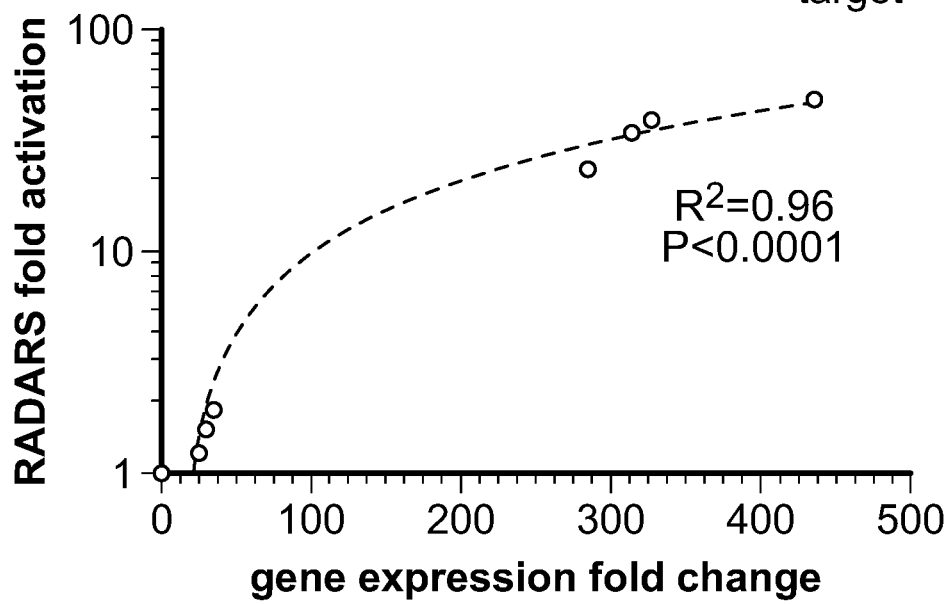
FIG. 38 is a scatterplot displaying a linear regression on the sensor activation fold change against qPCR detected gene expression fold changes.
Figure 39:
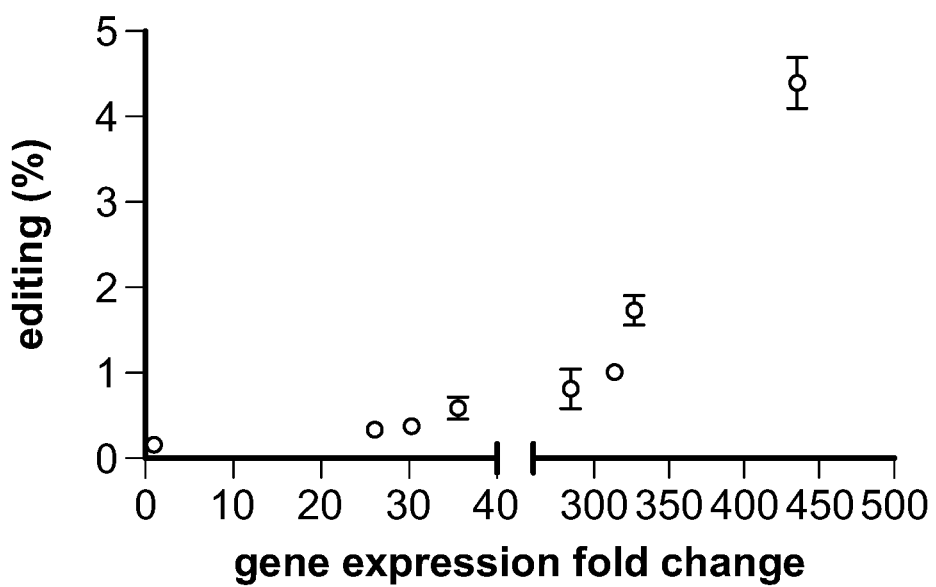
FIG. 39 is the corresponding edit of the adenosine in the UAG stop codon of the sensor across different IL6 gene expression levels to FIG. 38.

To further examine the quantitative value of ADAR sensors, we produced a wide range of expression levels with both transfected and virally integrated versions of our inducible IL-6 expression system and measured the luciferase response of the 7-site avidity binding guide with dual stop codons (FIG. 36A). We found that the ADAR sensor luciferase activation was linearly correlated with the concentration of the target transgene as confirmed by qPCR (FIG. 37, FIG. 38, R2=0.96). Correspondingly, RNA editing of the first stop codon in the ADAR sensor guide had a strong correlation with the gene expression level (FIG. 39), showing ADAR sensors can quantitatively sense transcripts at both the RNA editing and payload level.

Figure 58A:
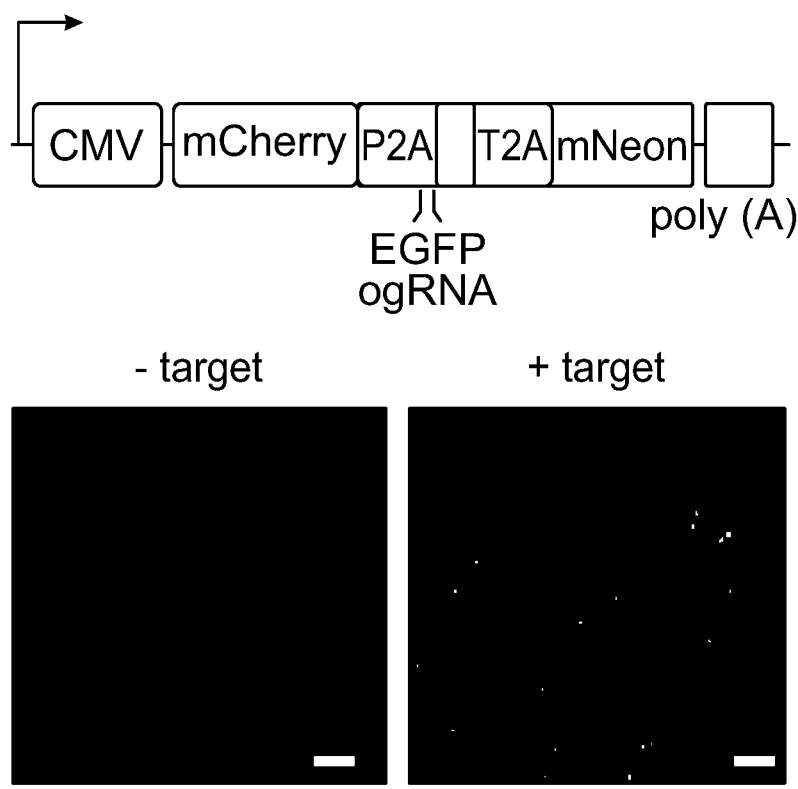
FIG. 58A is visual depiction of a schematic showing a fluorescent output RADARS construct, containing a constitutively expressed normalizing fluorescent protein (mCherry) upstream of a RADARS engineered guide RNA controlling mNeon fluorescent protein (top) and images of fluorescence RADARS showing HEK293FT cells expressing mNeon payload only in the presence of target transcript (out of frame EGFP). HEK293FT cells are transfected with EGFP-targeting RADARS, ADAR1p150, and f target (out of frame EGFP) as indicated (bottom). Scale bar, 100 microns.
Figure 58B:
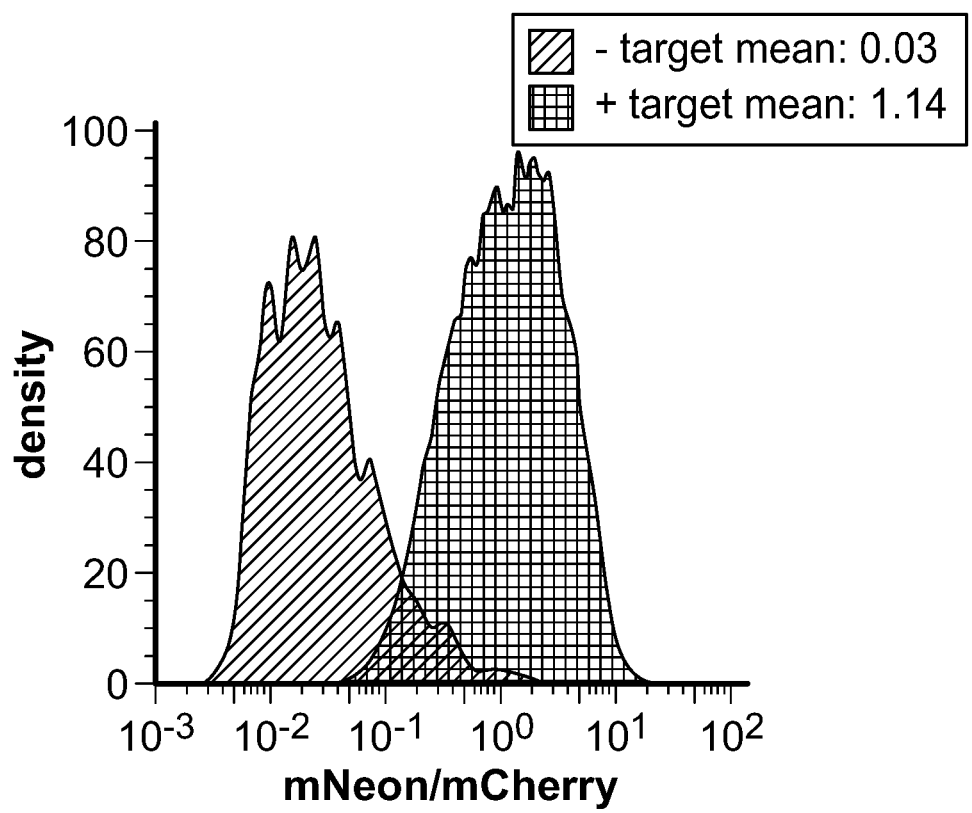
FIG. 58B is a visual depiction of flow cytometry analysis of fluorescent RADARS showing a histogram of mNeon/mCherry fluorescence, for HEK293FT cells transfected as in d), with the beige and blue distributions indicating target absence and target presence, respectively.
Figure 59A:
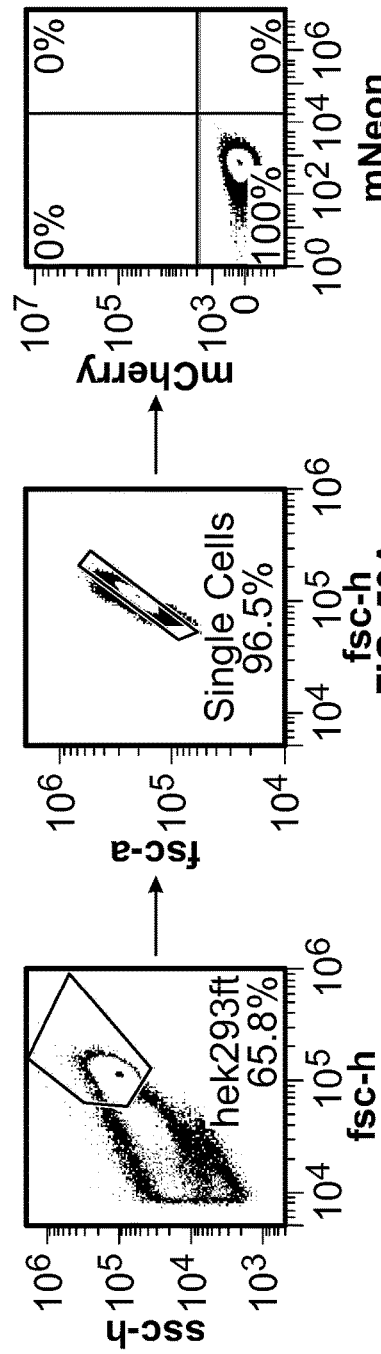
FIG. 59A is a visual depiction of the gating strategy used for flow cytometry analysis of fluorescent RADARS in HEK293 cells. Gates are drawn using a control population transfected with pUC19 plasmid.
Figure 59B:
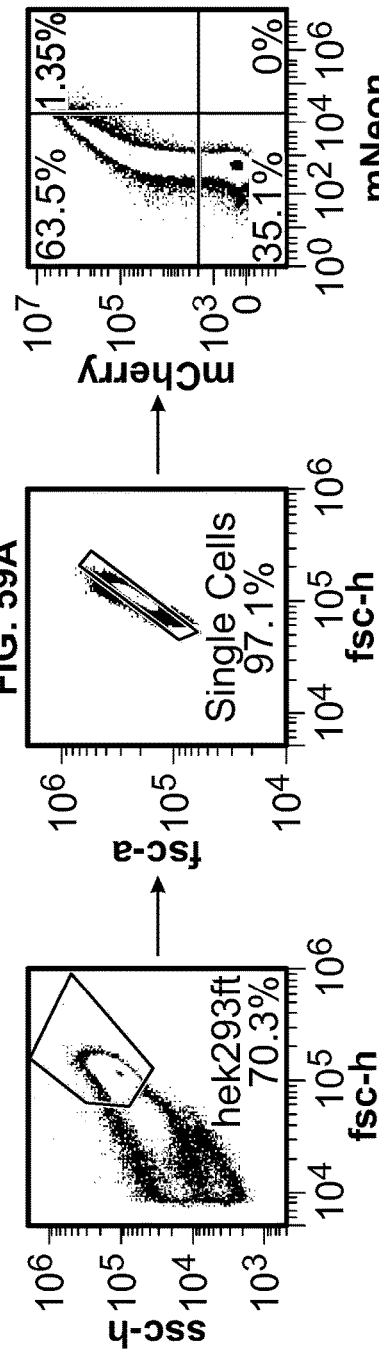
FIG. 59B is a visual depiction of the gates overlaid onto a population of cells transfected with EGFP-targeting RADARS, ADARp150, and pUC19 plasmid.
Figure 59C:
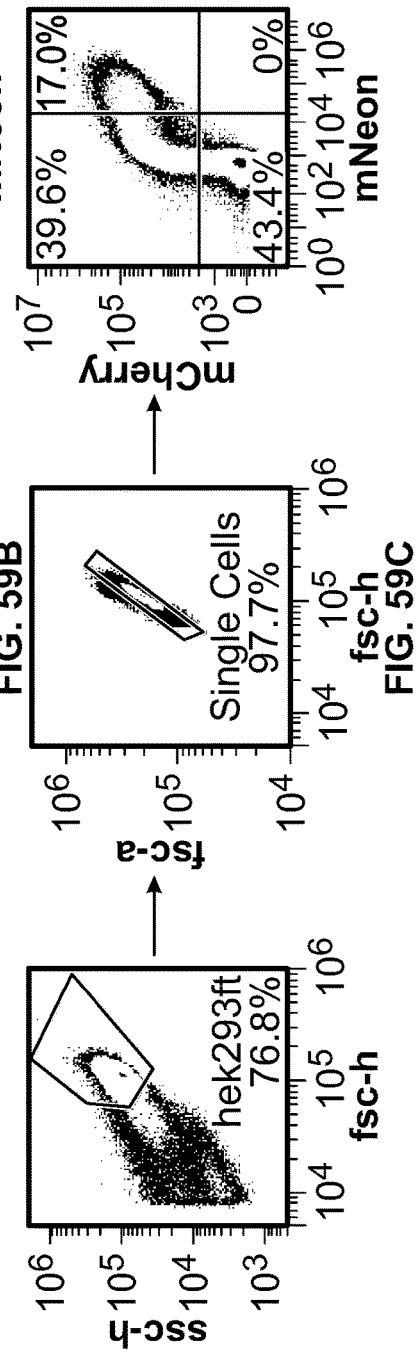
FIG. 59C is a visual depiction of the gates overlaid onto a population of cells transfected with EGFP-targeting RADARS, ADARp150, and EGFP-target (frame-shifted) plasmid.

To enable single-cell measurements with RADARSv2, we engineered a fluorescent payload for microscopy and flow-based readouts (FIG. 58A). We designed the fluorescent sensor as a single transcript, containing an upstream mCherry normalization control, separated by a self-cleaving peptide P2A sequence from the best EGFP-targeting engineered guide RNA, followed by a self-cleaving peptide sequence T2A, in front of a mNeon payload. We transfected HEK293FT cells with EGFP-targeting RADARS with or without combinations of exogenous ADAR1p150 or frame-shifted non-fluorescent EGFP target transcripts. We observed mNeon fluorescence signals by microscopy in the presence of the target transcript, and a negligible background in the absence of the target transcript (FIG. 58A). Quantification of fluorescent signals by flow cytometry revealed a shift in the distribution of mNeon/mCherry ratio, from 1.00% mNeon/mCherry positive cells in the absence of the target transcript, to 56.1% mNeon/mCherry positive cells in the presence of the target transcript, with a 38-fold increase in the ratio of the geometric means (FIG. 58B, FIG. 59A-C).

Figure 60A:
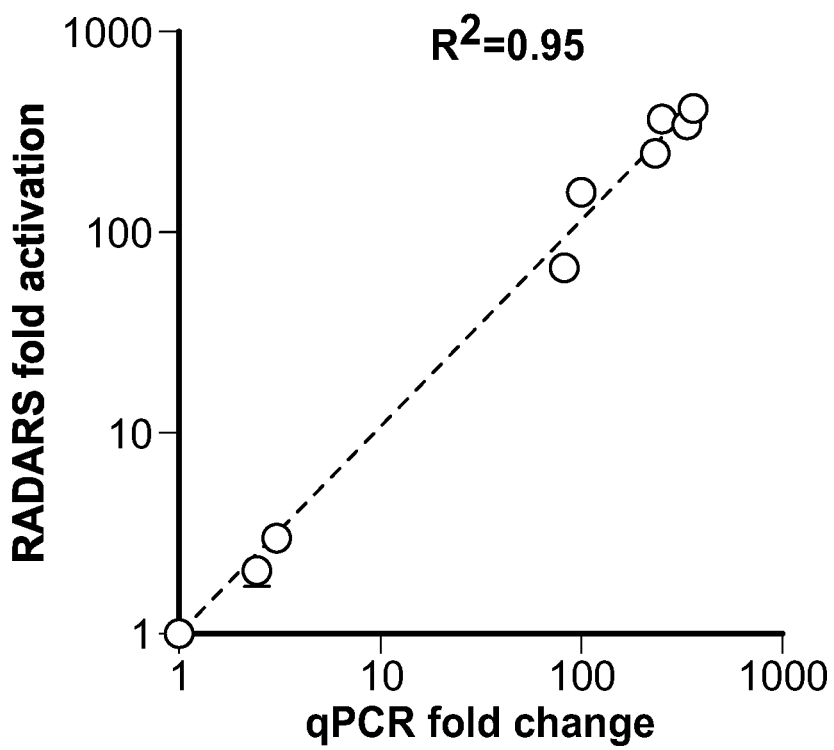
FIG. 60A is a visual depiction of RADARS fold activation relative to the basal condition (0ng/mL doxycycline in the integrated HEK293FT cells) is plotted against the IL6 gene expression change as determined by quantitative polymerase chain reaction (qPCR) on log 10–log 10 scale. Blue dashed line represents the linear regression results of the data. Data are mean of technical replicates (n=3)±s.e.m.
Figure 60B:
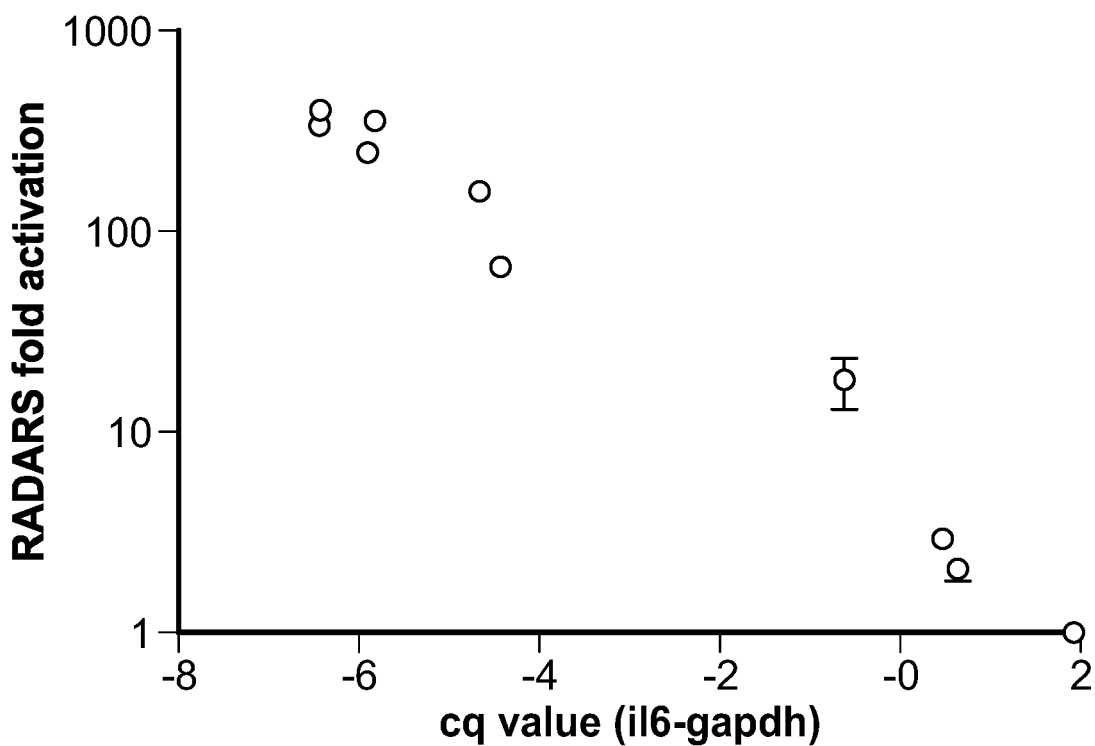
FIG. 60B is a visual depiction of the raw Cq value of IL6 transgene normalized by subtraction to GAPDH gene Cq number and the RADARS corresponding fold activation. Error bars indicate standard error of the mean (n=3 biological replicates).
Figure 60C:
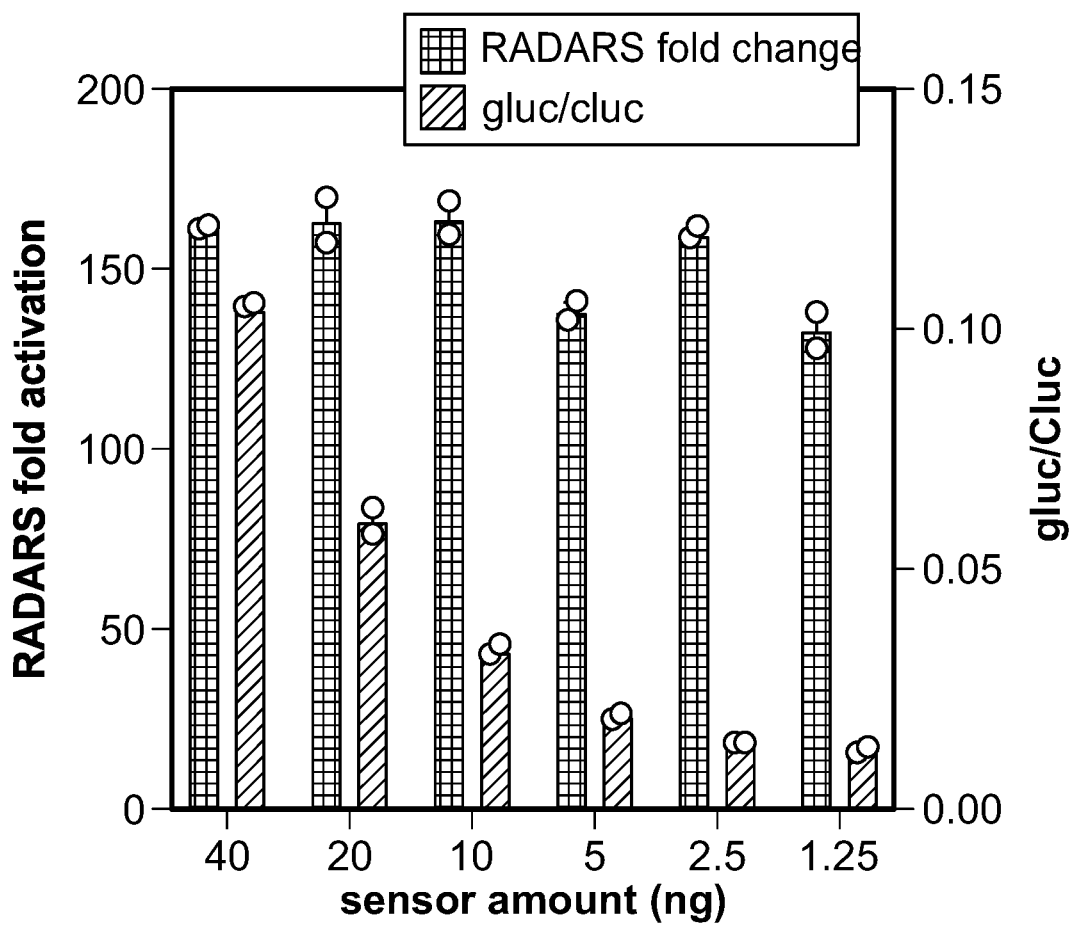
FIG. 60C is a visual depiction of the effect of titrating the best IL6 engineered guide RNA RADARS sensor amount on resulting activation and overall protein production in the plus target condition (gluc/cluc ratio). For conditions below 40 ng, the remaining plasmid amount was substituted with pUC19 plasmid. Error bars indicate standard error of the mean (n=3 technical replicates).

To further explore the quantitative accuracy of RADARS, we used transfected and virally integrated versions of a tetracycline-inducible IL-6 expression system to generate a wide range of expression levels and measured the luciferase response with the best IL-6 sensing engineered guide RNA. RADARS luciferase activation was quantitative and had a linear correlation with the concentration of the target transgene as confirmed by qPCR (FIG. 60A, FIG. 60B, R2=0.95). Furthermore, RADARS activation was invariant to the amount of sensor transfected, with robust activation rates across a large titration of sensor loads, allowing for tuning of total sensor output independent of overall sensor activation (FIG. 60C).

Figure 61:
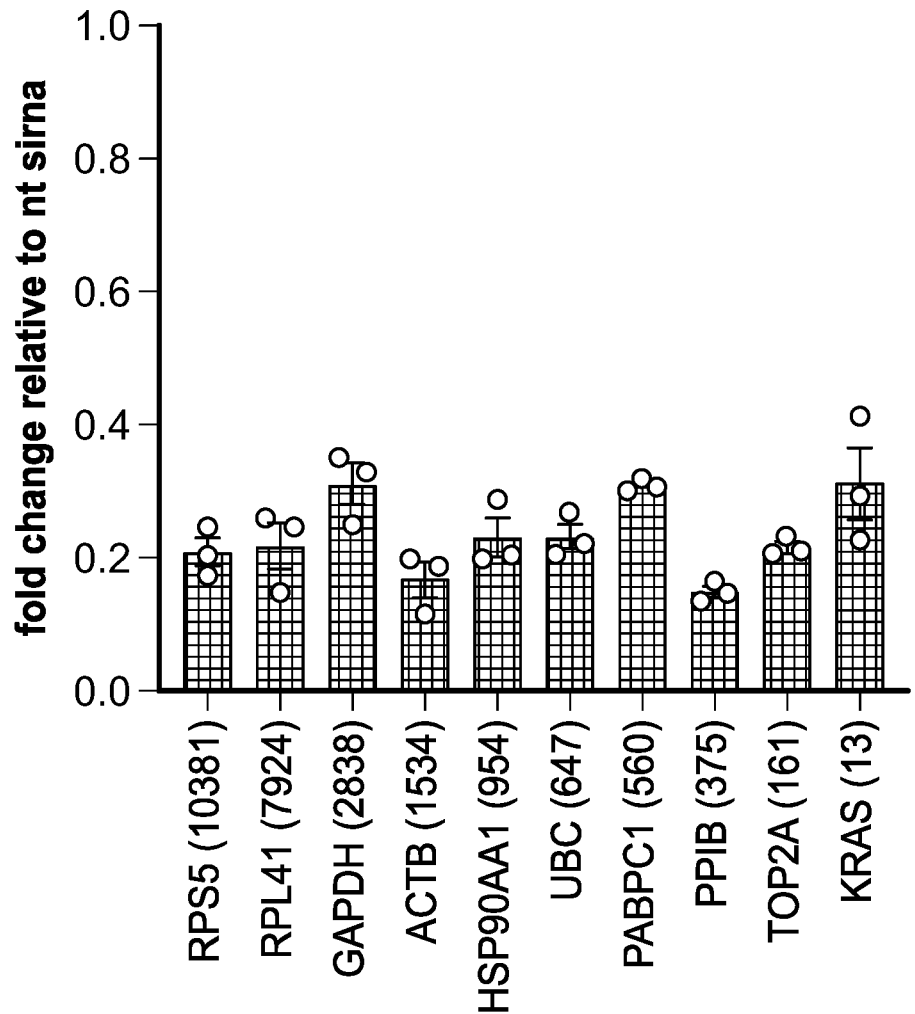
FIG. 61 is a visual depiction of the results of a validation experiment of siRNA knockdown of 10 endogenous transcripts as measured by qPCR expression. Fold change is calculated by the gene expression of the target transcript in the on-target siRNA group over the non-target siRNA group. (n=3 biological replicates).
Figure 62A:
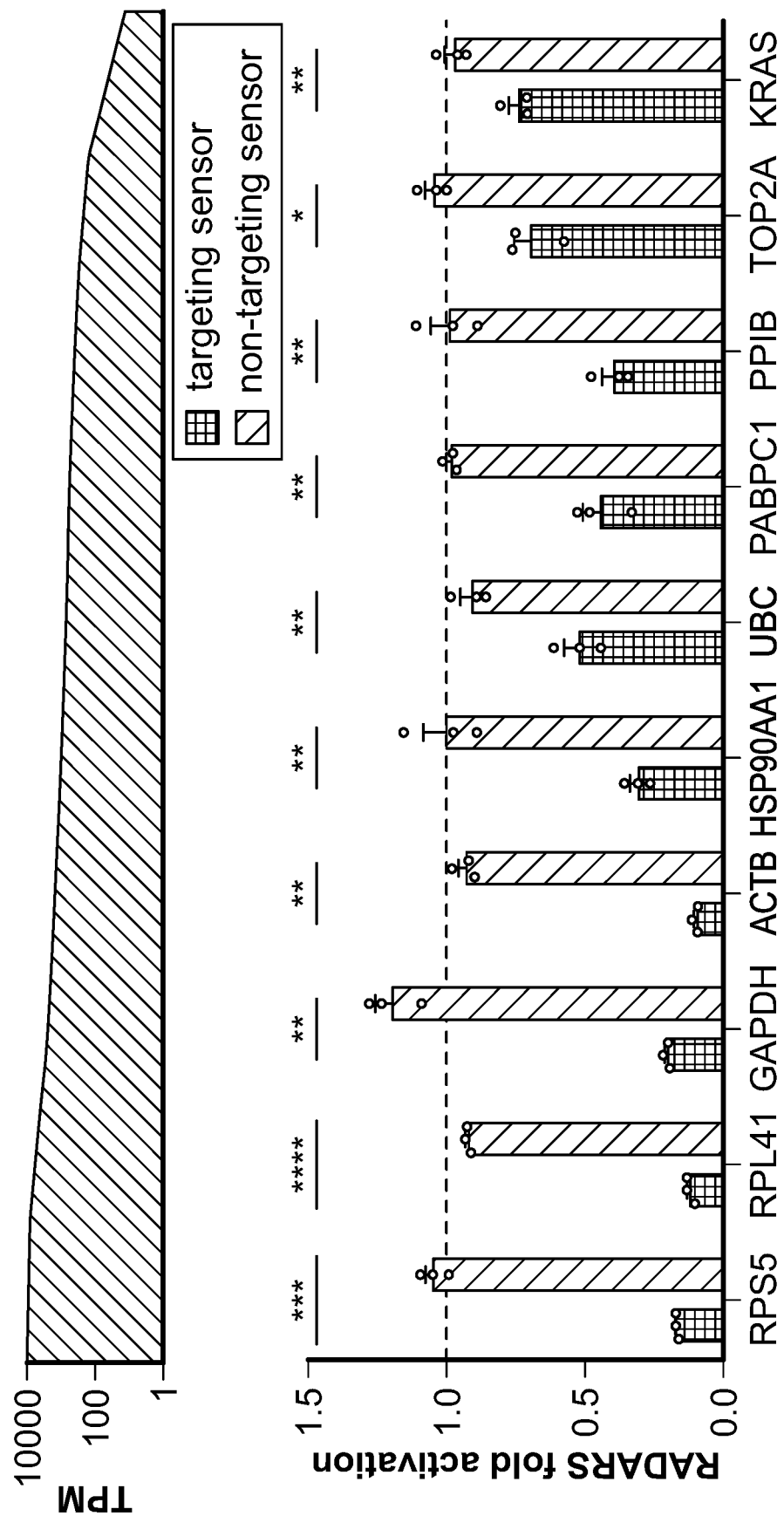
FIG. 62A (top) is visual depiction of the gene expression in transcripts per million (TPM) shown in log scale across ten genes ranging from 10,381 TPM (RSP5) to 13 TPM (KRAS). Bottom: RADARSv2 detection of transcripts in cells treated with 100 nM of targeting siRNA pool or non-targeting siRNA pool. The bars denote fold activation (Gluc/Cluc ratio of RADARS in the targeting siRNA group relative to the non-targeting siRNA group) of targeting RADARS and non-targeting RADARS constructs. Significance is determined via unpaired t-test between targeting and non-targeting RADARS with Welch correction assuming individual variance for each group (*, $p<0.05$. , $p<0.01$. *, $p<0.001$. ****, $p<0.0001$).
Figure 62B:
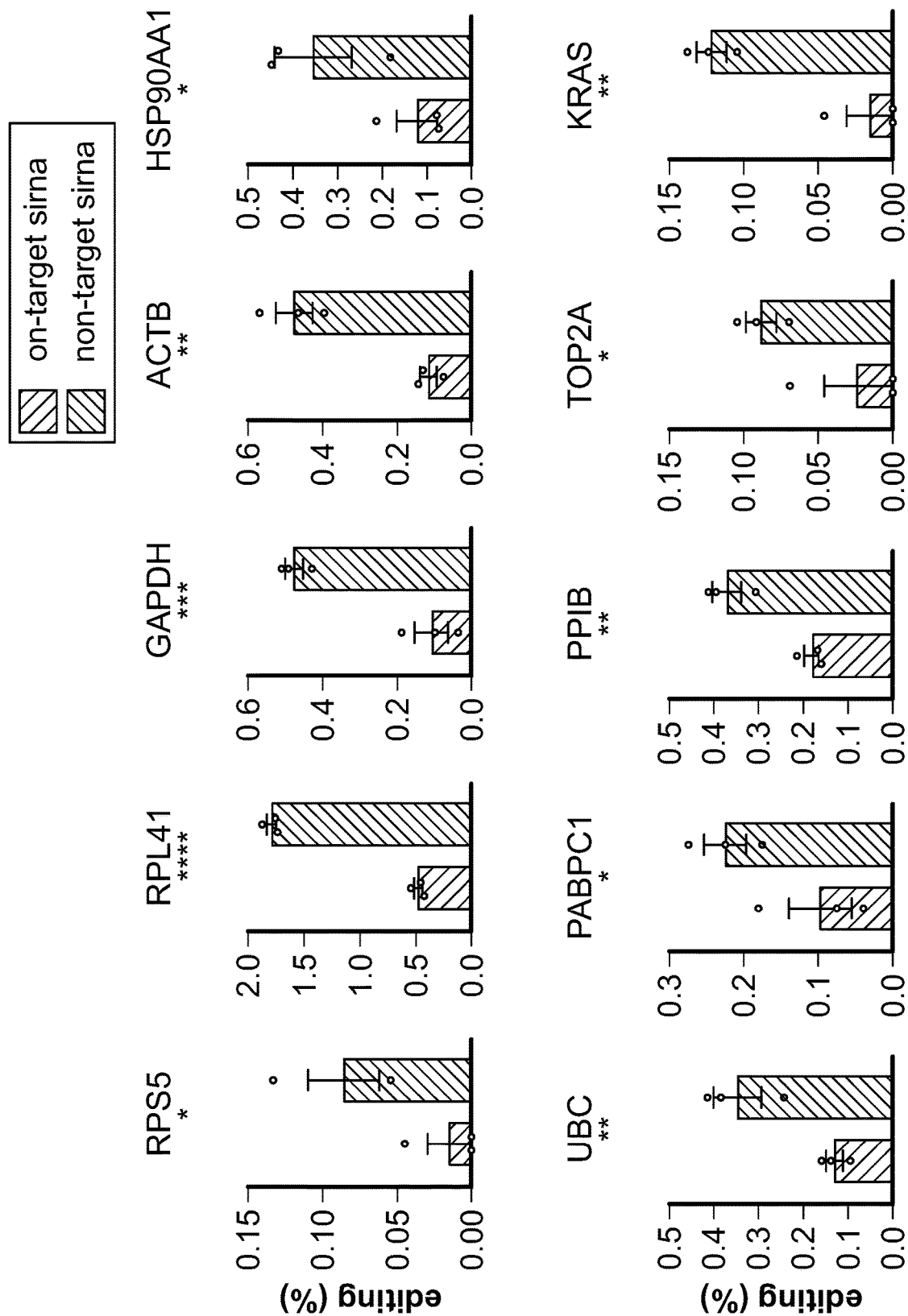
FIG. 62B is a graphical depiction of the editing rate of the UAG stop codon in the best performing sensor in each gene group from b. One-tailed unpaired t-test's carried between the ontarget siRNA group and the non-target siRNA group. (*, $p<0.05$. , $p<0.01$ *, $p<0.001$. ****, $p<0.0001$) Error bars indicate standard error of the mean (n=3 technical replicates).
Figure 63A:
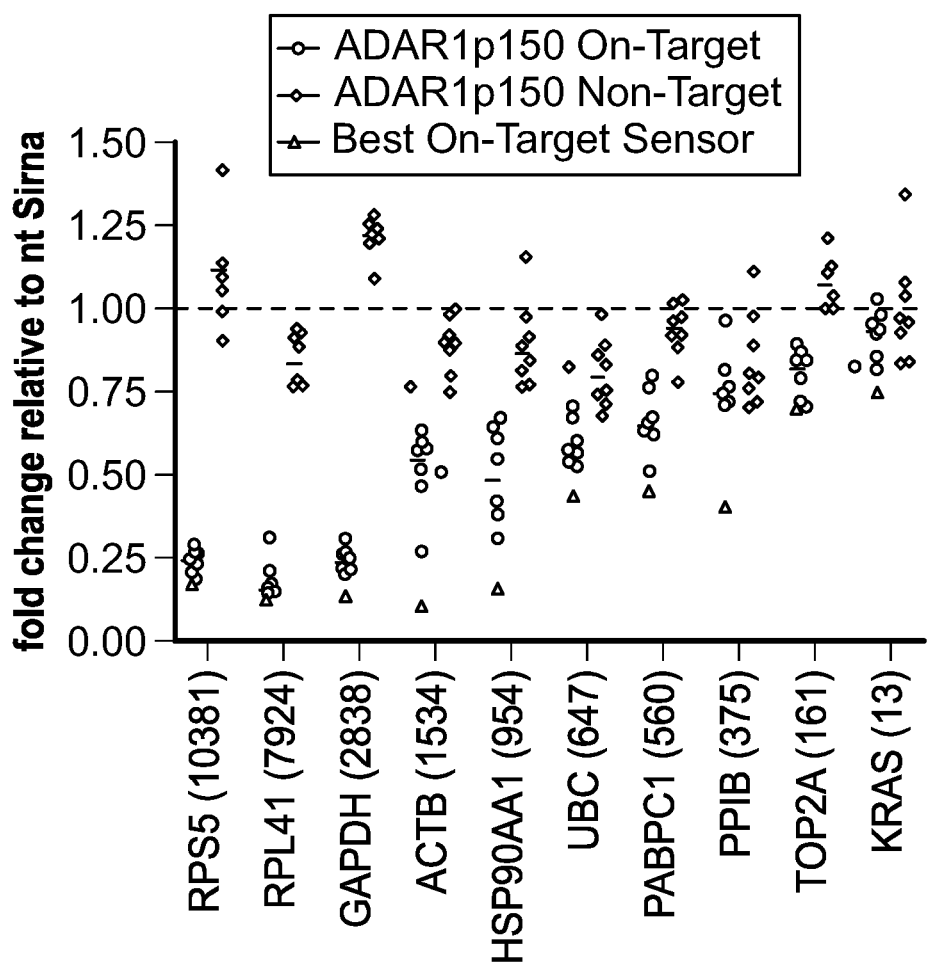
FIG. 63A is a graphical depiction of the performance of 8 randomly selected engineered guide RNAs targeting 10 endogenous transcripts and 8 randomly selected non-targeting engineered guide RNAs. Fold activation of RADARS is calculated by the Gluc/Cluc ratio in the on-target siRNA group over the non-target siRNA group. The best performing targeting sensors for each gene are labeled as yellow and examined in FIG. 63. Horizontal line represents the mean of each group.

We further designed sensors against a panel of 10 different transcripts, ranging in TPMs from ~10,000 to ~10 in HEK293FT cells for validation. For each transcript, we compared 8 different targeting engineered guide RNAs and 8 non-targeting engineered guide RNAs. Following siRNA transfection, we validated the knockdown of these 10 genes by qPCR (FIG. 61) and observed significant decreases in RADARS signal for each transcript compared to non-targeting sensor controls, engineered guide RNA robustness was associated with expression: for highly expressed genes, a majority of the eight different targeting engineered guide RNA detected target transcript knockdown, but with decreasing expression levels, fewer engineered guide RNAs successfully detected knockdown (FIG. 63A). Despite the RADARS sensitivity dropping at lower TPMs, at least one engineered guide RNA of the eight tested was capable of significantly detecting transcript knockdown (FIG. 62A). These data suggest that RADARS is sensitive to relative changes in gene expression across a wide range of expression levels. Measuring the editing rate of the UAG stop codon for the best performing sensor of each of the 10 target transcripts (FIG. 62B), we found that the overall editing rate is low, but there is a statistically significant reduction in editing rate when the target was knocked down for all 10 genes. Since RADARS is overexpressed relative to the endogenous target with a low turn-over rate, the editing rate of the stop codon will be less sensitive to copy-number fluctuations of the target.

Figure 63B:
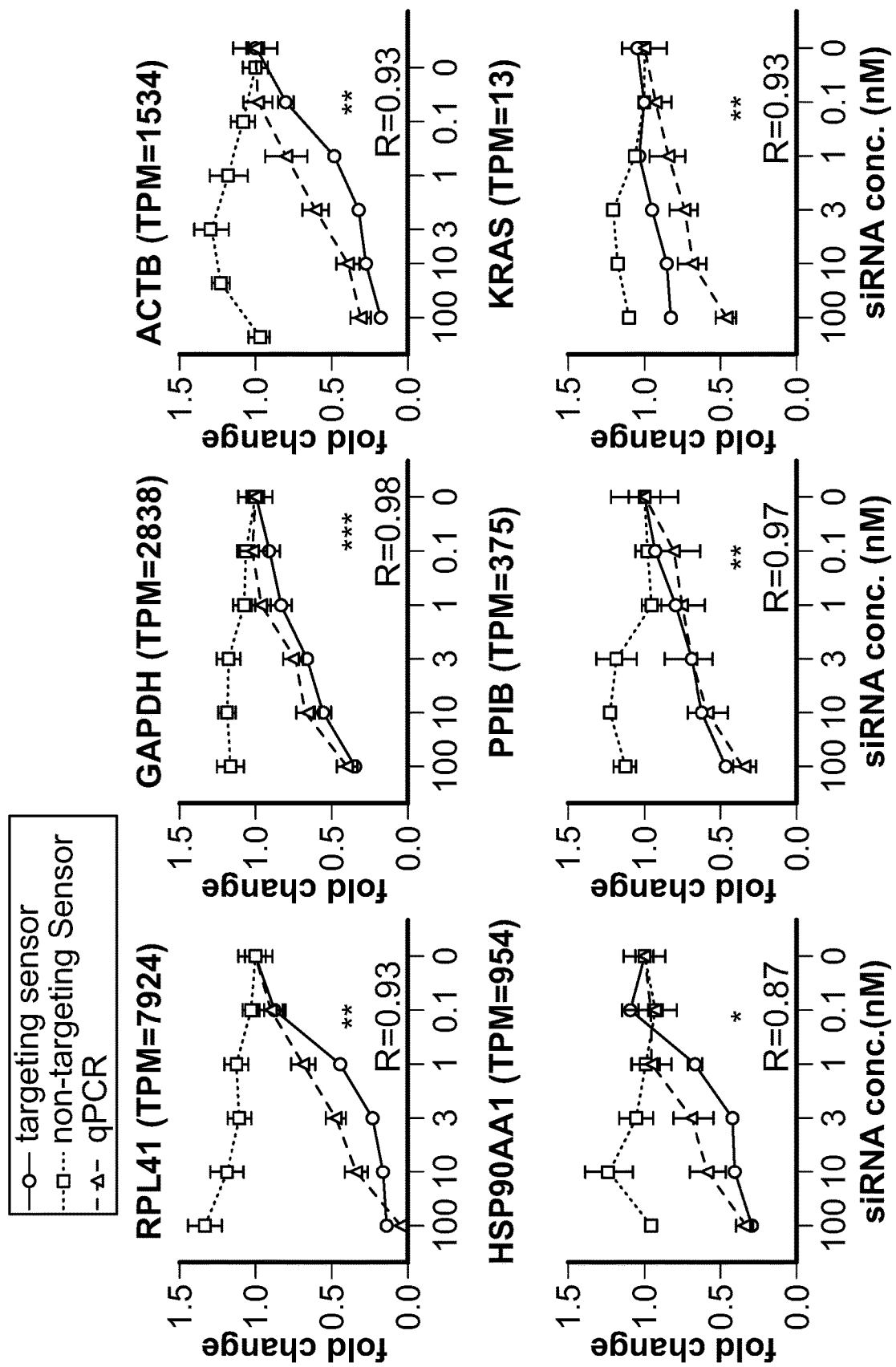
FIG. 63B is a visual depiction of RADARSv2 targeting RPL41, GAPDH, ACTB, HSP90AA1, PPIB, and KRAS, tracking the expression of these transcripts over a range of siRNA concentrations. The blue and beige lines represent fold activation of RADARS (Gluc/Cluc) ratio and fold change of qPCR-quantified expression, respectively, relative to 0 nM siRNA. The gray line represents the fold activation of non-targeting engineered guide RNAs (non-complementary to the target transcript). Data are mean of technical replicates (n=3)±s.e.m. (R value denotes pearson correlation between qPCR and targeting RADARS, *, $p<0.05$. , $p<0.01$. *, $p<0.001$).

We next sought to determine the sensitivity of RADARS by measuring changes in gene expression of endogenous targets. To test RADARS across a range of endogenous transcript expression levels, we applied sensors to measure transcriptional downregulation via siRNA (FIG. 63). We utilized commercially validated siRNA pools targeting 6 endogenous genes, divided between highly expressed genes RPL41, GAPDH, and ACTB, and the medium to lowly expressed genes HSP90AA1, PPIB, and KRAS. For each transcript, we first compared 8 different engineered guide RNAs for the highest sensitivity to knockdown (FIG. 63A).

Next, we titrated the amount of siRNA to generate a range of expression levels, which were confirmed by qPCR, and tracked changes in expression levels using the best engineered guide RNA supplemented with exogenous ADAR1p150. We observed that for all six genes, RADARS tracks qPCR-measured transcript levels with a high Pearson correlation (R>0.86, FIG. 61B). We found that for KRAS, which is expressed at TPM (transcripts per million) of 13 in HEK293FT cells (Karlsson et al., 2021), raw RADARS activation fold activation deviated from qPCR measured fold change presumably due to the loss of sensitivity at such low expression levels. However, the RADARS response was still highly correlated to the qPCR-determined KRAS levels (R=0.93, FIG. 61B).

Figure 64A:
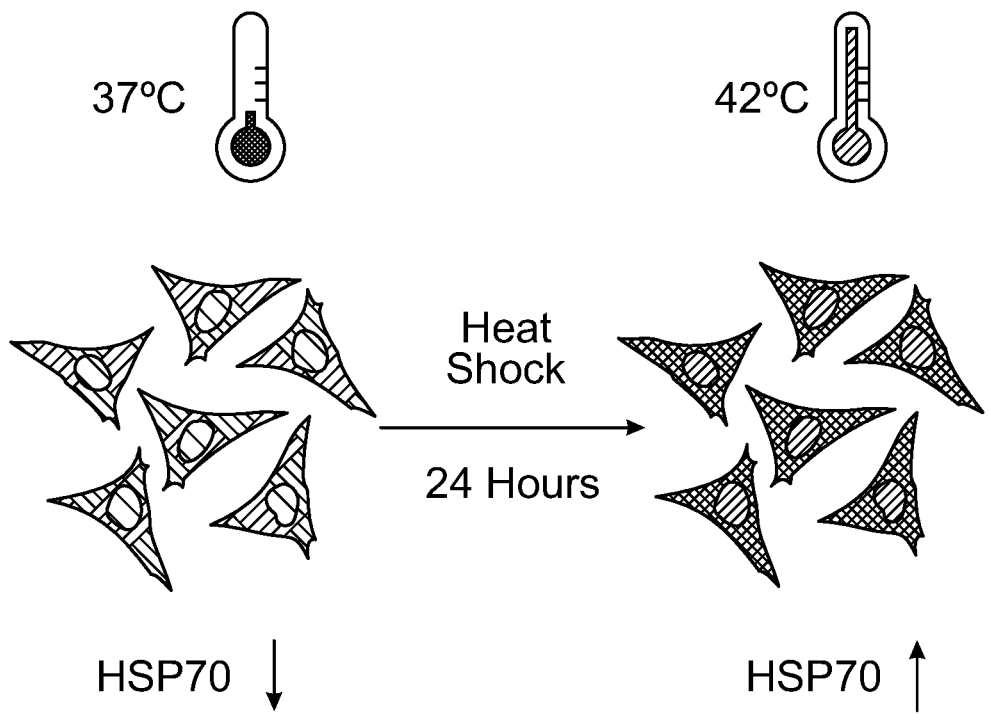
FIG. 64A is a visual schematic of heat shock protein family gene HSP70 upregulation during heat shock at 42 degrees Celsius.
Figure 64B:
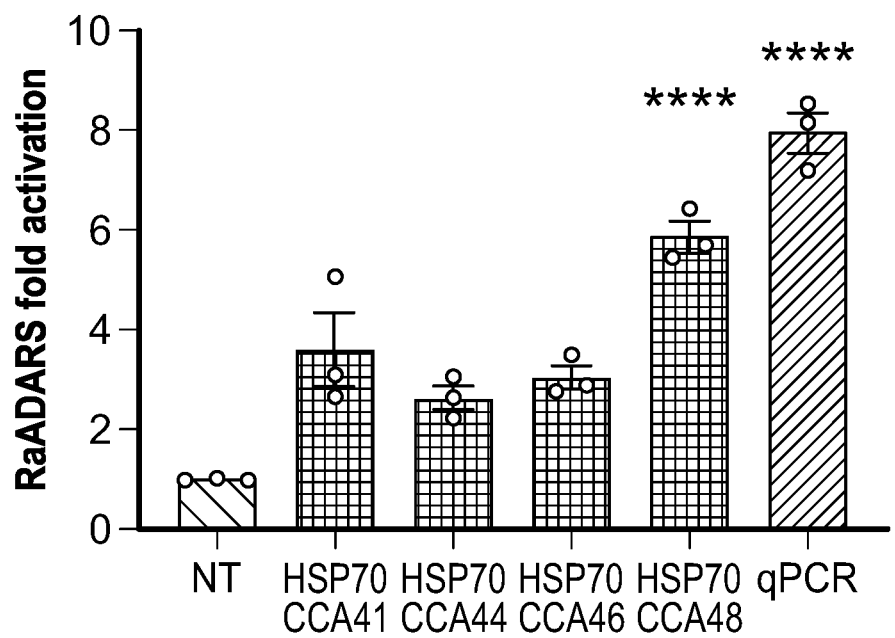
FIG. 64B is a visual depiction of results from an experiment in which four HSP70-targeting engineered guide RNAs targeting different CCA sites and a scrambled non-targeting (NT) engineered guide RNA, all with exogenous ADAR1p150 supplementation, were transfected into HeLa cells followed by 24 hours at 42° C. or 37° C. qPCR and RADARSv2 detected HSP70 expression differences between the 37 degrees Celsius (control) and 42 degrees Celsius (heat shock) groups. Sensor activation is calculated between the 42° C. and 37° C. groups and is normalized to the NT condition. Data are mean of technical replicates (n=3)±s.e.m.

Next, we investigated whether RADARS could sense upregulation of endogenous transcripts, using a cellular heat shock model that leads to upregulation of heat-shock family genes. We designed RADARSv2 engineered guide RNAs targeting HSP70, a dynamic heat-shock response protein, and transfected them into HeLa cells along with exogenous ADAR1p150 before exposing cells to heat-shock at 42° C. (FIG. 64A). RADARS had strong agreement with qPCR, with the best HSP70 targeting engineered guide RNA producing a 5.9-fold activation in response to heat shock, relative to a 7.2 fold increase in HSP70 transcript expression level as measured by qPCR (FIG. 64B). These results suggest that RADARS is sensitive to upregulation of endogenous transcripts and can detect relative gene expression changes with high fidelity.

Example 8. Logic Gates

Figure 40A:
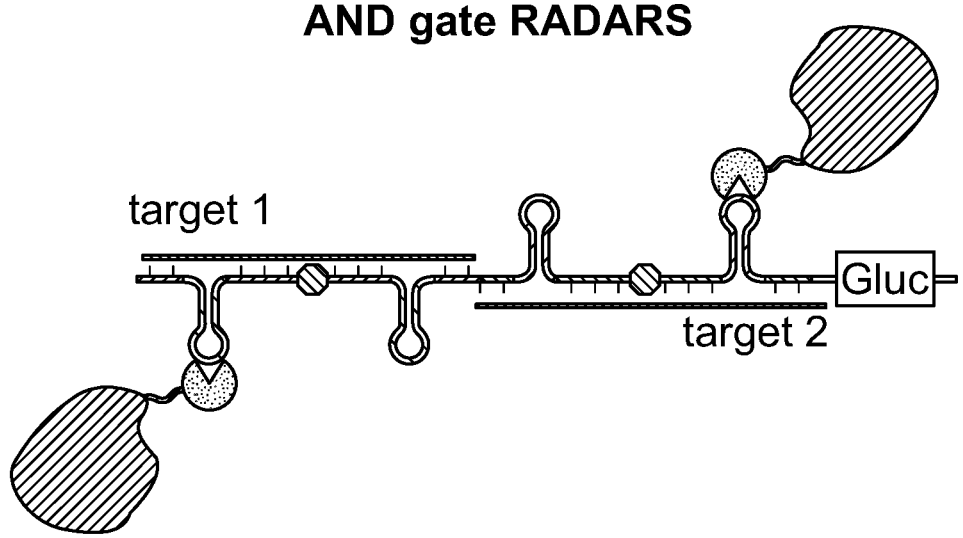
FIG. 40A is a schematic representation of a AND gate.
Figure 40B:
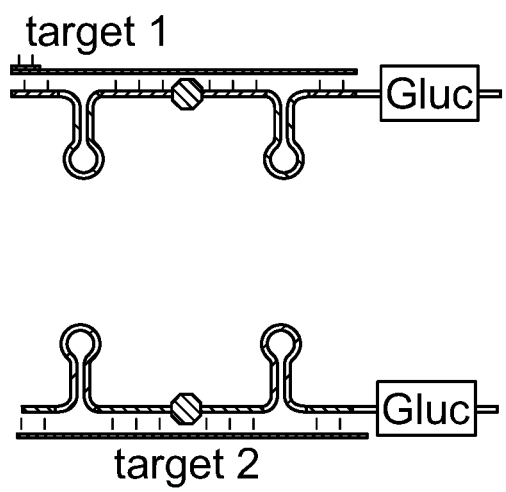
FIG. 40B is a schematic representation of an OR gate.
Figure 40C:
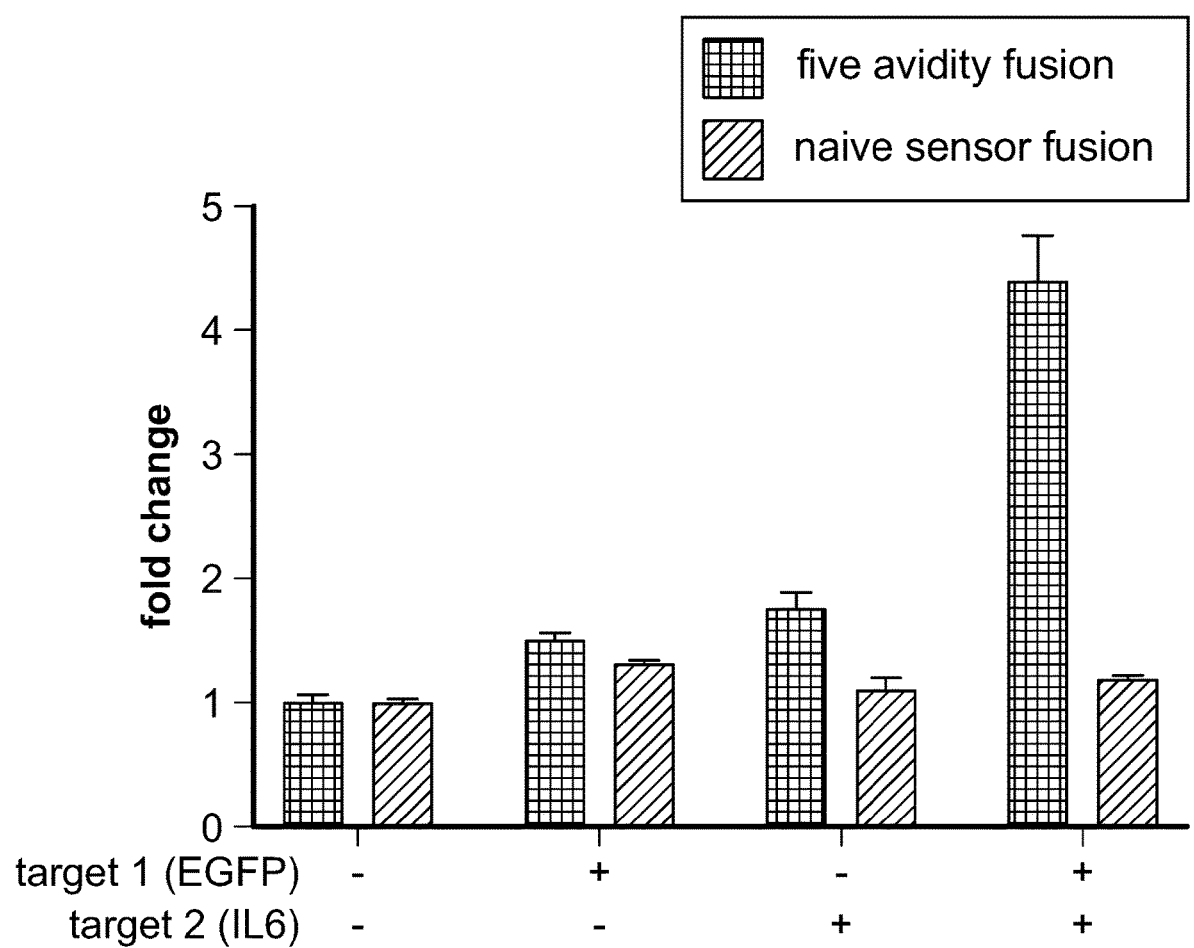
FIG. 40C is a graphical illustration comparing activation fold change of naive 51 nt guide AND gate sensor and five avidity guide AND gate sensor across all four combinations of IL6 and EGFP target induction.

We also set out to determine if the ADAR sensors of the present disclosure could be multiplexed into a logic system, which could comprise AND gates and OR gates. These AND OR approaches are schematically shown in FIG. 40A (AND) and FIG. 40B (OR). An AND gate can only fully deliver a payload if both target strands are present. However, an OR gate can deliver a payload in the presence of either 1 of the target strands, and not both. To generate a rudimentary AND gate, we connected two single 51 nt guides, targeting EGFP and IL6 respectively, in tandem with an MS2 hairpin loop. However, this design performed poorly, due to a combination of low signal and background readthrough (FIG. 40A).

Figure 65A:
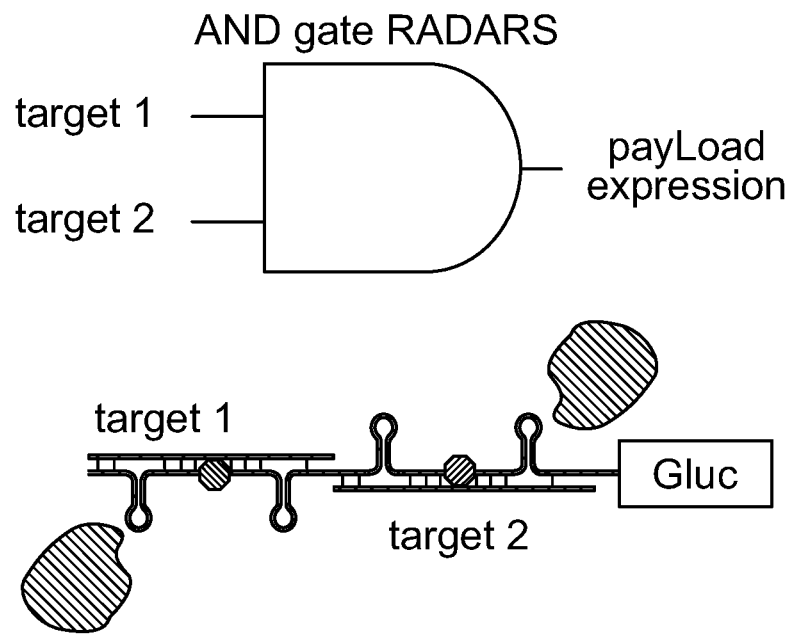
FIG. 65A is a visual schematic of two input AND gate with RADARS.
Figure 65B:
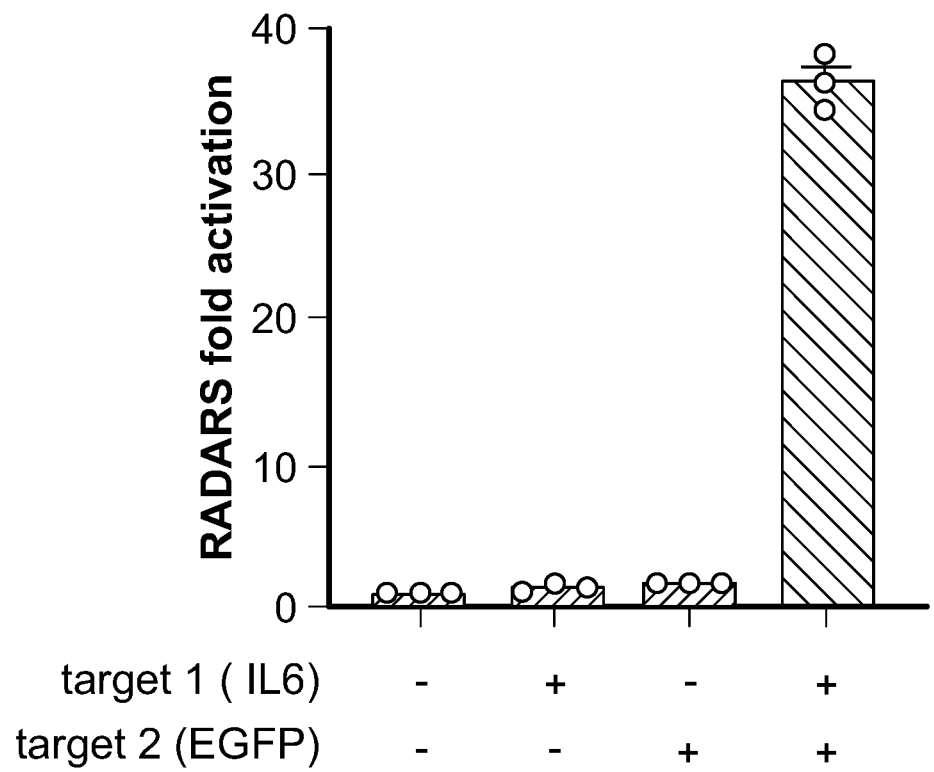
FIG. 65B is a graphical depiction of normalized sensor activation of AND gate RADARS for EGFP and IL6 transcript inputs across all four possible target combinations. Data are mean of technical replicates (n=3) ±s.e.m.

To improve AND gate signal, we used the RADARSv2 design and found that the resulting AND gate sensor behaved in a target specific manner, requiring both targets to reach full activation, with only minor leakage in the single-target conditions (FIG. 65A, FIG. 65B). The AND logic strand exhibited 36 fold activation in the presence of both target transcripts with only 1.3-1.5 fold activation when only one target RNA was present (FIG. 65B).

To engineer an OR gate logic, we co-transfected two five-binding site avidity sensors targeting EGFP and IL6. These sensors responded to EGFP or IL6 target transcripts in a manner consistent with an OR gate (FIG. 41B). The OR logic sensors exhibited a significantly increased fold change in the presence of each gene individually, but not in the absence of both genes. In total, these results suggest the modularity of ADAR SENSOR enables logical computations to be performed on mRNA in living cells.

Figure 66A:
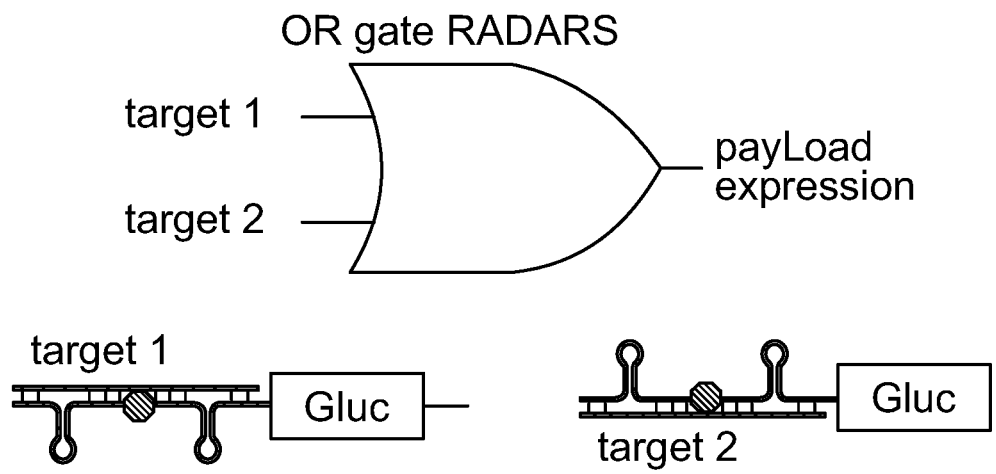
FIG. 66A is a visual schematic of two input OR gate logic with RADARS.
Figure 66B:
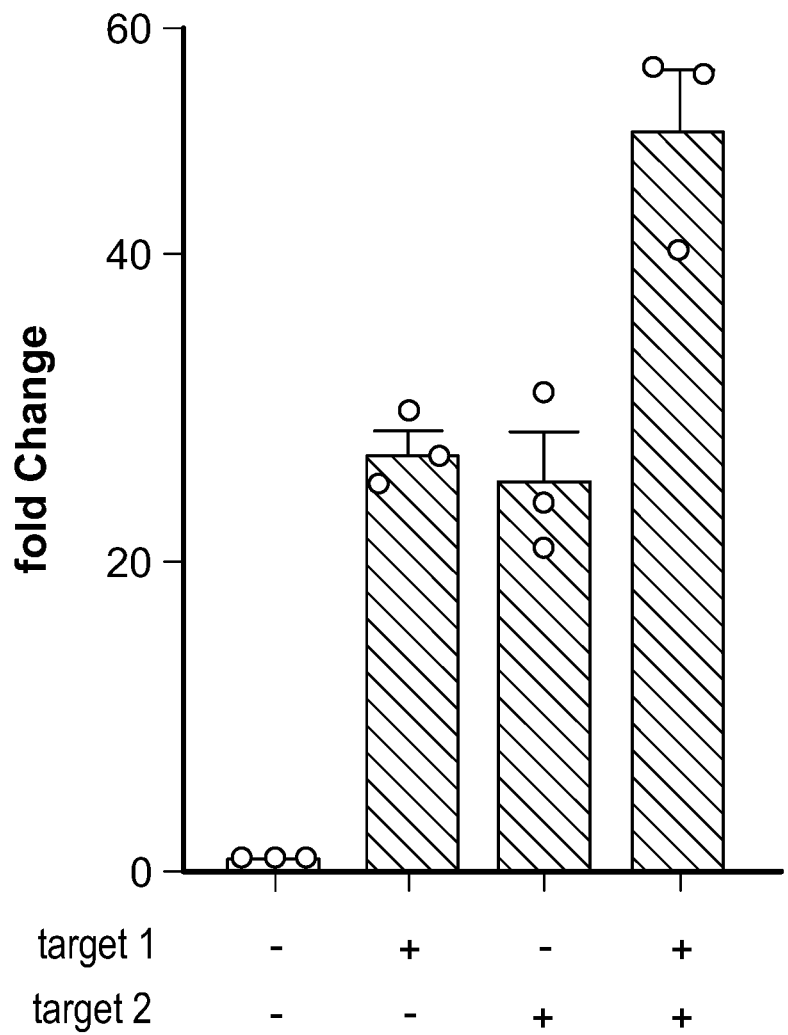
FIG. 66B is a graphical depiction of sensor activation of OR gate RADARS for all possible EGFP and IL6 transcript input combinations. Data are mean of technical replicates (n=3)±s.e.m.

To improve OR gate logic (FIG. 66A), we co-transfected two engineered guide RNA RADARSv2 (upstream ORF, out-of-frame stop codon) targeting EGFP and IL6 transcripts and saw that the sensors respond to EGFP or IL6 target transcripts in a manner consistent with an OR gate (FIG. 66B).

Example. 9 Use of ADAR Sensors to Induce Apoptosis in Target Cells

Figure 42A:
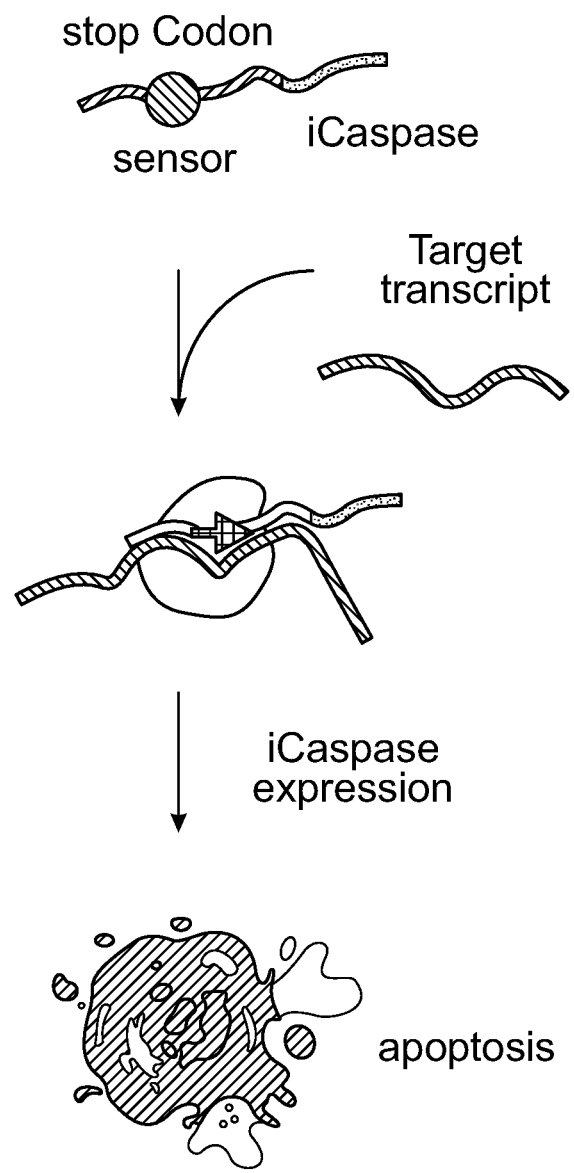
FIG. 42A is a schematic of an IL6 responsive caspase using ADAR SENSOR with a five-avidity sensor targeting human IL6 transcript. Sensor activation expresses a FKBP self-dimerizing Caspase9.
Figure 42B:
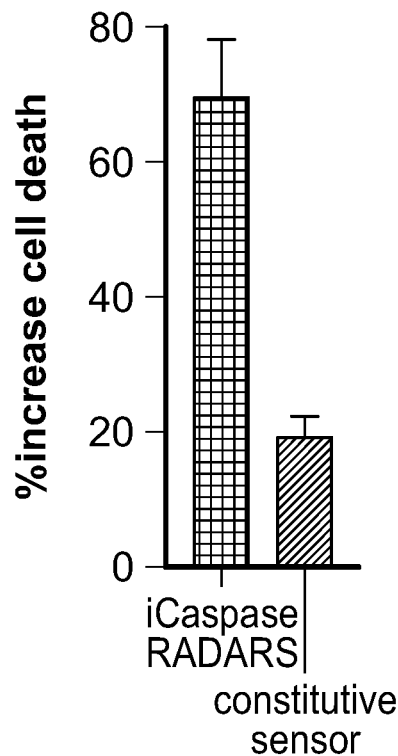
FIG. 42B is a graphical illustration of the fold change of cell death (apoptosis) in response to ADAR SENSOR activation by IL6 transcript detection. Positive control sensors involve a scramble guide sequence in front of the iCaspase with no stop codon in frame. Cell death fold change is determined by calculating the fold change of cell viability in the + target compared to the − target conditions.
Figure 42C:
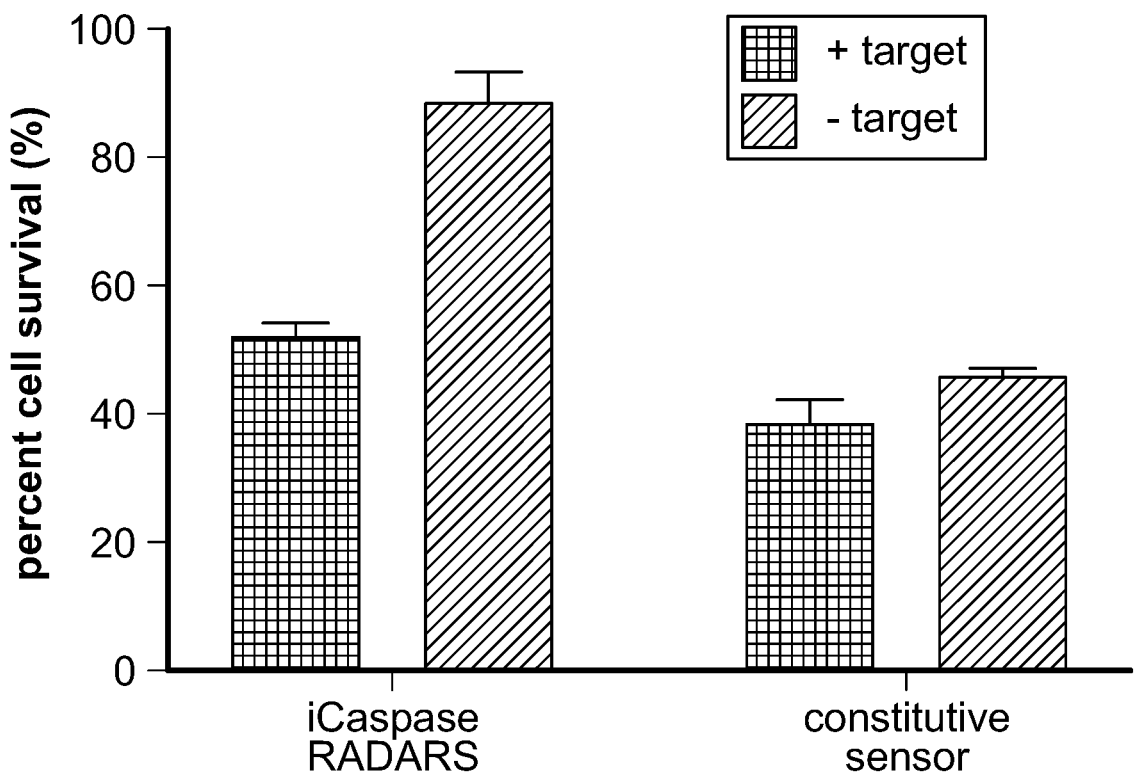
FIG. 42C is a bar plot comparing percent cell survival values of IL6 responsive iCaspase ADAR SENSOR and a no stop codon control in the + target and − target groups.

To determine if the ADAR sensors of the disclosure could be used to non-reporter payloads, we determined if the ADAR sensors could induce apoptotic cell death in a targeted group of cells. To apply ADAR sensors for cell state-specific killing, we engineered a payload with the therapeutically relevant iCaspase-9 (Straathof et al. 2005) (FIG. 42A). An iCaspase payload was engineered to a sensor strand that could target human IL6. Mammalian cells were transfected with the caspase ADAR sensor, target, and MCP-ADAR2dd. Twenty-four hours after transfection, cells were split 1:5 into fresh media and the +drug samples were supplemented with 10 nM of AP20187 (Sigma Aldrich). After 24 hours of additional growth, cells were assayed for viability by CellTiter-Glo Luminescent Cell Viability Assay (Promega). Control caspase was a sensor strand with a scrambled sensor region (i.e., it does not specifically target IL6) and a caspase with no intervening stop codon. Using the CellTiter-Glo Assay (Promega), cell death was measured as fold change in the luminescence value of cell lysates of the + target group over the − target group. We found that fusing an IL6 sensor using the dual stop codon seven avidity guide in front of the caspase selectively killed IL-6 expressing cells, with minimum toxicity in the absence of IL-6 induction (FIG. 42B, C). The IL6 responsive caspase exhibited a significant increase in the induction of apoptotic cell death, indicating that the ADAR sensors may be used to induce cell death in a target group of cells. See FIG. 42B. The percent cell survival in cells treated with an IL6 responsive caspase and those with a caspase and no stop codon was also analyzed, in cells with and without target transcript (FIG. 42C).

Next, we used a highly specific SERPINA1-targeting engineered guide RNA for cell specific-killing by combining the engineered guide RNA with iCaspase-9 payload (FIG. 67A) (Straathof et al., 2005). We co-transfected the SERPINA1-iCaspase9 RADARS with ADARp150 into A549, HeLa, and HepG2 cells, and assayed cell viability 48 hours after transfection. We found that the SERPINA1− targeting RADARS-iCaspase selectively killed HepG2 cells with minimum toxicity in other cell types, and the non-targeting negative controls showed no differential death (FIG. 673, FIG. 67C).

Example 10. Use of ADAR Sensors to Track Cell States and Cell Types

Figure 43A:
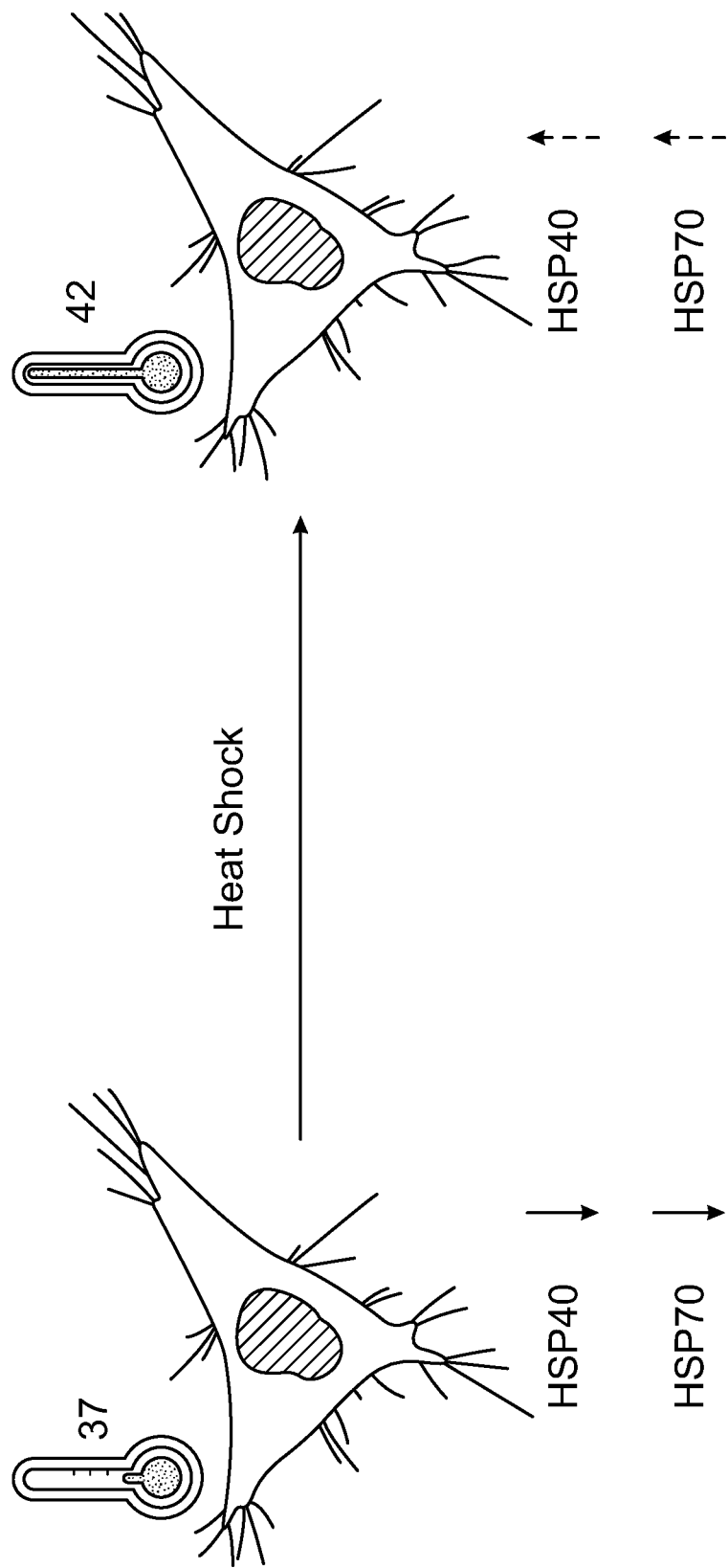
FIG. 43A is a visual representation of an experiment to examine the efficiency of ADAR sensors in a heat shock Assay. Heat shock of Hela cells at 42° C. is used to induce upregulation of HSP40 and HSP70 gene expression. HSP70 and HSP40 targeting sensors along with MCP-ADAR2dd (E488Q, T490A) or alone are transfected into Hela cells followed by 24 hours at 42° C. or 37° C.
Figure 43B:
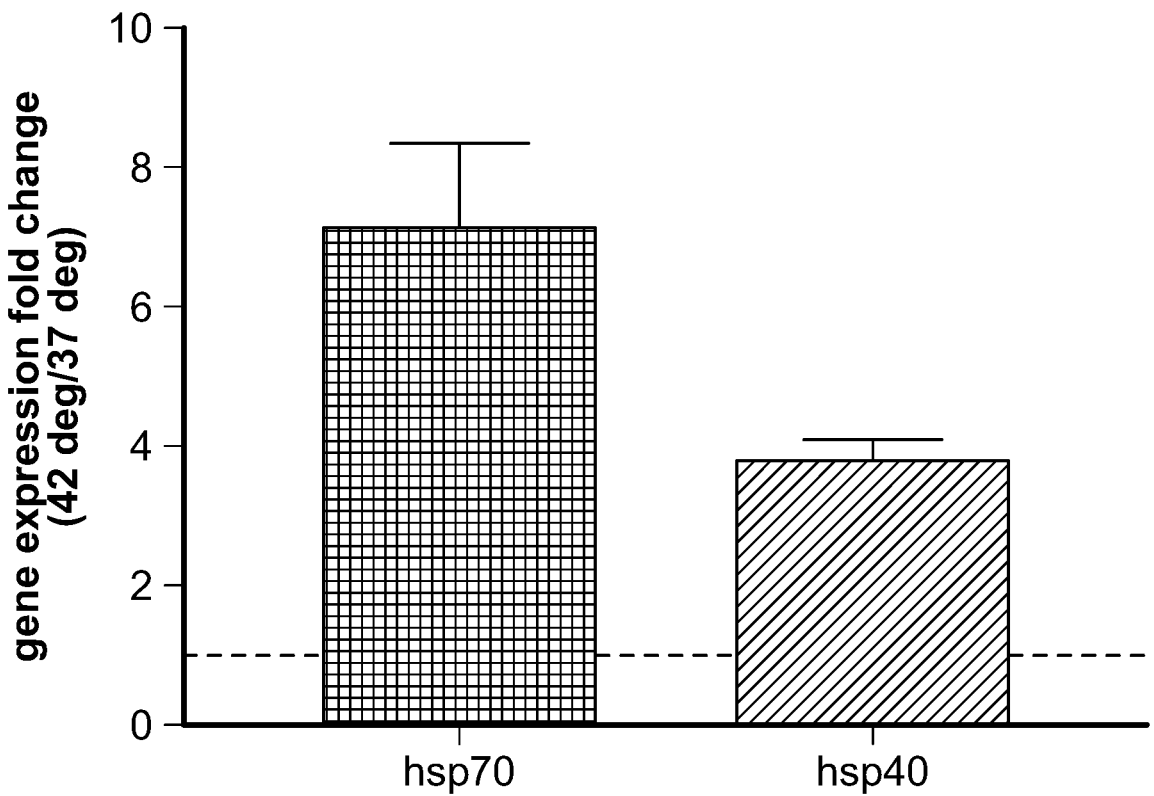
FIG. 43B qPCR validation of HSP40 and HSP70 levels upregulated after 24 hours of heat shock.
Figure 43C:
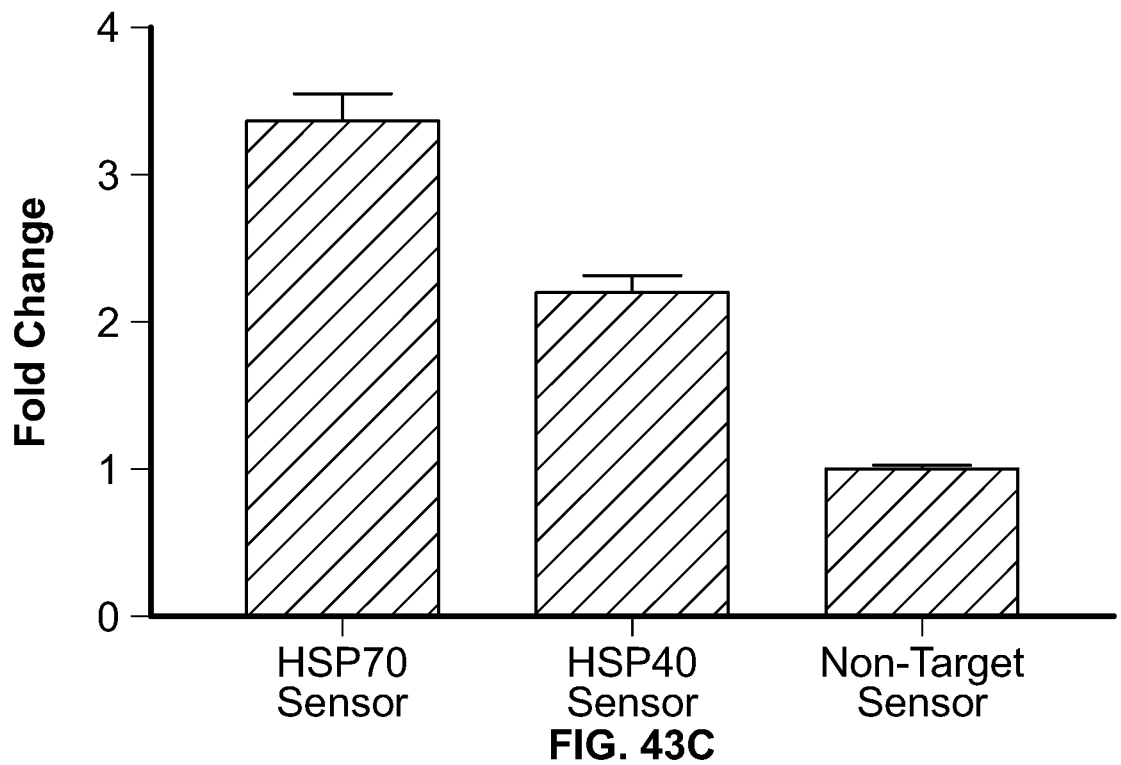
FIG. 43C Sensor activation is calculated between the 42° C. and 37° C. groups and is normalized to a sensor with a scrambled non-targeting guide to account for protein degradation changes.

To determine if the developed ADAR sensors could be employed to track cell states, the heat shock response of HeLa cells was first examined. Two sets of Hela cells were transfected with ADAR sensors, with guides designed to target the heat shock family genes, including HSP70 and HSP40. HSP70 and HSP40 can be upregulated in a heat shock model in vitro (FIG. 43A, B). ADAR sensors with either the 5 site or 7 site avidity binding guide designs detected both HSP70 and HSP40 upregulation in cells exposed to heat shock (FIG. 43A). HeLa cells (ATCC CCL-2) were transfected with either HSP40 or HSP70 ADAR sensors. 24 hours post transfection, a portion of cells are moved to 42 degrees Celsius (5% CO2) for 24 hours. Media was harvested at the end of 24 hours of heat shock and subjected to luciferase measurements. To control for non-specific changes to translation as a result of heat shock, we transfected a scrambled non-targeting guide. Normalizing against the non-targeting guide, we found up to 3-fold activation of the ADAR sensors in response to heat shock (FIG. 43C).

Figure 68:
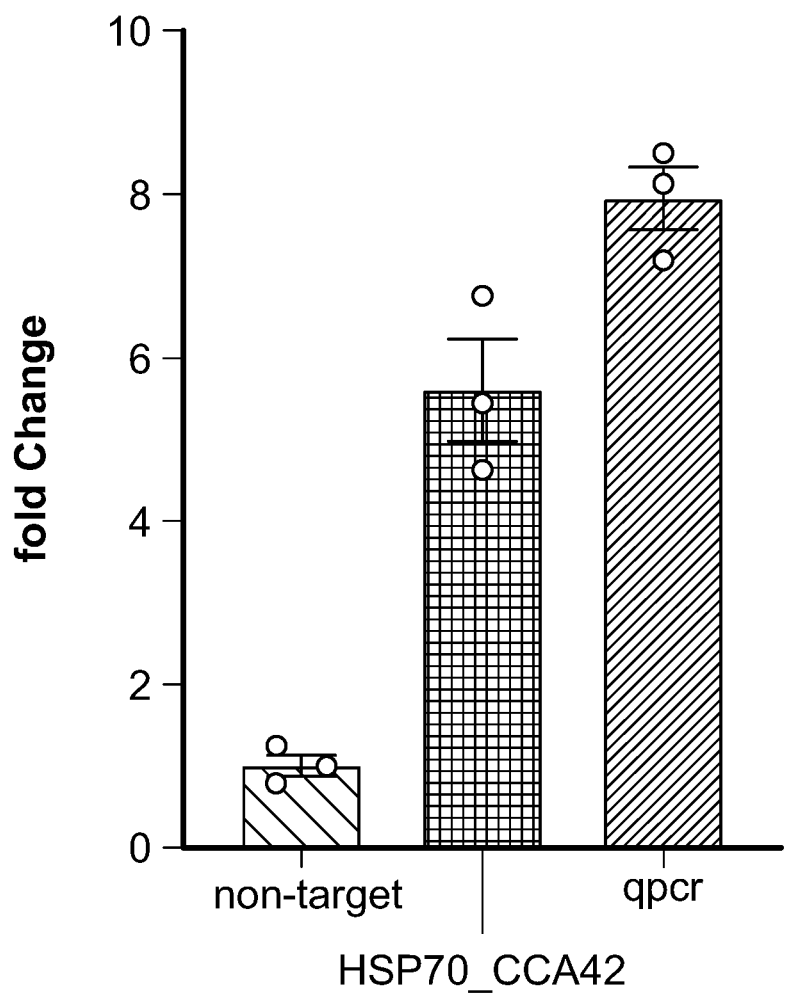
FIG. 68 is a graphical depiction of the results of an experiment in which the best HSP70 targeting RADARS construct on the HSP70 transcript and a scrambled non-targeting (NT) RADARS construct, without exogenous ADAR were transfected into HeLa cells followed by 24 hours at 42° C. or 37° C. qPCR and RADARSv2 detected HSP70 expression differences between the 37 degrees Celsius (control) and 42 degrees Celsius (heat shock) groups. Sensor activation is calculated between the 42° C. and 37° C. groups and is normalized to the NT condition, which is a sensor with a scrambled non-targeting engineered guide RNA (NT) to control for changes in protein production. Data are mean of technical replicates (n=3)±s.e.m.

We repeated the heat shock experiment (FIG. 64) with the RADARSv2 design, only delivering the RADARSv2 sensor without ADAR supplementation and designed sensors. We found that the best HSP70 sensor (CCA42) could leverage endogenous ADAR inside Hela cells to track the upregulation of HSP70 during heat shock (FIG. 68), and thus demonstrate the feasibility of a single-component RADARSv2 system to be deployed using endogenous ADAR.

Figure 44A:
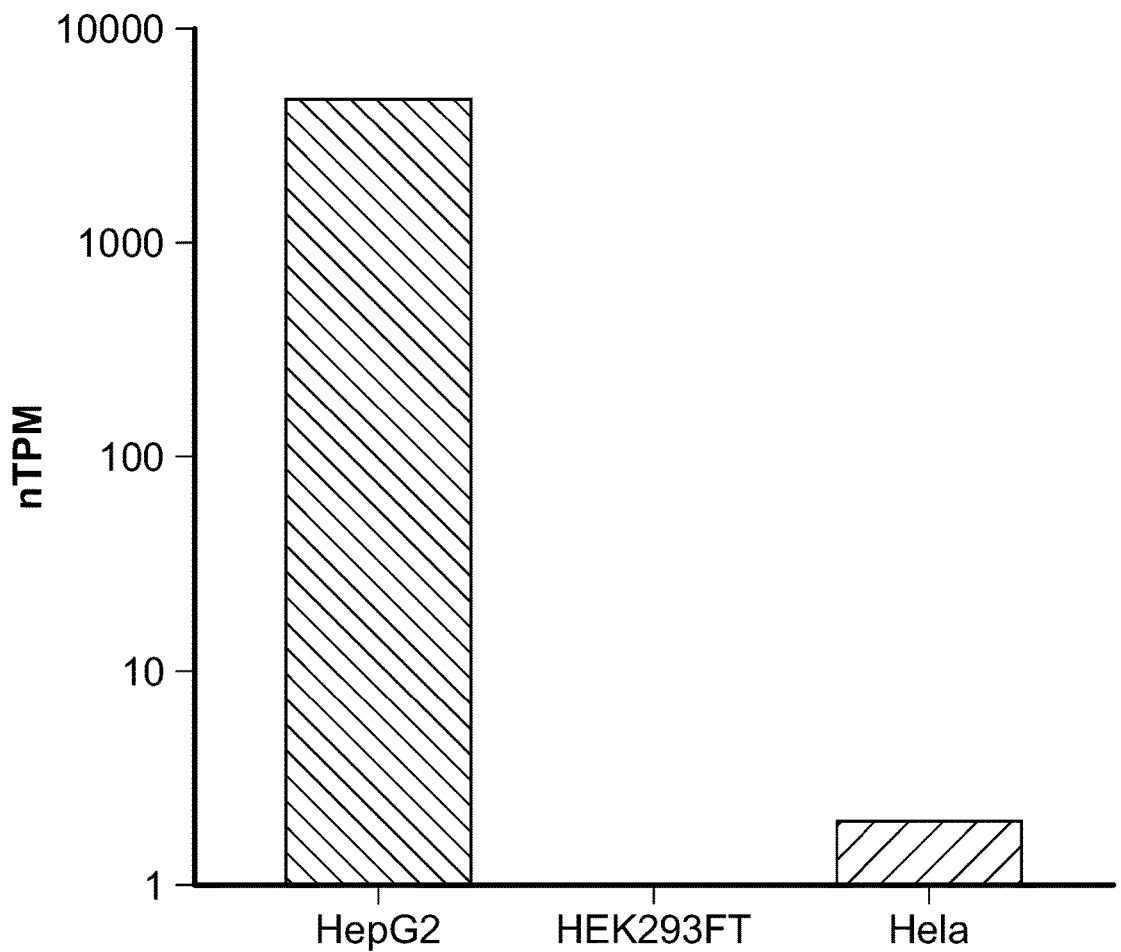
FIG. 44A is a visual representation of an analysis of SERPINA1 in three cell types which differentially express SERPINA1.
Figure 44B:
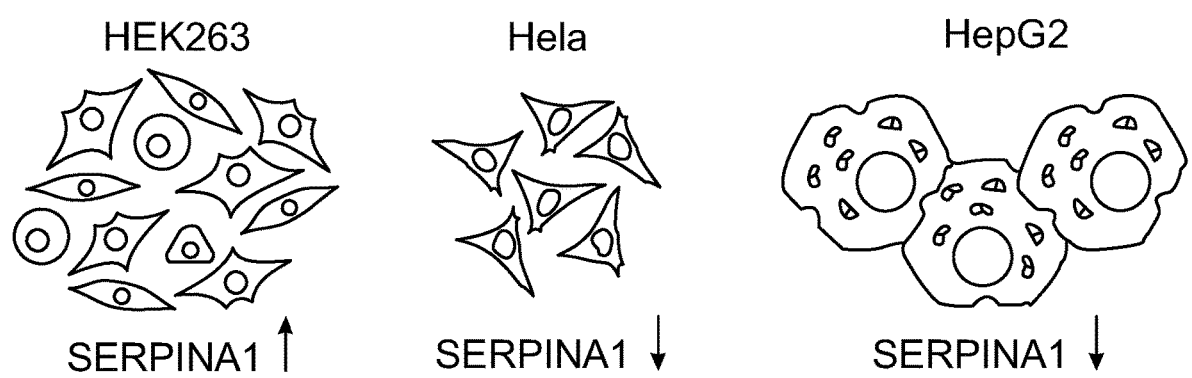
FIG. 44B. The SERPINA1-sensing five avidity sensor is transfected either with or without exogenous MCP-ADAR2dd (E488Q, T490A) in three different cell types (HEK293FT, Hela, and HepG2 cells).
Figure 44C:
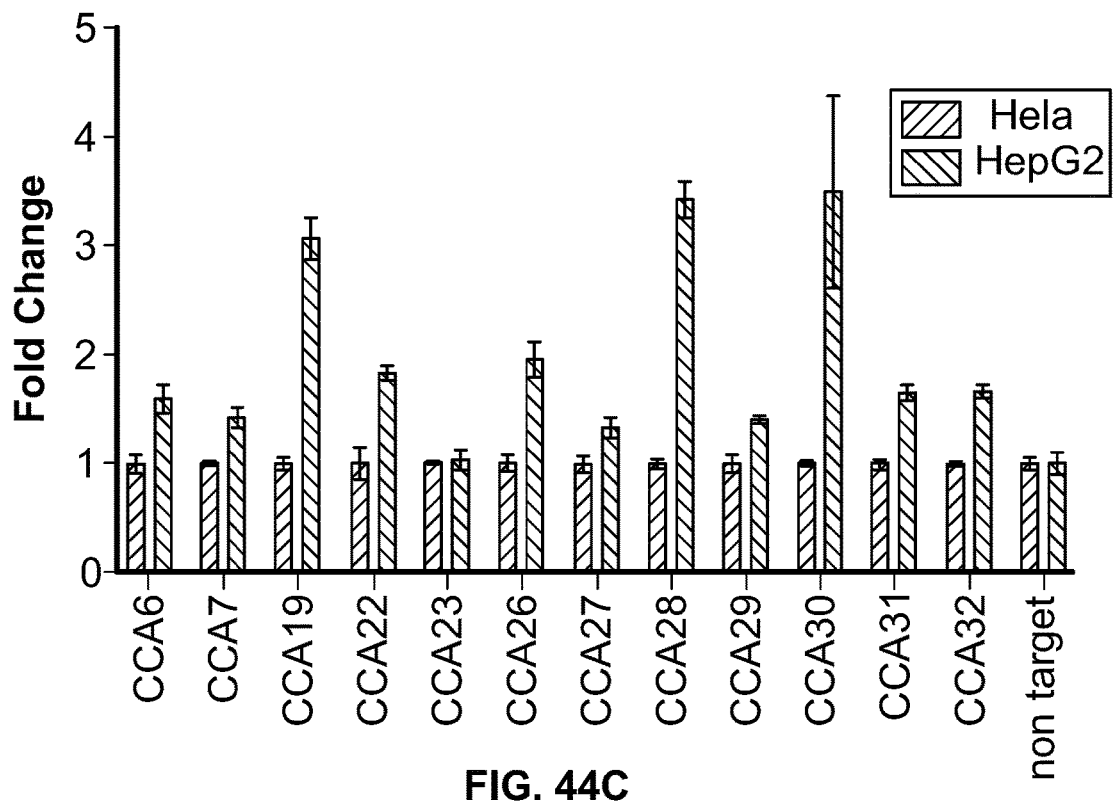
FIG. 44C is a bar plot comparing sensor activation fold changes between Hela cells and HepG2 cells across SERPINA1 sensors targeting different CCA sites.
Figure 44D:
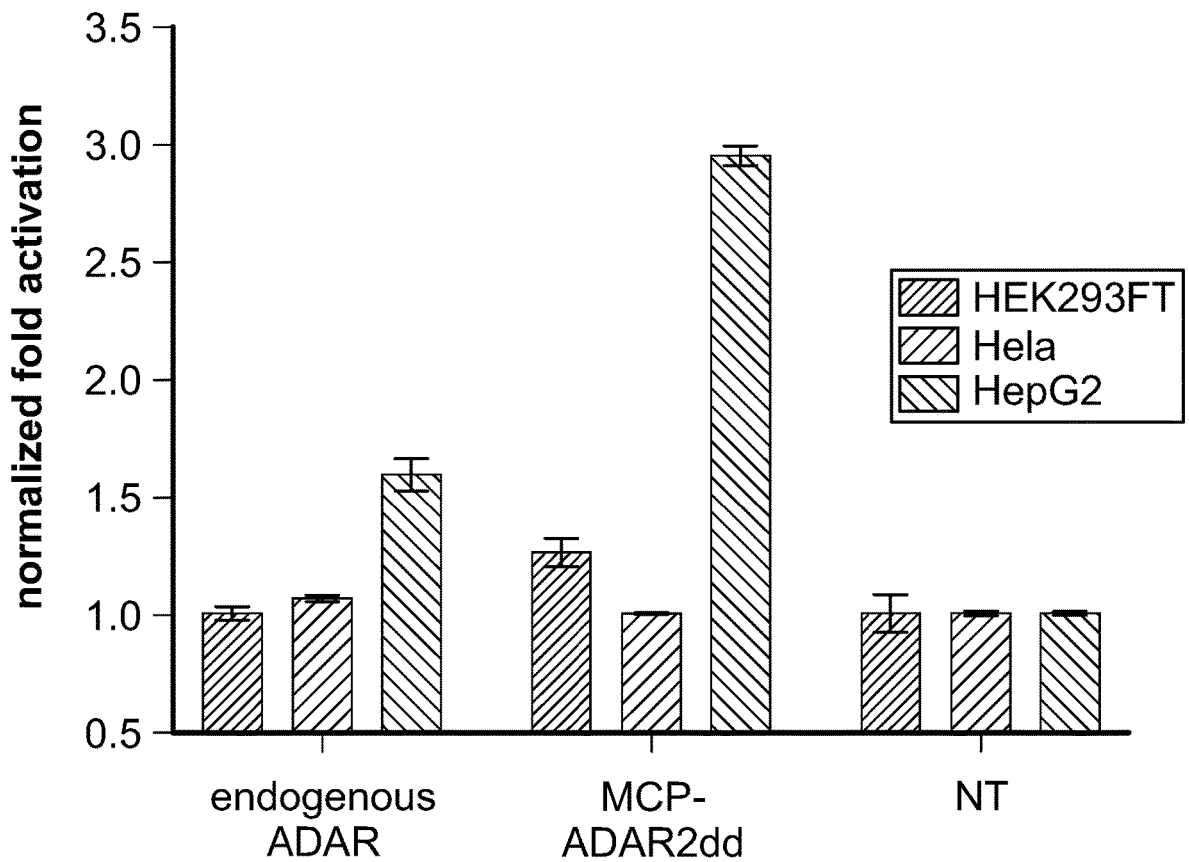
FIG. 44D Sensor activation is determined by calculating the raw luciferase values of SERPINA1 sensor normalized by a scrambled non-targeting guide sensor to account for protein production/secretion and background ADAR activity differences between cell types, followed by normalization to the gluc/cluc ratio in HEK293FT cells.

Cell type differences represent the primary variation of gene expression in tissues. We therefore set out to determine if ADAR sensors could accurately track cell type differences. First, to identify marker transcripts for cell type distinction, we performed a differential gene analysis between HEK293. Hela and HepG2 cells (FIG. 44A), selecting SERPINA1, a liver serine protease inhibitor with therapeutically relevant pathogenic variants (Boëlle et al., 2019), as a marker only expressed in HepG2 cells and not the other cell lines (FIG. 44B). We designed a panel of ADAR sensors with guides targeting SERPINA1 and tested their ability to distinguish between HepG2 and Hela cells, finding that the CCA30 guide design had the highest activation fold-change between HepG2 and Hela cells (FIG. 44C). We transfected the SERPINA1 (CCA30) targeting sensor into the three different cell types alongside a non-targeting scrambled sensor designed to control for background ADAR editing, transfection variance, protein production, and secretion differences between the three cell types. Each cell type was transfected with a CCA30 SERPINA1 sensor with an MS2 hairpin connected 5 avidity region, either with or without MCP-ADAR2dd. The fold change (FIG. 44D) is calculated by the raw luciferase values of SERPINA1 sensor normalized by a scramble non-targeting sensor to account for protein production/secretion and background ADAR kinetic differences between cell types, followed by normalization to the ratio in HEK cell for cell types comparison.

Figure 45:
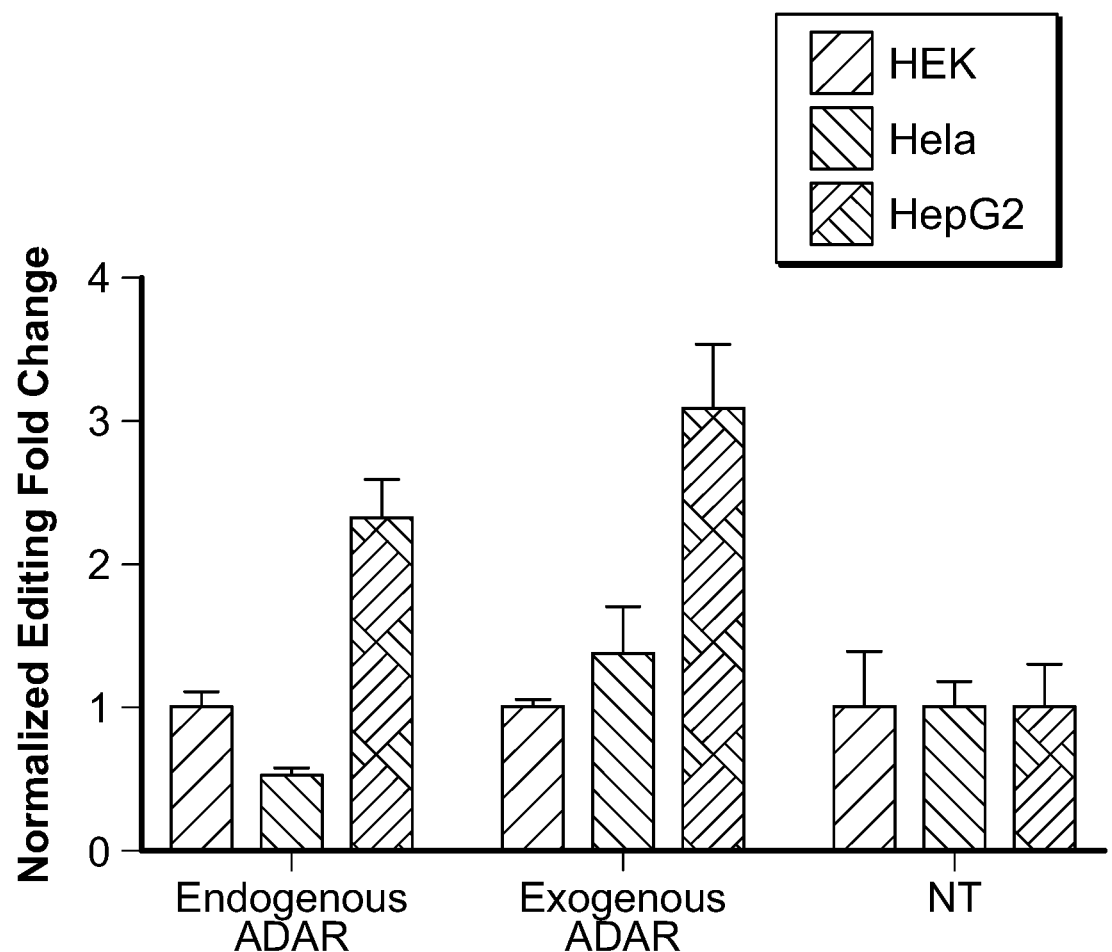
FIG. 45 is a graphical representation of Normalized Fold change of editing rate at the SERPINA1 Five avidity sensor in different cell types (HEK293. Hela and HepG2).

The normalized fold change of editing rate in all three cell types was also analyzed, in the presence of endogenous ADAR. Supplemental ADAR, and a control (FIG. 45). Various CCA sites on the SERPINA1 transcript were also used as targets.

Figure 46:
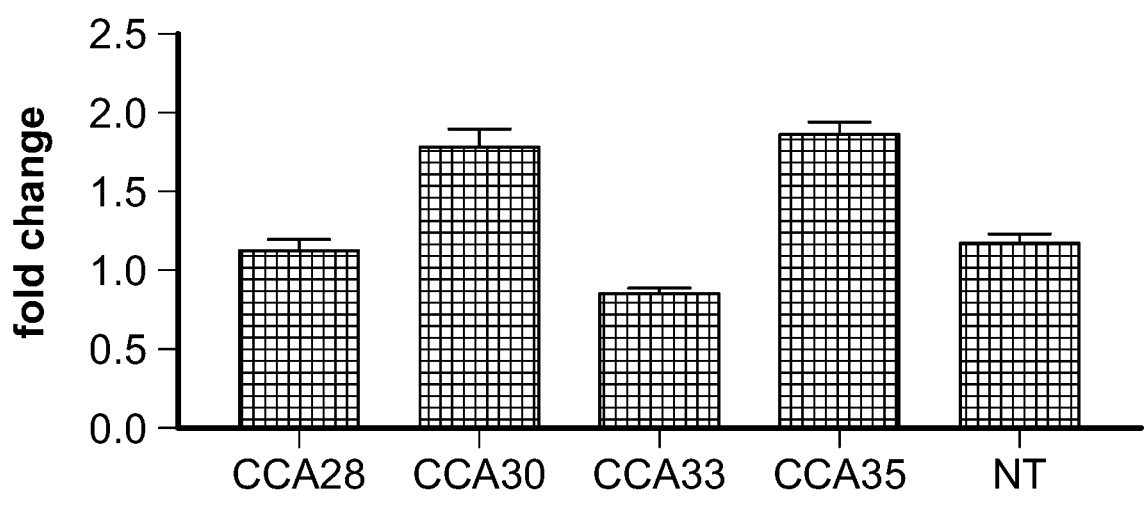
FIG. 46 A barplot comparing mRNA SERPINA1 sensor activation fold change targeting different CCA sites on the SERPINA1 transcript in Hepa1-6 cells with transiently transfected tetracycline inducible SERPINA1 expression.

To model liver-specific cell targeting in vitro, we expressed the human SERPINA1 transcript in Hepa-1-6 cells, in vitro synthesized the top CCA SERPINA1 sensors as mRNA, and transfected mRNA sensor alone into Hepa-1-6 cells. We found that both SERPINA1 sensors targeting CCA30 and CCA35 are able to recruit endogenous ADAR in Hepa-1-6 cells to sense induction of SERPINA1 transcripts (FIG. 46).

Figure 69A:
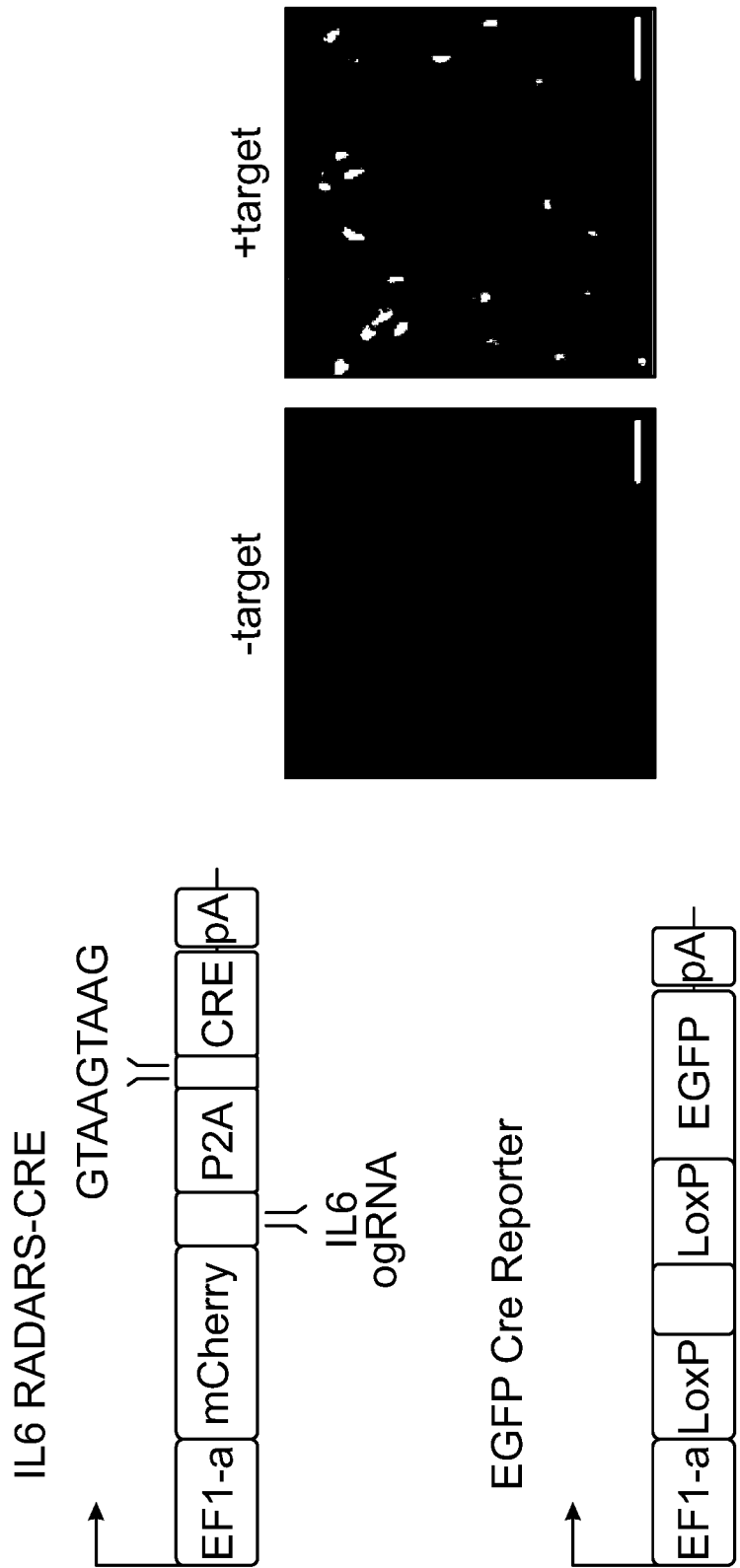
FIG. 69A is a visual schematic of dual loxP EGFP Cre reporter and IL6 RADARS-CRE. Right: HEK293FT fluorescence at 48 hours post-transfection of dual loxP EGFP reporter, ADAR1p150, and IL6-targeting RADARS with Cre payload with or without IL6 target. Images are shown for the − target and + target conditions. White scale bar denotes 100 microns.
Figure 69B:
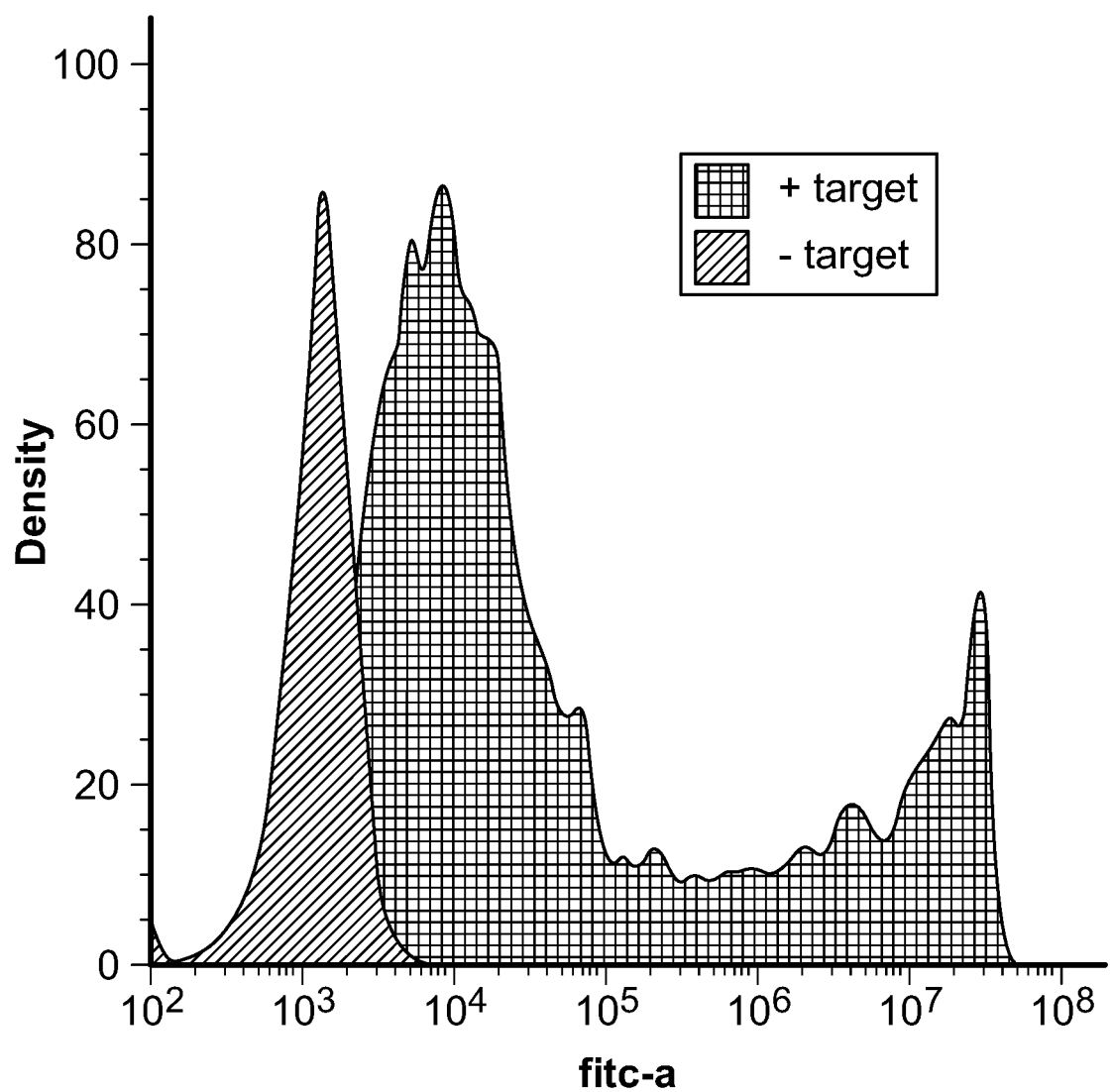
FIG. 69B is a visual depiction of the results of an experiment in which cells from FIG. 69A are harvested for flow analysis of EGFP expression.

To evaluate RADARSv2 for cell type discrimination, we first leveraged the modular nature of RADARS to engineer a system for permanent genetic labeling of a cellular population. We designed a dual loxP system for conditional, permanent labeling cells with EGFP upon Cre expression, and tested this reporter in combination with ADAR1p150 and an IL6-targeting engineered guide RNA with a Cre payload in HEK293FT cells. Upon IL6 induction, we observed significant production of EGFP protein, with minimal signal in the absence of target RNA (FIG. 69A, FIG. 69B).

Figure 70B:
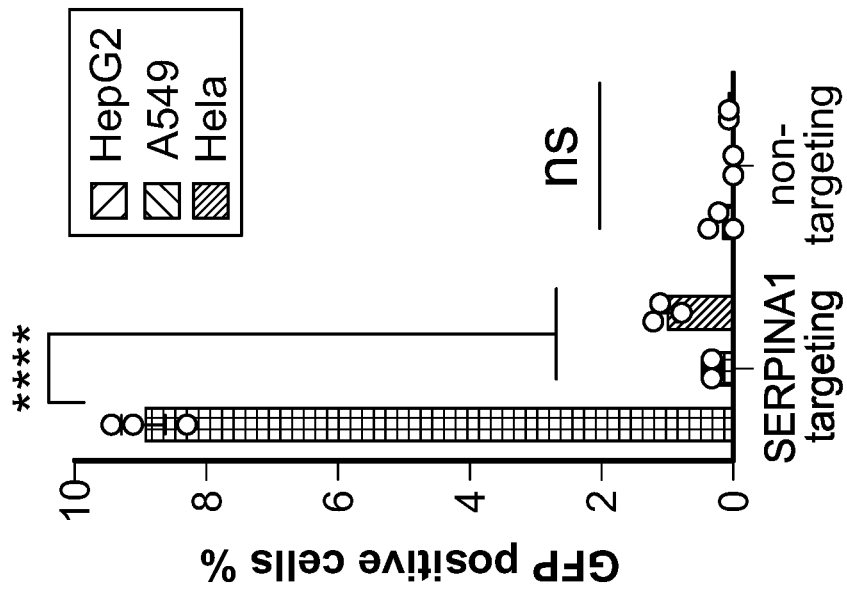
FIG. 70B is a visual depiction of results of flow cytometry analyzed percent GFP+ cells for Hela. HepG2, and A549 cells 48 hours post-transfection with SERPINA1-targeting RADARS constructs expressing Cre with exogenous ADAR1p150. Data are mean of technical replicates (n=3)±s.e.m.
Figure 70A:
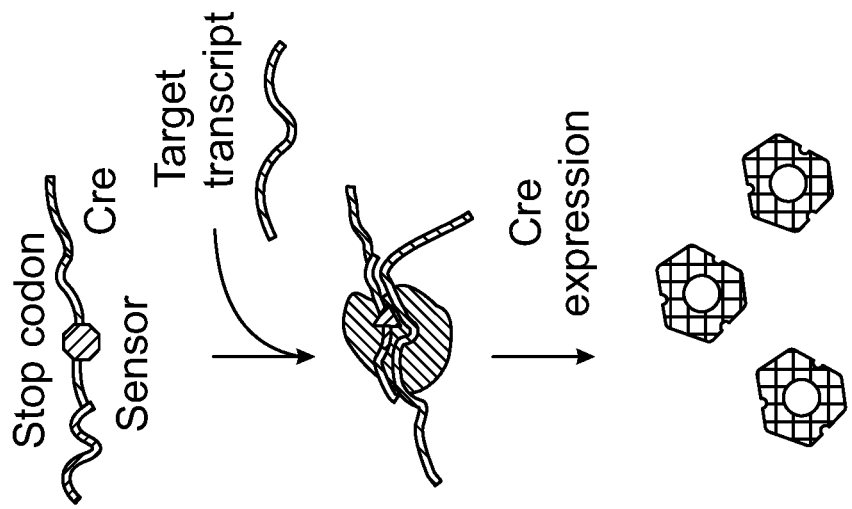
FIG. 70A is a visual schematic of a SERPINA1− targeting RADARS construct with a Cre payload.
Figure 70C:
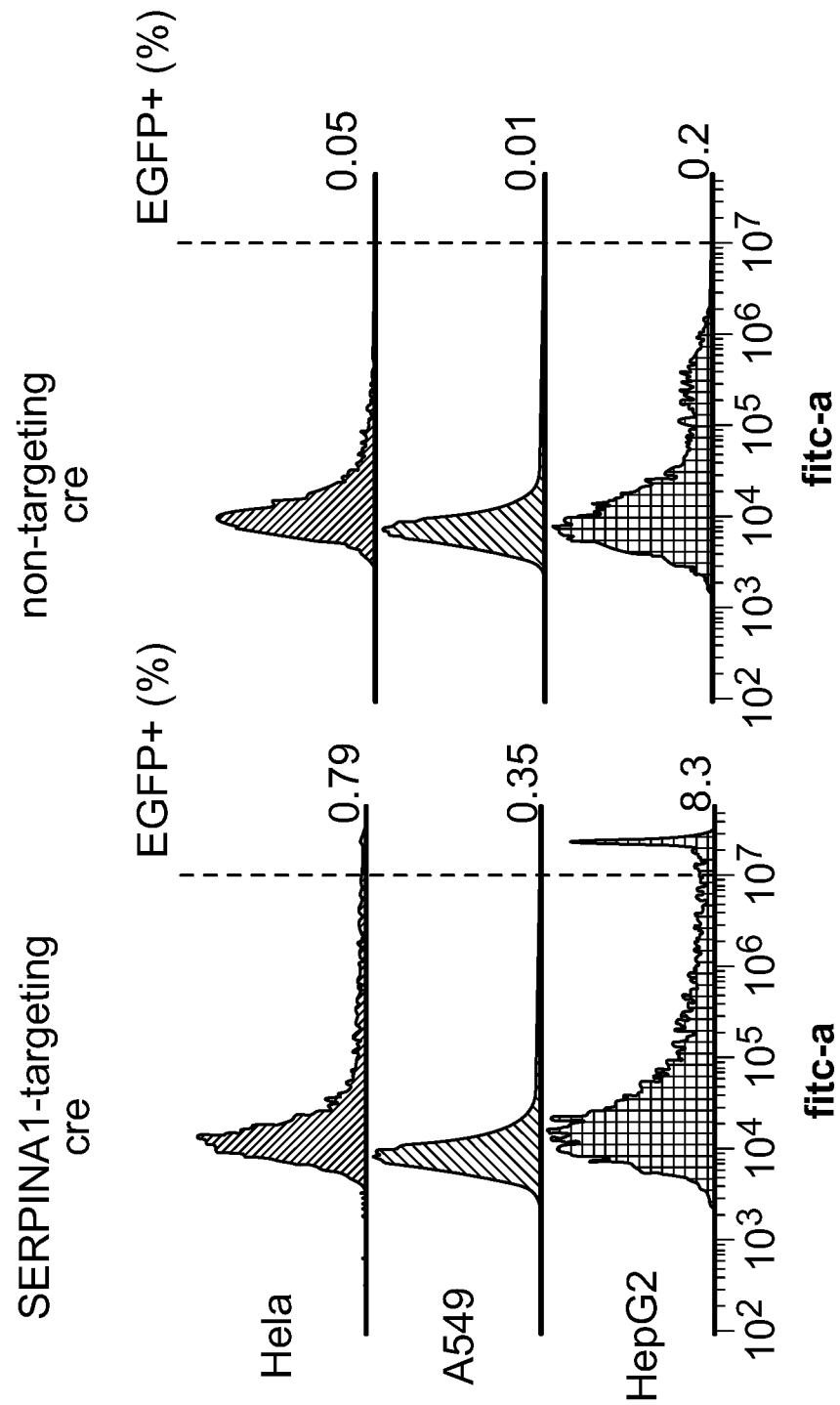
FIG. 70C is a visual depiction of EGFP expression quantified by flow cytometry at 48 hours post-transfection of CRE reporter, ADAR1p150, and IL6-targeting RADARS with Cre payload with or without IL6 target. Distribution of EGFP signals is analyzed by flow cytometry for Hela, A549 and HepG2 cells. For all three cell types, GFP positive cells are defined as a population of cells with FITC channel EGFP intensity above $10^7$.

Using the RADARSv2 design, we then identified SERPINA1 as a differentially expressed marker gene of liver-derived cell line HepG2 compared to two non-liver cell lines without SERPINA1 expression, A549 and HeLa (Karlsson et al., 2021). Using a SERPINA1-targeting engineered guide RNA to selectively activate Cre in HepG2 cells (FIG. 70A), we co-transfected this sensor with ADAR1p150 and Cre loxP reporter into HepG2, Hela, and A549 cells and benchmarked activation against a non-targeting RADARS construct. The non-targeting engineered guide RNA showed no reporter activation in any cell type, whereas the targeting engineered guide RNA showed significant EGFP reporter activation only in HepG2 cells (FIG. 70B, FIG. 70C). These results establish that the RADARS system can distinguish cell types based on specific markers, and engineered guide RNA and payloads can be modularly combined for cell type-specific expression of various transgenes.

Example 11. In Vivo Use of ADAR Sensors

Figure 47A:
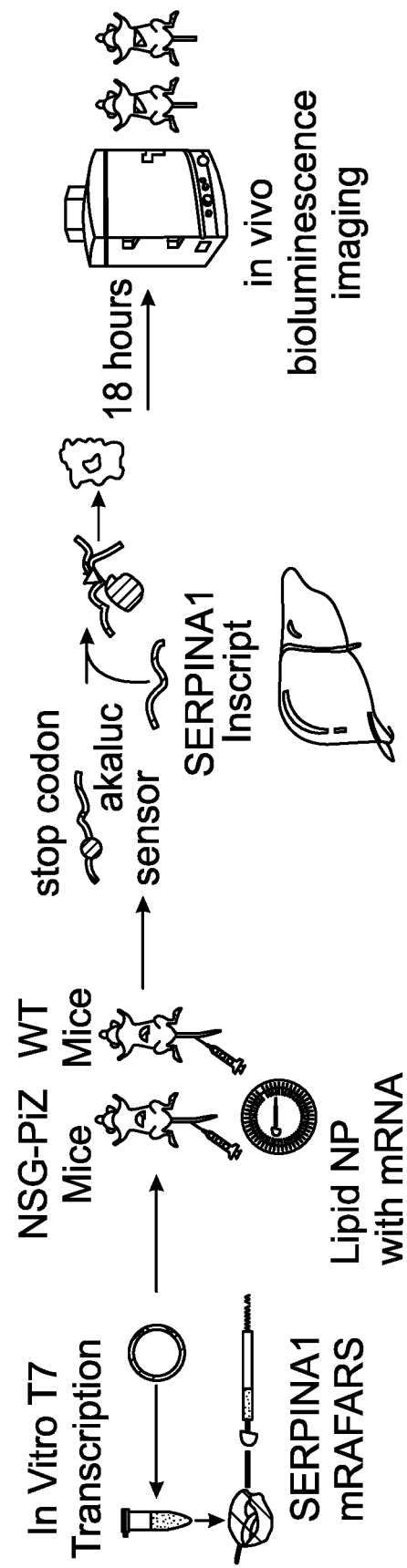
FIG. 47A is a schematic illustration of in vivo sensing experiment of the human SERPINA1 transcript using SERPINA1 mADAR sensor construct. SERPINA1 targeting sensor mRNA with Akaluc output is produced in vitro with 25% 5-methylcytosine and 0% pseudouridine. Constitutive Akaluc (no stop codon) and a non-targeting guide (with stop codon) sensor constructs are synthesized with the same protocol. All mRNAs are packaged with lipid nanoparticles and tail-vein injected into either wild-type mice or NSG-Piz mice with human SERPINA1 PiZ mutant cassette. In vivo sensor activation is measured 18 hours post injection.
Figure 71A:
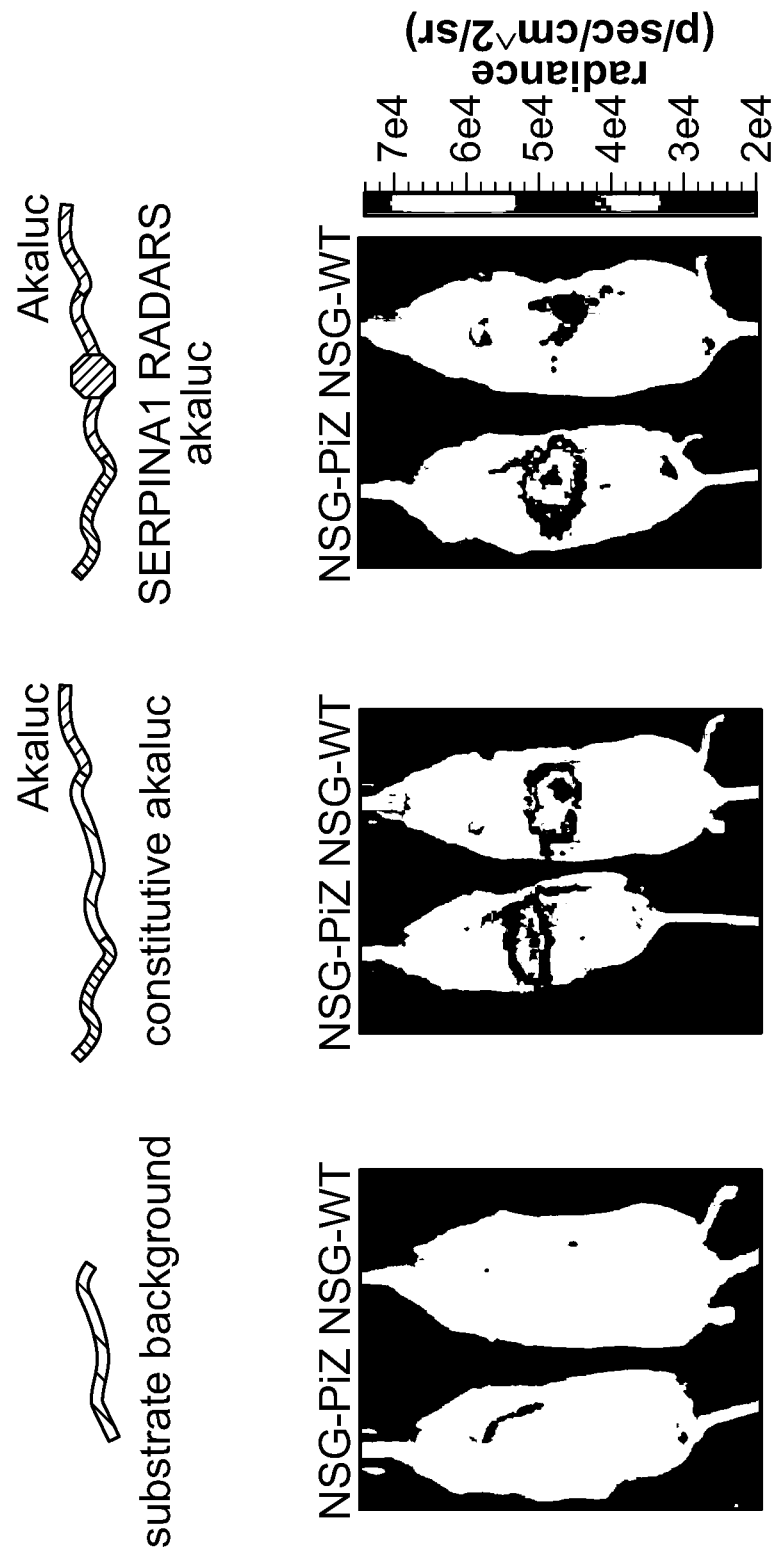
FIG. 71A is a visual depiction of bioluminescence images of sensor activation for various synthetic mRNA RADARS constructs.
Figure 71C:
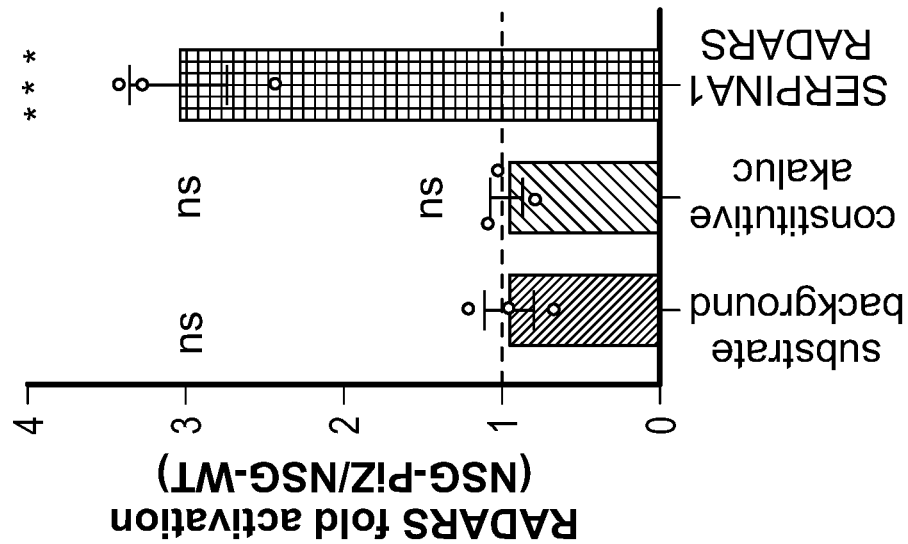
FIG. 71C is a graphical comparison of Akaluc-generated radiance is calculated for the liver and compared between the wild type and the NSG-PiZ mutant mice. The fold activation between the NGS-PiZ mice and the NSG-WT mice is calculated for each RADARS construct. Significance is tested for each group compared to the substrate background via a two tailed unpaired t-test, N=3 mice (NS, p>0.05. *, p<0.001.).
Figure 71B:
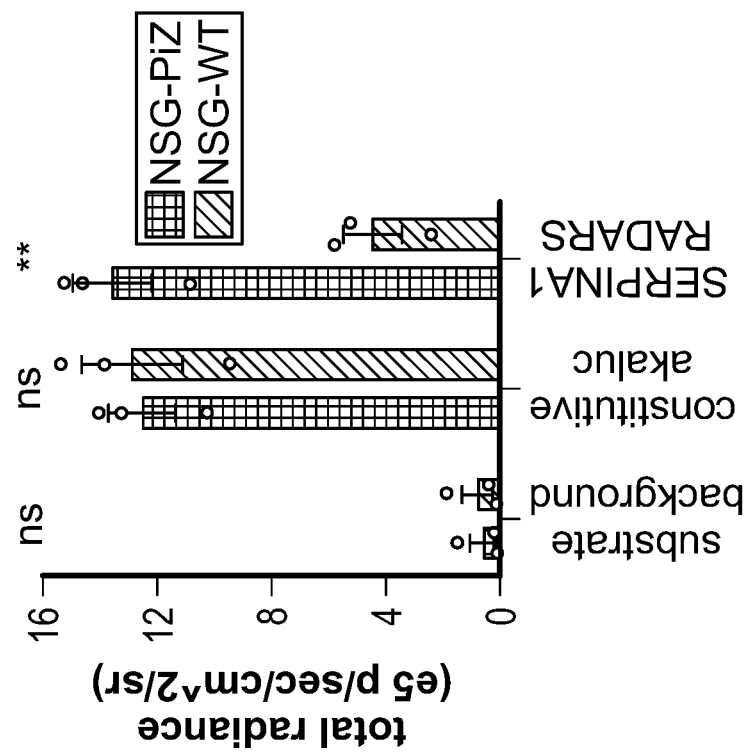
FIG. 71B is a graphical comparison of Akaluc luminescence radiance in the liver in NSG-PiZ mice and NSG-WT mice across substrate background, constitutive sensor, and SERPINA1 #CCA32 targeting RADARS. Data are mean of technical replicates (n=3)±s.e.m. Significance is determined between the NSG-WT and NSG-PiZ samples radiance via a two tailed unpaired t-test, N=3 mice. (NS, p>0.05. , p<0.01.)

To determine if ADAR sensors could be used in vivo, we next tested a SERPINA1 sensor in mice. We synthesized ADAR sensors targeting the CCA30 and CCA35 sites of human SERPINA1 in a construct that expresses Akaluciferase (Akaluc), which allows for facile non-invasive luminescent imaging to confirm cell-specific ADAR sensor activation (Yeh et al. 2019) (FIG. 47). Prior to bioluminescence imaging, 8- to 10-week-old Albino B6 and NSG-PiZ mice were anesthetized with 3% isoflurane and injected with 5 μg of synthesized mRNA via retro-orbital injection using in vivo-jetRNA transfection reagent (Polyplus). At 18 hours post-injection, the mice were anesthetized again with 3% isoflurane and immediately administered 100 μl of 15 mM AkaLumine-HCL (Sigma Aldrich) for imaging. Ventral bioluminescence images were acquired using an IVIS Spectrum In Vivo Imaging System (PerkinElmer). The following conditions were used for image acquisition: exposure time=60 sec, binning=medium; 4, field of view=12.5×12.5 cm, and f/stop=1. Bioluminescent images were analyzed using Living Image 4.3 software (PerkinElmer). As albino B6 mice do not express human SERPINA1, they represent a negative control (having no site for CCA30 or CCA35 binding). No additional ADAR enzyme was administered to the mice, to determine if endogenous ADAR alone could edit the administered ADAR sensors. The SERPINA1-sensing mRNA RADARS designs had significant activation (p=0.007, N=3 mice, one way ANOVA) of Akaluc expression in the NSG-PiZ mice relative to the NSG-WT mice, and we observed no significant differences between the two strains in substrate only background luciferase and constitutive Akaluc mRNA RADARS conditions (FIG. 71A-C).

Figure 47B:
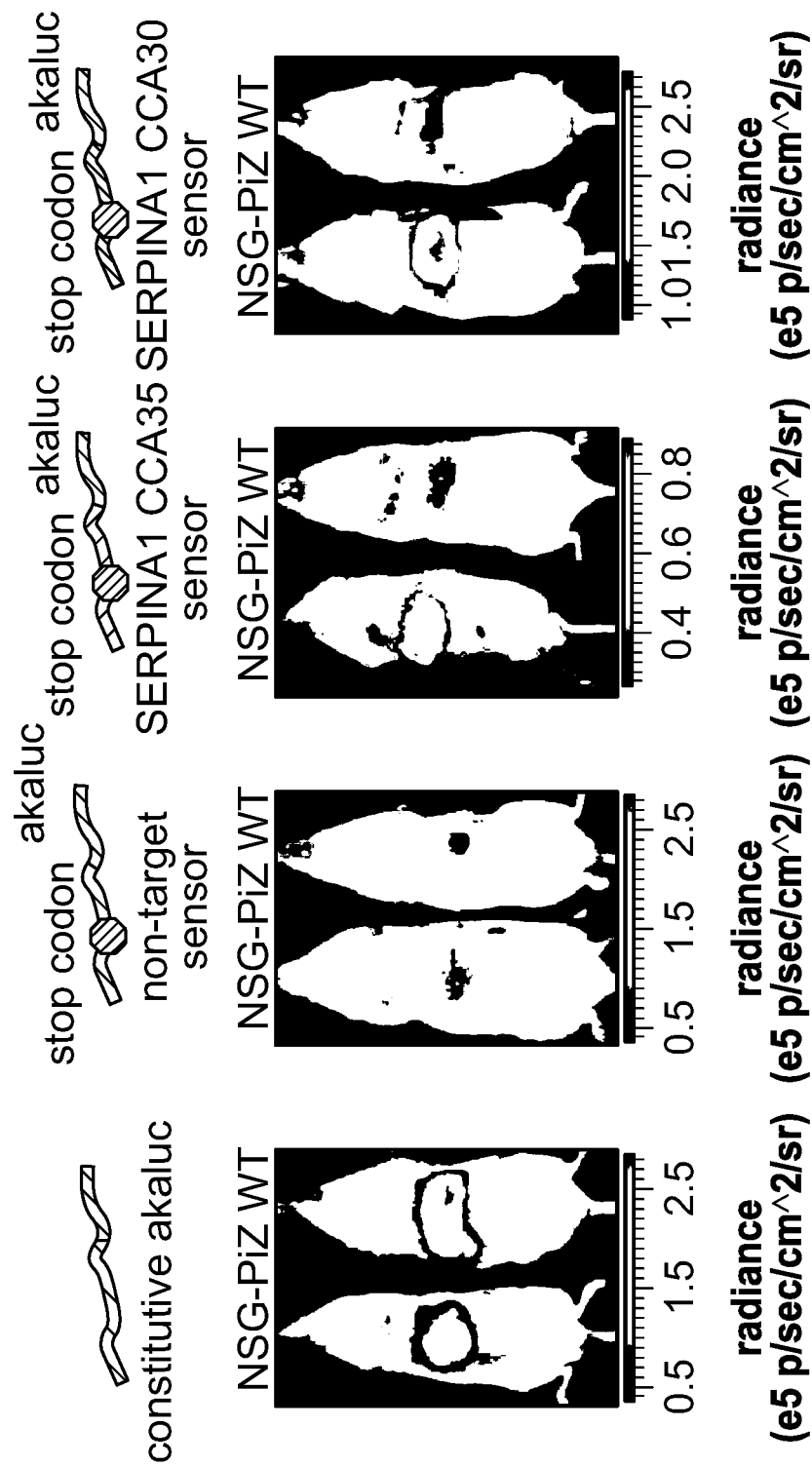
FIG. 47B displays representative images of sensor activation for various synthetic mRNA ADAR sensor constructs.
Figure 48A:
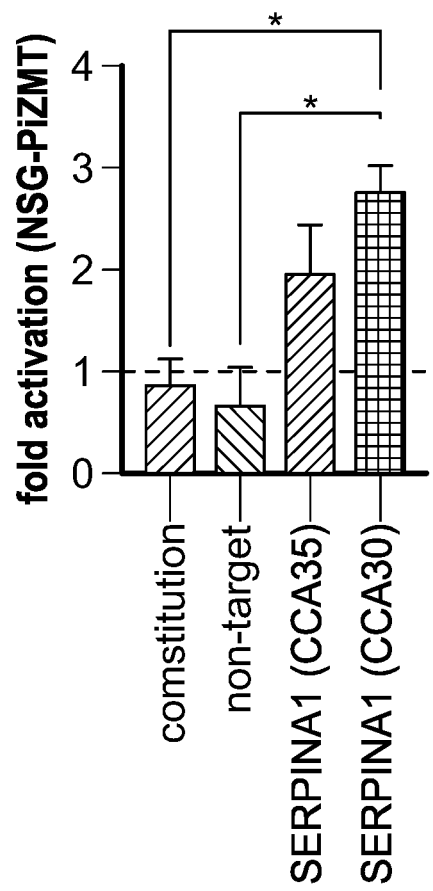
FIG. 48A is a graphical illustration of Akaluc generated radiance calculated for the liver and compared between the wild type and the NSG-PiZ mutant mice. The fold change between the NGS-PiZ mice and the WT mice is calculated for each ADAR SENSOR construct. Significance is determined via a two tailed t-test, N=2 mice. *, p<0.05. A p value smaller than 0.05 is denoted with an asterisk for statistical significance.
Figure 48B:
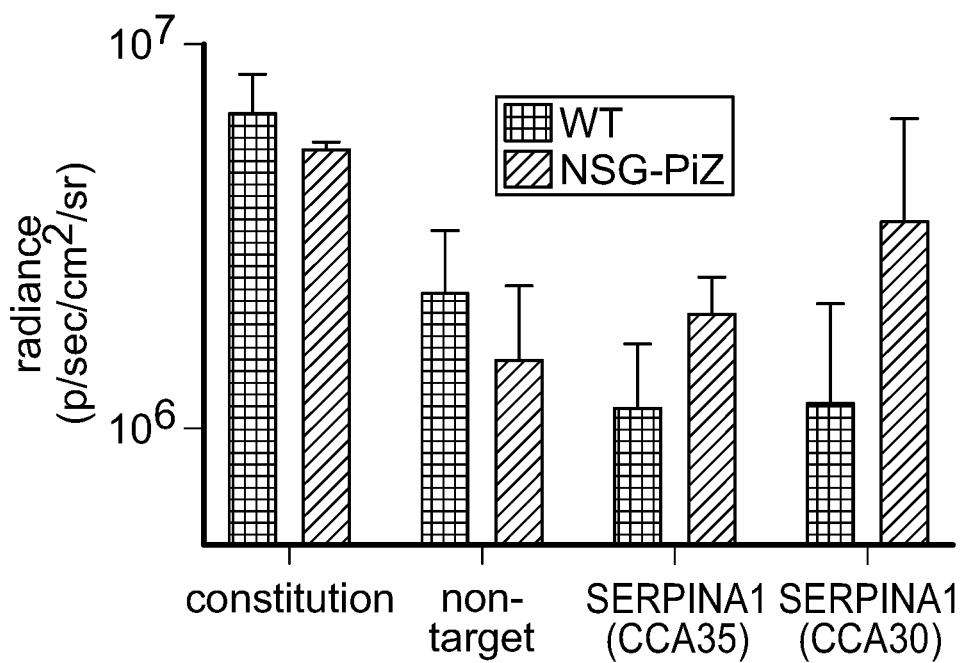
FIG. 48B is a barplot comparing Akaluc luminescence radiance in the NSG-PiZ mice and WT mice across non-targeting sensor, constitutive sensor, SERPINA1 CCA35 targeting sensor, and SERPINA1 CCA30 targeting sensor.

In addition to ADAR sensors targeting the CCA30 and CCA35 sites of SERPINA1, we also designed an Akaluc payload with either a constitutive ADAR sensor expressing Akaluciferase lacking the stop codon, or a scrambled non-targeting guide. (See FIG. 47B). 3 sensor systems were examined. The SERPINA1-sensing ADAR sensor designs had significant activation (p=0.04, N=2 mice, two tailed unpaired t-test) of Akaluc expression in the NSG-PiZ mice relative to the WT mice, and control guides had no significant difference between the two strains (FIG. 47B, FIG. 48). This activation demonstrates that ADAR SENSOR can be delivered as synthetic mRNA to sense cellular state in vivo with endogenous ADAR

Further Considerations

Figure 49A:
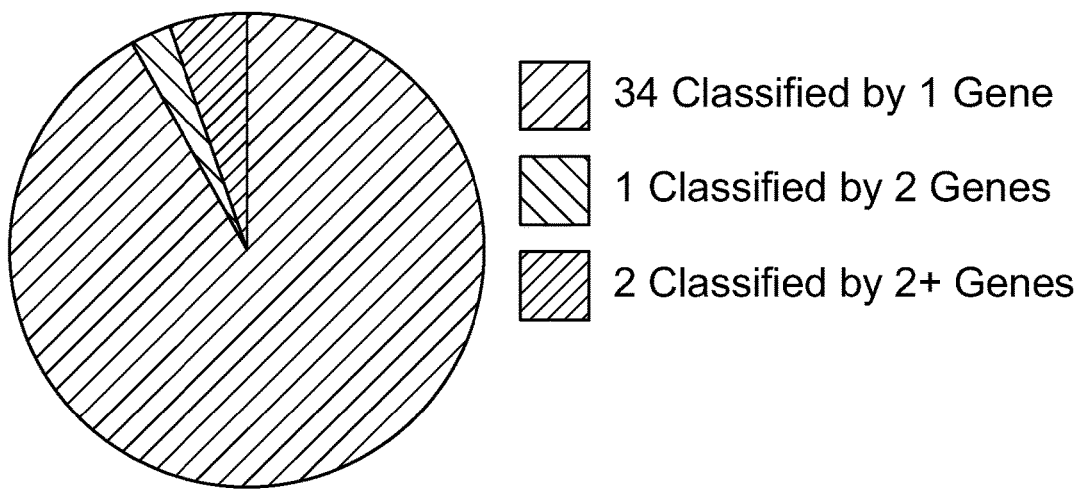
FIG. 49A is a graphical illustration of a differential gene analysis of 37 tissues using human protein atlas and GTEX dataset on minimum number of genes needed to classify a tissue according to gene, as well as the number of protein-coding genes FIG. 49B enriched in a specific tissue, enhanced in a specific tissue, or with low specificity.
Figure 49B:
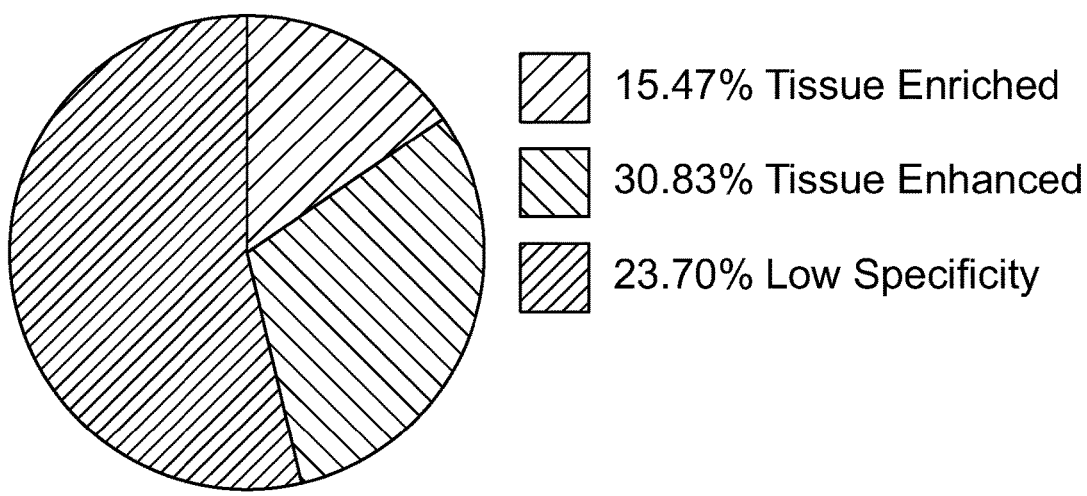
FIG. 49C is a heatmap showing relative transcript abundance of 34 mRNAs that uniquely define a tissue across 34 different tissue types.
Figure 49C:
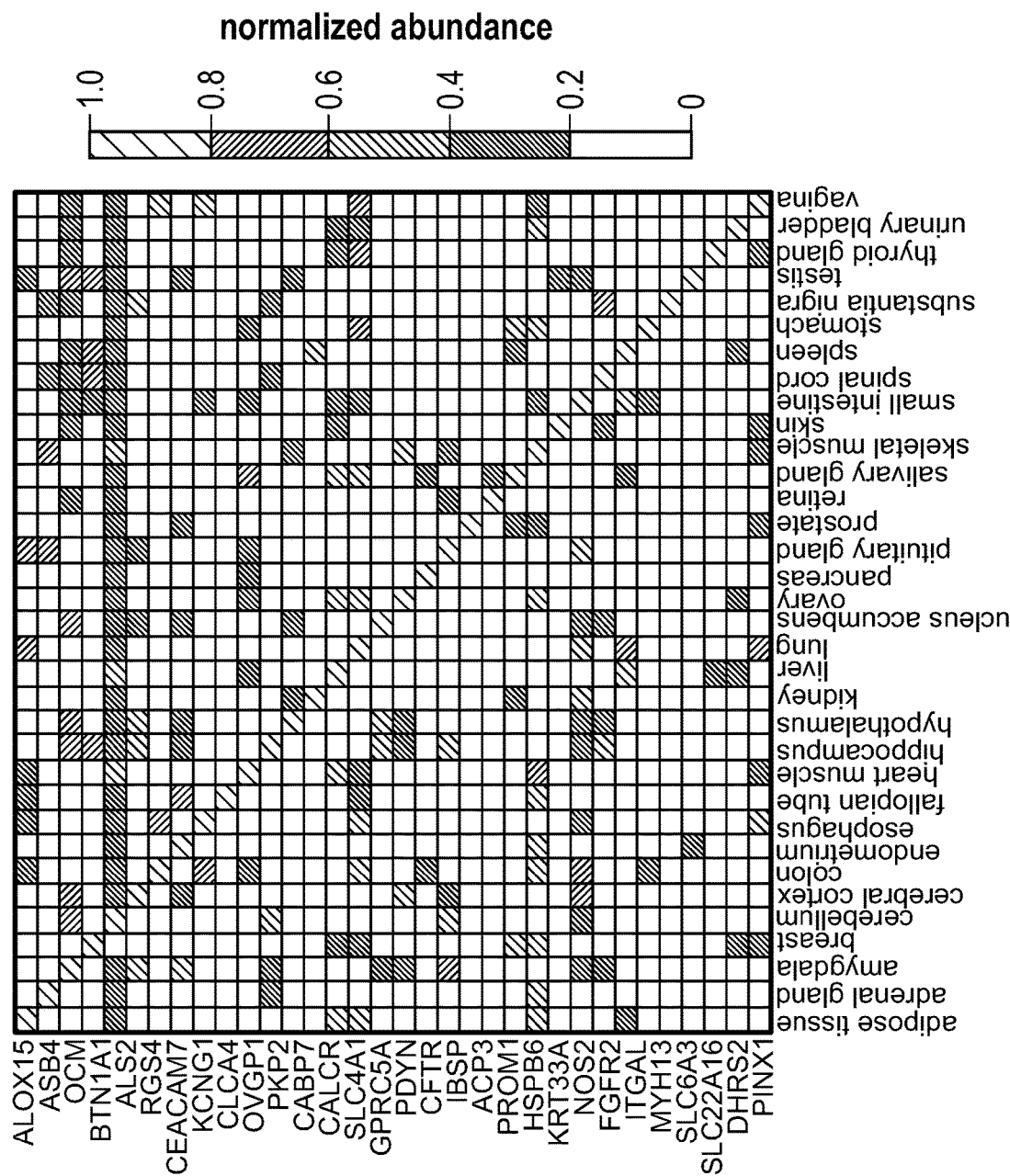
Figures 51A, 51B:
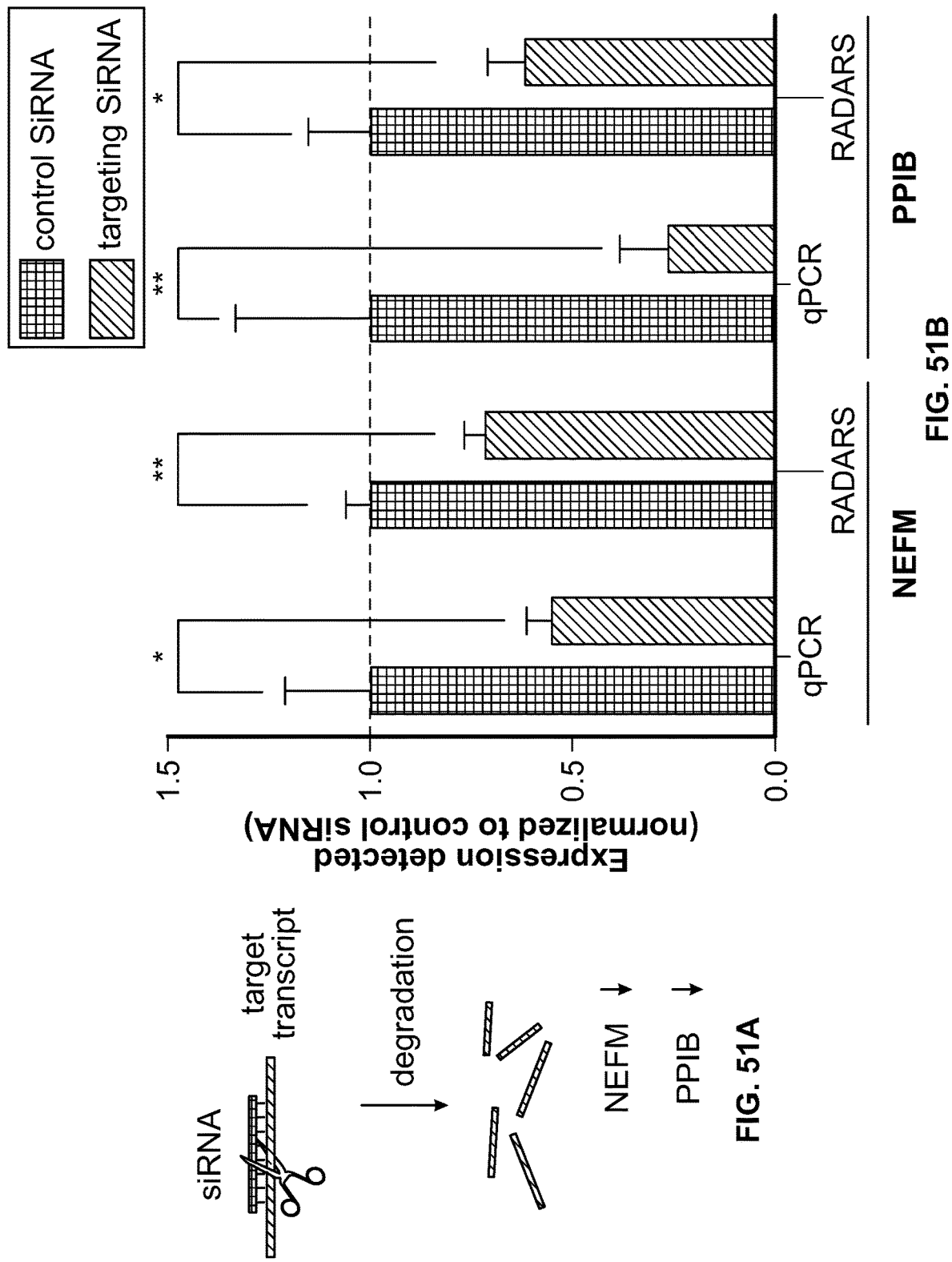
FIG. 51A is a graphical illustration showing depression of RADARS signal corresponding to endogenous target knockdown. Schematic of siRNA knockdown of endogenous transcripts.
FIG. 51B qPCR and fluorescent RADARS detected expression difference between siRNA targeting PPIB or NEFM versus a control non-targeting siRNA in HEK293FT cells. For RADARs sensor activation is calculated for the targeting siRNA and normalized to the control siRNA. Data are mean of technical replicates (n≥3)±s.d.

Analysis of public tissue gene expression data (GTEx Consortium 2013), shows that 34 out of 37 tissues could be distinguished with a single gene by a sensor with 3-fold sensitivity (FIG. 49A), with 3 additional tissues classified by combinations of genes, demonstrating direct applications for both the sensitivity and logical inputs of ADAR sensors (FIG. 49).

Figure 72A:
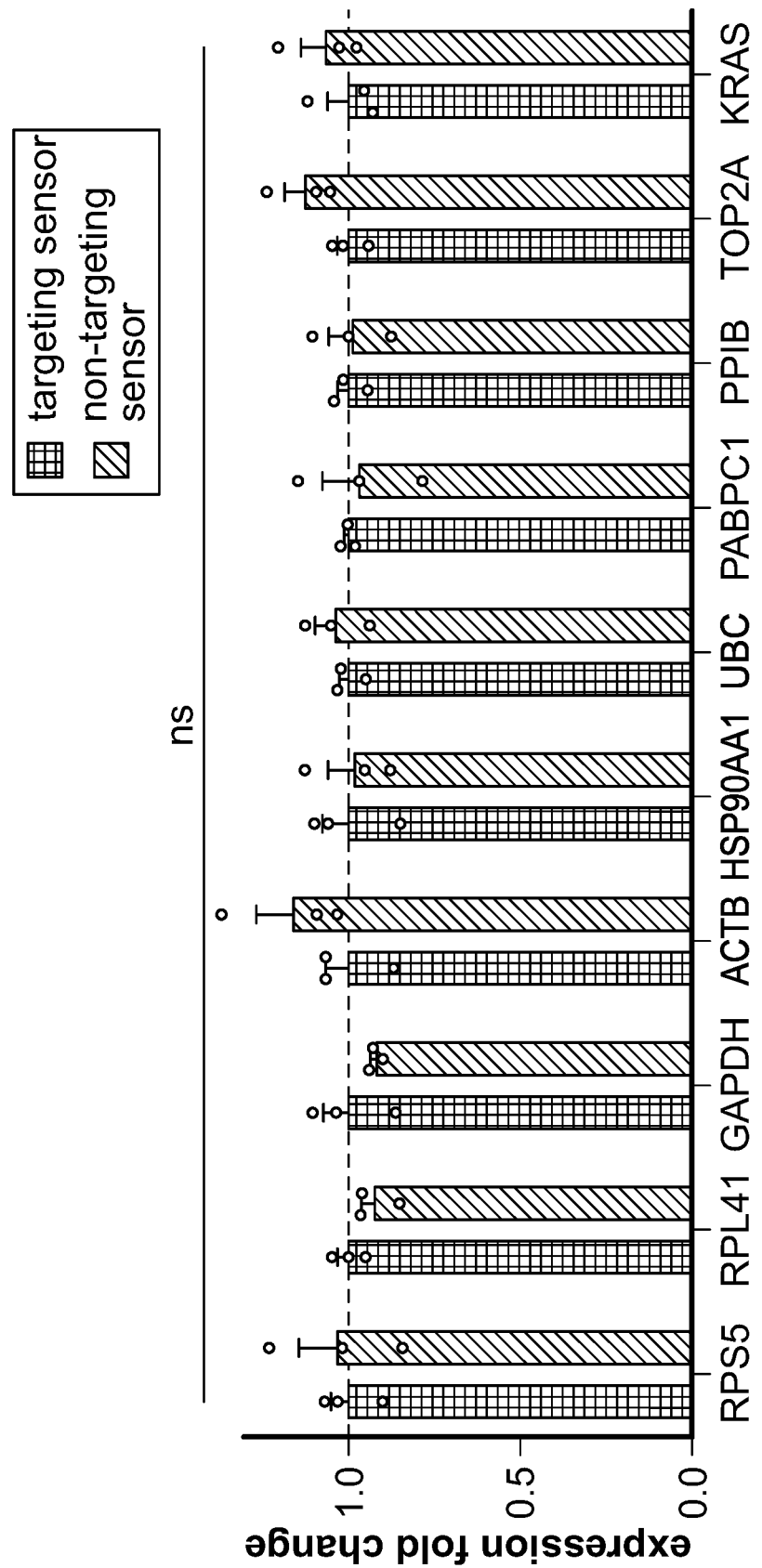
FIG. 72A is a graphical depiction of transcript expression levels, as quantified by qPCR, of 10 endogenous genes from HEK293FT cells transfected with either targeting or non-targeting (NT) RADARS constructs with exogenous ADAR1p150 supplementation. Data shown is normalized to the Targeting RADARS. Significance between the targeting and non-targeting RADARS is determined via an unpaired t-test with Welch correction assuming individual variance for each group (Ns, p>0.05).
Figure 72B:
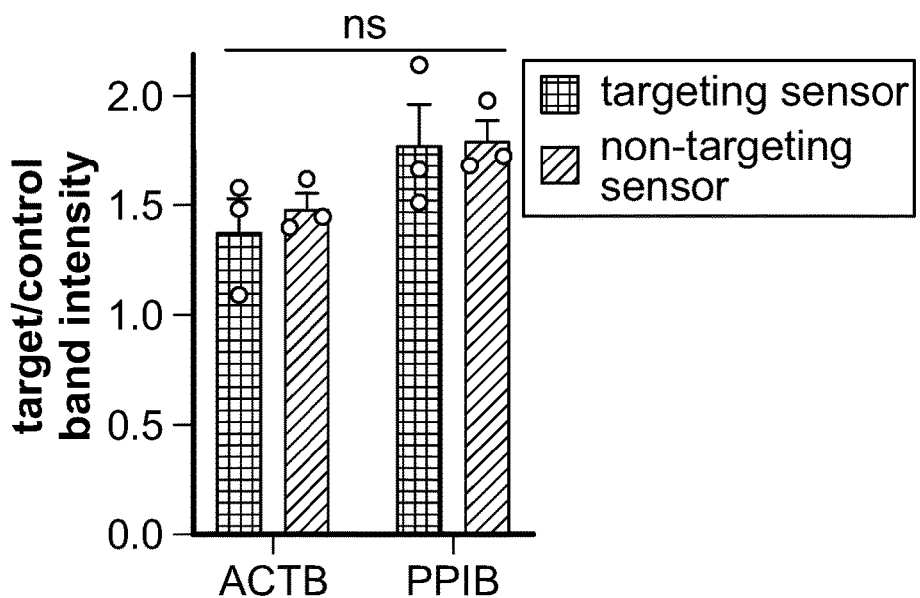
FIG. 72B is a graphical depiction of protein expression, as quantified by Western blot, of endogenous ACTB and PPIB in HEK293FT cells transfected with ACTB/PPIB targeting RADARS or non-targeting RADARS (with ADAR1p150 supplementation). Significance between the targeting and non-targeting RADARS is determined with an unpaired t-test with Welch correction assuming individual variance for each group (Ns, p>0.05).
Figure 72C:
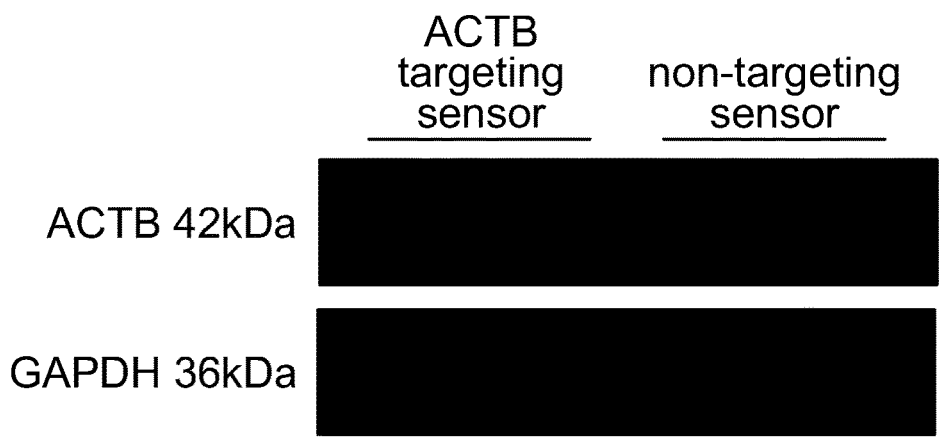
FIG. 72C and FIG. 72D are visual depictions of the effect of sensor-target hybridization on protein production is analyzed by Western blot. ACTB (FIG. 72C) and PPIB (FIG. 72D) protein levels are shown in response to RADARS hybridization and GAPDH is used as a normalizing protein control.
Figure 72D:
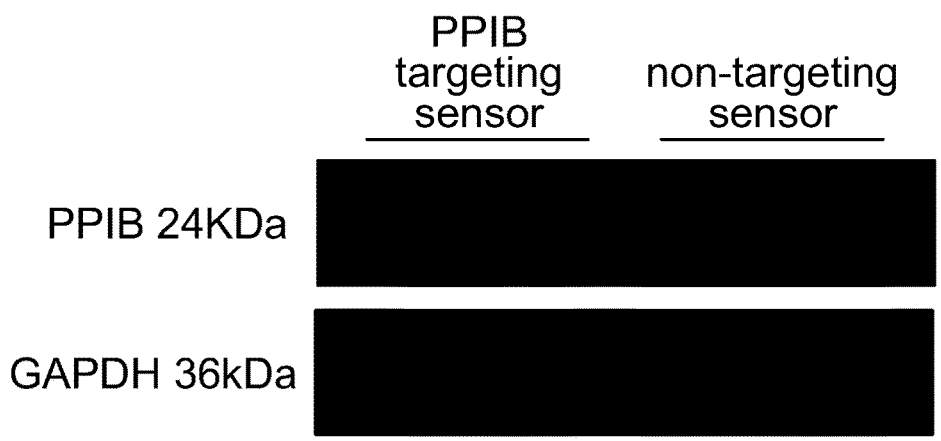

Example 12. Examination of Off-Target Effects and Disruption to Regular Cell Processes Since the RADARSv2 mechanism involves formation of a long hybridization region between the sensor engineered guide RNA and the target transcript, we investigated whether this duplex would perturb target transcript levels via either Dicer knockdown or transcript stabilization. We compared target expression for each of the endogenous transcripts knocked down via siRNA (FIG. 63A) between the top engineered guide RNA condition and a non-targeting engineered guide RNA sensor, finding no significant change in the target transcript expression (FIG. 72A). Additionally, to confirm that the resulting engineered guide RNA-target hybridization did not interfere with endogenous translation, we co-transfected HEK293FT cells with ADAR1p150 and either ACTB or PPIB-targeting engineered guide RNAs, and quantified target protein levels by western blot. Similar to the mRNA levels, we observed that protein levels of ACTB and PPIB were unchanged in targeting engineered guide RNA conditions relative to non-targeting engineered guide RNAs, demonstrating no appreciable effect on target expression by RADARS (FIG. 72B, FIG. 72C-D).

Figure 73A:
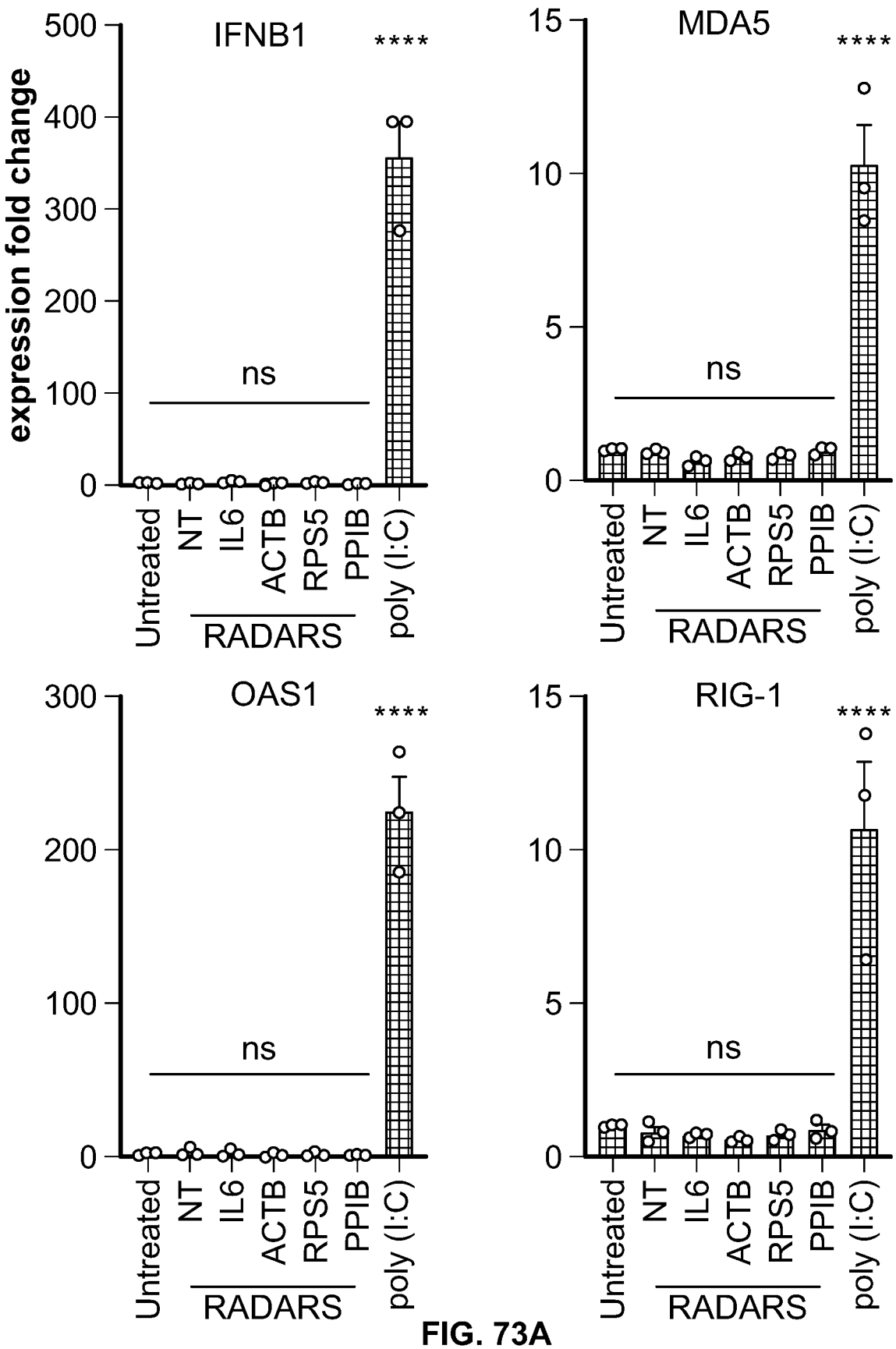
FIG. 73A is a graphical depiction of qPCR detected expression levels of Interferon beta, OAS1, RIG-1 and MDA5 upon transfection with RADARS constructs targeting either IL6, ACTB, RPS5, or PPIB, non-targeting (NT) RADARS, and high molecular weight poly (I:C). Significance is determined by a one way ANOVA test between untreated group, RADARS group, and poly (I:C) group (Ns, p>0.05. ****, p<0.0001).
Figure 73B:
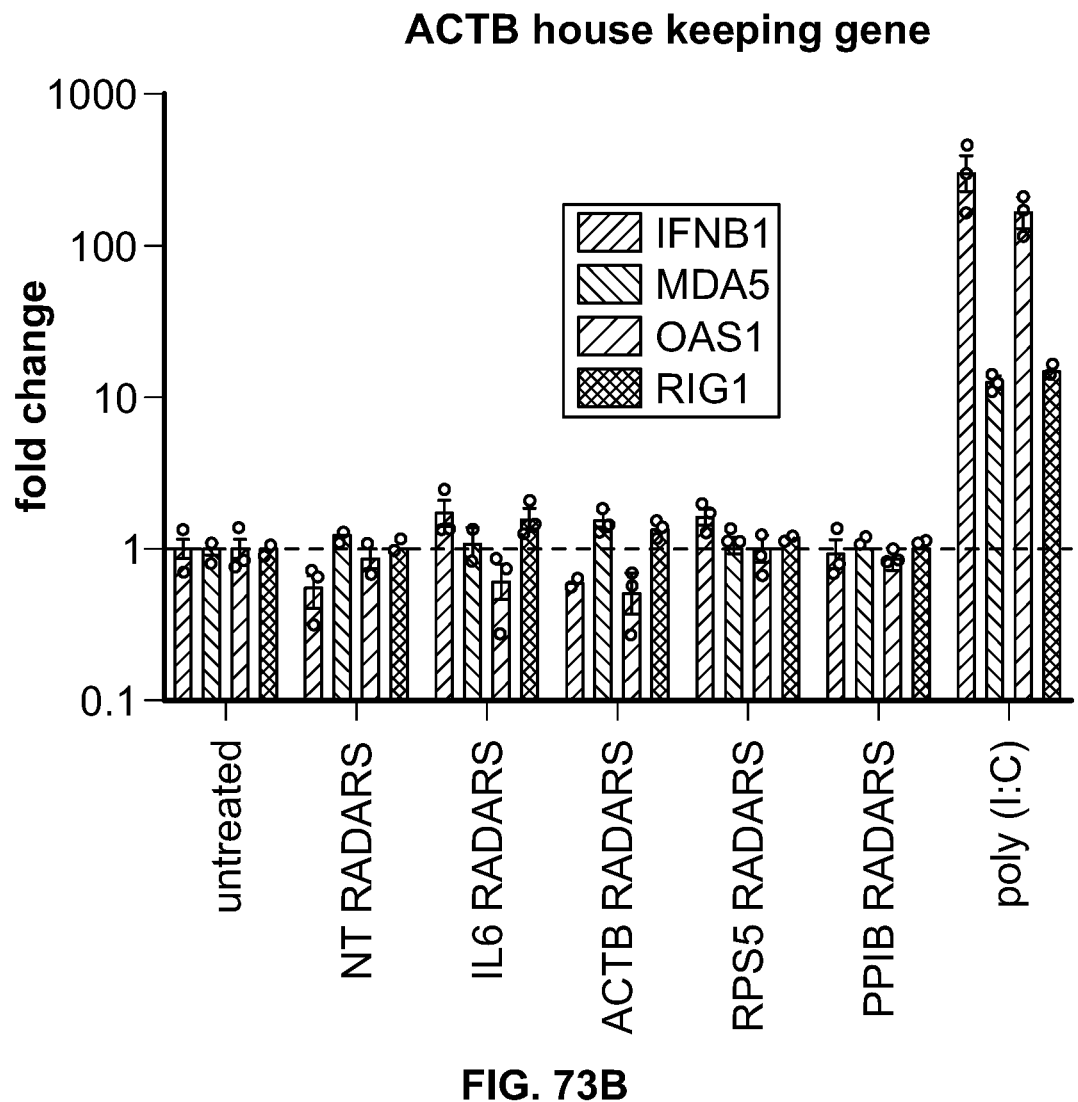
FIG. 73B is a graphical depiction of qPCR detected gene expression fold change of four dsRNA responsive genes (IFNb, OAS1, MDA5 and RIG-1) in response to RADARS in HEK293FT cells using ACTB as the normalizing gene.
Figure 73C:
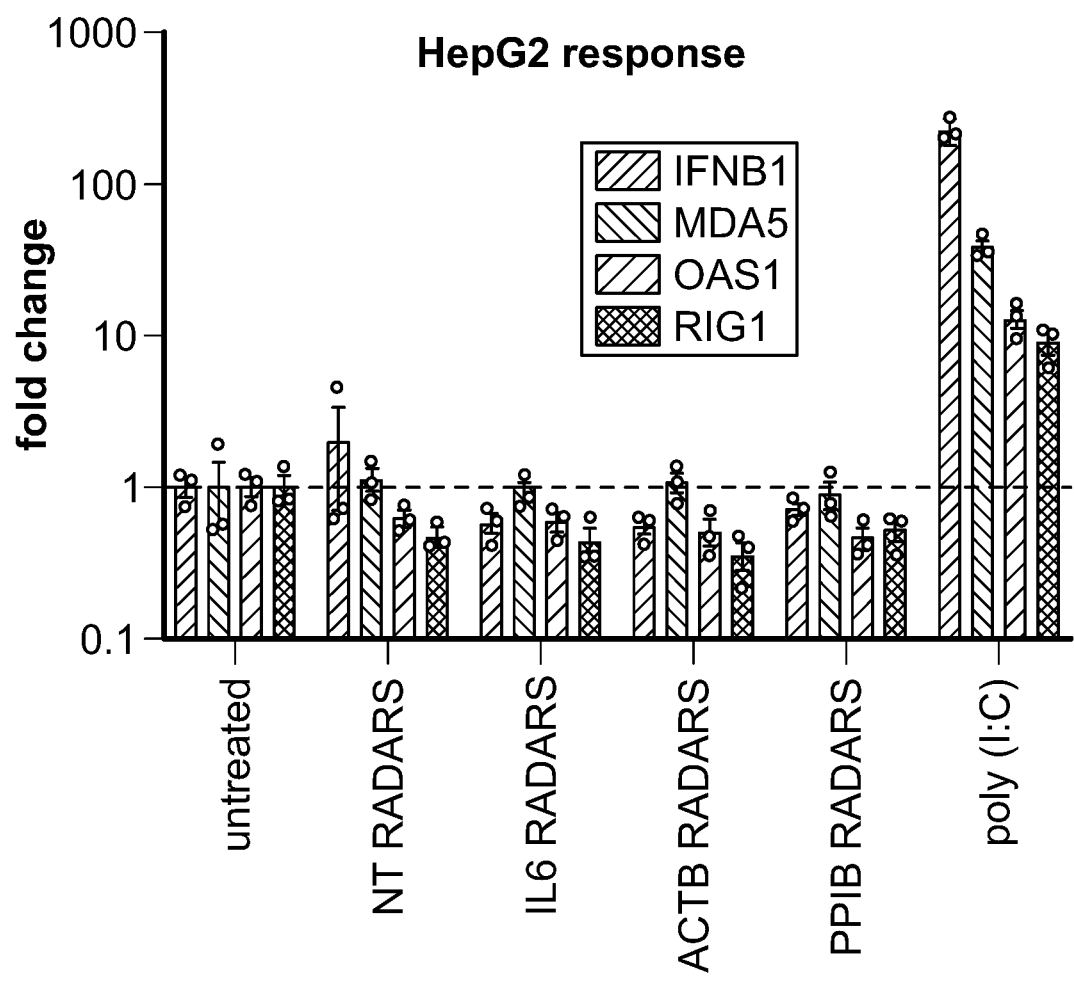
FIG. 73C is a graphical depiction of qPCR detected gene expression fold change of four dsRNA responsive genes (IFNb, OAS1, MDA5 and RIG-1) in response to RADARS or poly (I:C) in HepG2 cells with GAPDH as the normalizing gene.

The formation of dsRNAs in cells can activate immune response pathways, and, thus we next surveyed RADARS-induced upregulation of major endogenous innate immunity signaling pathways involved in dsRNA response (IFNB1, MDA5, OAS1, and RIG-1) by qPCR, using both ACTB and GAPDH as normalizing genes (FIG. 73A, FIG. 73B). To compare to a positive control, we tested RADARS constructs targeting ACTB, PPIB, RPS5, and exogenously introduced IL6 transgene alongside high molecular weight poly (I:C), which acts as an analog dsRNA and activates these four pathways. We found RADARS constructs did not significantly upregulate any of the four dsRNA response transcripts, while poly (I:C) caused significant activation of all four pathways (FIG. 73A). To generalize our findings across cell lines, we tested the same set of RADARS constructs in the HepG2 human hepatocellular carcinoma cell line and observed that RADARS sensors did not trigger any dsRNA responses (FIG. 73C).

Figure 74A:
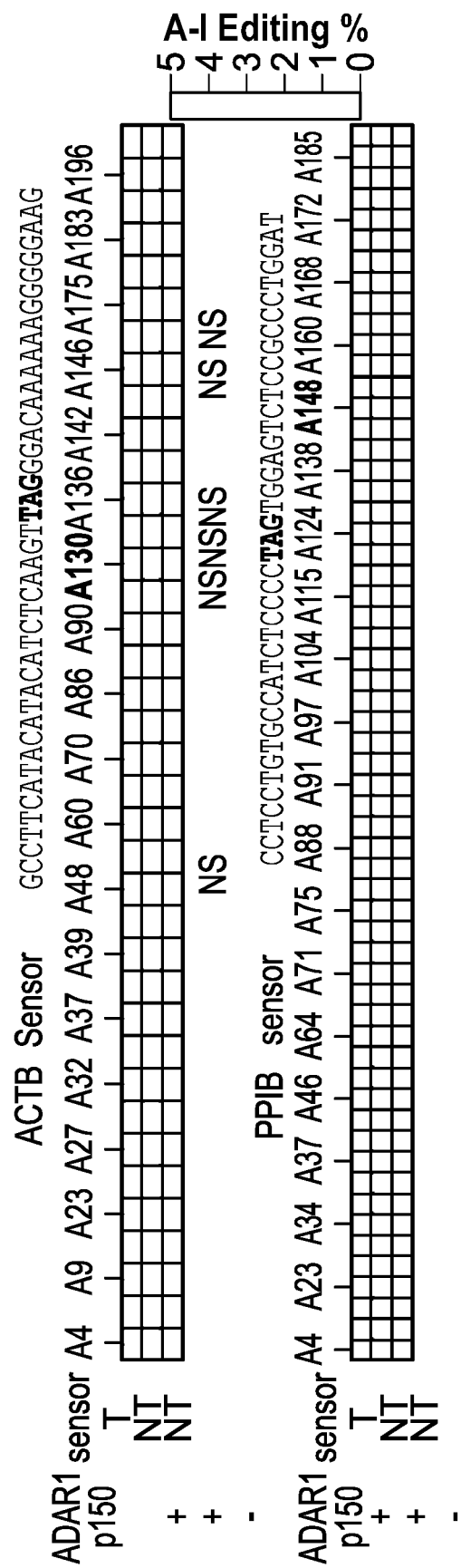
FIG. 74A is a visual depiction of the quantification of RNA editing in the 200 bp hybridization region of RADARS to the target transcript, for ACTB, PPIB, and a NT engineered guide RNA. A to I (G) conversion is depicted in a heatmap. Figure discloses SEQ ID NOS 6 and 7, respectively, in order of appearance. (NS, p>0.05)

Lastly, we explored whether ADAR1p150 overexpression generated off-target editing in the transcriptome, which has been observed with therapeutic ADAR-based RNA editing approaches (Cox et al., 2017; Qu et al., 2019; Reautschnig et al., 2022). We first profiled the region surrounding the hybridization duplex of PPIB and ACTB transcript with the RADARS engineered guide RNA, finding no significant off-target editing due to either the sensor hybridization or ADAR1p150 overexpression (FIG. 74A). To survey potential off-targets in an unbiased fashion, we next performed polyA mRNA sequencing of cells expressing PPIB sensors and ADAR1p150. We found that the combination of ADAR1p150 overexpression with PPIB targeting RADARS resulted in only 23 detectable sites in the transcriptome, all with below 10% editing (FIG. 74B). Furthermore, in the absence of ADARp150 overexpression with non-targeting engineered guide RNA, we find no significant editing of sites. In contrast, when we analyzed published RNA-seq data from MCP-ADAR2(E488Q) deaminase domain overexpression, we detected >10,000 sites with significant A→I RNA editing, highlighting the impact of deaminase construct selection on off-target profiles (FIG. 74C).

Figure 75A:
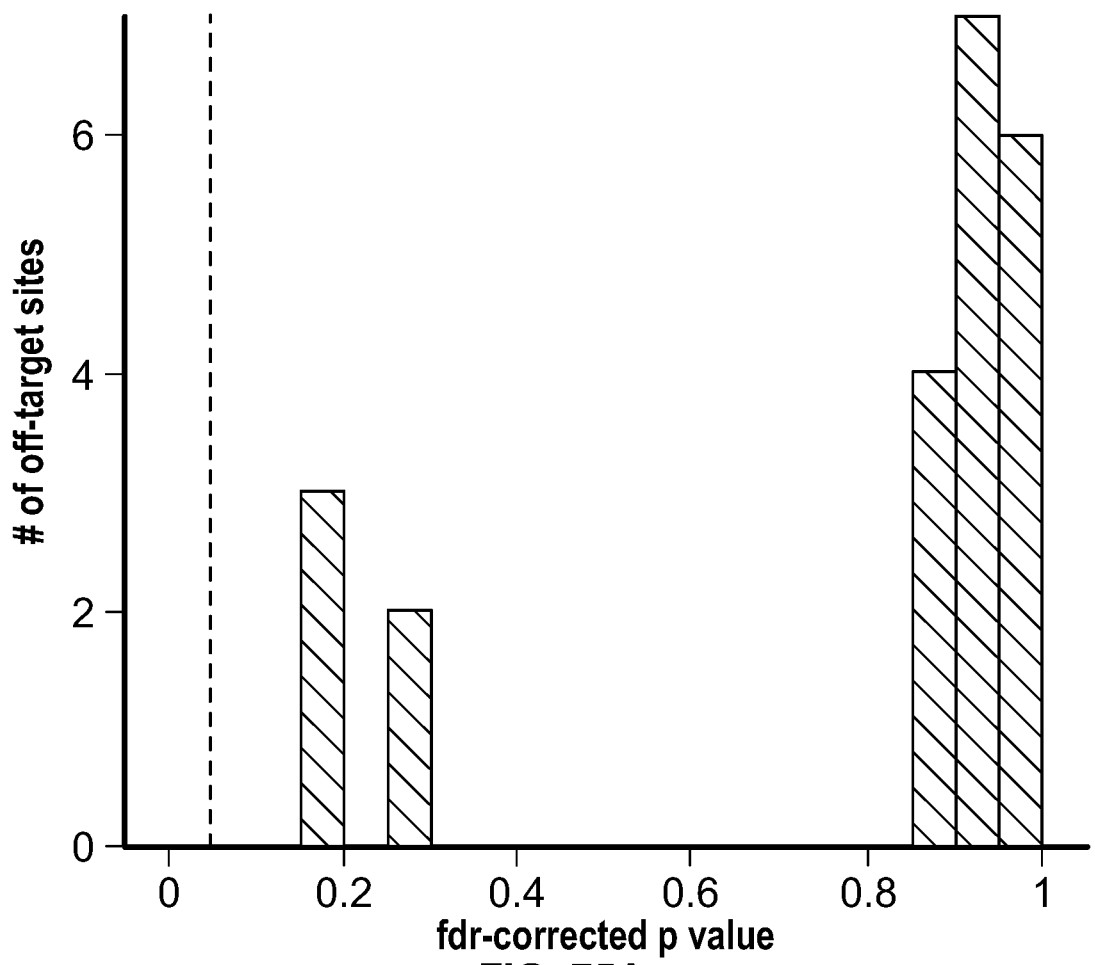
FIG. 75A is a graphical depiction of the analysis of sequence homology between transcriptome off targets (n=23 sites) and PPIB homology region targeted. Corresponding fdr-corrected p-values for the significance of local alignment (Monte Carlo permutation test) between 200 bp surrounding each off-target site and the PPIB homology region targeted by the engineered guide RNA (red line denotes p=0.05).
Figure 75B:
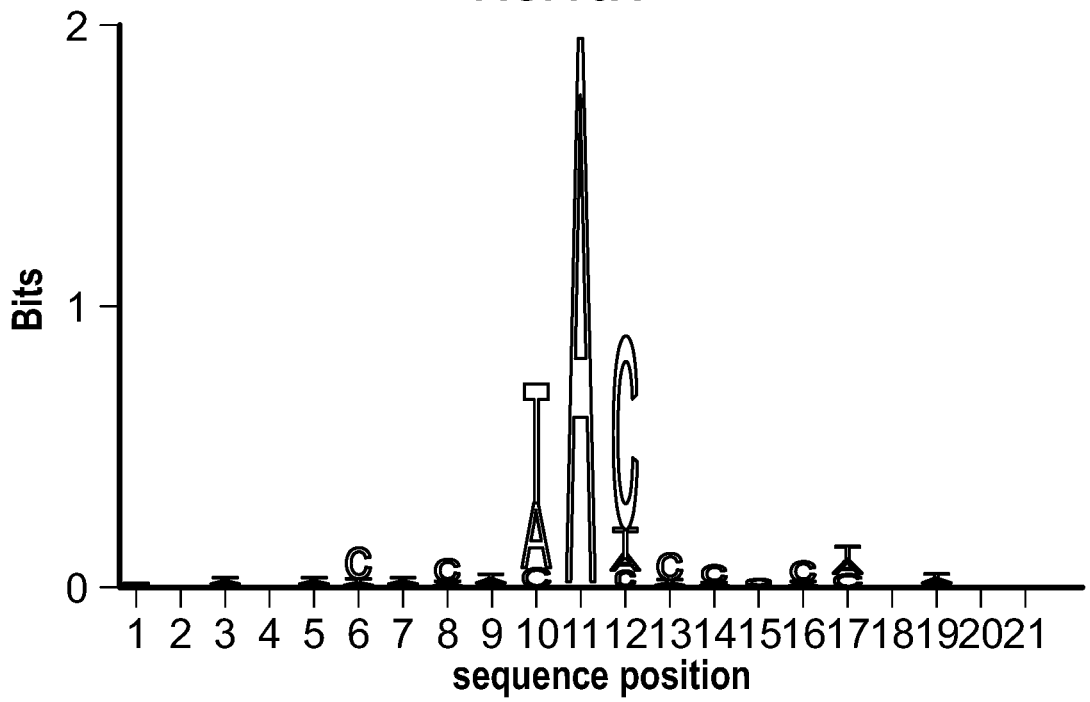
FIG. 75B is a visual depiction of sequence logo analysis of the off-target edit sites from ADAR1p150 overexpression along with PPIB targeting RADARS.

We did not find significant homology in the engineered guide RNA and sequences surrounding the off-target editing site (FIG. 75A). Performing the same sequencing and analysis for a different engineered guide RNA targeting exogenous IL6 target in the presence of ADARp150 overexpression shows a low rate of significant off-target editing (42 sites all less than 10% editing, FIG. 74B). Importantly 22/23 PPIB off-target sites were shared between the two different engineered guide RNA samples. Finally, we found that the sequence motif of the bases surrounding the edit site closely resembles the preferred substrate of ADAR1(Eggington et al., 2011) (FIG. 75B). Overall, these observations imply that RADARS generates relatively few non-specific RNA edits in the transcriptome when utilized with ADARp150 overexpression.

---

What is claimed is:

1. An RNA sensor system comprising:
   a) a synthetic single-stranded RNA (ssRNA) construct comprising (i) a sensor domain, the sensor domain comprising a first hybridization region and an ADAR editable stop codon, and (ii) a payload; and
   b) an adenosine deaminase acting on RNA (ADAR) deaminase;
   wherein the first hybridization region of the synthetic ssRNA sensor construct comprises a degree of sequence complementarity to a second ssRNA, the second ssRNA being an endogenous ssRNA target in a human cell, the degree of complementarity being sufficient to permit hybridization of the first hybridization region to the endogenous ssRNA target to form a bimolecular double-stranded RNA (dsRNA) duplex of the synthetic ssRNA and the second ssRNA comprising a mispairing within the stop codon of the synthetic ssRNA sensor domain, and wherein the dsRNA duplex is a substrate for the ADAR deaminase;
   wherein the mispairing is editable by the ADAR deaminase, which editing can effectively remove the editable stop codon so as to enable translation of the payload from the synthetic single stranded RNA construct.

2. The RNA sensor system of claim 1, wherein the mispairing within the stop codon of the synthetic ssRNA sensor domain comprises an adenosine to cytosine mispairing comprising an adenosine in the synthetic ssRNA sensor domain that is directly opposite to a cytosine in the endogenous ssRNA target in the dsRNA duplex.

3. The RNA sensor system of claim 2, wherein the adenosine of the synthetic ssRNA sensor domain in the mispairing within the stop codon is edited to an inosine by the ADAR deaminase.

4. The RNA sensor system of claim 1, comprising more than one mispairing within the bimolecular dsRNA duplex.

5. The RNA sensor system of claim 1, wherein the payload comprises a reporter protein, a transcription factor, an enzyme, a transgene protein, or a therapeutic protein.

6. The RNA sensor system of claim 5, wherein the payload comprises a therapeutic protein.

7. The RNA sensor system of claim 1, wherein the payload comprises a fluorescent reporter.

8. The RNA sensor system of claim 7, wherein the payload comprises an eGFP reporter or a luciferase reporter.

9. The RNA sensor system of claim 1, wherein the payload comprises a caspase.

10. The RNA sensor system of claim 1, wherein the ADAR is endogenous or exogenous.

11. The RNA sensor system of claim 1, wherein the ADAR deaminase comprises an RNA editing for programmable A to I (G) replacement (REPAIR) molecule, a Cas13b-ADAR fusion molecule, a Cas13d-ADAR fusion molecule, a Cas7-11-ADAR fusion molecule, and MS2-ADAR fusion molecule, a deaminase domain of ADAR2, a full-length ADAR2, or a truncated ADAR2.

12. The RNA sensor system of claim 1, wherein the synthetic ssRNA sensor domain further comprises a normalizing gene.

13. The RNA sensor system of claim 1, wherein the synthetic ssRNA sensor is a circular RNA.

14. A cell logic system comprising:
   a) an AND gate comprising:
   (i) a synthetic single stranded RNA (ssRNA) sensor construct comprising (1) one or more payloads, and (2) a sensor domain comprising multiple ADAR-editable stop codons, and at least a first hybridization region and a second hybridization region, the first and second hybridization regions comprising a degree of sequence complementarity to different ssRNA targets; and
   (ii) an adenosine deaminase acting on RNA (ADAR) deaminase;
   wherein the first hybridization region of the synthetic ssRNA sensor domain comprises a degree of sequence complementarity sufficient to permit hybridization of the first hybridization region to a first endogenous ssRNA target to form an RNA complex of the first hybridization region to the first endogenous ssRNA that comprises one of the multiple ADAR-editable stop codons and is a substrate for the ADAR deaminase, wherein the second hybridization region of the synthetic ssRNA sensor comprises a degree of sequence complementarity sufficient to permit hybridization of the second hybridization region to the second endogenous ssRNA target to form an RNA complex of the second hybridization region to the second endogenous ssRNA target that comprises one of the multiple ADAR-editable stop codons and is a substrate for the ADAR deaminase;
   wherein the substrate comprises a mispairing within the ADAR-editable stop codon;
   which editing can effectively remove the stop codon so as to enable translation of the one or more payloads; or
   b) an OR gate comprising:
   (i) multiple independent synthetic ssRNA sensor constructs, each synthetic ssRNA sensor construct comprising (1) one or more payloads, (2) an ADAR-editable stop codon, and (3) at least a first hybridization region with a degree of sequence complementarity to at least one endogenous ssRNA target; and
   (ii) an adenosine deaminase acting on RNA (ADAR) deaminase;
   wherein the first hybridization region of each synthetic ssRNA sensor construct comprises a degree of sequence complementarity sufficient to permit hybridization of the first hybridization region to the at least one endogenous ssRNA target to form a double-stranded RNA (dsRNA) duplex of the synthetic ssRNA and the endogenous ssRNA target that is a substrate for an ADAR deaminase comprising a mispairing within at least one ADAR-editable stop codon of the synthetic sensor domain;
   wherein the substrate comprises a mispairing within the ADAR-editable stop codon; and which editing can effectively remove the stop codon so as to enable translation of the one or more payloads.

* * * * *